US012612442B2

(12) United States Patent
Russell et al.

(10) Patent No.: US 12,612,442 B2
(45) Date of Patent: Apr. 28, 2026

(54) G12-SPECIFIC DESIGNER RECEPTOR EXCLUSIVELY ACTIVATED BY DESIGNER DRUGS

(71) Applicant: CELL NETWORKS GMBH, Heidelberg (DE)

(72) Inventors: Robert Bruce Russell, Heidelberg (DE); Asuka Inoue, Miyagi (JP)

(73) Assignee: CELL NETWORKS GMBH, Heidelberg (DE)

( * ) Notice: Subject to any disclaimer, the term of this patent is extended or adjusted under 35 U.S.C. 154(b) by 1134 days.

(21) Appl. No.: 17/615,000

(22) PCT Filed: May 29, 2020

(86) PCT No.: PCT/EP2020/064937
§ 371 (c)(1),
(2) Date: Nov. 29, 2021

(87) PCT Pub. No.: WO2020/239967
PCT Pub. Date: Dec. 3, 2020

(65) Prior Publication Data
US 2022/0220185 A1       Jul. 14, 2022

(30) Foreign Application Priority Data
May 29, 2019    (EP) .................................... 19177387

(51) Int. Cl.
| | |
|---|---|
| C07K 14/705 | (2006.01) |
| C07K 19/00 | (2006.01) |
| C12N 9/12 | (2006.01) |
| C12N 9/14 | (2006.01) |

(52) U.S. Cl.
CPC .............. *C07K 14/705* (2013.01); *C12N 9/12* (2013.01); *C12N 9/14* (2013.01); *C12Y 207/11013* (2013.01); *C12Y 306/05002* (2013.01)

(58) Field of Classification Search
None
See application file for complete search history.

(56) References Cited

U.S. PATENT DOCUMENTS

| | | | |
|---|---|---|---|
| 9,670,266 B2 | 6/2017 | Kobilka et al. ...... | C07K 14/723 |
| 2006/0008831 A1 | 1/2006 | Sreekumar et al. .............. | 435/6 |

FOREIGN PATENT DOCUMENTS

| | | | | |
|---|---|---|---|---|
| WO | WO 2008/016356 | 2/2008 | ............... | C12Q 1/68 |
| WO | WO 2015/155360 | 10/2015 | ............. | C12N 5/071 |

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser: Boston, pp. 491-495.*

International Preliminary Report on Patentability issued in PCT/EP2020/064937, dated Nov. 16, 2021, 8 pages.

International Search Report and Written Opinion issued in PCT/EP2020/064937, dated Nov. 19, 2020, 13 pages.

Partial European Search Report issued in EPO Patent Appln. Serial No. 19177387.8-1126, dated Dec. 17, 2019, 16 pages.

Extended European Search Report issued in EPO Patent Appln. Serial No. 19177387.8-1126, dated Apr. 14, 2020, 19 pages.

Altschul et al. "Basic Local Alignment Search Tool" *Journal of Molecular Biology* 215, 403-410, May 15, 1990 8 pages.

Armbruster et al., "Evolving the lock to fit the key to create a family of G protein-coupled receptors potently activated by an inert ligand" *Proc Natl Acad Sci* USA vol. 104, No. 12, Mar. 20, 2007, 6 pages.

Ataei, et al. "A novel luminescent biosensor for rapid monitoring of IP3 by split luciferase complementary assay" *Biosensors and Bioelectronics* vol. 41, Mar. 15, 2013, pp. 642-648, abstract only, 2 pages.

Capper et al. "How the ubiquitous GPCR receptor family selectively activates signalling pathways". Nature 558, 529-530, 2018, abstract only, 1 page.

Cervantes-Villagrana et al., "Gβγ signaling to the chemotactic effector P-REX1 and mammalian cell migration is directly regulated by $G\alpha_q$ and $G\alpha_{13}$ proteins" *Journal of Biological Chemistry* 294(2) 531-546, Nov. 16, 2018, 17 pages.

Chen et al., "Gpr132 sensing of lactate mediates tumor-macrophage interplay to promote breast cancer metastasis" *Proc Natl Acad Sci*, vol. 114, No. 3, 580-585 Jan. 17, 2017, 6 page.

Csardi et al., "The igraph software package for complex network research" InterJournal Complex Systems 2005, 9 pages.

Denker et al., "Promotion of the GTP-liganded State of the $G_{o\alpha}$ Protein by Deletion of the C Terminus" *Journal of Biological Chemistry*, vol. 267, No. 14, May 15, 1992, 9998-10002, 5 pages.

Devost et al., "Conformational Profiling of the AII Angiotensin II Receptor Reflects Biased Agonism, G Prtein Coupling, and Cellular Context" *Journal of Biological Chemistry*, vol. 292 No. 13, Mar. 31, 2017, 5443-5456, 14 pages.

Dijkstra, "A Note on Two Problems in Connexion with Graphs" *Numerische Mathematik* 1, 269-271, 1959, 3 pages.

Dixon et al., "NanoLuc Complementation Reporter Optimized for Accurate Measurement of Protein Interactions in Cells" *ACS Chemical Biology* 2016, 11, 400-408, Nov. 16, 2015, 9 pages.

Dorsam et al., "Central role of the $P2Y_{12}$ receptor in platelet activation" *The Journal of Clinical Investment* vol. 113, No. 3, Feb. 2004, 340-345, 6 pages.

Dou et al., "L1pred: A Sequence-Based Prediction Tool for Catalytic Residues in Enzymes with the L1-logreg Classifier" PLoS, vol. 7, Issue 4, Apr. 2012, 7 pages.

Eddy, Sean R., "Profile hidden Markov models" *Bioinformatics Review*, vol. 14, No. 9, Jul. 23, 1998, 755-763, 9 pages.

(Continued)

*Primary Examiner* — Christine J Saoud
*Assistant Examiner* — Jon M Lockard
(74) *Attorney, Agent, or Firm* — HAYES SOLOWAY P.C.

(57) ABSTRACT

Disclosed is a Designer Receptor Exclusively Activated by Designer Drugs (DREADD), and an amino acid sequence for determining coupling or no coupling between G-protein and G-protein coupled receptor (GPCR) mediated by a GPCR ligand in a cell based assay.

1 Claim, 17 Drawing Sheets

Specification includes a Sequence Listing.

(56)        References Cited

OTHER PUBLICATIONS

Ehlert et al., "A simple method for estimation of agonist activity at receptor subtypes: comparison of native and cloned M3 muscarinic receptors in guinea pig ileum and transfected cells" *Journal of Pharmacology and Experimental Therapeutics*, 289(2); 981-92. May 1999, abstract only, 2 pages.

Finn et al., "The Pfam protein families database: towards a more sustainable future" *Nucleic Acids Research* vol. 44, Dec. 15, 2015, D279-D285, 7 pages.

Flock et al., "Universal allosteric mechanism for Gα activation by GPCRs" *Nature* 524, 173-179, Aug. 13, 2015, 26 pages.

Gales et al., "Real-time monitoring of receptor and G-protein interactions in living cells" *Nature Methods* vol. 2, No. 3, Mar. 2005, 177-184, 8 pages.

Guettier et al., "A chemical-genetic approach to study G protein regulation of β cell function in vivo" *PNAS* vol. 106, No. 45, 19197-19202, Nov. 10, 2009, 6 pages.

Harding et al., "The IUPHAR/BPS Guide to Pharmacology in 2018: updates and expansion to encompass the new guide to Immunopharmacology" Nucleic Acids Res 46, D1091-D1106., 16 pages.

Hauser, et al. "Trends in GPCR drug discovery: new agents, targets and indications" Nat Rev Drug Discov 16, 829-842. Dec. 1, 2017, 33 pages.

Hauser, et al., "Pharmacogenomics of GPCR Drug Targets". Cell 172, 41-54 e19. Jan. 11, 2018, 34 pages.

Herroeder, et a;. "Guanine nucleotide-binding proteins of the G12 family shape immune functions by controlling CD4+ T cell adhesiveness and motility". Immunity 30, 708-720, May 22, 2009, 13 pages.

Horn, et al. "Receptors coupling to G proteins: is there a signal behind the sequence?" Proteins 41, 448-459. Oct. 19, 2000, abstract only, 2 pages.

Hu et al. "Development of novel ligand binding assay for relaxin family peptide receptor 3 and 4 using NanoLuc complementation" *Amino Acids*, May 16, 2018, 9 pages.

Inoue et al., "Illuminating G-Protein-Coupling Selectivity of GPCRs" *Cell*, 177, 1933-1947, Jun. 13, 2019, 41 pages.

Inoue, et al. "TGFalpha shedding assay: an accurate and versatile method for detecting GPCR activation", Nature Methods 9, 1021-1029.Oct. 2012, 11 pages.

Insel, et al. "Forskolin as a tool for examining adenylyl cyclase expression, regulation, and G protein signaling." Cell Mol Neurobiol 23, 305-314. Jun. 2003, abstract only, 2 pages.

Isberg et al. "GPCRdb: an information system for G protein-coupled receptors" Nucleic Acids Res 45, 2936, Nov. 17, 2015, 9 pages.

Kihara, et al. "Lysophospholipid receptor nomenclature review: IUPHAR Review 8". British Journal of Pharmacology 171, 3575-3594. Feb. 12, 2014, 20 pages.

Laschet et al., "A dynamic and screening-compatible nanoluciferase-based complementation assay enables profiling of individual GPCR-G protein interations" *Journal of Biological Chemistry*, Dec. 28, 2018, 25 pages.

Leng et al. "Novel split-luciferase-based genetically encoded biosensors for noninvasive visualization of Rho GTPases". PLoS One 8, e62230. Apr. 16, 2013, 12 pages.

Martin, et al. "The head and neck cancer cell oncogenome: a platform for the development of precision molecular therapies" Oncotarget 5, 8906-8923, Nov. 4, 2014, 18 pages.

Muppidi, et al. "Loss of signalling via Galpha13 in germinal centre B-cell-derived lymphoma" Nature 516, 254-258. Dec. 11, 2014, 25 pages.

Nichols et al. "Engineered G-protein coupled receptors are powerful tools to investigate biological processes and behaviors" *Frontiers in Molecular Neuroscience* vol. 2, Art. 16, Oct. 23, 2009, 10 pages.

O'Hayre, et al. "Inactivating mutations in GNA13 and RHOA in Burkitt's lymphoma and diffuse large B-cell lymphoma: a tumor suppressor function for the Galpha13/RhoA axis in B cells" Oncogene 35, 3771-3780. Jul. 21, 2016, 21 pages.

Patel, et al. "A novel mutation in the P2Y12 receptor and a function-reducing polymorphism in protease- activated receptor 1 in a patient with chronic bleeding" J Thromb Haemost 12, 716-725. Jan. 27, 2014, 10 pages.

Pedregosa et al. "Scikit-learn: Machine Learning in Python" J Machine Learning Res 12, 2825-2830. Oct. 2011, 6 pages.

"Psoriasis associated human protein Seq Id No. 7530" Aug. 21, 2008, 1 page.

Rasmussen, et al. "Crystal structure of the $\beta_2$Adrenergic receptor-Gs protein complex" Nature 477, 549-555. Mar. 29, 2021, 23 pages.

Rodriguez, et al. "Evolution-guided discovery and recoding of allosteric pathway specificity determinants in psychoactive bioamine receptors" Proc Natl Acad Sci U S A 107, 7787-7792. Mar. 16, 2010, 6 pages.

Sauliere, et al. "Deciphering biased-agonism complexity reveals a new active AT1 receptor entity" Nat Chem Biol 8, 622-630. May 27, 2021, abstract only, 2 pages.

Schrage, et al. "The experimental power of FR900359 to study Gq-regulated biological processes". Nature Communications Dec. 14, 2015, 17 pages.

"Sequence 9 from U.S. Pat. No. 9,670,266" Dec. 13, 2017, 1 page.

Sgourakis, N.G., et al. "Prediction of the coupling specificity of GPCRs to four families of G-proteins using hidden Markov models and artificial neural networks". Bioinformatics 21, 4101-4106. Sep. 20, 2005, 6 pages.

Sgourakis, et al. "A method for the prediction of GPCRs coupling specificity to G-proteins using refined profile Hidden Markov Models" BMC Bioinformatics, 6:104, Apr. 22, 2005, 12 pages.

Singh et al., "PRECOG: PREdicting COupling probabilities of G-protein coupled receptors" *Nucleic Acids Research*, vol. 47. W395-W401, May 1, 2019, 7 pages.

Sievers, et al. "Fast, scalable generation of high-quality protein multiple sequence alignments using Clustal Omega" Mol Syst Biol 7, 539. Oct. 11, 2011, 6 pages.

Stallaert, et al. "Purinergic Receptor Transactivation by the $\beta_2$-Adrenergic Receptor Increases Intracellular $Ca^{2+}$ in Nonexcitable Cells" Mol Pharmacol 91, 533-544. Mar. 2017, 12 pages.

Sugimoto, et al. "Prostaglandin E receptors" J Biol Chem 282, 11613-11617. Apr. 20, 2007, 5 pages.

Suzuki et al. "Regulation and physiological functions of G12/13-mediated signaling pathways" Neurosignals 17, 55-70. Feb. 12, 2009, 16 pages.

Thomsen, et al. "Functional assays for sercening GPCR targets" Current opinion in biotechnology 16, 655-665. Oct. 28, 2005, 11 pages.

Urban, et al. "DREADDs (designer receptors exclusively activated by designer drugs): chemogenetic tools with therapeutic utility" Annu Rev Pharmacol Toxicol 55, 399-417. Sep. 25, 2014, abstract only, 2 pages.

Velankar, et al. "SIFTS: Structure Integration with Function, Taxonomy and Sequences resource" Nucleic Acids Res 41, D483-489. Nov. 29, 2021, 7 pages.

Violin, et al. "Biased ligands at G-protein-coupled receptors: promise and progress" Trends Pharmacol Sci 35, 308-316. Jul. 2014, abstract only, 2 pages.

Waterhouse, et al. "Jalview Version 2—a multiple sequence alignment editor and analysis workbench" Bioinformatics vol. 25 No. 9, 1189-1191. 2009, 3 pages.

Weinstein, et al. "Integrated methods for the construction of three-dimensional models and computational probing of structure-function relations in G protein-coupled receptors" Methods in Neuroscience, 25, 366-428, 1995 Abstract only, 2 pages.

Wess, et al. "Novel designer receptors to probe GPCR signaling and physiology" Trends Pharmacol Sci 34, 385-392, Jul. 2013, 15 pages.

Wettschureck, et al. "Mammalian G proteins and their cell type specific functions" Physiol Rev 85, 1159-1204.2005, 46 pages.

Wheeler, et al. "Skylign: a tool for creating informative, interactive logos representing sequence alignments and profile hidden Markov models" BMC Bioinformatics 15, 7, 2014, 9 pages.

Wong, S.K. "G protein selectivity is regulated by multiple intracellular regions of GPCRs" Neurosignals 12, 1-12. 2003, 12 pages.

(56)               References Cited

OTHER PUBLICATIONS

Woodward, et al. "International Union of Basic and Clinical Pharmacology. LXXXIII: Classification of Prostanoid Receptors, Updating 15 Years of Progress" Pharmacol Rev 63, 471-538. 2011, 68 pages.

Yabuki, Y. et al. "GRIFFIN: a system for predicting GPCR-G-protein coupling selectivity using a support vector machine and a hidden Markov model" Nucleic Acids Res 33, W148-153. Apr. 26, 2005, 6 pages.

* cited by examiner

■ Predicted couplings for uncharacterized GPCRs

▨ Experimental couplings
(GtoPdb + Chimerice G-protein assay)

SEQUENCE LISTING

<160> NUMBER OF SEQ ID NOS: 114

<210> SEQ ID NO 1
<211> LENGTH: 502
<212> TYPE: PRT
<213> ORGANISM: Homo sapiens
<220> FEATURE:
<223> OTHER INFORMATION: DREADD M3D

<400> SEQUENCE: 1

Met Asp Tyr Lys Asp Asp Asp Asp Lys Gly Ser Thr Leu His Asn Asn

-continued

```
1                 5                 10                15

Ser Thr Thr Ser Pro Leu Phe Pro Asn Ile Ser Ser Ser Trp Ile His
            20                25                30

Ser Pro Ser Asp Ala Gly Leu Pro Pro Gly Thr Val Thr His Phe Gly
            35                40                45

Ser Tyr Asn Val Ser Arg Ala Ala Gly Asn Phe Ser Ser Pro Asp Gly
       50                55                60

Thr Thr Asp Asp Pro Leu Gly Gly His Thr Val Trp Gln Val Val Phe
65                70                75                80

Ile Ala Phe Leu Thr Gly Ile Leu Ala Leu Val Thr Ile Ile Gly Asn
                 85                90                95

Ile Leu Val Ile Val Ser Phe Lys Val Asn Lys Gln Leu Lys Thr Val
            100               105               110

Asn Asn Tyr Phe Leu Leu Ser Leu Ala Cys Ala Asp Leu Ile Ile Gly
            115               120               125

Val Ile Ser Met Asn Leu Phe Thr Thr Tyr Ile Ile Met Asn Arg Trp
       130               135               140

Ala Leu Gly Asn Leu Ala Cys Asp Leu Trp Leu Ala Ile Asp Cys Val
145               150               155               160

Ala Ser Asn Ala Ser Val Met Asn Leu Leu Val Ile Ser Phe Asp Arg
                 165               170               175

Tyr Phe Ser Ile Thr Arg Pro Leu Thr Tyr Arg Ala Lys Arg Thr Thr
            180               185               190

Lys Arg Ala Gly Val Met Ile Gly Leu Ala Trp Val Ile Ser Phe Val
            195               200               205

Leu Trp Ala Pro Ala Ile Leu Phe Trp Gln Tyr Phe Val Gly Lys Arg
       210               215               220

Thr Val Pro Pro Gly Glu Cys Phe Ile Gln Phe Leu Ser Glu Pro Thr
225               230               235               240

Ile Thr Phe Gly Thr Ala Ile Ala Gly Phe Tyr Met Pro Val Thr Ile
                 245               250               255

Met Thr Ile Leu Tyr Trp Arg Ile Tyr Lys Glu Thr Glu Lys Arg Thr
            260               265               270

Lys Glu Leu Ala Gly Leu Gln Ala Ser Gly Thr Glu Ala Glu Thr Glu
            275               280               285

Asn Phe Val His Pro Thr Gly Ser Ser Arg Ser Cys Ser Ser Tyr Glu
       290               295               300

Leu Gln Gln Gln Ser Met Lys Arg Ser Asn Arg Arg Lys Tyr Gly Arg
305               310               315               320

Cys His Phe Trp Phe Thr Thr Lys Ser Trp Lys Pro Ser Ser Glu Gln
                 325               330               335

Met Asp Gln Asp His Ser Ser Ser Asp Ser Trp Asn Asn Asn Asp Ala
            340               345               350

Ala Ala Ser Leu Glu Asn Ser Ala Ser Ser Asp Glu Glu Asp Ile Gly
            355               360               365

Ser Glu Thr Arg Ala Ile Tyr Ser Ile Val Leu Lys Leu Pro Gly His
       370               375               380

Ser Thr Ile Leu Asn Ser Thr Lys Leu Pro Ser Ser Asp Asn Leu Gln
385               390               395               400

Val Pro Glu Glu Glu Leu Gly Met Val Asp Leu Glu Arg Lys Ala Asp
                 405               410               415

Lys Leu Gln Ala Gln Lys Ser Val Asp Asp Gly Gly Ser Phe Pro Lys
            420               425               430
```

```
Ser Phe Ser Lys Leu Pro Ile Gln Leu Glu Ser Ala Val Asp Thr Ala
        435                 440                 445

Lys Thr Ser Asp Val Asn Ser Ser Val Gly Lys Ser Thr Ala Thr Leu
        450                 455                 460

Pro Leu Ser Phe Lys Glu Ala Thr Leu Ala Lys Arg Phe Ala Leu Lys
465                 470                 475                 480

Thr Arg Ser Gln Ile Thr Lys Arg Lys Arg Met Ser Leu Val Lys Glu
                485                 490                 495

Lys Lys Ala Ala Gln Thr
        500
```

```
<210> SEQ ID NO 2
<211> LENGTH: 388
<212> TYPE: PRT
<213> ORGANISM: Homo sapiens
<220> FEATURE:
<223> OTHER INFORMATION: M3D-GPR183/ICL3

<400> SEQUENCE: 2

Met Asp Tyr Lys Asp Asp Asp Lys Gly Ser Thr Leu His Asn Asn
1               5                   10                  15

Ser Thr Thr Ser Pro Leu Phe Pro Asn Ile Ser Ser Ser Trp Ile His
            20                  25                  30

Ser Pro Ser Asp Ala Gly Leu Pro Pro Gly Thr Val Thr His Phe Gly
            35                  40                  45

Ser Tyr Asn Val Ser Arg Ala Ala Gly Asn Phe Ser Ser Pro Asp Gly
        50                  55                  60

Thr Thr Asp Asp Pro Leu Gly Gly His Thr Val Trp Gln Val Val Phe
65                  70                  75                  80

Ile Ala Phe Leu Thr Gly Ile Leu Ala Leu Val Thr Ile Ile Gly Asn
                85                  90                  95

Ile Leu Val Ile Val Ser Phe Lys Val Asn Lys Gln Leu Lys Thr Val
            100                 105                 110

Asn Asn Tyr Phe Leu Leu Ser Leu Ala Cys Ala Asp Leu Ile Ile Gly
        115                 120                 125

Val Ile Ser Met Asn Leu Phe Thr Thr Tyr Ile Ile Met Asn Arg Trp
    130                 135                 140

Ala Leu Gly Asn Leu Ala Cys Asp Leu Trp Leu Ala Ile Asp Cys Val
145                 150                 155                 160

Ala Ser Asn Ala Ser Val Met Asn Leu Leu Val Ile Ser Phe Asp Arg
                165                 170                 175

Tyr Phe Ser Ile Thr Arg Pro Leu Thr Tyr Arg Ala Lys Arg Thr Thr
            180                 185                 190

Lys Arg Ala Gly Val Met Ile Gly Leu Ala Trp Val Ile Ser Phe Val
        195                 200                 205

Leu Trp Ala Pro Ala Ile Leu Phe Trp Gln Tyr Phe Val Gly Lys Arg
    210                 215                 220

Thr Val Pro Pro Gly Glu Cys Phe Ile Gln Phe Leu Ser Glu Pro Thr
225                 230                 235                 240

Ile Thr Phe Gly Thr Ala Ile Ala Gly Phe Tyr Met Pro Val Thr Ile
                245                 250                 255

Met Thr Ile Leu Tyr Trp Arg Ile Tyr Lys Glu Thr Glu Arg Thr Ala
            260                 265                 270

Lys Gln Asn Pro Leu Thr Glu Lys Ser Gly Val Glu Lys Lys Ala Ala
        275                 280                 285
```

```
Gln Thr Leu Ser Ala Ile Leu Leu Ala Phe Ile Ile Thr Trp Thr Pro
    290                 295                 300

Tyr Asn Ile Met Val Leu Val Asn Thr Phe Cys Asp Ser Cys Ile Pro
305                 310                 315                 320

Lys Thr Phe Trp Asn Leu Gly Tyr Trp Leu Cys Tyr Ile Asn Ser Thr
                325                 330                 335

Val Asn Pro Val Cys Tyr Ala Leu Cys Asn Lys Thr Phe Arg Thr Thr
                340                 345                 350

Phe Lys Met Leu Leu Leu Cys Gln Cys Asp Lys Lys Lys Arg Arg Lys
                355                 360                 365

Gln Gln Tyr Gln Gln Arg Gln Ser Val Ile Phe His Lys Arg Ala Pro
        370                 375                 380

Glu Gln Ala Leu
385

<210> SEQ ID NO 3
<211> LENGTH: 383
<212> TYPE: PRT
<213> ORGANISM: Homo sapiens
<220> FEATURE:
<223> OTHER INFORMATION: M3D-GPR132/ICL3

<400> SEQUENCE: 3

Met Asp Tyr Lys Asp Asp Asp Lys Gly Ser Thr Leu His Asn Asn
1               5               10              15

Ser Thr Thr Ser Pro Leu Phe Pro Asn Ile Ser Ser Ser Trp Ile His
                20                  25                  30

Ser Pro Ser Asp Ala Gly Leu Pro Pro Gly Thr Val Thr His Phe Gly
            35                  40                  45

Ser Tyr Asn Val Ser Arg Ala Ala Gly Asn Phe Ser Ser Pro Asp Gly
    50                  55                  60

Thr Thr Asp Asp Pro Leu Gly Gly His Thr Val Trp Gln Val Val Phe
65                  70                  75                  80

Ile Ala Phe Leu Thr Gly Ile Leu Ala Leu Val Thr Ile Ile Gly Asn r
                85                  90                  95

Ile Leu Val Ile Val Ser Phe Lys Val Asn Lys Gln Leu Lys Thr Val
                100                 105                 110

Asn Asn Tyr Phe Leu Leu Ser Leu Ala Cys Ala Asp Leu Ile Ile Gly
            115                 120                 125

Val Ile Ser Met Asn Leu Phe Thr Thr Tyr Ile Ile Met Asn Arg Trp
    130                 135                 140

Ala Leu Gly Asn Leu Ala Cys Asp Leu Trp Leu Ala Ile Asp Cys Val
145                 150                 155                 160

Ala Ser Asn Ala Ser Val Met Asn Leu Leu Val Ile Ser Phe Asp Arg
                165                 170                 175

Tyr Phe Ser Ile Thr Arg Pro Leu Thr Tyr Arg Ala Lys Arg Thr Thr
                180                 185                 190

Lys Arg Ala Gly Val Met Ile Gly Leu Ala Trp Val Ile Ser Phe Val
            195                 200                 205

Leu Trp Ala Pro Ala Ile Leu Phe Trp Gln Tyr Phe Val Gly Lys Arg
        210                 215                 220

Thr Val Pro Pro Gly Glu Cys Phe Ile Gln Phe Leu Ser Glu Pro Thr
225                 230                 235                 240

Ile Thr Phe Gly Thr Ala Ile Ala Gly Phe Tyr Met Pro Val Thr Ile
                245                 250                 255
```

```
Met Thr Ile Leu Tyr Trp Arg Ile Tyr Lys Glu Thr Glu Gln Ser Met
        260                 265             270

Gly Leu Ser Ala Ala Gln Glu Lys Lys Ala Ala Gln Thr Leu Ser Ala
        275                 280             285

Ile Leu Leu Ala Phe Ile Ile Thr Trp Thr Pro Tyr Asn Ile Met Val
        290                 295             300

Leu Val Asn Thr Phe Cys Asp Ser Cys Ile Pro Lys Thr Phe Trp Asn
305                 310             315                 320

Leu Gly Tyr Trp Leu Cys Tyr Ile Asn Ser Thr Val Asn Pro Val Cys
                325             330             335

Tyr Ala Leu Cys Asn Lys Thr Phe Arg Thr Thr Phe Lys Met Leu Leu
        340                 345             350

Leu Cys Gln Cys Asp Lys Lys Lys Arg Arg Lys Gln Gln Tyr Gln Gln
        355                 360             365

Arg Gln Ser Val Ile Phe His Lys Arg Ala Pro Glu Gln Ala Leu
        370                 375             380
```

```
<210> SEQ ID NO 4
<211> LENGTH: 388
<212> TYPE: PRT
<213> ORGANISM: Homo sapiens
<220> FEATURE:
<223> OTHER INFORMATION: M3D-GPR183/ICL3 (1.57V)

<400> SEQUENCE: 4
```

```
Met Asp Tyr Lys Asp Asp Asp Asp Lys Gly Ser Thr Leu His Asn Asn
1               5               10              15

Ser Thr Thr Ser Pro Leu Phe Pro Asn Ile Ser Ser Ser Trp Ile His
        20              25              30

Ser Pro Ser Asp Ala Gly Leu Pro Pro Gly Thr Val Thr His Phe Gly
        35              40              45

Ser Tyr Asn Val Ser Arg Ala Ala Gly Asn Phe Ser Ser Pro Asp Gly
        50              55              60

Thr Thr Asp Asp Pro Leu Gly Gly His Thr Val Trp Gln Val Val Phe
65              70              75              80

Ile Ala Phe Leu Thr Gly Ile Leu Ala Leu Val Thr Ile Ile Gly Asn
        85              90              95

Ile Leu Val Ile Val Ser Val Lys Val Asn Lys Gln Leu Lys Thr Val
        100             105             110

Asn Asn Tyr Phe Leu Leu Ser Leu Ala Cys Ala Asp Leu Ile Ile Gly
        115             120             125

Val Ile Ser Met Asn Leu Phe Thr Thr Tyr Ile Ile Met Asn Arg Trp
        130             135             140

Ala Leu Gly Asn Leu Ala Cys Asp Leu Trp Leu Ala Ile Asp Cys Val
145             150             155             160

Ala Ser Asn Ala Ser Val Met Asn Leu Leu Val Ile Ser Phe Asp Arg
        165             170             175

Tyr Phe Ser Ile Thr Arg Pro Leu Thr Tyr Arg Ala Lys Arg Thr Thr
        180             185             190

Lys Arg Ala Gly Val Met Ile Gly Leu Ala Trp Val Ile Ser Phe Val
        195             200             205

Leu Trp Ala Pro Ala Ile Leu Phe Trp Gln Tyr Phe Val Gly Lys Arg
        210             215             220

Thr Val Pro Pro Gly Glu Cys Phe Ile Gln Phe Leu Ser Glu Pro Thr
225             230             235             240
```

```
Ile Thr Phe Gly Thr Ala Ile Ala Gly Phe Tyr Met Pro Val Thr Ile
            245                 250                 255

Met Thr Ile Leu Tyr Trp Arg Ile Tyr Lys Glu Thr Glu Arg Thr Ala
            260                 265                 270

Lys Gln Asn Pro Leu Thr Glu Lys Ser Gly Val Glu Lys Lys Ala Ala
            275                 280                 285

Gln Thr Leu Ser Ala Ile Leu Leu Ala Phe Ile Ile Thr Trp Thr Pro
        290                 295                 300

Tyr Asn Ile Met Val Leu Val Asn Thr Phe Cys Asp Ser Cys Ile Pro
305                 310                 315                 320

Lys Thr Phe Trp Asn Leu Gly Tyr Trp Leu Cys Tyr Ile Asn Ser Thr
                325                 330                 335

Val Asn Pro Val Cys Tyr Ala Leu Cys Asn Lys Thr Phe Arg Thr Thr
            340                 345                 350

Phe Lys Met Leu Leu Leu Cys Gln Cys Asp Lys Lys Arg Arg Lys
            355                 360                 365

Gln Gln Tyr Gln Gln Arg Gln Ser Val Ile Phe His Lys Arg Ala Pro
        370                 375                 380

Glu Gln Ala Leu
385
```

<210> SEQ ID NO 5
<211> LENGTH: 582
<212> TYPE: PRT
<213> ORGANISM: Homo sapiens
<220> FEATURE:
<223> OTHER INFORMATION: G\'ce\'b1s-Lg (GNAS-LgBiT)

<400> SEQUENCE: 5

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Gly Gly Ser Gly Gly Gly Gly Ser Gly Gly Ser Ser Ser Gly Gly
            115                 120                 125

Val Phe Thr Leu Glu Asp Phe Val Gly Asp Trp Glu Gln Thr Ala Ala
        130                 135                 140

Tyr Asn Leu Asp Gln Val Leu Glu Gln Gly Gly Val Ser Ser Leu Leu
145                 150                 155                 160

Gln Asn Leu Ala Val Ser Val Thr Pro Ile Gln Arg Ile Val Arg Ser
                165                 170                 175

Gly Glu Asn Ala Leu Lys Ile Asp Ile His Val Ile Ile Pro Tyr Glu
            180                 185                 190

Gly Leu Ser Ala Asp Gln Met Ala Gln Ile Glu Glu Val Phe Lys Val
            195                 200                 205
```

-continued

```
Val Tyr Pro Val Asp Asp His His Phe Lys Val Ile Leu Pro Tyr Gly
    210             215             220

Thr Leu Val Ile Asp Gly Val Thr Pro Asn Met Leu Asn Tyr Phe Gly
225             230             235             240

Arg Pro Tyr Glu Gly Ile Ala Val Phe Asp Gly Lys Lys Ile Thr Val
            245             250             255

Thr Gly Thr Leu Trp Asn Gly Asn Lys Ile Ile Asp Glu Arg Leu Ile
            260             265             270

Thr Pro Asp Gly Ser Met Leu Phe Arg Val Thr Ile Asn Ser Gly Gly
            275             280             285

Ser Gly Gly Gly Gly Ser Gly Gly Ser Ser Ser Gly Gly Val Pro Pro
    290             295             300

Val Glu Leu Ala Asn Pro Glu Asn Gln Phe Arg Val Asp Tyr Ile Leu
305             310             315             320

Ser Val Met Asn Val Pro Asp Phe Asp Phe Pro Pro Glu Phe Tyr Glu
            325             330             335

His Ala Lys Ala Leu Trp Glu Asp Glu Gly Val Arg Ala Cys Tyr Glu
            340             345             350

Arg Ser Asn Glu Tyr Gln Leu Ile Asp Cys Ala Gln Tyr Phe Leu Asp
            355             360             365

Lys Ile Asp Val Ile Lys Gln Ala Asp Tyr Val Pro Ser Asp Gln Asp
    370             375             380

Leu Leu Arg Cys Arg Val Leu Thr Ser Gly Ile Phe Glu Thr Lys Phe
385             390             395             400

Gln Val Asp Lys Val Asn Phe His Met Phe Asp Val Gly Gly Gln Arg
            405             410             415

Asp Glu Arg Arg Lys Trp Ile Gln Cys Phe Asn Asp Val Thr Ala Ile
            420             425             430

Ile Phe Val Val Ala Ser Ser Tyr Asn Met Val Ile Arg Glu Asp
            435             440             445

Asn Gln Thr Asn Arg Leu Gln Glu Ala Leu Asn Leu Phe Lys Ser Ile
    450             455             460

Trp Asn Asn Arg Trp Leu Arg Thr Ile Ser Val Ile Leu Phe Leu Asn
465             470             475             480

Lys Gln Asp Leu Leu Ala Glu Lys Val Leu Ala Gly Lys Ser Lys Ile
            485             490             495

Glu Asp Tyr Phe Pro Glu Phe Ala Arg Tyr Thr Thr Pro Glu Asp Ala
            500             505             510

Thr Pro Glu Pro Gly Glu Asp Pro Arg Val Thr Arg Ala Lys Tyr Phe
            515             520             525

Ile Arg Asp Glu Phe Leu Arg Ile Ser Thr Ala Ser Gly Asp Gly Arg
    530             535             540

His Tyr Cys Tyr Pro His Phe Thr Cys Ala Val Asp Thr Glu Asn Ile
545             550             555             560

Arg Arg Val Phe Asn Asp Cys Arg Asp Ile Ile Gln Arg Met His Leu
            565             570             575

Arg Gln Tyr Glu Leu Leu
            580
```

<210> SEQ ID NO 6
<211> LENGTH: 542
<212> TYPE: PRT
<213> ORGANISM: Homo sapiens
<220> FEATURE:

<223> OTHER INFORMATION: G\'ce\'b1i1-Lg (GNAI1-LgBiT)

<400> SEQUENCE: 6

```
Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
        50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Gly Gly Ser Gly Gly
                85                  90                  95

Gly Gly Ser Gly Gly Ser Ser Ser Gly Gly Val Phe Thr Leu Glu Asp
            100                 105                 110

Phe Val Gly Asp Trp Glu Gln Thr Ala Ala Tyr Asn Leu Asp Gln Val
            115                 120                 125

Leu Glu Gln Gly Gly Val Ser Ser Leu Leu Gln Asn Leu Ala Val Ser
        130                 135                 140

Val Thr Pro Ile Gln Arg Ile Val Arg Ser Gly Glu Asn Ala Leu Lys
145                 150                 155                 160

Ile Asp Ile His Val Ile Ile Pro Tyr Glu Gly Leu Ser Ala Asp Gln
                165                 170                 175

Met Ala Gln Ile Glu Glu Val Phe Lys Val Val Tyr Pro Val Asp Asp
            180                 185                 190

His His Phe Lys Val Ile Leu Pro Tyr Gly Thr Leu Val Ile Asp Gly
            195                 200                 205

Val Thr Pro Asn Met Leu Asn Tyr Phe Gly Arg Pro Tyr Glu Gly Ile
        210                 215                 220

Ala Val Phe Asp Gly Lys Lys Ile Thr Val Thr Gly Thr Leu Trp Asn
225                 230                 235                 240

Gly Asn Lys Ile Ile Asp Glu Arg Leu Ile Thr Pro Asp Gly Ser Met
                245                 250                 255

Leu Phe Arg Val Thr Ile Asn Ser Gly Gly Ser Gly Gly Gly Gly Ser
            260                 265                 270

Gly Gly Ser Ser Ser Gly Gly Lys Ile Asp Phe Gly Asp Ser Ala Arg
            275                 280                 285

Ala Asp Asp Ala Arg Gln Leu Phe Val Leu Ala Gly Ala Ala Glu Glu
        290                 295                 300

Gly Phe Met Thr Ala Glu Leu Ala Gly Val Ile Lys Arg Leu Trp Lys
305                 310                 315                 320

Asp Ser Gly Val Gln Ala Cys Phe Asn Arg Ser Arg Glu Tyr Gln Leu
                325                 330                 335

Asn Asp Ser Ala Ala Tyr Tyr Leu Asn Asp Leu Asp Arg Ile Ala Gln
            340                 345                 350

Pro Asn Tyr Ile Pro Thr Gln Gln Asp Val Leu Arg Thr Arg Val Lys
            355                 360                 365

Thr Thr Gly Ile Val Glu Thr His Phe Thr Phe Lys Asp Leu His Phe
        370                 375                 380

Lys Met Phe Asp Val Gly Gly Gln Arg Ser Glu Arg Lys Lys Trp Ile
385                 390                 395                 400
```

```
His Cys Phe Glu Gly Val Thr Ala Ile Ile Phe Cys Val Ala Leu Ser
            405                 410                 415

Asp Tyr Asp Leu Val Leu Ala Glu Asp Glu Glu Met Asn Arg Met His
        420                 425                 430

Glu Ser Met Lys Leu Phe Asp Ser Ile Cys Asn Asn Lys Trp Phe Thr
        435                 440                 445

Asp Thr Ser Ile Ile Leu Phe Leu Asn Lys Lys Asp Leu Phe Glu Glu
    450                 455                 460

Lys Ile Lys Lys Ser Pro Leu Thr Ile Cys Tyr Pro Glu Tyr Ala Gly
465                 470                 475                 480

Ser Asn Thr Tyr Glu Glu Ala Ala Ala Tyr Ile Gln Cys Gln Phe Glu
                485                 490                 495

Asp Leu Asn Lys Arg Lys Asp Thr Lys Glu Ile Tyr Thr His Phe Thr
            500                 505                 510

Cys Ala Thr Asp Thr Lys Asn Val Gln Phe Val Phe Asp Ala Val Thr
        515                 520                 525

Asp Val Ile Ile Lys Asn Asn Leu Lys Asp Cys Gly Leu Phe
    530                 535                 540
```

<210> SEQ ID NO 7
<211> LENGTH: 543
<212> TYPE: PRT
<213> ORGANISM: Homo sapiens
<220> FEATURE:
<223> OTHER INFORMATION: G\'ce\'b1i2-Lg (GNAI2-LgBiT)

<400> SEQUENCE: 7

```
Met Gly Cys Thr Val Ser Ala Glu Asp Lys Ala Ala Ala Glu Arg Ser
1               5                   10                  15

Lys Met Ile Asp Lys Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Glu
    50                  55                  60

Glu Cys Arg Gln Tyr Arg Ala Val Val Tyr Ser Asn Thr Ile Gln Ser
65                  70                  75                  80

Ile Met Ala Ile Val Lys Ala Met Gly Asn Leu Gly Gly Ser Gly Gly
                85                  90                  95

Gly Gly Ser Gly Gly Ser Ser Ser Gly Gly Val Phe Thr Leu Glu Asp
            100                 105                 110

Phe Val Gly Asp Trp Glu Gln Thr Ala Ala Tyr Asn Leu Asp Gln Val
        115                 120                 125

Leu Glu Gln Gly Gly Val Ser Ser Leu Leu Gln Asn Leu Ala Val Ser
        130                 135                 140

Val Thr Pro Ile Gln Arg Ile Val Arg Ser Gly Glu Asn Ala Leu Lys
145                 150                 155                 160

Ile Asp Ile His Val Ile Ile Pro Tyr Glu Gly Leu Ser Ala Asp Gln
                165                 170                 175

Met Ala Gln Ile Glu Glu Val Phe Lys Val Val Tyr Pro Val Asp Asp
            180                 185                 190

His His Phe Lys Val Ile Leu Pro Tyr Gly Thr Leu Val Ile Asp Gly
        195                 200                 205

Val Thr Pro Asn Met Leu Asn Tyr Phe Gly Arg Pro Tyr Glu Gly Ile
    210                 215                 220
```

```
Ala Val Phe Asp Gly Lys Lys Ile Thr Val Thr Gly Thr Leu Trp Asn
225             230                 235                 240

Gly Asn Lys Ile Ile Asp Glu Arg Leu Ile Thr Pro Asp Gly Ser Met
                245                 250                 255

Leu Phe Arg Val Thr Ile Asn Ser Gly Gly Ser Gly Gly Gly Gly Ser
            260                 265                 270

Gly Gly Ser Ser Ser Gly Gly Gln Ile Asp Phe Ala Asp Pro Ser Arg
            275                 280                 285

Ala Asp Asp Ala Arg Gln Leu Phe Ala Leu Ser Cys Thr Ala Glu Glu
        290                 295                 300

Gln Gly Val Leu Pro Asp Asp Leu Ser Gly Val Ile Arg Arg Leu Trp
305                 310                 315                 320

Ala Asp His Gly Val Gln Ala Cys Phe Gly Arg Ser Arg Glu Tyr Gln
            325                 330                 335

Leu Asn Asp Ser Ala Ala Tyr Tyr Leu Asn Asp Leu Glu Arg Ile Ala
            340                 345                 350

Gln Ser Asp Tyr Ile Pro Thr Gln Gln Asp Val Leu Arg Thr Arg Val
            355                 360                 365

Lys Thr Thr Gly Ile Val Glu Thr His Phe Thr Phe Lys Asp Leu His
        370                 375                 380

Phe Lys Met Phe Asp Val Gly Gly Gln Arg Ser Glu Arg Lys Lys Trp
385                 390                 395                 400

Ile His Cys Phe Glu Gly Val Thr Ala Ile Ile Phe Cys Val Ala Leu
                405                 410                 415

Ser Ala Tyr Asp Leu Val Leu Ala Glu Asp Glu Glu Met Asn Arg Met
            420                 425                 430

His Glu Ser Met Lys Leu Phe Asp Ser Ile Cys Asn Asn Lys Trp Phe
            435                 440                 445

Thr Asp Thr Ser Ile Ile Leu Phe Leu Asn Lys Lys Asp Leu Phe Glu
        450                 455                 460

Glu Lys Ile Thr His Ser Pro Leu Thr Ile Cys Phe Pro Glu Tyr Thr
465                 470                 475                 480

Gly Ala Asn Lys Tyr Asp Glu Ala Ala Ser Tyr Ile Gln Ser Lys Phe
                485                 490                 495

Glu Asp Leu Asn Lys Arg Lys Asp Thr Lys Glu Ile Tyr Thr His Phe
            500                 505                 510

Thr Cys Ala Thr Asp Thr Lys Asn Val Gln Phe Val Phe Asp Ala Val
            515                 520                 525

Thr Asp Val Ile Ile Lys Asn Asn Leu Lys Asp Cys Gly Leu Phe
        530                 535                 540
```

<210> SEQ ID NO 8
<211> LENGTH: 542
<212> TYPE: PRT
<213> ORGANISM: Homo sapiens
<220> FEATURE:
<223> OTHER INFORMATION: G\'ce\'b1i3-Lg (GNAI3-LgBiT)

<400> SEQUENCE: 8

```
Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Lys
                20                  25                  30

Glu Val Lys Leu Leu Leu Leu Gly Ala Gly Glu Ser Gly Lys Ser Thr
            35                  40                  45
```

-continued

```
Ile Val Lys Gln Met Lys Ile Ile His Glu Asp Gly Tyr Ser Glu Asp
    50              55                  60

Glu Cys Lys Gln Tyr Lys Val Val Val Tyr Ser Asn Thr Ile Gln Ser
65              70                  75                  80

Ile Ile Ala Ile Ile Arg Ala Met Gly Arg Leu Gly Gly Ser Gly Gly
                85                  90                  95

Gly Gly Ser Gly Gly Ser Ser Ser Gly Gly Val Phe Thr Leu Glu Asp
            100                 105                 110

Phe Val Gly Asp Trp Glu Gln Thr Ala Ala Tyr Asn Leu Asp Gln Val
            115                 120                 125

Leu Glu Gln Gly Gly Val Ser Ser Leu Leu Gln Asn Leu Ala Val Ser
    130                 135                 140

Val Thr Pro Ile Gln Arg Ile Val Arg Ser Gly Glu Asn Ala Leu Lys
145                 150                 155                 160

Ile Asp Ile His Val Ile Ile Pro Tyr Glu Gly Leu Ser Ala Asp Gln
                165                 170                 175

Met Ala Gln Ile Glu Glu Val Phe Lys Val Val Tyr Pro Val Asp Asp
                180                 185                 190

His His Phe Lys Val Ile Leu Pro Tyr Gly Thr Leu Val Ile Asp Gly
            195                 200                 205

Val Thr Pro Asn Met Leu Asn Tyr Phe Gly Arg Pro Tyr Glu Gly Ile
    210                 215                 220

Ala Val Phe Asp Gly Lys Lys Ile Thr Val Thr Gly Thr Leu Trp Asn
225                 230                 235                 240

Gly Asn Lys Ile Ile Asp Glu Arg Leu Ile Thr Pro Asp Gly Ser Met
                245                 250                 255

Leu Phe Arg Val Thr Ile Asn Ser Gly Gly Ser Gly Gly Gly Gly Ser
            260                 265                 270

Gly Gly Ser Ser Ser Gly Gly Lys Ile Asp Phe Gly Glu Ala Ala Arg
            275                 280                 285

Ala Asp Asp Ala Arg Gln Leu Phe Val Leu Ala Gly Ser Ala Glu Glu
    290                 295                 300

Gly Val Met Thr Pro Glu Leu Ala Gly Val Ile Lys Arg Leu Trp Arg
305                 310                 315                 320

Asp Gly Gly Val Gln Ala Cys Phe Ser Arg Ser Arg Glu Tyr Gln Leu
            325                 330                 335

Asn Asp Ser Ala Ser Tyr Tyr Leu Asn Asp Leu Asp Arg Ile Ser Gln
            340                 345                 350

Ser Asn Tyr Ile Pro Thr Gln Gln Asp Val Leu Arg Thr Arg Val Lys
            355                 360                 365

Thr Thr Gly Ile Val Glu Thr His Phe Thr Phe Lys Asp Leu Tyr Phe
    370                 375                 380

Lys Met Phe Asp Val Gly Gly Gln Arg Ser Glu Arg Lys Lys Trp Ile
385                 390                 395                 400

His Cys Phe Glu Gly Val Thr Ala Ile Ile Phe Cys Val Ala Leu Ser
            405                 410                 415

Asp Tyr Asp Leu Val Leu Ala Glu Asp Glu Glu Met Asn Arg Met His
            420                 425                 430

Glu Ser Met Lys Leu Phe Asp Ser Ile Cys Asn Asn Lys Trp Phe Thr
            435                 440                 445

Glu Thr Ser Ile Ile Leu Phe Leu Asn Lys Lys Asp Leu Phe Glu Glu
    450                 455                 460

Lys Ile Lys Arg Ser Pro Leu Thr Ile Cys Tyr Pro Glu Tyr Thr Gly
```

-continued

```
465             470             475             480

Ser Asn Thr Tyr Glu Glu Ala Ala Tyr Ile Gln Cys Gln Phe Glu
                485             490             495

Asp Leu Asn Arg Arg Lys Asp Thr Lys Glu Ile Tyr Thr His Phe Thr
            500             505             510

Cys Ala Thr Asp Thr Lys Asn Val Gln Phe Val Phe Asp Ala Val Thr
            515             520             525

Asp Val Ile Ile Lys Asn Asn Leu Lys Glu Cys Gly Leu Tyr
        530             535             540

<210> SEQ ID NO 9
<211> LENGTH: 542
<212> TYPE: PRT
<213> ORGANISM: Homo sapiens
<220> FEATURE:
<223> OTHER INFORMATION: G\'ce\'b1o-Lg (GNAO1-LgBiT)

<400> SEQUENCE: 9

Met Gly Cys Thr Leu Ser Ala Glu Glu Arg Ala Ala Leu Glu Arg Ser
1               5               10              15

Lys Ala Ile Glu Lys Asn Leu Lys Glu Asp Gly Ile Ser Ala Ala Lys
            20              25              30

Asp Val Lys Leu Leu Leu Leu Gly Ala Gly Glu Ser Gly Lys Ser Thr
        35              40              45

Ile Val Lys Gln Met Lys Ile Ile His Glu Asp Gly Phe Ser Gly Glu
        50              55              60

Asp Val Lys Gln Tyr Lys Pro Val Val Tyr Ser Asn Thr Ile Gln Ser
65              70              75              80

Leu Ala Ala Ile Val Arg Ala Met Asp Thr Leu Gly Gly Ser Gly Gly
            85              90              95

Gly Gly Ser Gly Gly Ser Ser Ser Gly Gly Val Phe Thr Leu Glu Asp
            100             105             110

Phe Val Gly Asp Trp Glu Gln Thr Ala Ala Tyr Asn Leu Asp Gln Val
            115             120             125

Leu Glu Gln Gly Gly Val Ser Ser Leu Leu Gln Asn Leu Ala Val Ser
        130             135             140

Val Thr Pro Ile Gln Arg Ile Val Arg Ser Gly Glu Asn Ala Leu Lys
145             150             155             160

Ile Asp Ile His Val Ile Ile Pro Tyr Glu Gly Leu Ser Ala Asp Gln
            165             170             175

Met Ala Gln Ile Glu Glu Val Phe Lys Val Val Tyr Pro Val Asp Asp
            180             185             190

His His Phe Lys Val Ile Leu Pro Tyr Gly Thr Leu Val Ile Asp Gly
            195             200             205

Val Thr Pro Asn Met Leu Asn Tyr Phe Gly Arg Pro Tyr Glu Gly Ile
        210             215             220

Ala Val Phe Asp Gly Lys Lys Ile Thr Val Thr Gly Thr Leu Trp Asn
225             230             235             240

Gly Asn Lys Ile Ile Asp Glu Arg Leu Ile Thr Pro Asp Gly Ser Met
            245             250             255

Leu Phe Arg Val Thr Ile Asn Ser Gly Gly Ser Gly Gly Gly Gly Ser
            260             265             270

Gly Gly Ser Ser Ser Gly Gly Gly Ile Glu Tyr Gly Asp Lys Glu Arg
        275             280             285

Lys Ala Asp Ala Lys Met Val Cys Asp Val Val Ser Arg Met Glu Asp
```

```
            290                 295                 300

Thr Glu Pro Phe Ser Ala Glu Leu Leu Ser Ala Met Met Arg Leu Trp
305                 310                 315                 320

Gly Asp Ser Gly Ile Gln Glu Cys Phe Asn Arg Ser Arg Glu Tyr Gln
                325                 330                 335

Leu Asn Asp Ser Ala Lys Tyr Tyr Leu Asp Ser Leu Asp Arg Ile Gly
                340                 345                 350

Ala Ala Asp Tyr Gln Pro Thr Glu Gln Asp Ile Leu Arg Thr Arg Val
            355                 360                 365

Lys Thr Thr Gly Ile Val Glu Thr His Phe Thr Phe Lys Asn Leu His
        370                 375                 380

Phe Arg Leu Phe Asp Val Gly Gly Gln Arg Ser Glu Arg Lys Lys Trp
385                 390                 395                 400

Ile His Cys Phe Glu Asp Val Thr Ala Ile Ile Phe Cys Val Ala Leu
                405                 410                 415

Ser Gly Tyr Asp Gln Val Leu His Glu Asp Glu Thr Thr Asn Arg Met
                420                 425                 430

His Glu Ser Leu Met Leu Phe Asp Ser Ile Cys Asn Asn Lys Phe Phe
            435                 440                 445

Ile Asp Thr Ser Ile Ile Leu Phe Leu Asn Lys Lys Asp Leu Phe Gly
        450                 455                 460

Glu Lys Ile Lys Lys Ser Pro Leu Thr Ile Cys Phe Pro Glu Tyr Thr
465                 470                 475                 480

Gly Pro Asn Thr Tyr Glu Asp Ala Ala Ala Tyr Ile Gln Ala Gln Phe
                485                 490                 495

Glu Ser Lys Asn Arg Ser Pro Asn Lys Glu Ile Tyr Cys His Met Thr
                500                 505                 510

Cys Ala Thr Asp Thr Asn Asn Ile Gln Val Val Phe Asp Ala Val Thr
            515                 520                 525

Asp Ile Ile Ile Ala Asn Asn Leu Arg Gly Cys Gly Leu Tyr
    530                 535                 540
```

```
<210> SEQ ID NO 10
<211> LENGTH: 547
<212> TYPE: PRT
<213> ORGANISM: Homo sapiens
<220> FEATURE:
<223> OTHER INFORMATION: G\'ce\'b1q-Lg (GNAQ-LgBiT)

<400> SEQUENCE: 10

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Gly Thr Gly
            35                  40                  45

Glu Ser Gly Lys Ser Thr Phe Ile Lys Gln Met Arg Ile Ile His Gly
        50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Gly Gly Ser Gly Gly Gly Gly Ser Gly Gly Ser Ser Ser Gly Gly
                100                 105                 110

Val Phe Thr Leu Glu Asp Phe Val Gly Asp Trp Glu Gln Thr Ala Ala
```

```
                115                 120                 125

Tyr Asn Leu Asp Gln Val Leu Glu Gln Gly Gly Val Ser Ser Leu Leu
    130                 135                 140

Gln Asn Leu Ala Val Ser Val Thr Pro Ile Gln Arg Ile Val Arg Ser
145                 150                 155                 160

Gly Glu Asn Ala Leu Lys Ile Asp Ile His Val Ile Ile Pro Tyr Glu
                165                 170                 175

Gly Leu Ser Ala Asp Gln Met Ala Gln Ile Glu Glu Val Phe Lys Val
                180                 185                 190

Val Tyr Pro Val Asp Asp His His Phe Lys Val Ile Leu Pro Tyr Gly
            195                 200                 205

Thr Leu Val Ile Asp Gly Val Thr Pro Asn Met Leu Asn Tyr Phe Gly
    210                 215                 220

Arg Pro Tyr Glu Gly Ile Ala Val Phe Asp Gly Lys Lys Ile Thr Val
225                 230                 235                 240

Thr Gly Thr Leu Trp Asn Gly Asn Lys Ile Ile Asp Glu Arg Leu Ile
                245                 250                 255

Thr Pro Asp Gly Ser Met Leu Phe Arg Val Thr Ile Asn Ser Gly Gly
                260                 265                 270

Ser Gly Gly Gly Gly Ser Gly Gly Ser Ser Ser Gly Gly Lys Ile Pro
            275                 280                 285

Tyr Lys Tyr Glu His Asn Lys Ala His Ala Gln Leu Val Arg Glu Val
    290                 295                 300

Asp Val Glu Lys Val Ser Ala Phe Glu Asn Pro Tyr Val Asp Ala Ile
305                 310                 315                 320

Lys Ser Leu Trp Asn Asp Pro Gly Ile Gln Glu Cys Tyr Asp Arg Arg
                325                 330                 335

Arg Glu Tyr Gln Leu Ser Asp Ser Thr Lys Tyr Tyr Leu Asn Asp Leu
                340                 345                 350

Asp Arg Val Ala Asp Pro Ala Tyr Leu Pro Thr Gln Gln Asp Val Leu
            355                 360                 365

Arg Val Arg Val Pro Thr Thr Gly Ile Ile Glu Tyr Pro Phe Asp Leu
    370                 375                 380

Gln Ser Val Ile Phe Arg Met Val Asp Val Gly Gly Gln Arg Ser Glu
385                 390                 395                 400

Arg Arg Lys Trp Ile His Cys Phe Glu Asn Val Thr Ser Ile Met Phe
                405                 410                 415

Leu Val Ala Leu Ser Glu Tyr Asp Gln Val Leu Val Glu Ser Asp Asn
                420                 425                 430

Glu Asn Arg Met Glu Glu Ser Lys Ala Leu Phe Arg Thr Ile Ile Thr
            435                 440                 445

Tyr Pro Trp Phe Gln Asn Ser Ser Val Ile Leu Phe Leu Asn Lys Lys
    450                 455                 460

Asp Leu Leu Glu Glu Lys Ile Met Tyr Ser His Leu Val Asp Tyr Phe
465                 470                 475                 480

Pro Glu Tyr Asp Gly Pro Gln Arg Asp Ala Gln Ala Ala Arg Glu Phe
                485                 490                 495

Ile Leu Lys Met Phe Val Asp Leu Asn Pro Asp Ser Asp Lys Ile Ile
            500                 505                 510

Tyr Ser His Phe Thr Cys Ala Thr Asp Thr Glu Asn Ile Arg Phe Val
    515                 520                 525

Phe Ala Ala Val Lys Asp Thr Ile Leu Gln Leu Asn Leu Lys Glu Tyr
    530                 535                 540
```

Asn Leu Val
545

<210> SEQ ID NO 11
<211> LENGTH: 547
<212> TYPE: PRT
<213> ORGANISM: Homo sapiens
<220> FEATURE:
<223> OTHER INFORMATION: G\'ce\'b111-Lg (GNA11-LgBiT)

<400> SEQUENCE: 11

Met Thr Leu Glu Ser Met Met Ala Cys Cys Leu Ser Asp Glu Val Lys
1               5                   10                  15

Glu Ser Lys Arg Ile Asn Ala Glu Ile Glu Lys Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ala Gly Tyr Ser Glu Glu Asp Lys Arg Gly Phe Thr Lys Leu Val Tyr
65                  70                  75                  80

Gln Asn Ile Phe Thr Ala Met Gln Ala Met Ile Arg Ala Met Glu Thr
                85                  90                  95

Leu Gly Gly Ser Gly Gly Gly Gly Ser Gly Gly Ser Ser Gly Gly
            100                 105                 110

Val Phe Thr Leu Glu Asp Phe Val Gly Asp Trp Glu Gln Thr Ala Ala
            115                 120                 125

Tyr Asn Leu Asp Gln Val Leu Glu Gln Gly Gly Val Ser Ser Leu Leu
    130                 135                 140

Gln Asn Leu Ala Val Ser Val Thr Pro Ile Gln Arg Ile Val Arg Ser
145                 150                 155                 160

Gly Glu Asn Ala Leu Lys Ile Asp Ile His Val Ile Ile Pro Tyr Glu
                165                 170                 175

Gly Leu Ser Ala Asp Gln Met Ala Gln Ile Glu Glu Val Phe Lys Val
            180                 185                 190

Val Tyr Pro Val Asp Asp His His Phe Lys Val Ile Leu Pro Tyr Gly
            195                 200                 205

Thr Leu Val Ile Asp Gly Val Thr Pro Asn Met Leu Asn Tyr Phe Gly
    210                 215                 220

Arg Pro Tyr Glu Gly Ile Ala Val Phe Asp Gly Lys Lys Ile Thr Val
225                 230                 235                 240

Thr Gly Thr Leu Trp Asn Gly Asn Lys Ile Ile Asp Glu Arg Leu Ile
                245                 250                 255

Thr Pro Asp Gly Ser Met Leu Phe Arg Val Thr Ile Asn Ser Gly Gly
            260                 265                 270

Ser Gly Gly Gly Gly Ser Gly Gly Ser Ser Ser Gly Gly Lys Ile Leu
            275                 280                 285

Tyr Lys Tyr Glu Gln Asn Lys Ala Asn Ala Leu Leu Ile Arg Glu Val
    290                 295                 300

Asp Val Glu Lys Val Thr Thr Phe Glu His Gln Tyr Val Ser Ala Ile
305                 310                 315                 320

Lys Thr Leu Trp Glu Asp Pro Gly Ile Gln Glu Cys Tyr Asp Arg Arg
                325                 330                 335

Arg Glu Tyr Gln Leu Ser Asp Ser Ala Lys Tyr Tyr Leu Thr Asp Val
            340                 345                 350

-continued

```
Asp Arg Ile Ala Thr Leu Gly Tyr Leu Pro Thr Gln Gln Asp Val Leu
        355             360             365

Arg Val Arg Val Pro Thr Thr Gly Ile Ile Glu Tyr Pro Phe Asp Leu
        370             375             380

Glu Asn Ile Ile Phe Arg Met Val Asp Val Gly Gly Gln Arg Ser Glu
385             390             395             400

Arg Arg Lys Trp Ile His Cys Phe Glu Asn Val Thr Ser Ile Met Phe
            405             410             415

Leu Val Ala Leu Ser Glu Tyr Asp Gln Val Leu Val Glu Ser Asp Asn
            420             425             430

Glu Asn Arg Met Glu Glu Ser Lys Ala Leu Phe Arg Thr Ile Ile Thr
            435             440             445

Tyr Pro Trp Phe Gln Asn Ser Ser Val Ile Leu Phe Leu Asn Lys Lys
        450             455             460

Asp Leu Leu Glu Asp Lys Ile Leu Tyr Ser His Leu Val Asp Tyr Phe
465             470             475             480

Pro Glu Phe Asp Gly Pro Gln Arg Asp Ala Gln Ala Ala Arg Glu Phe
            485             490             495

Ile Leu Lys Met Phe Val Asp Leu Asn Pro Asp Ser Asp Lys Ile Ile
            500             505             510

Tyr Ser His Phe Thr Cys Ala Thr Asp Thr Glu Asn Ile Arg Phe Val
            515             520             525

Phe Ala Ala Val Lys Asp Thr Ile Leu Gln Leu Asn Leu Lys Glu Tyr
        530             535             540

Asn Leu Val
545
```

```
<210> SEQ ID NO 12
<211> LENGTH: 543
<212> TYPE: PRT
<213> ORGANISM: Homo sapiens
<220> FEATURE:
<223> OTHER INFORMATION: G\'ce\'b114-Lg (GNA14-LgBiT)

<400> SEQUENCE: 12
```

```
Met Ala Gly Cys Cys Cys Leu Ser Ala Glu Glu Lys Glu Ser Gln Arg
1               5               10              15

Ile Ser Ala Glu Ile Glu Arg Gln Leu Arg Arg Asp Lys Lys Asp Ala
            20              25              30

Arg Arg Glu Leu Lys Leu Leu Leu Leu Gly Thr Gly Glu Ser Gly Lys
            35              40              45

Ser Thr Phe Ile Lys Gln Met Arg Ile Ile His Gly Ser Gly Tyr Ser
        50              55              60

Asp Glu Asp Arg Lys Gly Phe Thr Lys Leu Val Tyr Gln Asn Ile Phe
65              70              75              80

Thr Ala Met Gln Ala Met Ile Arg Ala Met Asp Thr Leu Gly Gly Ser
            85              90              95

Gly Gly Gly Gly Ser Gly Gly Ser Ser Ser Gly Gly Val Phe Thr Leu
            100             105             110

Glu Asp Phe Val Gly Asp Trp Glu Gln Thr Ala Ala Tyr Asn Leu Asp
            115             120             125

Gln Val Leu Glu Gln Gly Gly Val Ser Ser Leu Leu Gln Asn Leu Ala
        130             135             140

Val Ser Val Thr Pro Ile Gln Arg Ile Val Arg Ser Gly Glu Asn Ala
145             150             155             160
```

```
Leu Lys Ile Asp Ile His Val Ile Ile Pro Tyr Glu Gly Leu Ser Ala
            165             170             175

Asp Gln Met Ala Gln Ile Glu Glu Val Phe Lys Val Val Tyr Pro Val
            180             185             190

Asp Asp His His Phe Lys Val Ile Leu Pro Tyr Gly Thr Leu Val Ile
            195             200             205

Asp Gly Val Thr Pro Asn Met Leu Asn Tyr Phe Gly Arg Pro Tyr Glu
        210             215             220

Gly Ile Ala Val Phe Asp Gly Lys Lys Ile Thr Val Thr Gly Thr Leu
225             230             235             240

Trp Asn Gly Asn Lys Ile Ile Asp Glu Arg Leu Ile Thr Pro Asp Gly
            245             250             255

Ser Met Leu Phe Arg Val Thr Ile Asn Ser Gly Gly Ser Gly Gly Gly
            260             265             270

Gly Ser Gly Gly Ser Ser Ser Gly Gly Arg Ile Gln Tyr Val Cys Glu
            275             280             285

Gln Asn Lys Glu Asn Ala Gln Ile Ile Arg Glu Val Glu Val Asp Lys
        290             295             300

Val Ser Met Leu Ser Arg Glu Gln Val Glu Ala Ile Lys Gln Leu Trp
305             310             315             320

Gln Asp Pro Gly Ile Gln Glu Cys Tyr Asp Arg Arg Arg Glu Tyr Gln
            325             330             335

Leu Ser Asp Ser Ala Lys Tyr Tyr Leu Thr Asp Ile Asp Arg Ile Ala
            340             345             350

Thr Pro Ser Phe Val Pro Thr Gln Gln Asp Val Leu Arg Val Arg Val
            355             360             365

Pro Thr Thr Gly Ile Ile Glu Tyr Pro Phe Asp Leu Glu Asn Ile Ile
        370             375             380

Phe Arg Met Val Asp Val Gly Gly Gln Arg Ser Glu Arg Arg Lys Trp
385             390             395             400

Ile His Cys Phe Glu Ser Val Thr Ser Ile Ile Phe Leu Val Ala Leu
            405             410             415

Ser Glu Tyr Asp Gln Val Leu Ala Glu Cys Asp Asn Glu Asn Arg Met
            420             425             430

Glu Glu Ser Lys Ala Leu Phe Lys Thr Ile Ile Thr Tyr Pro Trp Phe
            435             440             445

Leu Asn Ser Ser Val Ile Leu Phe Leu Asn Lys Lys Asp Leu Leu Glu
        450             455             460

Glu Lys Ile Met Tyr Ser His Leu Ile Ser Tyr Phe Pro Glu Tyr Thr
465             470             475             480

Gly Pro Lys Gln Asp Val Arg Ala Ala Arg Asp Phe Ile Leu Lys Leu
            485             490             495

Tyr Gln Asp Gln Asn Pro Asp Lys Glu Lys Val Ile Tyr Ser His Phe
            500             505             510

Thr Cys Ala Thr Asp Thr Asp Asn Ile Arg Phe Val Phe Ala Ala Val
            515             520             525

Lys Asp Thr Ile Leu Gln Leu Asn Leu Arg Glu Phe Asn Leu Val
        530             535             540
```

```
<210> SEQ ID NO 13
<211> LENGTH: 562
<212> TYPE: PRT
<213> ORGANISM: Homo sapiens
<220> FEATURE:
```

-continued

<223> OTHER INFORMATION: G\'ce\'b116-Lg (GNA15-LgBiT)

<400> SEQUENCE: 13

```
Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gly Gly Ser Gly Gly Gly Ser Gly Gly Ser Ser
            100                 105                 110

Ser Gly Gly Val Phe Thr Leu Glu Asp Phe Val Gly Asp Trp Glu Gln
            115                 120                 125

Thr Ala Ala Tyr Asn Leu Asp Gln Val Leu Glu Gln Gly Gly Val Ser
            130                 135                 140

Ser Leu Leu Gln Asn Leu Ala Val Ser Val Thr Pro Ile Gln Arg Ile
145                 150                 155                 160

Val Arg Ser Gly Glu Asn Ala Leu Lys Ile Asp Ile His Val Ile Ile
                165                 170                 175

Pro Tyr Glu Gly Leu Ser Ala Asp Gln Met Ala Gln Ile Glu Glu Val
            180                 185                 190

Phe Lys Val Val Tyr Pro Val Asp Asp His His Phe Lys Val Ile Leu
            195                 200                 205

Pro Tyr Gly Thr Leu Val Ile Asp Gly Val Thr Pro Asn Met Leu Asn
    210                 215                 220

Tyr Phe Gly Arg Pro Tyr Glu Gly Ile Ala Val Phe Asp Gly Lys Lys
225                 230                 235                 240

Ile Thr Val Thr Gly Thr Leu Trp Asn Gly Asn Lys Ile Ile Asp Glu
                245                 250                 255

Arg Leu Ile Thr Pro Asp Gly Ser Met Leu Phe Arg Val Thr Ile Asn
            260                 265                 270

Ser Gly Gly Ser Gly Gly Gly Gly Ser Gly Gly Ser Ser Ser Gly Gly
        275                 280                 285

Gln Ile Pro Phe Ser Arg Pro Glu Ser Lys His His Ala Ser Leu Val
    290                 295                 300

Met Ser Gln Asp Pro Tyr Lys Val Thr Thr Phe Glu Lys Arg Tyr Ala
305                 310                 315                 320

Ala Ala Met Gln Trp Leu Trp Arg Asp Ala Gly Ile Arg Ala Tyr Tyr
            325                 330                 335

Glu Arg Arg Arg Glu Phe His Leu Leu Asp Ser Ala Val Tyr Tyr Leu
            340                 345                 350

Ser His Leu Glu Arg Ile Thr Glu Glu Gly Tyr Val Pro Thr Ala Gln
        355                 360                 365

Asp Val Leu Arg Ser Arg Met Pro Thr Thr Gly Ile Asn Glu Tyr Cys
    370                 375                 380

Phe Ser Val Gln Lys Thr Asn Leu Arg Ile Val Asp Val Gly Gly Gln
385                 390                 395                 400
```

```
Lys Ser Glu Arg Lys Lys Trp Ile His Cys Phe Glu Asn Val Ile Ala
                405             410             415

Leu Ile Tyr Leu Ala Ser Leu Ser Glu Tyr Asp Gln Cys Leu Glu Glu
            420             425             430

Asn Asn Gln Glu Asn Arg Met Lys Glu Ser Leu Ala Leu Phe Gly Thr
            435             440             445

Ile Leu Glu Leu Pro Trp Phe Lys Ser Thr Ser Val Ile Leu Phe Leu
        450             455             460

Asn Lys Thr Asp Ile Leu Glu Glu Lys Ile Pro Thr Ser His Leu Ala
465             470             475             480

Thr Tyr Phe Pro Ser Phe Gln Gly Pro Lys Gln Asp Ala Glu Ala Ala
            485             490             495

Lys Arg Phe Ile Leu Asp Met Tyr Thr Arg Met Tyr Thr Gly Cys Val
            500             505             510

Asp Gly Pro Glu Gly Ser Lys Lys Gly Ala Arg Ser Arg Arg Leu Phe
            515             520             525

Ser His Tyr Thr Cys Ala Thr Asp Thr Gln Asn Ile Arg Lys Val Phe
        530             535             540

Lys Asp Val Arg Asp Ser Val Leu Ala Arg Tyr Leu Asp Glu Ile Asn
545             550             555             560

Leu Leu
```

```
<210> SEQ ID NO 14
<211> LENGTH: 569
<212> TYPE: PRT
<213> ORGANISM: Homo sapiens
<220> FEATURE:
<223> OTHER INFORMATION: G\'ce\'b112-Lg (GNA12-LgBiT)

<400> SEQUENCE: 14

Met Ser Gly Val Val Arg Thr Leu Ser Arg Cys Leu Leu Pro Ala Glu
1               5               10              15

Ala Gly Gly Ala Arg Glu Arg Arg Ala Gly Ser Gly Ala Arg Asp Ala
            20              25              30

Glu Arg Glu Ala Arg Arg Arg Ser Arg Asp Ile Asp Ala Leu Leu Ala
        35              40              45

Arg Glu Arg Arg Ala Val Arg Arg Leu Val Lys Ile Leu Leu Leu Gly
    50              55              60

Ala Gly Glu Ser Gly Lys Ser Thr Phe Leu Lys Gln Met Arg Ile Ile
65              70              75              80

His Gly Arg Glu Phe Asp Gln Lys Ala Leu Leu Glu Phe Arg Asp Thr
            85              90              95

Ile Phe Asp Asn Ile Leu Lys Gly Ser Arg Val Leu Val Asp Ala Arg
            100             105             110

Asp Lys Leu Gly Gly Ser Gly Gly Gly Gly Ser Gly Gly Ser Ser Ser
        115             120             125

Gly Gly Val Phe Thr Leu Glu Asp Phe Val Gly Asp Trp Glu Gln Thr
        130             135             140

Ala Ala Tyr Asn Leu Asp Gln Val Leu Glu Gln Gly Gly Val Ser Ser
145             150             155             160

Leu Leu Gln Asn Leu Ala Val Ser Val Thr Pro Ile Gln Arg Ile Val
            165             170             175

Arg Ser Gly Glu Asn Ala Leu Lys Ile Asp Ile His Val Ile Ile Pro
            180             185             190

Tyr Glu Gly Leu Ser Ala Asp Gln Met Ala Gln Ile Glu Glu Val Phe
```

-continued

```
               195              200              205

Lys Val Val Tyr Pro Val Asp Asp His His Phe Lys Val Ile Leu Pro
    210              215              220

Tyr Gly Thr Leu Val Ile Asp Gly Val Thr Pro Asn Met Leu Asn Tyr
225              230              235              240

Phe Gly Arg Pro Tyr Glu Gly Ile Ala Val Phe Asp Gly Lys Lys Ile
                245              250              255

Thr Val Thr Gly Thr Leu Trp Asn Gly Asn Lys Ile Ile Asp Glu Arg
                260              265              270

Leu Ile Thr Pro Asp Gly Ser Met Leu Phe Arg Val Thr Ile Asn Ser
                275              280              285

Gly Gly Ser Gly Gly Gly Ser Gly Gly Ser Ser Ser Gly Gly Gly
    290              295              300

Ile Pro Trp Gln Tyr Ser Glu Asn Glu Lys His Gly Met Phe Leu Met
305              310              315              320

Ala Phe Glu Asn Lys Ala Gly Leu Pro Val Glu Pro Ala Thr Phe Gln
                325              330              335

Leu Tyr Val Pro Ala Leu Ser Ala Leu Trp Arg Asp Ser Gly Ile Arg
                340              345              350

Glu Ala Phe Ser Arg Arg Ser Glu Phe Gln Leu Gly Glu Ser Val Lys
                355              360              365

Tyr Phe Leu Asp Asn Leu Asp Arg Ile Gly Gln Leu Asn Tyr Phe Pro
    370              375              380

Ser Lys Gln Asp Ile Leu Leu Ala Arg Lys Ala Thr Lys Gly Ile Val
385              390              395              400

Glu His Asp Phe Val Ile Lys Lys Ile Pro Phe Lys Met Val Asp Val
                405              410              415

Gly Gly Gln Arg Ser Gln Arg Gln Lys Trp Phe Gln Cys Phe Asp Gly
                420              425              430

Ile Thr Ser Ile Leu Phe Met Val Ser Ser Ser Glu Tyr Asp Gln Val
    435              440              445

Leu Met Glu Asp Arg Arg Thr Asn Arg Leu Val Glu Ser Met Asn Ile
    450              455              460

Phe Glu Thr Ile Val Asn Asn Lys Leu Phe Phe Asn Val Ser Ile Ile
465              470              475              480

Leu Phe Leu Asn Lys Met Asp Leu Leu Val Glu Lys Val Lys Thr Val
                485              490              495

Ser Ile Lys Lys His Phe Pro Asp Phe Arg Gly Asp Pro His Arg Leu
                500              505              510

Glu Asp Val Gln Arg Tyr Leu Val Gln Cys Phe Asp Arg Lys Arg Arg
                515              520              525

Asn Arg Ser Lys Pro Leu Phe His His Phe Thr Thr Ala Ile Asp Thr
    530              535              540

Glu Asn Val Arg Phe Val Phe His Ala Val Lys Asp Thr Ile Leu Gln
545              550              555              560

Glu Asn Leu Lys Asp Ile Met Leu Gln
                565
```

<210> SEQ ID NO 15
<211> LENGTH: 565
<212> TYPE: PRT
<213> ORGANISM: Homo sapiens
<220> FEATURE:
<223> OTHER INFORMATION: G\'ce\'b113-Lg (GNA13-LgBiT)

```
<400> SEQUENCE: 15

Met Ala Asp Phe Leu Pro Ser Arg Ser Val Leu Ser Val Cys Phe Pro
1               5                   10                  15

Gly Cys Leu Leu Thr Ser Gly Glu Ala Glu Gln Gln Arg Lys Ser Lys
            20                  25                  30

Glu Ile Asp Lys Cys Leu Ser Arg Glu Lys Thr Tyr Val Lys Arg Leu
            35                  40                  45

Val Lys Ile Leu Leu Leu Gly Ala Gly Glu Ser Gly Lys Ser Thr Phe
    50                  55                  60

Leu Lys Gln Met Arg Ile Ile His Gly Gln Asp Phe Asp Gln Arg Ala
65                  70                  75                  80

Arg Glu Glu Phe Arg Pro Thr Ile Tyr Ser Asn Val Ile Lys Gly Met
                85                  90                  95

Arg Val Leu Val Asp Ala Arg Glu Lys Leu Gly Gly Ser Gly Gly Gly
            100                 105                 110

Gly Ser Gly Gly Ser Ser Ser Gly Gly Val Phe Thr Leu Glu Asp Phe
            115                 120                 125

Val Gly Asp Trp Glu Gln Thr Ala Ala Tyr Asn Leu Asp Gln Val Leu
    130                 135                 140

Glu Gln Gly Gly Val Ser Ser Leu Leu Gln Asn Leu Ala Val Ser Val
145                 150                 155                 160

Thr Pro Ile Gln Arg Ile Val Arg Ser Gly Glu Asn Ala Leu Lys Ile
                165                 170                 175

Asp Ile His Val Ile Ile Pro Tyr Glu Gly Leu Ser Ala Asp Gln Met
            180                 185                 190

Ala Gln Ile Glu Glu Val Phe Lys Val Val Tyr Pro Val Asp Asp His
            195                 200                 205

His Phe Lys Val Ile Leu Pro Tyr Gly Thr Leu Val Ile Asp Gly Val
    210                 215                 220

Thr Pro Asn Met Leu Asn Tyr Phe Gly Arg Pro Tyr Glu Gly Ile Ala
225                 230                 235                 240

Val Phe Asp Gly Lys Lys Ile Thr Val Thr Gly Thr Leu Trp Asn Gly
                245                 250                 255

Asn Lys Ile Ile Asp Glu Arg Leu Ile Thr Pro Asp Gly Ser Met Leu
            260                 265                 270

Phe Arg Val Thr Ile Asn Ser Gly Gly Ser Gly Gly Gly Ser Gly
            275                 280                 285

Gly Ser Ser Ser Gly Gly His Ile Pro Trp Gly Asp Asn Ser Asn Gln
    290                 295                 300

Gln His Gly Asp Lys Met Met Ser Phe Asp Thr Arg Ala Pro Met Ala
305                 310                 315                 320

Ala Gln Gly Met Val Glu Thr Arg Val Phe Leu Gln Tyr Leu Pro Ala
                325                 330                 335

Ile Arg Ala Leu Trp Ala Asp Ser Gly Ile Gln Asn Ala Tyr Asp Arg
            340                 345                 350

Arg Arg Glu Phe Gln Leu Gly Glu Ser Val Lys Tyr Phe Leu Asp Asn
            355                 360                 365

Leu Asp Lys Leu Gly Glu Pro Asp Tyr Ile Pro Ser Gln Gln Asp Ile
    370                 375                 380

Leu Leu Ala Arg Arg Pro Thr Lys Gly Ile His Glu Tyr Asp Phe Glu
385                 390                 395                 400

Ile Lys Asn Val Pro Phe Lys Met Val Asp Val Gly Gly Gln Arg Ser
                405                 410                 415
```

Glu Arg Lys Arg Trp Phe Glu Cys Phe Asp Ser Val Thr Ser Ile Leu
            420                 425                 430

Phe Leu Val Ser Ser Ser Glu Phe Asp Gln Val Leu Met Glu Asp Arg
            435                 440                 445

Leu Thr Asn Arg Leu Thr Glu Ser Leu Asn Ile Phe Glu Thr Ile Val
            450                 455                 460

Asn Asn Arg Val Phe Ser Asn Val Ser Ile Ile Leu Phe Leu Asn Lys
465                 470                 475                 480

Thr Asp Leu Leu Glu Glu Lys Val Gln Ile Val Ser Ile Lys Asp Tyr
                485                 490                 495

Phe Leu Glu Phe Glu Gly Asp Pro His Cys Leu Arg Asp Val Gln Lys
            500                 505                 510

Phe Leu Val Glu Cys Phe Arg Asn Lys Arg Arg Asp Gln Gln Gln Lys
            515                 520                 525

Pro Leu Tyr His His Phe Thr Thr Ala Ile Asn Thr Glu Asn Ile Arg
            530                 535                 540

Leu Val Phe Arg Asp Val Lys Asp Thr Ile Leu His Asp Asn Leu Lys
545                 550                 555                 560

Gln Leu Met Leu Gln
                565

<210> SEQ ID NO 16
<211> LENGTH: 366
<212> TYPE: PRT
<213> ORGANISM: Homo sapiens
<220> FEATURE:
<223> OTHER INFORMATION: Sm-G\'ce\'b21 (SmBiT-GNB1)

<400> SEQUENCE: 16

Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ser Glu Leu Asp Gln
            20                  25                  30

Leu Arg Gln Glu Ala Glu Gln Leu Lys Asn Gln Ile Arg Asp Ala Arg
            35                  40                  45

Lys Ala Cys Ala Asp Ala Thr Leu Ser Gln Ile Thr Asn Asn Ile Asp
        50                  55                  60

Pro Val Gly Arg Ile Gln Met Arg Thr Arg Arg Thr Leu Arg Gly His
65                  70                  75                  80

Leu Ala Lys Ile Tyr Ala Met His Trp Gly Thr Asp Ser Arg Leu Leu
                85                  90                  95

Val Ser Ala Ser Gln Asp Gly Lys Leu Ile Ile Trp Asp Ser Tyr Thr
            100                 105                 110

Thr Asn Lys Val His Ala Ile Pro Leu Arg Ser Ser Trp Val Met Thr
            115                 120                 125

Cys Ala Tyr Ala Pro Ser Gly Asn Tyr Val Ala Cys Gly Gly Leu Asp
        130                 135                 140

Asn Ile Cys Ser Ile Tyr Asn Leu Lys Thr Arg Glu Gly Asn Val Arg
145                 150                 155                 160

Val Ser Arg Glu Leu Ala Gly His Thr Gly Tyr Leu Ser Cys Cys Arg
                165                 170                 175

Phe Leu Asp Asp Asn Gln Ile Val Thr Ser Ser Gly Asp Thr Thr Cys
            180                 185                 190

Ala Leu Trp Asp Ile Glu Thr Gly Gln Gln Thr Thr Thr Phe Thr Gly
            195                 200                 205

```
His Thr Gly Asp Val Met Ser Leu Ser Leu Ala Pro Asp Thr Arg Leu
    210                 215                 220
```

```
Phe Val Ser Gly Ala Cys Asp Ala Ser Ala Lys Leu Trp Asp Val Arg
225                 230                 235                 240
```

```
Glu Gly Met Cys Arg Gln Thr Phe Thr Gly His Glu Ser Asp Ile Asn
                245                 250                 255
```

```
Ala Ile Cys Phe Phe Pro Asn Gly Asn Ala Phe Ala Thr Gly Ser Asp
                260                 265                 270
```

```
Asp Ala Thr Cys Arg Leu Phe Asp Leu Arg Ala Asp Gln Glu Leu Met
                275                 280                 285
```

```
Thr Tyr Ser His Asp Asn Ile Ile Cys Gly Ile Thr Ser Val Ser Phe
    290                 295                 300
```

```
Ser Lys Ser Gly Arg Leu Leu Leu Ala Gly Tyr Asp Asp Phe Asn Cys
305                 310                 315                 320
```

```
Asn Val Trp Asp Ala Leu Lys Ala Asp Arg Ala Gly Val Leu Ala Gly
                325                 330                 335
```

```
His Asp Asn Arg Val Ser Cys Leu Gly Val Thr Asp Asp Gly Met Ala
                340                 345                 350
```

```
Val Ala Thr Gly Ser Trp Asp Ser Phe Leu Lys Ile Trp Asn
                355                 360                 365
```

```
<210> SEQ ID NO 17
<211> LENGTH: 366
<212> TYPE: PRT
<213> ORGANISM: Homo sapiens
<220> FEATURE:
<223> OTHER INFORMATION: Sm-G\'ce\'b22 (SmBiT-GNB2)

<400> SEQUENCE: 17
```

```
Met Val Thr Gly Tyr Arg Leu Phe Glu Glu Ile Leu Gly Gly Ser Gly
1                   5                   10                  15
```

```
Gly Gly Gly Ser Gly Gly Ser Ser Ser Gly Gly Ser Glu Leu Glu Gln
                20                  25                  30
```

```
Leu Arg Gln Glu Ala Glu Gln Leu Arg Asn Gln Ile Arg Asp Ala Arg
        35                  40                  45
```

```
Lys Ala Cys Gly Asp Ser Thr Leu Thr Gln Ile Thr Ala Gly Leu Asp
    50                  55                  60
```

```
Pro Val Gly Arg Ile Gln Met Arg Thr Arg Arg Thr Leu Arg Gly His
65                  70                  75                  80
```

```
Leu Ala Lys Ile Tyr Ala Met His Trp Gly Thr Asp Ser Arg Leu Leu
                85                  90                  95
```

```
Val Ser Ala Ser Gln Asp Gly Lys Leu Ile Ile Trp Asp Ser Tyr Thr
                100                 105                 110
```

```
Thr Asn Lys Val His Ala Ile Pro Leu Arg Ser Ser Trp Val Met Thr
                115                 120                 125
```

```
Cys Ala Tyr Ala Pro Ser Gly Asn Phe Val Ala Cys Gly Gly Leu Asp
    130                 135                 140
```

```
Asn Ile Cys Ser Ile Tyr Ser Leu Lys Thr Arg Glu Gly Asn Val Arg
145                 150                 155                 160
```

```
Val Ser Arg Glu Leu Pro Gly His Thr Gly Tyr Leu Ser Cys Cys Arg
                165                 170                 175
```

```
Phe Leu Asp Asp Asn Gln Ile Ile Thr Ser Ser Gly Asp Thr Thr Cys
                180                 185                 190
```

```
Ala Leu Trp Asp Ile Glu Thr Gly Gln Gln Thr Val Gly Phe Ala Gly
                195                 200                 205
```

```
His Ser Gly Asp Val Met Ser Leu Ser Leu Ala Pro Asp Gly Arg Thr
    210                 215                 220

Phe Val Ser Gly Ala Cys Asp Ala Ser Ile Lys Leu Trp Asp Val Arg
225                 230                 235                 240

Asp Ser Met Cys Arg Gln Thr Phe Ile Gly His Glu Ser Asp Ile Asn
                245                 250                 255

Ala Val Ala Phe Phe Pro Asn Gly Tyr Ala Phe Thr Thr Gly Ser Asp
                260                 265                 270

Asp Ala Thr Cys Arg Leu Phe Asp Leu Arg Ala Asp Gln Glu Leu Leu
                275                 280                 285

Met Tyr Ser His Asp Asn Ile Ile Cys Gly Ile Thr Ser Val Ala Phe
    290                 295                 300

Ser Arg Ser Gly Arg Leu Leu Leu Ala Gly Tyr Asp Asp Phe Asn Cys
305                 310                 315                 320

Asn Ile Trp Asp Ala Met Lys Gly Asp Arg Ala Gly Val Leu Ala Gly
                325                 330                 335

His Asp Asn Arg Val Ser Cys Leu Gly Val Thr Asp Asp Gly Met Ala
                340                 345                 350

Val Ala Thr Gly Ser Trp Asp Ser Phe Leu Lys Ile Trp Asn
        355                 360                 365
```

```
<210> SEQ ID NO 18
<211> LENGTH: 366
<212> TYPE: PRT
<213> ORGANISM: Homo sapiens
<220> FEATURE:
<223> OTHER INFORMATION: Sm-G\'ce\'b23 (SmBiT-GNB3)

<400> SEQUENCE: 18
```

```
Met Val Thr Gly Tyr Arg Leu Phe Glu Glu Ile Leu Gly Gly Ser Gly
1                   5                   10                  15

Gly Gly Gly Ser Gly Gly Ser Ser Ser Gly Gly Gly Glu Met Glu Gln
                20                  25                  30

Leu Arg Gln Glu Ala Glu Gln Leu Lys Lys Gln Ile Ala Asp Ala Arg
        35                  40                  45

Lys Ala Cys Ala Asp Val Thr Leu Ala Glu Leu Val Ser Gly Leu Glu
    50                  55                  60

Val Val Gly Arg Val Gln Met Arg Thr Arg Arg Thr Leu Arg Gly His
65                  70                  75                  80

Leu Ala Lys Ile Tyr Ala Met His Trp Ala Thr Asp Ser Lys Leu Leu
                85                  90                  95

Val Ser Ala Ser Gln Asp Gly Lys Leu Ile Val Trp Asp Ser Tyr Thr
                100                 105                 110

Thr Asn Lys Val His Ala Ile Pro Leu Arg Ser Ser Trp Val Met Thr
                115                 120                 125

Cys Ala Tyr Ala Pro Ser Gly Asn Phe Val Ala Cys Gly Gly Leu Asp
    130                 135                 140

Asn Met Cys Ser Ile Tyr Asn Leu Lys Ser Arg Glu Gly Asn Val Lys
145                 150                 155                 160

Val Ser Arg Glu Leu Ser Ala His Thr Gly Tyr Leu Ser Cys Cys Arg
                165                 170                 175

Phe Leu Asp Asp Asn Asn Ile Val Thr Ser Ser Gly Asp Thr Thr Cys
                180                 185                 190

Ala Leu Trp Asp Ile Glu Thr Gly Gln Gln Lys Thr Val Phe Val Gly
        195                 200                 205
```

-continued

```
His Thr Gly Asp Cys Met Ser Leu Ala Val Ser Pro Asp Phe Asn Leu
    210                 215                 220

Phe Ile Ser Gly Ala Cys Asp Ala Ser Ala Lys Leu Trp Asp Val Arg
225                 230                 235                 240

Glu Gly Thr Cys Arg Gln Thr Phe Thr Gly His Glu Ser Asp Ile Asn
                245                 250                 255

Ala Ile Cys Phe Phe Pro Asn Gly Glu Ala Ile Cys Thr Gly Ser Asp
                260                 265                 270

Asp Ala Ser Cys Arg Leu Phe Asp Leu Arg Ala Asp Gln Glu Leu Ile
                275                 280                 285

Cys Phe Ser His Glu Ser Ile Ile Cys Gly Ile Thr Ser Val Ala Phe
    290                 295                 300

Ser Leu Ser Gly Arg Leu Leu Phe Ala Gly Tyr Asp Asp Phe Asn Cys
305                 310                 315                 320

Asn Val Trp Asp Ser Met Lys Ser Glu Arg Val Gly Ile Leu Ser Gly
                325                 330                 335

His Asp Asn Arg Val Ser Cys Leu Gly Val Thr Ala Asp Gly Met Ala
                340                 345                 350

Val Ala Thr Gly Ser Trp Asp Ser Phe Leu Lys Ile Trp Asn
                355                 360                 365
```

<210> SEQ ID NO 19
<211> LENGTH: 366
<212> TYPE: PRT
<213> ORGANISM: Homo sapiens
<220> FEATURE:
<223> OTHER INFORMATION: Sm-G\'ce\'b24 (SmBiT-GNB4)

<400> SEQUENCE: 19

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ser Glu Leu Glu Gln
                20                  25                  30

Leu Arg Gln Glu Ala Glu Gln Leu Arg Asn Gln Ile Gln Asp Ala Arg
            35                  40                  45

Lys Ala Cys Asn Asp Ala Thr Leu Val Gln Ile Thr Ser Asn Met Asp
    50                  55                  60

Ser Val Gly Arg Ile Gln Met Arg Thr Arg Arg Thr Leu Arg Gly His
65                  70                  75                  80

Leu Ala Lys Ile Tyr Ala Met His Trp Gly Tyr Asp Ser Arg Leu Leu
                85                  90                  95

Val Ser Ala Ser Gln Asp Gly Lys Leu Ile Ile Trp Asp Ser Tyr Thr
                100                 105                 110

Thr Asn Lys Met His Ala Ile Pro Leu Arg Ser Ser Trp Val Met Thr
            115                 120                 125

Cys Ala Tyr Ala Pro Ser Gly Asn Tyr Val Ala Cys Gly Gly Leu Asp
    130                 135                 140

Asn Ile Cys Ser Ile Tyr Asn Leu Lys Thr Arg Glu Gly Asn Val Arg
145                 150                 155                 160

Val Ser Arg Glu Leu Pro Gly His Thr Gly Tyr Leu Ser Cys Cys Arg
                165                 170                 175

Phe Leu Asp Asp Ser Gln Ile Val Thr Ser Ser Gly Asp Thr Thr Cys
                180                 185                 190

Ala Leu Trp Asp Ile Glu Thr Ala Gln Gln Thr Thr Thr Phe Thr Gly
            195                 200                 205
```

```
His Ser Gly Asp Val Met Ser Leu Ser Leu Ser Pro Asp Met Arg Thr
    210             215             220

Phe Val Ser Gly Ala Cys Asp Ala Ser Ser Lys Leu Trp Asp Ile Arg
225             230             235             240

Asp Gly Met Cys Arg Gln Ser Phe Thr Gly His Val Ser Asp Ile Asn
            245             250             255

Ala Val Ser Phe Phe Pro Asn Gly Tyr Ala Phe Ala Thr Gly Ser Asp
            260             265             270

Asp Ala Thr Cys Arg Leu Phe Asp Leu Arg Ala Asp Gln Glu Leu Leu
            275             280             285

Leu Tyr Ser His Asp Asn Ile Ile Cys Gly Ile Thr Ser Val Ala Phe
    290             295             300

Ser Lys Ser Gly Arg Leu Leu Leu Ala Gly Tyr Asp Asp Phe Asn Cys
305             310             315             320

Asn Val Trp Asp Thr Leu Lys Gly Asp Arg Ala Gly Val Leu Ala Gly
            325             330             335

His Asp Asn Arg Val Ser Cys Leu Gly Val Thr Asp Asp Gly Met Ala
            340             345             350

Val Ala Thr Gly Ser Trp Asp Ser Phe Leu Arg Ile Trp Asn
            355             360             365

<210> SEQ ID NO 20
<211> LENGTH: 421
<212> TYPE: PRT
<213> ORGANISM: Homo sapiens
<220> FEATURE:
<223> OTHER INFORMATION: Sm-G\'ce\'b25 (SmBiT-GNB5)

<400> SEQUENCE: 20

Met Val Thr Gly Tyr Arg Leu Phe Glu Glu Ile Leu Gly Gly Ser Gly
1               5               10              15

Gly Gly Gly Ser Gly Gly Ser Ser Ser Gly Gly Cys Asp Gln Thr Phe
            20              25              30

Leu Val Asn Val Phe Gly Ser Cys Asp Lys Cys Phe Lys Gln Arg Ala
        35              40              45

Leu Arg Pro Val Phe Lys Lys Ser Gln Gln Leu Ser Tyr Cys Ser Thr
    50              55              60

Cys Ala Glu Ile Met Ala Thr Glu Gly Leu His Glu Asn Glu Thr Leu
65              70              75              80

Ala Ser Leu Lys Ser Glu Ala Glu Ser Leu Lys Gly Lys Leu Glu Glu
            85              90              95

Glu Arg Ala Lys Leu His Asp Val Glu Leu His Gln Val Ala Glu Arg
            100             105             110

Val Glu Ala Leu Gly Gln Phe Val Met Lys Thr Arg Arg Thr Leu Lys
            115             120             125

Gly His Gly Asn Lys Val Leu Cys Met Asp Trp Cys Lys Asp Lys Arg
    130             135             140

Arg Ile Val Ser Ser Ser Gln Asp Gly Lys Val Ile Val Trp Asp Ser
145             150             155             160

Phe Thr Thr Asn Lys Glu His Ala Val Thr Met Pro Cys Thr Trp Val
            165             170             175

Met Ala Cys Ala Tyr Ala Pro Ser Gly Cys Ala Ile Ala Cys Gly Gly
            180             185             190

Leu Asp Asn Lys Cys Ser Val Tyr Pro Leu Thr Phe Asp Lys Asn Glu
    195             200             205
```

-continued

```
Asn Met Ala Ala Lys Lys Ser Val Ala Met His Thr Asn Tyr Leu
    210             215             220

Ser Ala Cys Ser Phe Thr Asn Ser Asp Met Gln Ile Leu Thr Ala Ser
225             230             235             240

Gly Asp Gly Thr Cys Ala Leu Trp Asp Val Glu Ser Gly Gln Leu Leu
            245             250             255

Gln Ser Phe His Gly His Gly Ala Asp Val Leu Cys Leu Asp Leu Ala
            260             265             270

Pro Ser Glu Thr Gly Asn Thr Phe Val Ser Gly Gly Cys Asp Lys Lys
        275             280             285

Ala Met Val Trp Asp Met Arg Ser Gly Gln Cys Val Gln Ala Phe Glu
    290             295             300

Thr His Glu Ser Asp Ile Asn Ser Val Arg Tyr Tyr Pro Ser Gly Asp
305             310             315             320

Ala Phe Ala Ser Gly Ser Asp Asp Ala Thr Cys Arg Leu Tyr Asp Leu
            325             330             335

Arg Ala Asp Arg Glu Val Ala Ile Tyr Ser Lys Glu Ser Ile Ile Phe
            340             345             350

Gly Ala Ser Ser Val Asp Phe Ser Leu Ser Gly Arg Leu Leu Phe Ala
            355             360             365

Gly Tyr Asn Asp Tyr Thr Ile Asn Val Trp Asp Val Leu Lys Gly Ser
    370             375             380

Arg Val Ser Ile Leu Phe Gly His Glu Asn Arg Val Ser Thr Leu Arg
385             390             395             400

Val Ser Pro Asp Gly Thr Ala Phe Cys Ser Gly Ser Trp Asp His Thr
            405             410             415

Leu Arg Val Trp Ala
            420
```

```
<210> SEQ ID NO 21
<211> LENGTH: 97
<212> TYPE: PRT
<213> ORGANISM: Homo sapiens
<220> FEATURE:
<223> OTHER INFORMATION: Sm-G\'ce\'b32 (SmBiT-GNG2)

<400> SEQUENCE: 21

Met Val Thr Gly Tyr Arg Leu Phe Glu Glu Ile Leu Gly Gly Ser Gly
1               5               10              15

Gly Gly Gly Ser Gly Gly Ser Ser Ser Gly Gly Ala Ser Asn Asn Thr
            20              25              30

Ala Ser Ile Ala Gln Ala Arg Lys Leu Val Glu Gln Leu Lys Met Glu
        35              40              45

Ala Asn Ile Asp Arg Ile Lys Val Ser Lys Ala Ala Ala Asp Leu Met
    50              55              60

Ala Tyr Cys Glu Ala His Ala Lys Glu Asp Pro Leu Leu Thr Pro Val
65              70              75              80

Pro Ala Ser Glu Asn Pro Phe Arg Glu Lys Lys Phe Phe Cys Ala Ile
            85              90              95

Leu
```

```
<210> SEQ ID NO 22
<211> LENGTH: 101
<212> TYPE: PRT
<213> ORGANISM: Homo sapiens
<220> FEATURE:
```

<223> OTHER INFORMATION: Sm-G\'ce\'b33 (SmBiT-GNG3)

<400> SEQUENCE: 22

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Lys Gly Glu Thr Pro
            20                  25                  30

Val Asn Ser Thr Met Ser Ile Gly Gln Ala Arg Lys Met Val Glu Gln
        35                  40                  45

Leu Lys Ile Glu Ala Ser Leu Cys Arg Ile Lys Val Ser Lys Ala Ala
    50                  55                  60

Ala Asp Leu Met Thr Tyr Cys Asp Ala His Ala Cys Glu Asp Pro Leu
65                  70                  75                  80

Ile Thr Pro Val Pro Thr Ser Glu Asn Pro Phe Arg Glu Lys Lys Phe
                85                  90                  95

Phe Cys Ala Leu Leu
            100
```

<210> SEQ ID NO 23
<211> LENGTH: 101
<212> TYPE: PRT
<213> ORGANISM: Homo sapiens
<220> FEATURE:
<223> OTHER INFORMATION: Sm-G\'ce\'b34 (SmBiT-GNG4)

<400> SEQUENCE: 23

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Lys Glu Gly Met Ser
            20                  25                  30

Asn Asn Ser Thr Thr Ser Ile Ser Gln Ala Arg Lys Ala Val Glu Gln
        35                  40                  45

Leu Lys Met Glu Ala Cys Met Asp Arg Val Lys Val Ser Gln Ala Ala
    50                  55                  60

Ala Asp Leu Leu Ala Tyr Cys Glu Ala His Val Arg Glu Asp Pro Leu
65                  70                  75                  80

Ile Ile Pro Val Pro Ala Ser Glu Asn Pro Phe Arg Glu Lys Lys Phe
                85                  90                  95

Phe Cys Thr Ile Leu
            100
```

<210> SEQ ID NO 24
<211> LENGTH: 94
<212> TYPE: PRT
<213> ORGANISM: Homo sapiens
<220> FEATURE:
<223> OTHER INFORMATION: Sm-G\'ce\'b35 (SmBiT-GNG5)

<400> SEQUENCE: 24

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ser Gly Ser Ser Ser
            20                  25                  30

Val Ala Ala Met Lys Lys Val Val Gln Gln Leu Arg Leu Glu Ala Gly
        35                  40                  45

Leu Asn Arg Val Lys Val Ser Gln Ala Ala Ala Asp Leu Lys Gln Phe
    50                  55                  60

Cys Leu Gln Asn Ala Gln His Asp Pro Leu Leu Thr Gly Val Ser Ser
```

65                    70                   75                    80

Ser Thr Asn Pro Phe Arg Pro Gln Lys Val Cys Ser Phe Leu
                      85                   90

<210> SEQ ID NO 25
<211> LENGTH: 94
<212> TYPE: PRT
<213> ORGANISM: Homo sapiens
<220> FEATURE:
<223> OTHER INFORMATION: Sm-G\'ce\'b37 (SmBiT-GNG7)

<400> SEQUENCE: 25

Met Val Thr Gly Tyr Arg Leu Phe Glu Glu Ile Leu Gly Gly Ser Gly
1                   5                   10                   15

Gly Gly Gly Ser Gly Gly Ser Ser Ser Gly Gly Ser Ala Thr Asn Asn
                    20                  25                  30

Ile Ala Gln Ala Arg Lys Leu Val Glu Gln Leu Arg Ile Glu Ala Gly
                35                  40                  45

Ile Glu Arg Ile Lys Val Ser Lys Ala Ala Ser Asp Leu Met Ser Tyr
        50                  55                  60

Cys Glu Gln His Ala Arg Asn Asp Pro Leu Leu Val Gly Val Pro Ala
65                  70                  75                  80

Ser Glu Asn Pro Phe Lys Asp Lys Lys Pro Cys Ile Ile Leu
                    85                  90

<210> SEQ ID NO 26
<211> LENGTH: 96
<212> TYPE: PRT
<213> ORGANISM: Homo sapiens
<220> FEATURE:
<223> OTHER INFORMATION: Sm-G\'ce\'b38 (SmBiT-GNG8)

<400> SEQUENCE: 26

Met Val Thr Gly Tyr Arg Leu Phe Glu Glu Ile Leu Gly Gly Ser Gly
1                   5                   10                   15

Gly Gly Gly Ser Gly Gly Ser Ser Ser Gly Gly Ser Asn Asn Met Ala
                    20                  25                  30

Lys Ile Ala Glu Ala Arg Lys Thr Val Glu Gln Leu Lys Leu Glu Val
                35                  40                  45

Asn Ile Asp Arg Met Lys Val Ser Gln Ala Ala Ala Glu Leu Leu Ala
        50                  55                  60

Phe Cys Glu Thr His Ala Lys Asp Asp Pro Leu Val Thr Pro Val Pro
65                  70                  75                  80

Ala Ala Glu Asn Pro Phe Arg Asp Lys Arg Leu Phe Cys Val Leu Leu
                    85                  90                  95

<210> SEQ ID NO 27
<211> LENGTH: 94
<212> TYPE: PRT
<213> ORGANISM: Homo sapiens
<220> FEATURE:
<223> OTHER INFORMATION: Sm-G\'ce\'b310 (SmBiT-GNG10)

<400> SEQUENCE: 27

Met Val Thr Gly Tyr Arg Leu Phe Glu Glu Ile Leu Gly Gly Ser Gly
1                   5                   10                   15

Gly Gly Gly Ser Gly Gly Ser Ser Ser Gly Gly Ser Ser Gly Ala Ser
                    20                  25                  30

Ala Ser Ala Leu Gln Arg Leu Val Glu Gln Leu Lys Leu Glu Ala Gly
                35                  40                  45

-continued

Val Glu Arg Ile Lys Val Ser Gln Ala Ala Ala Glu Leu Gln Gln Tyr
    50              55              60

Cys Met Gln Asn Ala Cys Lys Asp Ala Leu Leu Val Gly Val Pro Ala
65              70              75              80

Gly Ser Asn Pro Phe Arg Glu Pro Arg Ser Cys Ala Leu Leu
                85              90

<210> SEQ ID NO 28
<211> LENGTH: 99
<212> TYPE: PRT
<213> ORGANISM: Homo sapiens
<220> FEATURE:
<223> OTHER INFORMATION: Sm-G\'ce\'b311 (SmBiT-GNG11)

<400> SEQUENCE: 28

Met Val Thr Gly Tyr Arg Leu Phe Glu Glu Ile Leu Gly Gly Ser Gly
1               5               10              15

Gly Gly Gly Ser Gly Gly Ser Ser Ser Gly Gly Pro Ala Leu His Ile
            20              25              30

Glu Asp Leu Pro Glu Lys Glu Lys Leu Lys Met Glu Val Glu Gln Leu
            35              40              45

Arg Lys Glu Val Lys Leu Gln Arg Gln Gln Val Ser Lys Cys Ser Glu
    50              55              60

Glu Ile Lys Asn Tyr Ile Glu Glu Arg Ser Gly Glu Asp Pro Leu Val
65              70              75              80

Lys Gly Ile Pro Glu Asp Lys Asn Pro Phe Lys Glu Lys Gly Ser Cys
                85              90              95

Val Ile Ser

<210> SEQ ID NO 29
<211> LENGTH: 98
<212> TYPE: PRT
<213> ORGANISM: Homo sapiens
<220> FEATURE:
<223> OTHER INFORMATION: Sm-G\'ce\'b312 (SmBiT-GNG12)

<400> SEQUENCE: 29

Met Val Thr Gly Tyr Arg Leu Phe Glu Glu Ile Leu Gly Gly Ser Gly
1               5               10              15

Gly Gly Gly Ser Gly Gly Ser Ser Ser Gly Gly Ser Ser Lys Thr Ala
            20              25              30

Ser Thr Asn Asn Ile Ala Gln Ala Arg Arg Thr Val Gln Gln Leu Arg
        35              40              45

Leu Glu Ala Ser Ile Glu Arg Ile Lys Val Ser Lys Ala Ser Ala Asp
    50              55              60

Leu Met Ser Tyr Cys Glu Glu His Ala Arg Ser Asp Pro Leu Leu Ile
65              70              75              80

Gly Ile Pro Thr Ser Glu Asn Pro Phe Lys Asp Lys Lys Thr Cys Ile
                85              90              95

Ile Leu

<210> SEQ ID NO 30
<211> LENGTH: 93
<212> TYPE: PRT
<213> ORGANISM: Homo sapiens
<220> FEATURE:
<223> OTHER INFORMATION: Sm-G\'ce\'b313 (SmBiT-GNG13)

<400> SEQUENCE: 30

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Glu Glu Trp Asp Val
                20                  25                  30

Pro Gln Met Lys Lys Glu Val Glu Ser Leu Lys Tyr Gln Leu Ala Phe
            35                  40                  45

Gln Arg Glu Met Ala Ser Lys Thr Ile Pro Glu Leu Leu Lys Trp Ile
        50                  55                  60

Glu Asp Gly Ile Pro Lys Asp Pro Phe Leu Asn Pro Asp Leu Met Lys
65                  70                  75                  80

Asn Asn Pro Trp Val Glu Lys Gly Lys Cys Thr Ile Leu
                85                  90
```

<210> SEQ ID NO 31
<211> LENGTH: 100
<212> TYPE: PRT
<213> ORGANISM: Homo sapiens
<220> FEATURE:
<223> OTHER INFORMATION: Sm-G\'ce\'b3t1 (SmBiT-GNGT1)

<400> SEQUENCE: 31

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Pro Val Ile Asn Ile
                20                  25                  30

Glu Asp Leu Thr Glu Lys Asp Lys Leu Lys Met Glu Val Asp Gln Leu
            35                  40                  45

Lys Lys Glu Val Thr Leu Glu Arg Met Leu Val Ser Lys Cys Cys Glu
        50                  55                  60

Glu Val Arg Asp Tyr Val Glu Glu Arg Ser Gly Glu Asp Pro Leu Val
65                  70                  75                  80

Lys Gly Ile Pro Glu Asp Lys Asn Pro Phe Lys Glu Leu Lys Gly Gly
                85                  90                  95

Cys Val Ile Ser
            100
```

<210> SEQ ID NO 32
<211> LENGTH: 95
<212> TYPE: PRT
<213> ORGANISM: Homo sapiens
<220> FEATURE:
<223> OTHER INFORMATION: Sm-G\'ce\'b3 (SmBiT-GNGT2)

<400> SEQUENCE: 32

```
Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ala Gln Asp Leu Ser
                20                  25                  30

Glu Lys Asp Leu Leu Lys Met Glu Val Glu Gln Leu Lys Lys Glu Val
            35                  40                  45

Lys Asn Thr Arg Ile Pro Ile Ser Lys Ala Gly Lys Glu Ile Lys Glu
        50                  55                  60

Tyr Val Glu Ala Gln Ala Gly Asn Asp Pro Phe Leu Lys Gly Ile Pro
65                  70                  75                  80

Glu Asp Lys Asn Pro Phe Lys Glu Lys Gly Gly Cys Leu Ile Ser
                85                  90                  95
```

<210> SEQ ID NO 33
<211> LENGTH: 435
<212> TYPE: PRT
<213> ORGANISM: Homo sapiens
<220> FEATURE:
<223> OTHER INFORMATION: G\'ce\'b1s-Sm (GNAS-SmBiT)

<400> SEQUENCE: 33

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Gly Gly Ser Gly Gly Gly Gly Ser Gly Gly Ser Ser Ser Gly Gly
        115                 120                 125

Val Thr Gly Tyr Arg Leu Phe Glu Glu Ile Leu Gly Gly Ser Gly Gly
        130                 135                 140

Gly Gly Ser Gly Gly Ser Ser Ser Gly Gly Val Pro Pro Val Glu Leu
145                 150                 155                 160

Ala Asn Pro Glu Asn Gln Phe Arg Val Asp Tyr Ile Leu Ser Val Met
                165                 170                 175

Asn Val Pro Asp Phe Asp Phe Pro Pro Glu Phe Tyr Glu His Ala Lys
                180                 185                 190

Ala Leu Trp Glu Asp Glu Gly Val Arg Ala Cys Tyr Glu Arg Ser Asn
            195                 200                 205

Glu Tyr Gln Leu Ile Asp Cys Ala Gln Tyr Phe Leu Asp Lys Ile Asp
        210                 215                 220

Val Ile Lys Gln Ala Asp Tyr Val Pro Ser Asp Gln Asp Leu Leu Arg
225                 230                 235                 240

Cys Arg Val Leu Thr Ser Gly Ile Phe Glu Thr Lys Phe Gln Val Asp
                245                 250                 255

Lys Val Asn Phe His Met Phe Asp Val Gly Gly Gln Arg Asp Glu Arg
                260                 265                 270

Arg Lys Trp Ile Gln Cys Phe Asn Asp Val Thr Ala Ile Ile Phe Val
            275                 280                 285

Val Ala Ser Ser Ser Tyr Asn Met Val Ile Arg Glu Asp Asn Gln Thr
        290                 295                 300

Asn Arg Leu Gln Glu Ala Leu Asn Leu Phe Lys Ser Ile Trp Asn Asn
305                 310                 315                 320

Arg Trp Leu Arg Thr Ile Ser Val Ile Leu Phe Leu Asn Lys Gln Asp
            325                 330                 335

Leu Leu Ala Glu Lys Val Leu Ala Gly Lys Ser Lys Ile Glu Asp Tyr
            340                 345                 350

Phe Pro Glu Phe Ala Arg Tyr Thr Thr Pro Glu Asp Ala Thr Pro Glu
            355                 360                 365

Pro Gly Glu Asp Pro Arg Val Thr Arg Ala Lys Tyr Phe Ile Arg Asp

-continued

```
              370               375               380

Glu Phe Leu Arg Ile Ser Thr Ala Ser Gly Asp Gly Arg His Tyr Cys
385               390               395               400

Tyr Pro His Phe Thr Cys Ala Val Asp Thr Glu Asn Ile Arg Arg Val
              405               410               415

Phe Asn Asp Cys Arg Asp Ile Ile Gln Arg Met His Leu Arg Gln Tyr
              420               425               430

Glu Leu Leu
        435

<210> SEQ ID NO 34
<211> LENGTH: 568
<212> TYPE: PRT
<213> ORGANISM: Homo sapiens
<220> FEATURE:
<223> OTHER INFORMATION: G\'ce\'b1s-Lg (\'ce\'b1B-\'ce\'b1C)
      (GNAS-LgBiT-\'ce\'b1B-\'ce\'b1C)

<400> SEQUENCE: 34

Met Gly Cys Leu Gly Asn Ser Lys Thr Glu Asp Gln Arg Asn Glu Glu
1               5               10               15

Lys Ala Gln Arg Glu Ala Asn Lys Lys Ile Glu Lys Gln Leu Gln Lys
              20               25               30

Asp Lys Gln Val Tyr Arg Ala Thr His Arg Leu Leu Leu Leu Gly Ala
        35               40               45

Gly Glu Ser Gly Lys Ser Thr Ile Val Lys Gln Met Arg Ile Leu His
     50               55               60

Val Asn Gly Phe Asn Gly Asp Ser Glu Lys Ala Thr Lys Val Gln Asp
65               70               75               80

Ile Lys Asn Asn Leu Lys Glu Ala Ile Glu Thr Ile Val Ala Ala Met
              85               90               95

Ser Asn Leu Val Pro Pro Val Glu Leu Ala Asn Pro Glu Asn Gln Phe
              100               105               110

Arg Val Asp Tyr Ile Leu Ser Val Met Asn Val Pro Asp Phe Gly Gly
        115               120               125

Ser Gly Gly Gly Gly Ser Gly Gly Ser Ser Ser Gly Gly Val Phe Thr
     130               135               140

Leu Glu Asp Phe Val Gly Asp Trp Glu Gln Thr Ala Ala Tyr Asn Leu
145               150               155               160

Asp Gln Val Leu Glu Gln Gly Gly Val Ser Ser Leu Leu Gln Asn Leu
              165               170               175

Ala Val Ser Val Thr Pro Ile Gln Arg Ile Val Arg Ser Gly Glu Asn
              180               185               190

Ala Leu Lys Ile Asp Ile His Val Ile Ile Pro Tyr Glu Gly Leu Ser
        195               200               205

Ala Asp Gln Met Ala Gln Ile Glu Glu Val Phe Lys Val Val Tyr Pro
     210               215               220

Val Asp Asp His His Phe Lys Val Ile Leu Pro Tyr Gly Thr Leu Val
225               230               235               240

Ile Asp Gly Val Thr Pro Asn Met Leu Asn Tyr Phe Gly Arg Pro Tyr
              245               250               255

Glu Gly Ile Ala Val Phe Asp Gly Lys Lys Ile Thr Val Thr Gly Thr
              260               265               270

Leu Trp Asn Gly Asn Lys Ile Ile Asp Glu Arg Leu Ile Thr Pro Asp
        275               280               285
```

-continued

```
Gly Ser Met Leu Phe Arg Val Thr Ile Asn Ser Gly Gly Ser Gly Gly
    290                 295                 300

Gly Gly Ser Gly Gly Ser Ser Ser Gly Gly Asp Phe Pro Pro Glu Phe
305                 310                 315                 320

Tyr Glu His Ala Lys Ala Leu Trp Glu Asp Glu Gly Val Arg Ala Cys
                325                 330                 335

Tyr Glu Arg Ser Asn Glu Tyr Gln Leu Ile Asp Cys Ala Gln Tyr Phe
                340                 345                 350

Leu Asp Lys Ile Asp Val Ile Lys Gln Ala Asp Tyr Val Pro Ser Asp
                355                 360                 365

Gln Asp Leu Leu Arg Cys Arg Val Leu Thr Ser Gly Ile Phe Glu Thr
    370                 375                 380

Lys Phe Gln Val Asp Lys Val Asn Phe His Met Phe Asp Val Gly Gly
385                 390                 395                 400

Gln Arg Asp Glu Arg Arg Lys Trp Ile Gln Cys Phe Asn Asp Val Thr
                405                 410                 415

Ala Ile Ile Phe Val Val Ala Ser Ser Ser Tyr Asn Met Val Ile Arg
                420                 425                 430

Glu Asp Asn Gln Thr Asn Arg Leu Gln Glu Ala Leu Asn Leu Phe Lys
                435                 440                 445

Ser Ile Trp Asn Asn Arg Trp Leu Arg Thr Ile Ser Val Ile Leu Phe
    450                 455                 460

Leu Asn Lys Gln Asp Leu Leu Ala Glu Lys Val Leu Ala Gly Lys Ser
465                 470                 475                 480

Lys Ile Glu Asp Tyr Phe Pro Glu Phe Ala Arg Tyr Thr Thr Pro Glu
                485                 490                 495

Asp Ala Thr Pro Glu Pro Gly Glu Asp Pro Arg Val Thr Arg Ala Lys
                500                 505                 510

Tyr Phe Ile Arg Asp Glu Phe Leu Arg Ile Ser Thr Ala Ser Gly Asp
                515                 520                 525

Gly Arg His Tyr Cys Tyr Pro His Phe Thr Cys Ala Val Asp Thr Glu
    530                 535                 540

Asn Ile Arg Arg Val Phe Asn Asp Cys Arg Asp Ile Ile Gln Arg Met
545                 550                 555                 560

His Leu Arg Gln Tyr Glu Leu Leu
                565
```

```
<210> SEQ ID NO 35
<211> LENGTH: 421
<212> TYPE: PRT
<213> ORGANISM: Homo sapiens
<220> FEATURE:
<223> OTHER INFORMATION: G\'ce\'b1s-Sm (\'ce\'b1B-\'ce\'b1C)
      (GNAS-SmBiT-\'ce\'b1B-\'ce\'b1C)

<400> SEQUENCE: 35

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
                35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80
```

-continued

```
Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
               100                 105                 110

Arg Val Asp Tyr Ile Leu Ser Val Met Asn Val Pro Asp Phe Gly Gly
               115                 120                 125

Ser Gly Gly Gly Gly Ser Gly Gly Ser Ser Ser Gly Gly Val Thr Gly
           130                 135                 140

Tyr Arg Leu Phe Glu Glu Ile Leu Gly Gly Ser Gly Gly Gly Gly Ser
145                 150                 155                 160

Gly Gly Ser Ser Ser Gly Gly Asp Phe Pro Pro Glu Phe Tyr Glu His
               165                 170                 175

Ala Lys Ala Leu Trp Glu Asp Glu Gly Val Arg Ala Cys Tyr Glu Arg
               180                 185                 190

Ser Asn Glu Tyr Gln Leu Ile Asp Cys Ala Gln Tyr Phe Leu Asp Lys
               195                 200                 205

Ile Asp Val Ile Lys Gln Ala Asp Tyr Val Pro Ser Asp Gln Asp Leu
           210                 215                 220

Leu Arg Cys Arg Val Leu Thr Ser Gly Ile Phe Glu Thr Lys Phe Gln
225                 230                 235                 240

Val Asp Lys Val Asn Phe His Met Phe Asp Val Gly Gly Gln Arg Asp
               245                 250                 255

Glu Arg Arg Lys Trp Ile Gln Cys Phe Asn Asp Val Thr Ala Ile Ile
               260                 265                 270

Phe Val Val Ala Ser Ser Ser Tyr Asn Met Val Ile Arg Glu Asp Asn
               275                 280                 285

Gln Thr Asn Arg Leu Gln Glu Ala Leu Asn Leu Phe Lys Ser Ile Trp
           290                 295                 300

Asn Asn Arg Trp Leu Arg Thr Ile Ser Val Ile Leu Phe Leu Asn Lys
305                 310                 315                 320

Gln Asp Leu Leu Ala Glu Lys Val Leu Ala Gly Lys Ser Lys Ile Glu
               325                 330                 335

Asp Tyr Phe Pro Glu Phe Ala Arg Tyr Thr Thr Pro Glu Asp Ala Thr
               340                 345                 350

Pro Glu Pro Gly Glu Asp Pro Arg Val Thr Arg Ala Lys Tyr Phe Ile
               355                 360                 365

Arg Asp Glu Phe Leu Arg Ile Ser Thr Ala Ser Gly Asp Gly Arg His
           370                 375                 380

Tyr Cys Tyr Pro His Phe Thr Cys Ala Val Asp Thr Glu Asn Ile Arg
385                 390                 395                 400

Arg Val Phe Asn Asp Cys Arg Asp Ile Ile Gln Arg Met His Leu Arg
               405                 410                 415

Gln Tyr Glu Leu Leu
           420
```

```
<210> SEQ ID NO 36
<211> LENGTH: 582
<212> TYPE: PRT
<213> ORGANISM: Homo sapiens
<220> FEATURE:
<223> OTHER INFORMATION: G\'ce\'b1s-Lg (G2A/C3S) (GNAS-LgBiT-G2A-C3S)

<400> SEQUENCE: 36
```

```
Met Ala Ser Leu Gly Asn Ser Lys Thr Glu Asp Gln Arg Asn Glu Glu
1               5                   10                  15
```

```
Lys Ala Gln Arg Glu Ala Asn Lys Lys Ile Glu Lys Gln Leu Gln Lys
            20              25              30

Asp Lys Gln Val Tyr Arg Ala Thr His Arg Leu Leu Leu Leu Gly Ala
            35              40              45

Gly Glu Ser Gly Lys Ser Thr Ile Val Lys Gln Met Arg Ile Leu His
        50              55              60

Val Asn Gly Phe Asn Gly Glu Gly Gly Glu Glu Asp Pro Gln Ala Ala
65              70              75              80

Arg Ser Asn Ser Asp Gly Glu Lys Ala Thr Lys Val Gln Asp Ile Lys
                85              90              95

Asn Asn Leu Lys Glu Ala Ile Glu Thr Ile Val Ala Ala Met Ser Asn
            100             105             110

Leu Gly Gly Ser Gly Gly Gly Ser Gly Gly Ser Ser Ser Gly Gly
            115             120             125

Val Phe Thr Leu Glu Asp Phe Val Gly Asp Trp Glu Gln Thr Ala Ala
    130             135             140

Tyr Asn Leu Asp Gln Val Leu Glu Gln Gly Gly Val Ser Ser Leu Leu
145             150             155             160

Gln Asn Leu Ala Val Ser Val Thr Pro Ile Gln Arg Ile Val Arg Ser
            165             170             175

Gly Glu Asn Ala Leu Lys Ile Asp Ile His Val Ile Ile Pro Tyr Glu
            180             185             190

Gly Leu Ser Ala Asp Gln Met Ala Gln Ile Glu Glu Val Phe Lys Val
            195             200             205

Val Tyr Pro Val Asp Asp His His Phe Lys Val Ile Leu Pro Tyr Gly
    210             215             220

Thr Leu Val Ile Asp Gly Val Thr Pro Asn Met Leu Asn Tyr Phe Gly
225             230             235             240

Arg Pro Tyr Glu Gly Ile Ala Val Phe Asp Gly Lys Lys Ile Thr Val
            245             250             255

Thr Gly Thr Leu Trp Asn Gly Asn Lys Ile Ile Asp Glu Arg Leu Ile
            260             265             270

Thr Pro Asp Gly Ser Met Leu Phe Arg Val Thr Ile Asn Ser Gly Gly
            275             280             285

Ser Gly Gly Gly Gly Ser Gly Gly Ser Ser Ser Gly Gly Val Pro Pro
    290             295             300

Val Glu Leu Ala Asn Pro Glu Asn Gln Phe Arg Val Asp Tyr Ile Leu
305             310             315             320

Ser Val Met Asn Val Pro Asp Phe Asp Phe Pro Pro Glu Phe Tyr Glu
            325             330             335

His Ala Lys Ala Leu Trp Glu Asp Glu Gly Val Arg Ala Cys Tyr Glu
            340             345             350

Arg Ser Asn Glu Tyr Gln Leu Ile Asp Cys Ala Gln Tyr Phe Leu Asp
            355             360             365

Lys Ile Asp Val Ile Lys Gln Ala Asp Tyr Val Pro Ser Asp Gln Asp
            370             375             380

Leu Leu Arg Cys Arg Val Leu Thr Ser Gly Ile Phe Glu Thr Lys Phe
385             390             395             400

Gln Val Asp Lys Val Asn Phe His Met Phe Asp Val Gly Gly Gln Arg
            405             410             415

Asp Glu Arg Arg Lys Trp Ile Gln Cys Phe Asn Asp Val Thr Ala Ile
            420             425             430
```

-continued

```
Ile Phe Val Val Ala Ser Ser Ser Tyr Asn Met Val Ile Arg Glu Asp
        435             440             445

Asn Gln Thr Asn Arg Leu Gln Glu Ala Leu Asn Leu Phe Lys Ser Ile
    450             455             460

Trp Asn Asn Arg Trp Leu Arg Thr Ile Ser Val Ile Leu Phe Leu Asn
465             470             475             480

Lys Gln Asp Leu Leu Ala Glu Lys Val Leu Ala Gly Lys Ser Lys Ile
            485             490             495

Glu Asp Tyr Phe Pro Glu Phe Ala Arg Tyr Thr Thr Pro Glu Asp Ala
            500             505             510

Thr Pro Glu Pro Gly Glu Asp Pro Arg Val Thr Arg Ala Lys Tyr Phe
            515             520             525

Ile Arg Asp Glu Phe Leu Arg Ile Ser Thr Ala Ser Gly Asp Gly Arg
        530             535             540

His Tyr Cys Tyr Pro His Phe Thr Cys Ala Val Asp Thr Glu Asn Ile
545             550             555             560

Arg Arg Val Phe Asn Asp Cys Arg Asp Ile Ile Gln Arg Met His Leu
            565             570             575

Arg Gln Tyr Glu Leu Leu
            580
```

<210> SEQ ID NO 37
<211> LENGTH: 547
<212> TYPE: PRT
<213> ORGANISM: Homo sapiens
<220> FEATURE:
<223> OTHER INFORMATION: G\'ce\'b1q-Lg (R183C) (GNAQ-LgBiT-R183C)

<400> SEQUENCE: 37

```
Met Thr Leu Glu Ser Ile Met Ala Cys Cys Leu Ser Glu Glu Ala Lys
1               5               10              15

Glu Ala Arg Arg Ile Asn Asp Glu Ile Glu Arg Gln Leu Arg Arg Asp
            20              25              30

Lys Arg Asp Ala Arg Arg Glu Leu Lys Leu Leu Leu Gly Thr Gly
        35              40              45

Glu Ser Gly Lys Ser Thr Phe Ile Lys Gln Met Arg Ile Ile His Gly
    50              55              60

Ser Gly Tyr Ser Asp Glu Asp Lys Arg Gly Phe Thr Lys Leu Val Tyr
65              70              75              80

Gln Asn Ile Phe Thr Ala Met Gln Ala Met Ile Arg Ala Met Asp Thr
            85              90              95

Leu Gly Gly Ser Gly Gly Gly Ser Gly Gly Ser Ser Ser Gly Gly
            100             105             110

Val Phe Thr Leu Glu Asp Phe Val Gly Asp Trp Glu Gln Thr Ala Ala
            115             120             125

Tyr Asn Leu Asp Gln Val Leu Glu Gln Gly Gly Val Ser Ser Leu Leu
        130             135             140

Gln Asn Leu Ala Val Ser Val Thr Pro Ile Gln Arg Ile Val Arg Ser
145             150             155             160

Gly Glu Asn Ala Leu Lys Ile Asp Ile His Val Ile Ile Pro Tyr Glu
            165             170             175

Gly Leu Ser Ala Asp Gln Met Ala Gln Ile Glu Glu Val Phe Lys Val
            180             185             190

Val Tyr Pro Val Asp Asp His His Phe Lys Val Ile Leu Pro Tyr Gly
        195             200             205
```

```
Thr Leu Val Ile Asp Gly Val Thr Pro Asn Met Leu Asn Tyr Phe Gly
    210             215                 220

Arg Pro Tyr Glu Gly Ile Ala Val Phe Asp Gly Lys Lys Ile Thr Val
225             230                 235                 240

Thr Gly Thr Leu Trp Asn Gly Asn Lys Ile Ile Asp Glu Arg Leu Ile
            245                 250                 255

Thr Pro Asp Gly Ser Met Leu Phe Arg Val Thr Ile Asn Ser Gly Gly
            260                 265                 270

Ser Gly Gly Gly Gly Ser Gly Gly Ser Ser Ser Gly Gly Lys Ile Pro
            275                 280                 285

Tyr Lys Tyr Glu His Asn Lys Ala His Ala Gln Leu Val Arg Glu Val
    290                 295                 300

Asp Val Glu Lys Val Ser Ala Phe Glu Asn Pro Tyr Val Asp Ala Ile
305             310                 315                 320

Lys Ser Leu Trp Asn Asp Pro Gly Ile Gln Glu Cys Tyr Asp Arg Arg
            325                 330                 335

Arg Glu Tyr Gln Leu Ser Asp Ser Thr Lys Tyr Tyr Leu Asn Asp Leu
            340                 345                 350

Asp Arg Val Ala Asp Pro Ala Tyr Leu Pro Thr Gln Gln Asp Val Leu
            355                 360                 365

Arg Val Cys Val Pro Thr Thr Gly Ile Ile Glu Tyr Pro Phe Asp Leu
    370                 375                 380

Gln Ser Val Ile Phe Arg Met Val Asp Val Gly Gly Gln Arg Ser Glu
385                 390                 395                 400

Arg Arg Lys Trp Ile His Cys Phe Glu Asn Val Thr Ser Ile Met Phe
            405                 410                 415

Leu Val Ala Leu Ser Glu Tyr Asp Gln Val Leu Val Glu Ser Asp Asn
            420                 425                 430

Glu Asn Arg Met Glu Glu Ser Lys Ala Leu Phe Arg Thr Ile Ile Thr
            435                 440                 445

Tyr Pro Trp Phe Gln Asn Ser Ser Val Ile Leu Phe Leu Asn Lys Lys
    450                 455                 460

Asp Leu Leu Glu Glu Lys Ile Met Tyr Ser His Leu Val Asp Tyr Phe
465             470                 475                 480

Pro Glu Tyr Asp Gly Pro Gln Arg Asp Ala Gln Ala Ala Arg Glu Phe
            485                 490                 495

Ile Leu Lys Met Phe Val Asp Leu Asn Pro Asp Ser Asp Lys Ile Ile
            500                 505                 510

Tyr Ser His Phe Thr Cys Ala Thr Asp Thr Glu Asn Ile Arg Phe Val
            515                 520                 525

Phe Ala Ala Val Lys Asp Thr Ile Leu Gln Leu Asn Leu Lys Glu Tyr
    530                 535                 540

Asn Leu Val
545

<210> SEQ ID NO 38
<211> LENGTH: 547
<212> TYPE: PRT
<213> ORGANISM: Homo sapiens
<220> FEATURE:
<223> OTHER INFORMATION: G\'ce\'b1q-Lg (\'ce\'b1B-\'ce\'b1C)
      (GNAQ-LgBiT-\'ce\'b1B-\'ce\'b1C)

<400> SEQUENCE: 38

Met Thr Leu Glu Ser Ile Met Ala Cys Cys Leu Ser Glu Glu Ala Lys
1               5                   10                  15
```

```
Glu Ala Arg Arg Ile Asn Asp Glu Ile Glu Arg Gln Leu Arg Arg Asp
          20              25              30

Lys Arg Asp Ala Arg Arg Glu Leu Lys Leu Leu Leu Gly Thr Gly
          35              40              45

Glu Ser Gly Lys Ser Thr Phe Ile Lys Gln Met Arg Ile Ile His Gly
          50              55              60

Ser Gly Tyr Ser Asp Glu Asp Lys Arg Gly Phe Thr Lys Leu Val Tyr
65              70              75              80

Gln Asn Ile Phe Thr Ala Met Gln Ala Met Ile Arg Ala Met Asp Thr
              85              90              95

Leu Lys Ile Pro Tyr Lys Tyr Glu His Asn Lys Ala His Ala Gln Leu
              100             105             110

Val Arg Glu Val Asp Val Glu Lys Val Ser Ala Gly Gly Ser Gly Gly
          115             120             125

Gly Gly Ser Gly Gly Ser Ser Ser Gly Gly Val Phe Thr Leu Glu Asp
          130             135             140

Phe Val Gly Asp Trp Glu Gln Thr Ala Ala Tyr Asn Leu Asp Gln Val
145             150             155             160

Leu Glu Gln Gly Gly Val Ser Ser Leu Leu Gln Asn Leu Ala Val Ser
              165             170             175

Val Thr Pro Ile Gln Arg Ile Val Arg Ser Gly Glu Asn Ala Leu Lys
              180             185             190

Ile Asp Ile His Val Ile Ile Pro Tyr Glu Gly Leu Ser Ala Asp Gln
              195             200             205

Met Ala Gln Ile Glu Glu Val Phe Lys Val Val Tyr Pro Val Asp Asp
          210             215             220

His His Phe Lys Val Ile Leu Pro Tyr Gly Thr Leu Val Ile Asp Gly
225             230             235             240

Val Thr Pro Asn Met Leu Asn Tyr Phe Gly Arg Pro Tyr Glu Gly Ile
              245             250             255

Ala Val Phe Asp Gly Lys Lys Ile Thr Val Thr Gly Thr Leu Trp Asn
              260             265             270

Gly Asn Lys Ile Ile Asp Glu Arg Leu Ile Thr Pro Asp Gly Ser Met
              275             280             285

Leu Phe Arg Val Thr Ile Asn Ser Gly Gly Ser Gly Gly Gly Gly Ser
          290             295             300

Gly Gly Ser Ser Ser Gly Gly Phe Glu Asn Pro Tyr Val Asp Ala Ile
305             310             315             320

Lys Ser Leu Trp Asn Asp Pro Gly Ile Gln Glu Cys Tyr Asp Arg Arg
              325             330             335

Arg Glu Tyr Gln Leu Ser Asp Ser Thr Lys Tyr Tyr Leu Asn Asp Leu
              340             345             350

Asp Arg Val Ala Asp Pro Ala Tyr Leu Pro Thr Gln Gln Asp Val Leu
              355             360             365

Arg Val Arg Val Pro Thr Thr Gly Ile Ile Glu Tyr Pro Phe Asp Leu
          370             375             380

Gln Ser Val Ile Phe Arg Met Val Asp Val Gly Gly Gln Arg Ser Glu
385             390             395             400

Arg Arg Lys Trp Ile His Cys Phe Glu Asn Val Thr Ser Ile Met Phe
              405             410             415

Leu Val Ala Leu Ser Glu Tyr Asp Gln Val Leu Val Glu Ser Asp Asn
          420             425             430
```

-continued

```
Glu Asn Arg Met Glu Glu Ser Lys Ala Leu Phe Arg Thr Ile Ile Thr
    435                 440                 445

Tyr Pro Trp Phe Gln Asn Ser Ser Val Ile Leu Phe Leu Asn Lys Lys
    450                 455                 460

Asp Leu Leu Glu Glu Lys Ile Met Tyr Ser His Leu Val Asp Tyr Phe
465                 470                 475                 480

Pro Glu Tyr Asp Gly Pro Gln Arg Asp Ala Gln Ala Ala Arg Glu Phe
                485                 490                 495

Ile Leu Lys Met Phe Val Asp Leu Asn Pro Asp Ser Asp Lys Ile Ile
                500                 505                 510

Tyr Ser His Phe Thr Cys Ala Thr Asp Thr Glu Asn Ile Arg Phe Val
                515                 520                 525

Phe Ala Ala Val Lys Asp Thr Ile Leu Gln Leu Asn Leu Lys Glu Tyr
    530                 535                 540

Asn Leu Val
545

<210> SEQ ID NO 39
<211> LENGTH: 547
<212> TYPE: PRT
<213> ORGANISM: Homo sapiens
<220> FEATURE:
<223> OTHER INFORMATION: G\'ce\'b111-Lg (\'ce\'b1B-\'ce\'b1C)
      (GNA11-LgBiT-\'ce\'b1B-\'ce\'b1C)

<400> SEQUENCE: 39

Met Thr Leu Glu Ser Met Met Ala Cys Cys Leu Ser Asp Glu Val Lys
1               5                   10                  15

Glu Ser Lys Arg Ile Asn Ala Glu Ile Glu Lys Gln Leu Arg Arg Asp
                20                  25                  30

Lys Arg Asp Ala Arg Arg Glu Leu Lys Leu Leu Leu Gly Thr Gly
                35                  40                  45

Glu Ser Gly Lys Ser Thr Phe Ile Lys Gln Met Arg Ile Ile His Gly
    50                  55                  60

Ala Gly Tyr Ser Glu Glu Asp Lys Arg Gly Phe Thr Lys Leu Val Tyr
65                  70                  75                  80

Gln Asn Ile Phe Thr Ala Met Gln Ala Met Ile Arg Ala Met Glu Thr
                85                  90                  95

Leu Lys Ile Leu Tyr Lys Tyr Glu Gln Asn Lys Ala Asn Ala Leu Leu
                100                 105                 110

Ile Arg Glu Val Asp Val Glu Lys Val Thr Thr Gly Gly Ser Gly Gly
                115                 120                 125

Gly Gly Ser Gly Gly Ser Ser Ser Gly Gly Val Phe Thr Leu Glu Asp
    130                 135                 140

Phe Val Gly Asp Trp Glu Gln Thr Ala Ala Tyr Asn Leu Asp Gln Val
145                 150                 155                 160

Leu Glu Gln Gly Gly Val Ser Ser Leu Leu Gln Asn Leu Ala Val Ser
                165                 170                 175

Val Thr Pro Ile Gln Arg Ile Val Arg Ser Gly Glu Asn Ala Leu Lys
                180                 185                 190

Ile Asp Ile His Val Ile Ile Pro Tyr Glu Gly Leu Ser Ala Asp Gln
                195                 200                 205

Met Ala Gln Ile Glu Glu Val Phe Lys Val Val Tyr Pro Val Asp Asp
    210                 215                 220

His His Phe Lys Val Ile Leu Pro Tyr Gly Thr Leu Val Ile Asp Gly
225                 230                 235                 240
```

```
Val Thr Pro Asn Met Leu Asn Tyr Phe Gly Arg Pro Tyr Glu Gly Ile
                245                 250                 255

Ala Val Phe Asp Gly Lys Lys Ile Thr Val Thr Gly Thr Leu Trp Asn
                260                 265                 270

Gly Asn Lys Ile Ile Asp Glu Arg Leu Ile Thr Pro Asp Gly Ser Met
                275                 280                 285

Leu Phe Arg Val Thr Ile Asn Ser Gly Gly Ser Gly Gly Gly Gly Ser
        290                 295                 300

Gly Gly Ser Ser Gly Gly Phe Glu His Gln Tyr Val Ser Ala Ile
305                 310                 315                 320

Lys Thr Leu Trp Glu Asp Pro Gly Ile Gln Glu Cys Tyr Asp Arg Arg
                325                 330                 335

Arg Glu Tyr Gln Leu Ser Asp Ser Ala Lys Tyr Tyr Leu Thr Asp Val
                340                 345                 350

Asp Arg Ile Ala Thr Leu Gly Tyr Leu Pro Thr Gln Gln Asp Val Leu
                355                 360                 365

Arg Val Arg Val Pro Thr Thr Gly Ile Ile Glu Tyr Pro Phe Asp Leu
        370                 375                 380

Glu Asn Ile Ile Phe Arg Met Val Asp Val Gly Gly Gln Arg Ser Glu
385                 390                 395                 400

Arg Arg Lys Trp Ile His Cys Phe Glu Asn Val Thr Ser Ile Met Phe
                405                 410                 415

Leu Val Ala Leu Ser Glu Tyr Asp Gln Val Leu Val Glu Ser Asp Asn
                420                 425                 430

Glu Asn Arg Met Glu Glu Ser Lys Ala Leu Phe Arg Thr Ile Ile Thr
                435                 440                 445

Tyr Pro Trp Phe Gln Asn Ser Ser Val Ile Leu Phe Leu Asn Lys Lys
        450                 455                 460

Asp Leu Leu Glu Asp Lys Ile Leu Tyr Ser His Leu Val Asp Tyr Phe
465                 470                 475                 480

Pro Glu Phe Asp Gly Pro Gln Arg Asp Ala Gln Ala Ala Arg Glu Phe
                485                 490                 495

Ile Leu Lys Met Phe Val Asp Leu Asn Pro Asp Ser Asp Lys Ile Ile
                500                 505                 510

Tyr Ser His Phe Thr Cys Ala Thr Asp Thr Glu Asn Ile Arg Phe Val
                515                 520                 525

Phe Ala Ala Val Lys Asp Thr Ile Leu Gln Leu Asn Leu Lys Glu Tyr
        530                 535                 540

Asn Leu Val
545
```

```
<210> SEQ ID NO 40
<211> LENGTH: 543
<212> TYPE: PRT
<213> ORGANISM: Homo sapiens
<220> FEATURE:
<223> OTHER INFORMATION: G\'ce\'b114-Lg (\'ce\'b1B-\'ce\'b1C)
      (GNA14-LgBiT-\'ce\'b1B-\'ce\'b1C)

<400> SEQUENCE: 40

Met Ala Gly Cys Cys Cys Leu Ser Ala Glu Glu Lys Glu Ser Gln Arg
1                   5                   10                  15

Ile Ser Ala Glu Ile Glu Arg Gln Leu Arg Arg Asp Lys Lys Asp Ala
                20                  25                  30

Arg Arg Glu Leu Lys Leu Leu Leu Leu Gly Thr Gly Glu Ser Gly Lys
```

```
                35                    40                    45
Ser Thr Phe Ile Lys Gln Met Arg Ile Ile His Gly Ser Gly Tyr Ser
    50                    55                    60

Asp Glu Asp Arg Lys Gly Phe Thr Lys Leu Val Tyr Gln Asn Ile Phe
65                    70                    75                    80

Thr Ala Met Gln Ala Met Ile Arg Ala Met Asp Thr Leu Arg Ile Gln
                85                    90                    95

Tyr Val Cys Glu Gln Asn Lys Glu Asn Ala Gln Ile Ile Arg Glu Val
            100                   105                   110

Glu Val Asp Lys Val Ser Met Gly Gly Ser Gly Gly Gly Ser Gly
            115                   120                   125

Gly Ser Ser Ser Gly Gly Val Phe Thr Leu Glu Asp Phe Val Gly Asp
    130                   135                   140

Trp Glu Gln Thr Ala Ala Tyr Asn Leu Asp Gln Val Leu Glu Gln Gly
145                   150                   155                   160

Gly Val Ser Ser Leu Leu Gln Asn Leu Ala Val Ser Val Thr Pro Ile
            165                   170                   175

Gln Arg Ile Val Arg Ser Gly Glu Asn Ala Leu Lys Ile Asp Ile His
            180                   185                   190

Val Ile Ile Pro Tyr Glu Gly Leu Ser Ala Asp Gln Met Ala Gln Ile
            195                   200                   205

Glu Glu Val Phe Lys Val Val Tyr Pro Val Asp Asp His His Phe Lys
    210                   215                   220

Val Ile Leu Pro Tyr Gly Thr Leu Val Ile Asp Gly Val Thr Pro Asn
225                   230                   235                   240

Met Leu Asn Tyr Phe Gly Arg Pro Tyr Glu Gly Ile Ala Val Phe Asp
                245                   250                   255

Gly Lys Lys Ile Thr Val Thr Gly Thr Leu Trp Asn Gly Asn Lys Ile
            260                   265                   270

Ile Asp Glu Arg Leu Ile Thr Pro Asp Gly Ser Met Leu Phe Arg Val
            275                   280                   285

Thr Ile Asn Ser Gly Gly Ser Gly Gly Gly Ser Gly Gly Ser Ser
    290                   295                   300

Ser Gly Gly Leu Ser Arg Glu Gln Val Glu Ala Ile Lys Gln Leu Trp
305                   310                   315                   320

Gln Asp Pro Gly Ile Gln Glu Cys Tyr Asp Arg Arg Arg Glu Tyr Gln
            325                   330                   335

Leu Ser Asp Ser Ala Lys Tyr Tyr Leu Thr Asp Ile Asp Arg Ile Ala
            340                   345                   350

Thr Pro Ser Phe Val Pro Thr Gln Gln Asp Val Leu Arg Val Arg Val
            355                   360                   365

Pro Thr Thr Gly Ile Ile Glu Tyr Pro Phe Asp Leu Glu Asn Ile Ile
    370                   375                   380

Phe Arg Met Val Asp Val Gly Gly Gln Arg Ser Glu Arg Arg Lys Trp
385                   390                   395                   400

Ile His Cys Phe Glu Ser Val Thr Ser Ile Ile Phe Leu Val Ala Leu
            405                   410                   415

Ser Glu Tyr Asp Gln Val Leu Ala Glu Cys Asp Asn Glu Asn Arg Met
            420                   425                   430

Glu Glu Ser Lys Ala Leu Phe Lys Thr Ile Ile Thr Tyr Pro Trp Phe
            435                   440                   445

Leu Asn Ser Ser Val Ile Leu Phe Leu Asn Lys Lys Asp Leu Leu Glu
    450                   455                   460
```

-continued

```
Glu Lys Ile Met Tyr Ser His Leu Ile Ser Tyr Phe Pro Glu Tyr Thr
465                 470                 475                 480

Gly Pro Lys Gln Asp Val Arg Ala Ala Arg Asp Phe Ile Leu Lys Leu
                485                 490                 495

Tyr Gln Asp Gln Asn Pro Asp Lys Glu Lys Val Ile Tyr Ser His Phe
            500                 505                 510

Thr Cys Ala Thr Asp Thr Asp Asn Ile Arg Phe Val Phe Ala Ala Val
            515                 520                 525

Lys Asp Thr Ile Leu Gln Leu Asn Leu Arg Glu Phe Asn Leu Val
            530                 535                 540

<210> SEQ ID NO 41
<211> LENGTH: 562
<212> TYPE: PRT
<213> ORGANISM: Homo sapiens
<220> FEATURE:
<223> OTHER INFORMATION: G\'ce\'b116-Lg (\'ce\'b1B-\'ce\'b1C)
      (GNA15-LgBiT-\'ce\'b1B-\'ce\'b1C)

<400> SEQUENCE: 41

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
        50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Gly Gly
            115                 120                 125

Ser Gly Gly Gly Gly Ser Gly Gly Ser Ser Ser Gly Gly Val Phe Thr
        130                 135                 140

Leu Glu Asp Phe Val Gly Asp Trp Glu Gln Thr Ala Ala Tyr Asn Leu
145                 150                 155                 160

Asp Gln Val Leu Glu Gln Gly Gly Val Ser Ser Leu Leu Gln Asn Leu
                165                 170                 175

Ala Val Ser Val Thr Pro Ile Gln Arg Ile Val Arg Ser Gly Glu Asn
            180                 185                 190

Ala Leu Lys Ile Asp Ile His Val Ile Ile Pro Tyr Glu Gly Leu Ser
            195                 200                 205

Ala Asp Gln Met Ala Gln Ile Glu Glu Val Phe Lys Val Val Tyr Pro
            210                 215                 220

Val Asp Asp His His Phe Lys Val Ile Leu Pro Tyr Gly Thr Leu Val
225                 230                 235                 240

Ile Asp Gly Val Thr Pro Asn Met Leu Asn Tyr Phe Gly Arg Pro Tyr
                245                 250                 255

Glu Gly Ile Ala Val Phe Asp Gly Lys Lys Ile Thr Val Thr Gly Thr
            260                 265                 270

Leu Trp Asn Gly Asn Lys Ile Ile Asp Glu Arg Leu Ile Thr Pro Asp
```

-continued

```
            275                 280                 285
Gly Ser Met Leu Phe Arg Val Thr Ile Asn Ser Gly Gly Ser Gly Gly
    290                 295                 300
Gly Gly Ser Gly Gly Ser Ser Ser Gly Gly Phe Glu Lys Arg Tyr Ala
305                 310                 315                 320
Ala Ala Met Gln Trp Leu Trp Arg Asp Ala Gly Ile Arg Ala Tyr Tyr
                325                 330                 335
Glu Arg Arg Arg Glu Phe His Leu Leu Asp Ser Ala Val Tyr Tyr Leu
            340                 345                 350
Ser His Leu Glu Arg Ile Thr Glu Glu Gly Tyr Val Pro Thr Ala Gln
            355                 360                 365
Asp Val Leu Arg Ser Arg Met Pro Thr Thr Gly Ile Asn Glu Tyr Cys
    370                 375                 380
Phe Ser Val Gln Lys Thr Asn Leu Arg Ile Val Asp Val Gly Gly Gln
385                 390                 395                 400
Lys Ser Glu Arg Lys Lys Trp Ile His Cys Phe Glu Asn Val Ile Ala
                405                 410                 415
Leu Ile Tyr Leu Ala Ser Leu Ser Glu Tyr Asp Gln Cys Leu Glu Glu
            420                 425                 430
Asn Asn Gln Glu Asn Arg Met Lys Glu Ser Leu Ala Leu Phe Gly Thr
            435                 440                 445
Ile Leu Glu Leu Pro Trp Phe Lys Ser Thr Ser Val Ile Leu Phe Leu
    450                 455                 460
Asn Lys Thr Asp Ile Leu Glu Glu Lys Ile Pro Thr Ser His Leu Ala
465                 470                 475                 480
Thr Tyr Phe Pro Ser Phe Gln Gly Pro Lys Gln Asp Ala Glu Ala Ala
                485                 490                 495
Lys Arg Phe Ile Leu Asp Met Tyr Thr Arg Met Tyr Thr Gly Cys Val
            500                 505                 510
Asp Gly Pro Glu Gly Ser Lys Lys Gly Ala Arg Ser Arg Arg Leu Phe
            515                 520                 525
Ser His Tyr Thr Cys Ala Thr Asp Thr Gln Asn Ile Arg Lys Val Phe
    530                 535                 540
Lys Asp Val Arg Asp Ser Val Leu Ala Arg Tyr Leu Asp Glu Ile Asn
545                 550                 555                 560
Leu Leu
```

```
<210> SEQ ID NO 42
<211> LENGTH: 513
<212> TYPE: PRT
<213> ORGANISM: Homo sapiens
<220> FEATURE:
<223> OTHER INFORMATION: Lg-G\'ce\'b21 (LgBiT-GNB1)

<400> SEQUENCE: 42
```

```
Met Val Phe Thr Leu Glu Asp Phe Val Gly Asp Trp Glu Gln Thr Ala
1               5                   10                  15
Ala Tyr Asn Leu Asp Gln Val Leu Glu Gln Gly Gly Val Ser Ser Leu
                20                  25                  30
Leu Gln Asn Leu Ala Val Ser Val Thr Pro Ile Gln Arg Ile Val Arg
            35                  40                  45
Ser Gly Glu Asn Ala Leu Lys Ile Asp Ile His Val Ile Ile Pro Tyr
    50                  55                  60
Glu Gly Leu Ser Ala Asp Gln Met Ala Gln Ile Glu Glu Val Phe Lys
65                  70                  75                  80
```

```
Val Val Tyr Pro Val Asp Asp His His Phe Lys Val Ile Leu Pro Tyr
            85              90                  95

Gly Thr Leu Val Ile Asp Gly Val Thr Pro Asn Met Leu Asn Tyr Phe
            100             105                 110

Gly Arg Pro Tyr Glu Gly Ile Ala Val Phe Asp Gly Lys Lys Ile Thr
            115             120                 125

Val Thr Gly Thr Leu Trp Asn Gly Asn Lys Ile Ile Asp Glu Arg Leu
    130             135             140

Ile Thr Pro Asp Gly Ser Met Leu Phe Arg Val Thr Ile Asn Ser Gly
145             150             155                 160

Gly Ser Gly Gly Gly Gly Ser Gly Gly Ser Ser Ser Gly Gly Ser Glu
                165             170                 175

Leu Asp Gln Leu Arg Gln Glu Ala Glu Gln Leu Lys Asn Gln Ile Arg
            180             185             190

Asp Ala Arg Lys Ala Cys Ala Asp Ala Thr Leu Ser Gln Ile Thr Asn
            195             200             205

Asn Ile Asp Pro Val Gly Arg Ile Gln Met Arg Thr Arg Arg Thr Leu
    210             215             220

Arg Gly His Leu Ala Lys Ile Tyr Ala Met His Trp Gly Thr Asp Ser
225             230             235                 240

Arg Leu Leu Val Ser Ala Ser Gln Asp Gly Lys Leu Ile Ile Trp Asp
            245             250             255

Ser Tyr Thr Thr Asn Lys Val His Ala Ile Pro Leu Arg Ser Ser Trp
            260             265             270

Val Met Thr Cys Ala Tyr Ala Pro Ser Gly Asn Tyr Val Ala Cys Gly
            275             280             285

Gly Leu Asp Asn Ile Cys Ser Ile Tyr Asn Leu Lys Thr Arg Glu Gly
    290             295             300

Asn Val Arg Val Ser Arg Glu Leu Ala Gly His Thr Gly Tyr Leu Ser
305             310             315                 320

Cys Cys Arg Phe Leu Asp Asp Asn Gln Ile Val Thr Ser Ser Gly Asp
            325             330             335

Thr Thr Cys Ala Leu Trp Asp Ile Glu Thr Gly Gln Gln Thr Thr Thr
            340             345             350

Phe Thr Gly His Thr Gly Asp Val Met Ser Leu Ser Leu Ala Pro Asp
            355             360             365

Thr Arg Leu Phe Val Ser Gly Ala Cys Asp Ala Ser Ala Lys Leu Trp
    370             375             380

Asp Val Arg Glu Gly Met Cys Arg Gln Thr Phe Thr Gly His Glu Ser
385             390             395                 400

Asp Ile Asn Ala Ile Cys Phe Phe Pro Asn Gly Asn Ala Phe Ala Thr
            405             410             415

Gly Ser Asp Asp Ala Thr Cys Arg Leu Phe Asp Leu Arg Ala Asp Gln
            420             425             430

Glu Leu Met Thr Tyr Ser His Asp Asn Ile Ile Cys Gly Ile Thr Ser
            435             440             445

Val Ser Phe Ser Lys Ser Gly Arg Leu Leu Leu Ala Gly Tyr Asp Asp
    450             455             460

Phe Asn Cys Asn Val Trp Asp Ala Leu Lys Ala Asp Arg Ala Gly Val
465             470             475                 480

Leu Ala Gly His Asp Asn Arg Val Ser Cys Leu Gly Val Thr Asp Asp
                485             490                 495
```

Gly Met Ala Val Ala Thr Gly Ser Trp Asp Ser Phe Leu Lys Ile Trp
        500                     505                     510

Asn

<210> SEQ ID NO 43
<211> LENGTH: 244
<212> TYPE: PRT
<213> ORGANISM: Homo sapiens
<220> FEATURE:
<223> OTHER INFORMATION: Lg-G\'ce\'b32 (LgBiT-GNG2)

<400> SEQUENCE: 43

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser Gly
145                 150                 155                 160

Gly Ser Gly Gly Gly Gly Ser Gly Gly Ser Ser Ser Gly Gly Ala Ser
                165                 170                 175

Asn Asn Thr Ala Ser Ile Ala Gln Ala Arg Lys Leu Val Glu Gln Leu
            180                 185                 190

Lys Met Glu Ala Asn Ile Asp Arg Ile Lys Val Ser Lys Ala Ala Ala
        195                 200                 205

Asp Leu Met Ala Tyr Cys Glu Ala His Ala Lys Glu Asp Pro Leu Leu
    210                 215                 220

Thr Pro Val Pro Ala Ser Glu Asn Pro Phe Arg Glu Lys Lys Phe Phe
225                 230                 235                 240

Cys Ala Ile Leu

<210> SEQ ID NO 44
<211> LENGTH: 97
<212> TYPE: PRT
<213> ORGANISM: Homo sapiens
<220> FEATURE:
<223> OTHER INFORMATION: Sm-G\'ce\'b32 (C68S) (SmBiT-GNG2-C68S)

<400> SEQUENCE: 44

Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ala Ser Asn Asn Thr
            20                  25                  30

Ala Ser Ile Ala Gln Ala Arg Lys Leu Val Glu Gln Leu Lys Met Glu

```
                35                  40                  45

Ala Asn Ile Asp Arg Ile Lys Val Ser Lys Ala Ala Ala Asp Leu Met
    50                  55                  60

Ala Tyr Cys Glu Ala His Ala Lys Glu Asp Pro Leu Leu Thr Pro Val
65                  70                  75                  80

Pro Ala Ser Glu Asn Pro Phe Arg Glu Lys Lys Phe Phe Ser Ala Ile
                85                  90                  95

Leu

<210> SEQ ID NO 45
<211> LENGTH: 1242
<212> TYPE: PRT
<213> ORGANISM: Homo sapiens
<220> FEATURE:
<223> OTHER INFORMATION: Sm-PLC\'ce\'b21 (SmBiT-PLCB1)

<400> SEQUENCE: 45

Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ala Gly Ala Gln Pro
                20                  25                  30

Gly Val His Ala Leu Gln Leu Lys Pro Val Cys Val Ser Asp Ser Leu
            35                  40                  45

Lys Lys Gly Thr Lys Phe Val Lys Trp Asp Asp Asp Ser Thr Ile Val
    50                  55                  60

Thr Pro Ile Ile Leu Arg Thr Asp Pro Gln Gly Phe Phe Phe Tyr Trp
65                  70                  75                  80

Thr Asp Gln Asn Lys Glu Thr Glu Leu Leu Asp Leu Ser Leu Val Lys
                85                  90                  95

Asp Ala Arg Cys Gly Arg His Ala Lys Ala Pro Lys Asp Pro Lys Leu
                100                 105                 110

Arg Glu Leu Leu Asp Val Gly Asn Ile Gly Arg Leu Glu Gln Arg Met
            115                 120                 125

Ile Thr Val Val Tyr Gly Pro Asp Leu Val Asn Ile Ser His Leu Asn
    130                 135                 140

Leu Val Ala Phe Gln Glu Glu Val Ala Lys Glu Trp Thr Asn Glu Val
145                 150                 155                 160

Phe Ser Leu Ala Thr Asn Leu Leu Ala Gln Asn Met Ser Arg Asp Ala
                165                 170                 175

Phe Leu Glu Lys Ala Tyr Thr Lys Leu Lys Leu Gln Val Thr Pro Glu
            180                 185                 190

Gly Arg Ile Pro Leu Lys Asn Ile Tyr Arg Leu Phe Ser Ala Asp Arg
            195                 200                 205

Lys Arg Val Glu Thr Ala Leu Glu Ala Cys Ser Leu Pro Ser Ser Arg
    210                 215                 220

Asn Asp Ser Ile Pro Gln Glu Asp Phe Thr Pro Glu Val Tyr Arg Val
225                 230                 235                 240

Phe Leu Asn Asn Leu Cys Pro Arg Pro Glu Ile Asp Asn Ile Phe Ser
                245                 250                 255

Glu Phe Gly Ala Lys Ser Lys Pro Tyr Leu Thr Val Asp Gln Met Met
            260                 265                 270

Asp Phe Ile Asn Leu Lys Gln Arg Asp Pro Arg Leu Asn Glu Ile Leu
            275                 280                 285

Tyr Pro Pro Leu Lys Gln Glu Gln Val Gln Val Leu Ile Glu Lys Tyr
    290                 295                 300
```

```
Glu Pro Asn Asn Ser Leu Ala Arg Lys Gly Gln Ile Ser Val Asp Gly
305             310             315             320

Phe Met Arg Tyr Leu Ser Gly Glu Glu Asn Gly Val Val Ser Pro Glu
                325             330             335

Lys Leu Asp Leu Asn Glu Asp Met Ser Gln Pro Leu Ser His Tyr Phe
        340             345             350

Ile Asn Ser Ser His Asn Thr Tyr Leu Thr Ala Gly Gln Leu Ala Gly
        355             360             365

Asn Ser Ser Val Glu Met Tyr Arg Gln Val Leu Leu Ser Gly Cys Arg
    370             375             380

Cys Val Glu Leu Asp Cys Trp Lys Gly Arg Thr Ala Glu Glu Glu Pro
385             390             395             400

Val Ile Thr His Gly Phe Thr Met Thr Thr Glu Ile Ser Phe Lys Glu
                405             410             415

Val Ile Glu Ala Ile Ala Glu Cys Ala Phe Lys Thr Ser Pro Phe Pro
        420             425             430

Ile Leu Leu Ser Phe Glu Asn His Val Asp Ser Pro Lys Gln Gln Ala
        435             440             445

Lys Met Ala Glu Tyr Cys Arg Leu Ile Phe Gly Asp Ala Leu Leu Met
    450             455             460

Glu Pro Leu Glu Lys Tyr Pro Leu Glu Ser Gly Val Pro Leu Pro Ser
465             470             475             480

Pro Met Asp Leu Met Tyr Lys Ile Leu Val Lys Asn Lys Lys Lys Ser
        485             490             495

His Lys Ser Ser Glu Gly Ser Gly Lys Lys Lys Leu Ser Glu Gln Ala
        500             505             510

Ser Asn Thr Tyr Ser Asp Ser Ser Ser Met Phe Glu Pro Ser Ser Pro
    515             520             525

Gly Ala Gly Glu Ala Asp Thr Glu Ser Asp Asp Asp Asp Asp Asp Asp
    530             535             540

Asp Cys Lys Lys Ser Ser Met Asp Glu Gly Thr Ala Gly Ser Glu Ala
545             550             555             560

Met Ala Thr Glu Glu Met Ser Asn Leu Val Asn Tyr Ile Gln Pro Val
            565             570             575

Lys Phe Glu Ser Phe Glu Ile Ser Lys Lys Arg Asn Lys Ser Phe Glu
        580             585             590

Met Ser Ser Phe Val Glu Thr Lys Gly Leu Glu Gln Leu Thr Lys Ser
        595             600             605

Pro Val Glu Phe Val Glu Tyr Asn Lys Met Gln Leu Ser Arg Ile Tyr
    610             615             620

Pro Lys Gly Thr Arg Val Asp Ser Ser Asn Tyr Met Pro Gln Leu Phe
625             630             635             640

Trp Asn Ala Gly Cys Gln Met Val Ala Leu Asn Phe Gln Thr Met Asp
            645             650             655

Leu Ala Met Gln Ile Asn Met Gly Met Tyr Glu Tyr Asn Gly Lys Ser
        660             665             670

Gly Tyr Arg Leu Lys Pro Glu Phe Met Arg Arg Pro Asp Lys His Phe
    675             680             685

Asp Pro Phe Thr Glu Gly Ile Val Asp Gly Ile Val Ala Asn Thr Leu
    690             695             700

Ser Val Lys Ile Ile Ser Gly Gln Phe Leu Ser Asp Lys Lys Val Gly
705             710             715             720
```

-continued

```
Thr Tyr Val Glu Val Asp Met Phe Gly Leu Pro Val Asp Thr Arg Arg
            725                 730                 735

Lys Ala Phe Lys Thr Lys Thr Ser Gln Gly Asn Ala Val Asn Pro Val
            740                 745                 750

Trp Glu Glu Glu Pro Ile Val Phe Lys Lys Val Val Leu Pro Thr Leu
            755                 760                 765

Ala Cys Leu Arg Ile Ala Val Tyr Glu Glu Gly Gly Lys Phe Ile Gly
        770             775                 780

His Arg Ile Leu Pro Val Gln Ala Ile Arg Pro Gly Tyr His Tyr Ile
785             790                 795                 800

Cys Leu Arg Asn Glu Arg Asn Gln Pro Leu Thr Leu Pro Ala Val Phe
            805                 810                 815

Val Tyr Ile Glu Val Lys Asp Tyr Val Pro Asp Thr Tyr Ala Asp Val
            820                 825                 830

Ile Glu Ala Leu Ser Asn Pro Ile Arg Tyr Val Asn Leu Met Glu Gln
        835                 840                 845

Arg Ala Lys Gln Leu Ala Ala Leu Thr Leu Glu Asp Glu Glu Glu Val
    850                 855                 860

Lys Lys Glu Ala Asp Pro Gly Glu Thr Pro Ser Glu Ala Pro Ser Glu
865                 870                 875                 880

Ala Arg Thr Thr Pro Ala Glu Asn Gly Val Asn His Thr Thr Thr Leu
                885                 890                 895

Thr Pro Lys Pro Pro Ser Gln Ala Leu His Ser Gln Pro Ala Pro Gly
            900                 905                 910

Ser Val Lys Ala Pro Ala Lys Thr Glu Asp Leu Ile Gln Ser Val Leu
            915                 920                 925

Thr Glu Val Glu Ala Gln Thr Ile Glu Glu Leu Lys Gln Gln Lys Ser
    930                 935                 940

Phe Val Lys Leu Gln Lys Lys His Tyr Lys Glu Met Lys Asp Leu Val
945                 950                 955                 960

Lys Arg His His Lys Lys Thr Thr Asp Leu Ile Lys Glu His Thr Thr
                965                 970                 975

Lys Tyr Asn Glu Ile Gln Asn Asp Tyr Leu Arg Arg Arg Ala Ala Leu
            980                 985                 990

Glu Lys Ser Ala Lys Lys Asp Ser Lys Lys Ser Glu Pro Ser Ser
    995                 1000                1005

Pro Asp His Gly Ser Ser Thr Ile Glu Gln Asp Leu Ala Ala Leu Asp
    1010                1015                1020

Ala Glu Met Thr Gln Lys Leu Ile Asp Leu Lys Asp Lys Gln Gln Gln
1025                1030                1035                1040

Gln Leu Leu Asn Leu Arg Gln Glu Gln Tyr Tyr Ser Glu Lys Tyr Gln
                1045                1050                1055

Lys Arg Glu His Ile Lys Leu Leu Ile Gln Lys Leu Thr Asp Val Ala
            1060                1065                1070

Glu Glu Cys Gln Asn Asn Gln Leu Lys Lys Leu Lys Glu Ile Cys Glu
            1075                1080                1085

Lys Glu Lys Lys Glu Leu Lys Lys Lys Met Asp Lys Lys Arg Gln Glu
        1090                1095                1100

Lys Ile Thr Glu Ala Lys Ser Lys Asp Lys Ser Gln Met Glu Glu Glu
1105                1110                1115                1120

Lys Thr Glu Met Ile Arg Ser Tyr Ile Gln Glu Val Val Gln Tyr Ile
                1125                1130                1135

Lys Arg Leu Glu Glu Ala Gln Ser Lys Arg Gln Glu Lys Leu Val Glu
```

-continued

```
                   1140                1145                1150

Lys His Lys Glu Ile Arg Gln Gln Ile Leu Asp Glu Lys Pro Lys Leu
        1155                1160                1165

Gln Val Glu Leu Glu Gln Glu Tyr Gln Asp Lys Phe Lys Arg Leu Pro
    1170                1175                1180

Leu Glu Ile Leu Glu Phe Val Gln Glu Ala Met Lys Gly Lys Ile Ser
1185                1190                1195                1200

Glu Asp Ser Asn His Gly Ser Ala Pro Leu Ser Leu Ser Ser Asp Pro
                1205                1210                1215

Gly Lys Val Asn His Lys Thr Pro Ser Ser Glu Glu Leu Gly Gly Asp
                1220                1225                1230

Ile Pro Gly Lys Glu Phe Asp Thr Pro Leu
        1235                1240

<210> SEQ ID NO 46
<211> LENGTH: 1207
<212> TYPE: PRT
<213> ORGANISM: Homo sapiens
<220> FEATURE:
<223> OTHER INFORMATION: Sm-PLC\'ce\'b22 (SmBiT-PLCB2)

<400> SEQUENCE: 46

Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ser Leu Leu Asn Pro
            20                  25                  30

Val Leu Leu Pro Pro Lys Val Lys Ala Tyr Leu Ser Gln Gly Glu Arg
        35                  40                  45

Phe Ile Lys Trp Asp Asp Glu Thr Thr Val Ala Ser Pro Val Ile Leu
        50                  55                  60

Arg Val Asp Pro Lys Gly Tyr Tyr Leu Tyr Trp Thr Tyr Gln Ser Lys
65                  70                  75                  80

Glu Met Glu Phe Leu Asp Ile Thr Ser Ile Arg Asp Thr Arg Phe Gly
                85                  90                  95

Lys Phe Ala Lys Met Pro Lys Ser Gln Lys Leu Arg Asp Val Phe Asn
            100                 105                 110

Met Asp Phe Pro Asp Asn Ser Phe Leu Leu Lys Thr Leu Thr Val Val
        115                 120                 125

Ser Gly Pro Asp Met Val Asp Leu Thr Phe His Asn Phe Val Ser Tyr
    130                 135                 140

Lys Glu Asn Val Gly Lys Ala Trp Ala Glu Asp Val Leu Ala Leu Val
145                 150                 155                 160

Lys His Pro Leu Thr Ala Asn Ala Ser Arg Ser Thr Phe Leu Asp Lys
            165                 170                 175

Ile Leu Val Lys Leu Lys Met Gln Leu Asn Ser Glu Gly Lys Ile Pro
            180                 185                 190

Val Lys Asn Phe Phe Gln Met Phe Pro Ala Asp Arg Lys Arg Val Glu
        195                 200                 205

Ala Ala Leu Ser Ala Cys His Leu Pro Lys Gly Lys Asn Asp Ala Ile
    210                 215                 220

Asn Pro Glu Asp Phe Pro Glu Pro Val Tyr Lys Ser Phe Leu Met Ser
225                 230                 235                 240

Leu Cys Pro Arg Pro Glu Ile Asp Glu Ile Phe Thr Ser Tyr His Ala
            245                 250                 255

Lys Ala Lys Pro Tyr Met Thr Lys Glu His Leu Thr Lys Phe Ile Asn
```

```
              260                 265                 270
Gln Lys Gln Arg Asp Ser Arg Leu Asn Ser Leu Leu Phe Pro Pro Ala
              275                 280                 285

Arg Pro Asp Gln Val Gln Gly Leu Ile Asp Lys Tyr Glu Pro Ser Gly
              290                 295                 300

Ile Asn Ala Gln Arg Gly Gln Leu Ser Pro Glu Gly Met Val Trp Phe
305                 310                 315                 320

Leu Cys Gly Pro Glu Asn Ser Val Leu Ala Gln Asp Lys Leu Leu Leu
                  325                 330                 335

His His Asp Met Thr Gln Pro Leu Asn His Tyr Phe Ile Asn Ser Ser
              340                 345                 350

His Asn Thr Tyr Leu Thr Ala Gly Gln Phe Ser Gly Leu Ser Ser Ala
              355                 360                 365

Glu Met Tyr Arg Gln Val Leu Leu Ser Gly Cys Arg Cys Val Glu Leu
              370                 375                 380

Asp Cys Trp Lys Gly Lys Pro Pro Asp Glu Glu Pro Ile Ile Thr His
385                 390                 395                 400

Gly Phe Thr Met Thr Thr Asp Ile Phe Phe Lys Glu Ala Ile Glu Ala
                  405                 410                 415

Ile Ala Glu Ser Ala Phe Lys Thr Ser Pro Tyr Pro Ile Ile Leu Ser
                  420                 425                 430

Phe Glu Asn His Val Asp Ser Pro Arg Gln Gln Ala Lys Met Ala Glu
              435                 440                 445

Tyr Cys Arg Thr Ile Phe Gly Asp Met Leu Leu Thr Glu Pro Leu Glu
              450                 455                 460

Lys Phe Pro Leu Lys Pro Gly Val Pro Leu Pro Ser Pro Glu Asp Leu
465                 470                 475                 480

Arg Gly Lys Ile Leu Ile Lys Asn Lys Lys Asn Gln Phe Ser Gly Pro
                  485                 490                 495

Thr Ser Ser Ser Lys Asp Thr Gly Gly Glu Ala Glu Gly Ser Ser Pro
                  500                 505                 510

Pro Ser Ala Pro Ala Val Trp Ala Gly Glu Glu Gly Thr Glu Leu Glu
              515                 520                 525

Glu Glu Glu Val Glu Glu Glu Glu Glu Glu Ser Gly Asn Leu Asp
              530                 535                 540

Glu Glu Glu Ile Lys Lys Met Gln Ser Asp Glu Gly Thr Ala Gly Leu
545                 550                 555                 560

Glu Val Thr Ala Tyr Glu Glu Met Ser Ser Leu Val Asn Tyr Ile Gln
                  565                 570                 575

Pro Thr Lys Phe Val Ser Phe Glu Phe Ser Ala Gln Lys Asn Arg Ser
                  580                 585                 590

Tyr Val Ile Ser Ser Phe Thr Glu Leu Lys Ala Tyr Asp Leu Leu Ser
                  595                 600                 605

Lys Ala Ser Val Gln Phe Val Asp Tyr Asn Lys Arg Gln Met Ser Arg
              610                 615                 620

Ile Tyr Pro Lys Gly Thr Arg Met Asp Ser Ser Asn Tyr Met Pro Gln
625                 630                 635                 640

Met Phe Trp Asn Ala Gly Cys Gln Met Val Ala Leu Asn Phe Gln Thr
                  645                 650                 655

Met Asp Leu Pro Met Gln Gln Asn Met Ala Val Phe Glu Phe Asn Gly
                  660                 665                 670

Gln Ser Gly Tyr Leu Leu Lys His Glu Phe Met Arg Arg Pro Asp Lys
              675                 680                 685
```

-continued

```
Gln Phe Asn Pro Phe Ser Val Asp Arg Ile Asp Val Val Ala Thr
    690             695             700

Thr Leu Ser Ile Thr Val Ile Ser Gly Gln Phe Leu Ser Glu Arg Ser
705             710             715             720

Val Arg Thr Tyr Val Glu Val Glu Leu Phe Gly Leu Pro Gly Asp Pro
            725             730             735

Lys Arg Arg Tyr Arg Thr Lys Leu Ser Pro Ser Thr Asn Ser Ile Asn
        740             745             750

Pro Val Trp Lys Glu Glu Pro Phe Val Phe Glu Lys Ile Leu Met Pro
        755             760             765

Glu Leu Ala Ser Leu Arg Val Ala Val Met Glu Glu Gly Asn Lys Phe
    770             775             780

Leu Gly His Arg Ile Ile Pro Ile Asn Ala Leu Asn Ser Gly Tyr His
785             790             795             800

His Leu Cys Leu His Ser Glu Ser Asn Met Pro Leu Thr Met Pro Ala
            805             810             815

Leu Phe Ile Phe Leu Glu Met Lys Asp Tyr Ile Pro Gly Ala Trp Ala
            820             825             830

Asp Leu Thr Val Ala Leu Ala Asn Pro Ile Lys Phe Phe Ser Ala His
            835             840             845

Asp Thr Lys Ser Val Lys Leu Lys Glu Ala Met Gly Gly Leu Pro Glu
    850             855             860

Lys Pro Phe Pro Leu Ala Ser Pro Val Ala Ser Gln Val Asn Gly Ala
865             870             875             880

Leu Ala Pro Thr Ser Asn Gly Ser Pro Ala Ala Arg Ala Gly Ala Arg
            885             890             895

Glu Glu Ala Met Lys Glu Ala Ala Glu Pro Arg Thr Ala Ser Leu Glu
            900             905             910

Glu Leu Arg Glu Leu Lys Gly Val Val Lys Leu Gln Arg Arg His Glu
            915             920             925

Lys Glu Leu Arg Glu Leu Glu Arg Arg Gly Ala Arg Arg Trp Glu Glu
    930             935             940

Leu Leu Gln Arg Gly Ala Ala Gln Leu Ala Glu Leu Gly Pro Pro Gly
945             950             955             960

Val Gly Gly Val Gly Ala Cys Lys Leu Gly Pro Gly Lys Gly Ser Arg
            965             970             975

Lys Lys Arg Ser Leu Pro Arg Glu Glu Ser Ala Gly Ala Ala Pro Gly
            980             985             990

Glu Gly Pro Glu Gly Val Asp Gly Arg Val Arg Glu Leu Lys Asp Arg
            995             1000            1005

Leu Glu Leu Glu Leu Leu Arg Gln Gly Glu Glu Gln Tyr Glu Cys Val
    1010            1015            1020

Leu Lys Arg Lys Glu Gln His Val Ala Glu Gln Ile Ser Lys Met Met
1025            1030            1035            1040

Glu Leu Ala Arg Glu Lys Gln Ala Ala Glu Leu Lys Ala Leu Lys Glu
            1045            1050            1055

Thr Ser Glu Asn Asp Thr Lys Glu Met Lys Lys Lys Leu Glu Thr Lys
            1060            1065            1070

Arg Leu Glu Arg Ile Gln Gly Met Thr Lys Val Thr Thr Asp Lys Met
        1075            1080            1085

Ala Gln Glu Arg Leu Lys Arg Glu Ile Asn Asn Ser His Ile Gln Glu
    1090            1095            1100
```

```
Val Val Gln Val Ile Lys Gln Met Thr Glu Asn Leu Glu Arg His Gln
1105                1110                1115                1120

Glu Lys Leu Glu Glu Lys Gln Ala Ala Cys Leu Glu Gln Ile Arg Glu
                1125                1130                1135

Met Glu Lys Gln Phe Gln Lys Glu Ala Leu Ala Glu Tyr Glu Ala Arg
                1140                1145                1150

Met Lys Gly Leu Glu Ala Glu Val Lys Glu Ser Val Arg Ala Cys Leu
        1155                1160                1165

Arg Thr Cys Phe Pro Ser Glu Ala Lys Asp Lys Pro Glu Arg Ala Cys
        1170                1175                1180

Glu Cys Pro Pro Glu Leu Cys Glu Gln Asp Pro Leu Ile Ala Lys Ala
1185                1190                1195                1200

Asp Ala Gln Glu Ser Arg Leu
                1205

<210> SEQ ID NO 47
<211> LENGTH: 1260
<212> TYPE: PRT
<213> ORGANISM: Homo sapiens
<220> FEATURE:
<223> OTHER INFORMATION: Sm-PLC\'ce\'b23 (SmBiT-PLCB3)

<400> SEQUENCE: 47

Met Val Thr Gly Tyr Arg Leu Phe Glu Glu Ile Leu Gly Gly Ser Gly
1               5                   10                  15

Gly Gly Gly Ser Gly Gly Ser Ser Ser Gly Gly Ala Gly Ala Gln Pro
                20                  25                  30

Gly Val His Ala Leu Gln Leu Glu Pro Pro Thr Val Val Glu Thr Leu
        35                  40                  45

Arg Arg Gly Ser Lys Phe Ile Lys Trp Asp Glu Glu Thr Ser Ser Arg
    50                  55                  60

Asn Leu Val Thr Leu Arg Val Asp Pro Asn Gly Phe Phe Leu Tyr Trp
65                  70                  75                  80

Thr Gly Pro Asn Met Glu Val Asp Thr Leu Asp Ile Ser Ser Ile Arg
                85                  90                  95

Asp Thr Arg Thr Gly Arg Tyr Ala Arg Leu Pro Lys Asp Pro Lys Ile
                100                 105                 110

Arg Glu Val Leu Gly Phe Gly Gly Pro Asp Ala Arg Leu Glu Glu Lys
            115                 120                 125

Leu Met Thr Val Val Ser Gly Pro Asp Pro Val Asn Thr Val Phe Leu
    130                 135                 140

Asn Phe Met Ala Val Gln Asp Asp Thr Ala Lys Val Trp Ser Glu Glu
145                 150                 155                 160

Leu Phe Lys Leu Ala Met Asn Ile Leu Ala Gln Asn Ala Ser Arg Asn
                165                 170                 175

Thr Phe Leu Arg Lys Ala Tyr Thr Lys Leu Lys Leu Gln Val Asn Gln
                180                 185                 190

Asp Gly Arg Ile Pro Val Lys Asn Ile Leu Lys Met Phe Ser Ala Asp
            195                 200                 205

Lys Lys Arg Val Glu Thr Ala Leu Glu Ser Cys Gly Leu Lys Phe Asn
    210                 215                 220

Arg Ser Glu Ser Ile Arg Pro Asp Glu Phe Ser Leu Glu Ile Phe Glu
225                 230                 235                 240

Arg Phe Leu Asn Lys Leu Cys Leu Arg Pro Asp Ile Asp Lys Ile Leu
                245                 250                 255
```

```
Leu Glu Ile Gly Ala Lys Gly Lys Pro Tyr Leu Thr Leu Glu Gln Leu
            260             265             270

Met Asp Phe Ile Asn Gln Lys Gln Arg Asp Pro Arg Leu Asn Glu Val
            275             280             285

Leu Tyr Pro Pro Leu Arg Pro Ser Gln Ala Arg Leu Leu Ile Glu Lys
            290             295             300

Tyr Glu Pro Asn Gln Gln Phe Leu Glu Arg Asp Gln Met Ser Met Glu
305             310             315             320

Gly Phe Ser Arg Tyr Leu Gly Gly Glu Glu Asn Gly Ile Leu Pro Leu
            325             330             335

Glu Ala Leu Asp Leu Ser Thr Asp Met Thr Gln Pro Leu Ser Ala Tyr
            340             345             350

Phe Ile Asn Ser Ser His Asn Thr Tyr Leu Thr Ala Gly Gln Leu Ala
            355             360             365

Gly Thr Ser Ser Val Glu Met Tyr Arg Gln Ala Leu Leu Trp Gly Cys
            370             375             380

Arg Cys Val Glu Leu Asp Val Trp Lys Gly Arg Pro Pro Glu Glu Glu
385             390             395             400

Pro Phe Ile Thr His Gly Phe Thr Met Thr Thr Glu Val Pro Leu Arg
            405             410             415

Asp Val Leu Glu Ala Ile Ala Glu Thr Ala Phe Lys Thr Ser Pro Tyr
            420             425             430

Pro Val Ile Leu Ser Phe Glu Asn His Val Asp Ser Ala Lys Gln Gln
            435             440             445

Ala Lys Met Ala Glu Tyr Cys Arg Ser Ile Phe Gly Asp Ala Leu Leu
            450             455             460

Ile Glu Pro Leu Asp Lys Tyr Pro Leu Ala Pro Gly Val Pro Leu Pro
465             470             475             480

Ser Pro Gln Asp Leu Met Gly Arg Ile Leu Val Lys Asn Lys Lys Arg
            485             490             495

His Arg Pro Ser Ala Gly Gly Pro Asp Ser Ala Gly Arg Lys Arg Pro
            500             505             510

Leu Glu Gln Ser Asn Ser Ala Leu Ser Glu Ser Ser Ala Ala Thr Glu
            515             520             525

Pro Ser Ser Pro Gln Leu Gly Ser Pro Ser Ser Asp Ser Cys Pro Gly
            530             535             540

Leu Ser Asn Gly Glu Glu Val Gly Leu Glu Lys Pro Ser Leu Glu Pro
545             550             555             560

Gln Lys Ser Leu Gly Asp Glu Gly Leu Asn Arg Gly Pro Tyr Val Leu
            565             570             575

Gly Pro Ala Asp Arg Glu Asp Glu Glu Asp Glu Glu Glu Glu Glu
            580             585             590

Gln Thr Asp Pro Lys Lys Pro Thr Thr Asp Glu Gly Thr Ala Ser Ser
            595             600             605

Glu Val Asn Ala Thr Glu Glu Met Ser Thr Leu Val Asn Tyr Ile Glu
            610             615             620

Pro Val Lys Phe Lys Ser Phe Glu Ala Ala Arg Lys Arg Asn Lys Cys
625             630             635             640

Phe Glu Met Ser Ser Phe Val Glu Thr Lys Ala Met Glu Gln Leu Thr
            645             650             655

Lys Ser Pro Met Glu Phe Val Glu Tyr Asn Lys Gln Gln Leu Ser Arg
            660             665             670

Ile Tyr Pro Lys Gly Thr Arg Val Asp Ser Ser Asn Tyr Met Pro Gln
```

-continued

```
         675              680              685

Leu Phe Trp Asn Val Gly Cys Gln Leu Val Ala Leu Asn Phe Gln Thr
    690              695              700

Leu Asp Val Ala Met Gln Leu Asn Ala Gly Val Phe Glu Tyr Asn Gly
705              710              715              720

Arg Ser Gly Tyr Leu Leu Lys Pro Glu Phe Met Arg Arg Pro Asp Lys
                725              730              735

Ser Phe Asp Pro Phe Thr Glu Val Ile Val Asp Gly Ile Val Ala Asn
            740              745              750

Ala Leu Arg Val Lys Val Ile Ser Gly Gln Phe Leu Ser Asp Arg Lys
            755              760              765

Val Gly Ile Tyr Val Glu Val Asp Met Phe Gly Leu Pro Val Asp Thr
    770              775              780

Arg Arg Lys Tyr Arg Thr Arg Thr Ser Gln Gly Asn Ser Phe Asn Pro
785              790              795              800

Val Trp Asp Glu Glu Pro Phe Asp Phe Pro Lys Val Val Leu Pro Thr
            805              810              815

Leu Ala Ser Leu Arg Ile Ala Ala Phe Glu Glu Gly Gly Lys Phe Val
            820              825              830

Gly His Arg Ile Leu Pro Val Ser Ala Ile Arg Ser Gly Tyr His Tyr
            835              840              845

Val Cys Leu Arg Asn Glu Ala Asn Gln Pro Leu Cys Leu Pro Ala Leu
    850              855              860

Leu Ile Tyr Thr Glu Ala Ser Asp Tyr Ile Pro Asp Asp His Gln Asp
865              870              875              880

Tyr Ala Glu Ala Leu Ile Asn Pro Ile Lys His Val Ser Leu Met Asp
            885              890              895

Gln Arg Ala Arg Gln Leu Ala Ala Leu Ile Gly Glu Ser Glu Ala Gln
            900              905              910

Ala Gly Gln Glu Thr Cys Gln Asp Thr Gln Ser Gln Gln Leu Gly Ser
            915              920              925

Gln Pro Ser Ser Asn Pro Thr Pro Ser Pro Leu Asp Ala Ser Pro Arg
    930              935              940

Arg Pro Pro Gly Pro Thr Thr Ser Pro Ala Ser Thr Ser Leu Ser Ser
945              950              955              960

Pro Gly Gln Arg Asp Asp Leu Ile Ala Ser Ile Leu Ser Glu Val Ala
            965              970              975

Pro Thr Pro Leu Asp Glu Leu Arg Gly His Lys Ala Leu Val Lys Leu
            980              985              990

Arg Ser Arg Gln Glu Arg Asp Leu Arg Glu Leu Arg Lys Lys His Gln
            995              1000              1005

Arg Lys Ala Val Thr Leu Thr Arg Arg Leu Leu Asp Gly Leu Ala Gln
    1010              1015              1020

Ala Gln Ala Glu Gly Arg Cys Arg Leu Arg Pro Gly Ala Leu Gly Gly
1025              1030              1035              1040

Ala Ala Asp Val Glu Asp Thr Lys Glu Gly Glu Asp Glu Ala Lys Arg
            1045              1050              1055

Tyr Gln Glu Phe Gln Asn Arg Gln Val Gln Ser Leu Leu Glu Leu Arg
            1060              1065              1070

Glu Ala Gln Val Asp Ala Glu Ala Gln Arg Arg Leu Glu His Leu Arg
            1075              1080              1085

Gln Ala Leu Gln Arg Leu Arg Glu Val Val Leu Asp Ala Asn Thr Thr
    1090              1095              1100
```

```
Gln Phe Lys Arg Leu Lys Glu Met Asn Glu Arg Glu Lys Lys Glu Leu
1105            1110                1115                1120

Gln Lys Ile Leu Asp Arg Lys Arg His Asn Ser Ile Ser Glu Ala Lys
            1125                1130                1135

Met Arg Asp Lys His Lys Lys Glu Ala Glu Leu Thr Glu Ile Asn Arg
            1140                1145                1150

Arg His Ile Thr Glu Ser Val Asn Ser Ile Arg Arg Leu Glu Glu Ala
            1155                1160                1165

Gln Lys Gln Arg His Asp Arg Leu Val Ala Gly Gln Gln Gln Val Leu
        1170                1175                1180

Gln Gln Leu Ala Glu Glu Glu Pro Lys Leu Leu Ala Gln Leu Ala Gln
1185                1190                1195                1200

Glu Cys Gln Glu Gln Arg Ala Arg Leu Pro Gln Glu Ile Arg Arg Ser
            1205                1210                1215

Leu Leu Gly Glu Met Pro Glu Gly Leu Gly Asp Gly Pro Leu Val Ala
            1220                1225                1230

Cys Ala Ser Asn Gly His Ala Pro Gly Ser Ser Gly His Leu Ser Gly
            1235                1240                1245

Ala Asp Ser Glu Ser Gln Glu Glu Asn Thr Gln Leu
        1250                1255                1260

<210> SEQ ID NO 48
<211> LENGTH: 1220
<212> TYPE: PRT
<213> ORGANISM: Homo sapiens
<220> FEATURE:
<223> OTHER INFORMATION: Sm-PLC\'ce\'b24 (SmBiT-PLCB4)

<400> SEQUENCE: 48

Met Val Thr Gly Tyr Arg Leu Phe Glu Glu Ile Leu Gly Gly Ser Gly
1                5                10                15

Gly Gly Gly Ser Gly Gly Ser Ser Ser Gly Gly Ala Lys Pro Tyr Glu
            20                25                30

Phe Asn Trp Gln Lys Glu Val Pro Ser Phe Leu Gln Glu Gly Ala Val
        35                40                45

Phe Asp Arg Tyr Glu Glu Glu Ser Phe Val Phe Glu Pro Asn Cys Leu
    50                55                60

Phe Lys Val Asp Glu Phe Gly Phe Phe Leu Thr Trp Arg Ser Glu Gly
65                70                75                80

Lys Glu Gly Gln Val Leu Glu Cys Ser Leu Ile Asn Ser Ile Arg Ser
            85                90                95

Gly Ala Ile Pro Lys Asp Pro Lys Ile Leu Ala Ala Leu Glu Ala Val
            100                105                110

Gly Lys Ser Glu Asn Asp Leu Glu Gly Arg Ile Val Cys Val Cys Ser
        115                120                125

Gly Thr Asp Leu Val Asn Ile Ser Phe Thr Tyr Met Val Ala Glu Asn
    130                135                140

Pro Glu Val Thr Lys Gln Trp Val Glu Gly Leu Arg Ser Ile Ile His
145                150                155                160

Asn Phe Arg Ala Asn Asn Val Ser Pro Met Thr Cys Leu Lys Lys His
            165                170                175

Trp Met Lys Leu Ala Phe Met Thr Asn Thr Asn Gly Lys Ile Pro Val
            180                185                190

Arg Ser Ile Thr Arg Thr Phe Ala Ser Gly Lys Thr Glu Lys Val Ile
        195                200                205
```

-continued

```
Phe Gln Ala Leu Lys Glu Leu Gly Leu Pro Ser Gly Lys Asn Asp Glu
    210             215             220

Ile Glu Pro Thr Ala Phe Ser Tyr Glu Lys Phe Tyr Glu Leu Thr Gln
225             230             235             240

Lys Ile Cys Pro Arg Thr Asp Ile Glu Asp Leu Phe Lys Lys Ile Asn
            245             250             255

Gly Asp Lys Thr Asp Tyr Leu Thr Val Asp Gln Leu Val Ser Phe Leu
            260             265             270

Asn Glu His Gln Arg Asp Pro Arg Leu Asn Glu Ile Leu Phe Pro Phe
            275             280             285

Tyr Asp Ala Lys Arg Ala Met Gln Ile Ile Glu Met Tyr Glu Pro Asp
    290             295             300

Glu Asp Leu Lys Lys Lys Gly Leu Ile Ser Ser Asp Gly Phe Cys Arg
305             310             315             320

Tyr Leu Met Ser Asp Glu Asn Ala Pro Val Phe Leu Asp Arg Leu Glu
            325             330             335

Leu Tyr Gln Glu Met Asp His Pro Leu Ala His Tyr Phe Ile Ser Ser
            340             345             350

Ser His Asn Thr Tyr Leu Thr Gly Arg Gln Phe Gly Gly Lys Ser Ser
            355             360             365

Val Glu Met Tyr Arg Gln Val Leu Leu Ala Gly Cys Arg Cys Val Glu
    370             375             380

Leu Asp Cys Trp Asp Gly Lys Gly Glu Asp Gln Glu Pro Ile Ile Thr
385             390             395             400

His Gly Lys Ala Met Cys Thr Asp Ile Leu Phe Lys Asp Val Ile Gln
            405             410             415

Ala Ile Lys Glu Thr Ala Phe Val Thr Ser Glu Tyr Pro Val Ile Leu
            420             425             430

Ser Phe Glu Asn His Cys Ser Lys Tyr Gln Gln Tyr Lys Met Ser Lys
            435             440             445

Tyr Cys Glu Asp Leu Phe Gly Asp Leu Leu Leu Lys Gln Ala Leu Glu
    450             455             460

Ser His Pro Leu Glu Pro Gly Arg Ala Leu Pro Ser Pro Asn Asp Leu
465             470             475             480

Lys Arg Lys Ile Leu Ile Lys Asn Lys Arg Leu Lys Pro Glu Val Glu
            485             490             495

Lys Lys Gln Leu Glu Ala Leu Arg Ser Met Met Glu Ala Gly Glu Ser
            500             505             510

Ala Ser Pro Ala Asn Ile Leu Glu Asp Asp Asn Glu Glu Glu Ile Glu
            515             520             525

Ser Ala Asp Gln Glu Glu Glu Ala His Pro Glu Phe Lys Phe Gly Asn
    530             535             540

Glu Leu Ser Ala Asp Asp Leu Gly His Lys Glu Ala Val Ala Asn Ser
545             550             555             560

Val Lys Lys Gly Leu Val Thr Val Glu Asp Glu Gln Ala Trp Met Ala
            565             570             575

Ser Tyr Lys Tyr Val Gly Ala Thr Thr Asn Ile His Pro Tyr Leu Ser
            580             585             590

Thr Met Ile Asn Tyr Ala Gln Pro Val Lys Phe Gln Gly Phe His Val
            595             600             605

Ala Glu Glu Arg Asn Ile His Tyr Asn Met Ser Ser Phe Asn Glu Ser
    610             615             620
```

```
Val Gly Leu Gly Tyr Leu Lys Thr His Ala Ile Glu Phe Val Asn Tyr
625             630              635             640

Asn Lys Arg Gln Met Ser Arg Ile Tyr Pro Lys Gly Gly Arg Val Asp
                645             650             655

Ser Ser Asn Tyr Met Pro Gln Ile Phe Trp Asn Ala Gly Cys Gln Met
            660             665             670

Val Ser Leu Asn Tyr Gln Thr Pro Asp Leu Ala Met Gln Leu Asn Gln
        675             680             685

Gly Lys Phe Glu Tyr Asn Gly Ser Cys Gly Tyr Leu Leu Lys Pro Asp
        690             695             700

Phe Met Arg Arg Pro Asp Arg Thr Phe Asp Pro Phe Ser Glu Thr Pro
705             710             715             720

Val Asp Gly Val Ile Ala Ala Thr Cys Ser Val Gln Val Ile Ser Gly
                725             730             735

Gln Phe Leu Ser Asp Lys Lys Ile Gly Thr Tyr Val Glu Val Asp Met
            740             745             750

Tyr Gly Leu Pro Thr Asp Thr Ile Arg Lys Glu Phe Arg Thr Arg Met
        755             760             765

Val Met Asn Asn Gly Leu Asn Pro Val Tyr Asn Glu Glu Ser Phe Val
        770             775             780

Phe Arg Lys Val Ile Leu Pro Asp Leu Ala Val Leu Arg Ile Ala Val
785             790             795             800

Tyr Asp Asp Asn Asn Lys Leu Ile Gly Gln Arg Ile Leu Pro Leu Asp
                805             810             815

Gly Leu Gln Ala Gly Tyr Arg His Ile Ser Leu Arg Asn Glu Gly Asn
            820             825             830

Lys Pro Leu Ser Leu Pro Thr Ile Phe Cys Asn Ile Val Leu Lys Thr
            835             840             845

Tyr Val Pro Asp Gly Phe Gly Asp Ile Val Asp Ala Leu Ser Asp Pro
        850             855             860

Lys Lys Phe Leu Ser Ile Thr Glu Lys Arg Ala Asp Gln Met Arg Ala
865             870             875             880

Met Gly Ile Glu Thr Ser Asp Ile Ala Asp Val Pro Ser Asp Thr Ser
                885             890             895

Lys Asn Asp Lys Lys Gly Lys Ala Asn Thr Ala Lys Ala Asn Val Thr
            900             905             910

Pro Gln Ser Ser Ser Glu Leu Arg Pro Thr Thr Thr Ala Ala Leu Ala
        915             920             925

Ser Gly Val Glu Ala Lys Lys Gly Ile Glu Leu Ile Pro Gln Val Arg
        930             935             940

Ile Glu Asp Leu Lys Gln Met Lys Ala Tyr Leu Lys His Leu Lys Lys
945             950             955             960

Gln Gln Lys Glu Leu Asn Ser Leu Lys Lys Lys His Ala Lys Glu His
            965             970             975

Ser Thr Met Gln Lys Leu His Cys Thr Gln Val Asp Lys Ile Val Ala
            980             985             990

Gln Tyr Asp Lys Glu Lys Ser Thr His Glu Lys Ile Leu Glu Lys Ala
        995             1000            1005

Met Lys Lys Lys Gly Gly Ser Asn Cys Leu Glu Met Lys Lys Glu Thr
    1010            1015            1020

Glu Ile Lys Ile Gln Thr Leu Thr Ser Asp His Lys Ser Lys Val Lys
1025            1030            1035            1040

Glu Ile Val Ala Gln His Thr Lys Glu Trp Ser Glu Met Ile Asn Thr
```

-continued

```
                      1045              1050              1055

His Ser Ala Glu Glu Gln Glu Ile Arg Asp Leu His Leu Ser Gln Gln
                1060              1065              1070

Cys Glu Leu Leu Lys Lys Leu Leu Ile Asn Ala His Glu Gln Gln Thr
          1075              1080              1085

Gln Gln Leu Lys Leu Ser His Asp Arg Glu Ser Lys Glu Met Arg Ala
          1090              1095              1100

His Gln Ala Lys Ile Ser Met Glu Asn Ser Lys Ala Ile Ser Gln Asp
1105              1110              1115              1120

Lys Ser Ile Lys Asn Lys Ala Glu Arg Glu Arg Arg Val Arg Glu Leu
                1125              1130              1135

Asn Ser Ser Asn Thr Lys Lys Phe Leu Glu Glu Arg Lys Arg Leu Ala
                1140              1145              1150

Met Lys Gln Ser Lys Glu Met Asp Gln Leu Lys Lys Val Gln Leu Glu
          1155              1160              1165

His Leu Glu Phe Leu Glu Lys Gln Asn Glu Gln Leu Leu Lys Ser Cys
          1170              1175              1180

His Ala Val Ser Gln Thr Gln Gly Glu Gly Asp Ala Ala Asp Gly Glu
1185              1190              1195              1200

Ile Gly Ser Arg Asp Gly Pro Gln Thr Ser Asn Ser Ser Met Lys Leu
                1205              1210              1215

Gln Asn Ala Asn
          1220
```

```
<210> SEQ ID NO 49
<211> LENGTH: 158
<212> TYPE: PRT
<213> ORGANISM: Homo sapiens
<220> FEATURE:
<223> OTHER INFORMATION: LgBiT luciferase fragment

<400> SEQUENCE: 49

Val Phe Thr Leu Glu Asp Phe Val Gly Asp Trp Glu Gln Thr Ala Ala
1               5                   10                  15

Tyr Asn Leu Asp Gln Val Leu Glu Gln Gly Gly Val Ser Ser Leu Leu
                20                  25                  30

Gln Asn Leu Ala Val Ser Val Thr Pro Ile Gln Arg Ile Val Arg Ser
          35                  40                  45

Gly Glu Asn Ala Leu Lys Ile Asp Ile His Val Ile Ile Pro Tyr Glu
          50                  55                  60

Gly Leu Ser Ala Asp Gln Met Ala Gln Ile Glu Glu Val Phe Lys Val
65                  70                  75                  80

Val Tyr Pro Val Asp Asp His His Phe Lys Val Ile Leu Pro Tyr Gly
                85                  90                  95

Thr Leu Val Ile Asp Gly Val Thr Pro Asn Met Leu Asn Tyr Phe Gly
                100                 105                 110

Arg Pro Tyr Glu Gly Ile Ala Val Phe Asp Gly Lys Lys Ile Thr Val
          115                 120                 125

Thr Gly Thr Leu Trp Asn Gly Asn Lys Ile Ile Asp Glu Arg Leu Ile
          130                 135                 140

Thr Pro Asp Gly Ser Met Leu Phe Arg Val Thr Ile Asn Ser
145                 150                 155
```

```
<210> SEQ ID NO 50
<211> LENGTH: 12
<212> TYPE: PRT
```

-continued

<213> ORGANISM: Homo sapiens

<400> SEQUENCE: 50

Met Val Thr Gly Tyr Arg Leu Phe Glu Glu Ile Leu
1               5               10

<210> SEQ ID NO 51
<211> LENGTH: 15
<212> TYPE: PRT
<213> ORGANISM: Homo sapiens

<400> SEQUENCE: 51

Gly Gly Ser Gly Gly Gly Gly Ser Gly Gly Ser Ser Ser Gly Gly
1               5               10                  15

<210> SEQ ID NO 52
<211> LENGTH: 8
<212> TYPE: PRT
<213> ORGANISM: Homo sapiens

<400> SEQUENCE: 52

Asp Tyr Lys Asp Asp Asp Asp Lys
1               5

<210> SEQ ID NO 53
<211> LENGTH: 14
<212> TYPE: PRT
<213> ORGANISM: Homo sapiens
<220> FEATURE:
<223> OTHER INFORMATION: Flag epitope DREADD without linker GS / GSG

<400> SEQUENCE: 53

Arg Thr Ala Lys Gln Asn Pro Leu Thr Glu Lys Ser Gly Val
1               5               10

<210> SEQ ID NO 54
<211> LENGTH: 9
<212> TYPE: PRT
<213> ORGANISM: Homo sapiens

<400> SEQUENCE: 54

Gln Ser Met Gly Leu Ser Ala Ala Gln
1               5

<210> SEQ ID NO 55
<211> LENGTH: 367
<212> TYPE: PRT
<213> ORGANISM: Homo sapiens
<220> FEATURE:
<223> OTHER INFORMATION: Lg-RhoA (LgBiT-RHOA)

<400> SEQUENCE: 55

Met Val Phe Thr Leu Glu Asp Phe Val Gly Asp Trp Glu Gln Thr Ala
1               5               10                  15

Ala Tyr Asn Leu Asp Gln Val Leu Glu Gln Gly Gly Val Ser Ser Leu
                20                  25                  30

Leu Gln Asn Leu Ala Val Ser Val Thr Pro Ile Gln Arg Ile Val Arg
            35                  40                  45

Ser Gly Glu Asn Ala Leu Lys Ile Asp Ile His Val Ile Ile Pro Tyr
        50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr

-continued

```
                    85                    90                    95
Gly Thr Leu Val Ile Asp Gly Val Thr Pro Asn Met Leu Asn Tyr Phe
            100                   105                   110
Gly Arg Pro Tyr Glu Gly Ile Ala Val Phe Asp Gly Lys Lys Ile Thr
            115                   120                   125
Val Thr Gly Thr Leu Trp Asn Gly Asn Lys Ile Ile Asp Glu Arg Leu
            130                   135                   140
Ile Thr Pro Asp Gly Ser Met Leu Phe Arg Val Thr Ile Asn Ser Gly
145                   150                   155                   160
Gly Ser Gly Gly Gly Gly Ser Gly Gly Ser Ser Ser Gly Gly Thr Ala
                    165                   170                   175
Ala Ile Arg Lys Lys Leu Val Ile Val Gly Asp Gly Ala Cys Gly Lys
            180                   185                   190
Thr Cys Leu Leu Ile Val Phe Ser Lys Asp Gln Phe Pro Glu Val Tyr
            195                   200                   205
Val Pro Thr Val Phe Glu Asn Tyr Val Ala Asp Ile Glu Val Asp Gly
            210                   215                   220
Lys Gln Val Glu Leu Ala Leu Trp Asp Thr Ala Gly Gln Glu Asp Tyr
225                   230                   235                   240
Asp Arg Leu Arg Pro Leu Ser Tyr Pro Asp Thr Asp Val Ile Leu Met
                    245                   250                   255
Cys Phe Ser Ile Asp Ser Pro Asp Ser Leu Glu Asn Ile Pro Glu Lys
                    260                   265                   270
Trp Thr Pro Glu Val Lys His Phe Cys Pro Asn Val Pro Ile Ile Leu
                    275                   280                   285
Val Gly Asn Lys Lys Asp Leu Arg Asn Asp Glu His Thr Arg Arg Glu
            290                   295                   300
Leu Ala Lys Met Lys Gln Glu Pro Val Lys Pro Glu Glu Gly Arg Asp
305                   310                   315                   320
Met Ala Asn Arg Ile Gly Ala Phe Gly Tyr Met Glu Cys Ser Ala Lys
                    325                   330                   335
Thr Lys Asp Gly Val Arg Glu Val Phe Glu Met Ala Thr Arg Ala Ala
            340                   345                   350
Leu Gln Ala Arg Arg Gly Lys Lys Lys Ser Gly Cys Leu Val Leu
            355                   360                   365
```

```
<210> SEQ ID NO 56
<211> LENGTH: 127
<212> TYPE: PRT
<213> ORGANISM: Homo sapiens
<220> FEATURE:
<223> OTHER INFORMATION: Sm-PKN1 (SmBiT-PKN1-GBD)

<400> SEQUENCE: 56

Met Val Thr Gly Tyr Arg Leu Phe Glu Glu Ile Leu Gly Gly Ser Gly
1                   5                     10                    15
Gly Gly Gly Ser Gly Gly Ser Ser Gly Gly Glu Ser Glu Pro Arg
            20                    25                    30
Ser Trp Ser Leu Leu Glu Gln Leu Gly Leu Ala Gly Ala Asp Leu Ala
            35                    40                    45
Ala Pro Gly Val Gln Gln Gln Leu Glu Leu Glu Arg Glu Arg Leu Arg
            50                    55                    60
Arg Glu Ile Arg Lys Glu Leu Lys Leu Lys Glu Gly Ala Glu Asn Leu
65                    70                    75                    80
Arg Arg Ala Thr Thr Asp Leu Gly Arg Ser Leu Gly Pro Val Glu Leu
```

```
                    85               90              95
Leu Leu Arg Gly Ser Ser Arg Arg Leu Asp Leu Leu His Gln Gln Leu
            100             105             110

Gln Glu Leu His Ala His Val Val Leu Pro Asp Pro Ala Ala Thr
        115             120             125

<210> SEQ ID NO 57
<211> LENGTH: 581
<212> TYPE: PRT
<213> ORGANISM: Homo sapiens
<220> FEATURE:
<223> OTHER INFORMATION: Lg-IP3R2-Sm (LgBiT-ITPR2-IBC-SmBiT)

<400> SEQUENCE: 57

Met Val Phe Thr Leu Glu Asp Phe Val Gly Asp Trp Glu Gln Thr Ala
1               5               10              15

Ala Tyr Asn Leu Asp Gln Val Leu Glu Gln Gly Gly Val Ser Ser Leu
            20              25              30

Leu Gln Asn Leu Ala Val Ser Val Thr Pro Ile Gln Arg Ile Val Arg
        35              40              45

Ser Gly Glu Asn Ala Leu Lys Ile Asp Ile His Val Ile Ile Pro Tyr
    50              55              60

Glu Gly Leu Ser Ala Asp Gln Met Ala Gln Ile Glu Glu Val Phe Lys
65              70              75              80

Val Val Tyr Pro Val Asp Asp His His Phe Lys Val Ile Leu Pro Tyr
                85              90              95

Gly Thr Leu Val Ile Asp Gly Val Thr Pro Asn Met Leu Asn Tyr Phe
            100             105             110

Gly Arg Pro Tyr Glu Gly Ile Ala Val Phe Asp Gly Lys Lys Ile Thr
        115             120             125

Val Thr Gly Thr Leu Trp Asn Gly Asn Lys Ile Ile Asp Glu Arg Leu
    130             135             140

Ile Thr Pro Asp Gly Ser Met Leu Phe Arg Val Thr Ile Asn Ser Gly
145             150             155             160

Gly Ser Gly Gly Gly Gly Ser Gly Gly Ser Ser Ser Gly Gly Thr Lys
            165             170             175

Tyr Ser Ser Tyr Arg Glu Asp Val Leu Lys Gly Gly Asp Val Val Arg
        180             185             190

Leu Phe His Ala Glu Gln Glu Lys Phe Leu Thr Cys Asp Glu Tyr Glu
        195             200             205

Lys Lys Gln His Ile Phe Leu Arg Thr Thr Leu Arg Gln Ser Ala Thr
    210             215             220

Ser Ala Thr Ser Ser Lys Ala Leu Trp Glu Ile Glu Val Val His His
225             230             235             240

Asp Pro Cys Arg Gly Gly Ala Gly Gln Trp Asn Ser Leu Phe Arg Phe
            245             250             255

Lys His Leu Ala Thr Gly Asn Tyr Leu Ala Ala Glu Leu Asn Pro Asp
        260             265             270

Tyr Arg Asp Ala Gln Asn Glu Gly Lys Asn Val Arg Asp Gly Val Pro
        275             280             285

Pro Thr Ser Lys Lys Lys Arg Gln Ala Gly Glu Lys Ile Met Tyr Thr
    290             295             300

Leu Val Ser Val Pro His Gly Asn Asp Ile Ala Ser Leu Phe Glu Leu
305             310             315             320

Asp Ala Thr Thr Leu Gln Arg Ala Asp Cys Leu Val Pro Arg Asn Ser
```

```
                    325                 330                 335
Tyr Val Arg Leu Arg His Leu Cys Thr Asn Thr Trp Val Thr Ser Thr
            340                 345                 350
Ser Ile Pro Ile Asp Thr Asp Glu Glu Arg Pro Val Met Leu Lys Ile
                355                 360                 365
Gly Thr Cys Gln Thr Lys Glu Asp Lys Glu Ala Phe Ala Ile Val Ser
            370                 375                 380
Val Pro Leu Ser Glu Val Arg Asp Leu Asp Phe Ala Asn Asp Ala Asn
385                 390                 395                 400
Lys Val Leu Ala Thr Thr Val Lys Lys Leu Glu Asn Gly Thr Ile Thr
                405                 410                 415
Gln Asn Glu Arg Arg Phe Val Thr Lys Leu Leu Glu Asp Leu Ile Phe
            420                 425                 430
Phe Val Ala Asp Val Pro Asn Asn Gly Gln Glu Val Leu Asp Val Val
            435                 440                 445
Ile Thr Lys Pro Asn Arg Glu Arg Gln Lys Leu Met Arg Glu Gln Asn
        450                 455                 460
Ile Leu Ala Gln Val Phe Gly Ile Leu Lys Ala Pro Phe Lys Glu Lys
465                 470                 475                 480
Ala Gly Glu Gly Ser Met Leu Arg Leu Glu Asp Leu Gly Asp Gln Arg
                485                 490                 495
Tyr Ala Pro Tyr Lys Tyr Met Leu Arg Leu Cys Tyr Arg Val Leu Arg
            500                 505                 510
His Ser Gln Gln Asp Tyr Arg Lys Asn Gln Glu Tyr Ile Ala Lys Asn
            515                 520                 525
Phe Cys Val Met Gln Ser Gln Ile Gly Tyr Asp Ile Leu Ala Glu Asp
        530                 535                 540
Thr Ile Thr Ala Leu Leu His Asn Asn Arg Lys Gly Gly Ser Gly Gly
545                 550                 555                 560
Gly Gly Ser Gly Gly Ser Ser Ser Gly Gly Val Thr Gly Tyr Arg Leu
            565                 570                 575
Phe Glu Glu Ile Leu
            580
```

<210> SEQ ID NO 58
<211> LENGTH: 352
<212> TYPE: PRT
<213> ORGANISM: Homo sapiens
<220> FEATURE:
<223> OTHER INFORMATION: G\'ce\'b1q (\'e2\u710 \'88\u8224 \'86C)

<400> SEQUENCE: 58

```
Met Thr Leu Glu Ser Ile Met Ala Cys Cys Leu Ser Glu Glu Ala Lys
1               5                   10                  15
Glu Ala Arg Arg Ile Asn Asp Glu Ile Glu Arg Gln Leu Arg Arg Asp
            20                  25                  30
Lys Arg Asp Ala Arg Arg Glu Leu Lys Leu Leu Leu Leu Gly Thr Gly
        35                  40                  45
Glu Ser Gly Lys Ser Thr Phe Ile Lys Gln Met Arg Ile Ile His Gly
        50                  55                  60
Ser Gly Tyr Ser Asp Glu Asp Lys Arg Gly Phe Thr Lys Leu Val Tyr
65                  70                  75                  80
Gln Asn Ile Phe Thr Ala Met Gln Ala Met Ile Arg Ala Met Asp Thr
                85                  90                  95
Leu Lys Ile Pro Tyr Lys Tyr Glu His Asn Lys Ala His Ala Gln Leu
```

-continued

```
                100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
        130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
                195                 200                 205

Gln Arg Ser Glu Arg Arg Lys Trp Ile His Cys Phe Glu Asn Val Thr
        210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
                275                 280                 285

Val Asp Tyr Phe Pro Glu Tyr Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350
```

```
<210> SEQ ID NO 59
<211> LENGTH: 359
<212> TYPE: PRT
<213> ORGANISM: Homo sapiens
<220> FEATURE:
<223> OTHER INFORMATION: G\'ce\'b1q/s

<400> SEQUENCE: 59
```

```
Met Thr Leu Glu Ser Ile Met Ala Cys Cys Leu Ser Glu Glu Ala Lys
1                   5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Gly Thr Gly
        35                  40                  45

Glu Ser Gly Lys Ser Thr Phe Ile Lys Gln Met Arg Ile Ile His Gly
        50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Glu Asn Pro Tyr
```

```
                    115                     120                     125

Val Asp Ala Ile Lys Ser Leu Trp Asn Asp Pro Gly Ile Gln Glu Cys
    130                     135                     140

Tyr Asp Arg Arg Arg Glu Tyr Gln Leu Ser Asp Ser Thr Lys Tyr Tyr
145                     150                     155                     160

Leu Asn Asp Leu Asp Arg Val Ala Asp Pro Ala Tyr Leu Pro Thr Gln
                    165                     170                     175

Gln Asp Val Leu Arg Val Arg Val Pro Thr Thr Gly Ile Ile Glu Tyr
                    180                     185                     190

Pro Phe Asp Leu Gln Ser Val Ile Phe Arg Met Val Asp Val Gly Gly
                    195                     200                     205

Gln Arg Ser Glu Arg Arg Lys Trp Ile His Cys Phe Glu Asn Val Thr
    210                     215                     220

Ser Ile Met Phe Leu Val Ala Leu Ser Glu Tyr Asp Gln Val Leu Val
225                     230                     235                     240

Glu Ser Asp Asn Glu Asn Arg Met Glu Glu Ser Lys Ala Leu Phe Arg
                    245                     250                     255

Thr Ile Ile Thr Tyr Pro Trp Phe Gln Asn Ser Ser Val Ile Leu Phe
                    260                     265                     270

Leu Asn Lys Lys Asp Leu Leu Glu Glu Lys Ile Met Tyr Ser His Leu
                    275                     280                     285

Val Asp Tyr Phe Pro Glu Tyr Asp Gly Pro Gln Arg Asp Ala Gln Ala
    290                     295                     300

Ala Arg Glu Phe Ile Leu Lys Met Phe Val Asp Leu Asn Pro Asp Ser
305                     310                     315                     320

Asp Lys Ile Ile Tyr Ser His Phe Thr Cys Ala Thr Asp Thr Glu Asn
                    325                     330                     335

Ile Arg Phe Val Phe Ala Ala Val Lys Asp Thr Ile Leu Gln Leu Asn
                    340                     345                     350

Leu Arg Gln Tyr Glu Leu Leu
        355

<210> SEQ ID NO 60
<211> LENGTH: 359
<212> TYPE: PRT
<213> ORGANISM: Homo sapiens
<220> FEATURE:
<223> OTHER INFORMATION: G\'ce\'blq/olf

<400> SEQUENCE: 60

Met Thr Leu Glu Ser Ile Met Ala Cys Cys Leu Ser Glu Glu Ala Lys
1                   5                       10                      15

Glu Ala Arg Arg Ile Asn Asp Glu Ile Glu Arg Gln Leu Arg Arg Asp
                    20                      25                      30

Lys Arg Asp Ala Arg Arg Glu Leu Lys Leu Leu Leu Gly Thr Gly
            35                      40                      45

Glu Ser Gly Lys Ser Thr Phe Ile Lys Gln Met Arg Ile Ile His Gly
        50                      55                      60

Ser Gly Tyr Ser Asp Glu Asp Lys Arg Gly Phe Thr Lys Leu Val Tyr
65                      70                      75                      80

Gln Asn Ile Phe Thr Ala Met Gln Ala Met Ile Arg Ala Met Asp Thr
                    85                      90                      95

Leu Lys Ile Pro Tyr Lys Tyr Glu His Asn Lys Ala His Ala Gln Leu
                    100                     105                     110

Val Arg Glu Val Asp Val Glu Lys Val Ser Ala Phe Glu Asn Pro Tyr
```

-continued

```
            115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
                195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
    275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Gln Tyr Glu Leu Leu
        355

<210> SEQ ID NO 61
<211> LENGTH: 359
<212> TYPE: PRT
<213> ORGANISM: Homo sapiens
<220> FEATURE:
<223> OTHER INFORMATION: G\'ce\'b1q/i1

<400> SEQUENCE: 61

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Glu Asn Pro Tyr
```

```
                115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
                195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
    275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Asp Cys Gly Leu Phe
          355

<210> SEQ ID NO 62
<211> LENGTH: 359
<212> TYPE: PRT
<213> ORGANISM: Homo sapiens
<220> FEATURE:
<223> OTHER INFORMATION: G\'ce\'b1q/i3

<400> SEQUENCE: 62

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
          20                  25                  30

Lys Arg Asp Ala Arg Arg Glu Leu Lys Leu Leu Leu Gly Thr Gly
          35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
          100                 105                 110

Val Arg Glu Val Asp Val Glu Lys Val Ser Ala Phe Glu Asn Pro Tyr
```

-continued

```
                115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
                195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
                275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Cys Gly Leu Tyr
        355
```

```
<210> SEQ ID NO 63
<211> LENGTH: 359
<212> TYPE: PRT
<213> ORGANISM: Homo sapiens
<220> FEATURE:
<223> OTHER INFORMATION: G\'ce\'b1q/o

<400> SEQUENCE: 63

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
```

-continued

```
        115              120              125
Val Asp Ala Ile Lys Ser Leu Trp Asn Asp Pro Gly Ile Gln Glu Cys
    130              135              140

Tyr Asp Arg Arg Arg Glu Tyr Gln Leu Ser Asp Ser Thr Lys Tyr Tyr
145              150              155              160

Leu Asn Asp Leu Asp Arg Val Ala Asp Pro Ala Tyr Leu Pro Thr Gln
             165              170              175

Gln Asp Val Leu Arg Val Arg Val Pro Thr Thr Gly Ile Ile Glu Tyr
             180              185              190

Pro Phe Asp Leu Gln Ser Val Ile Phe Arg Met Val Asp Val Gly Gly
             195              200              205

Gln Arg Ser Glu Arg Arg Lys Trp Ile His Cys Phe Glu Asn Val Thr
    210              215              220

Ser Ile Met Phe Leu Val Ala Leu Ser Glu Tyr Asp Gln Val Leu Val
225              230              235              240

Glu Ser Asp Asn Glu Asn Arg Met Glu Glu Ser Lys Ala Leu Phe Arg
             245              250              255

Thr Ile Ile Thr Tyr Pro Trp Phe Gln Asn Ser Ser Val Ile Leu Phe
             260              265              270

Leu Asn Lys Lys Asp Leu Leu Glu Glu Lys Ile Met Tyr Ser His Leu
    275              280              285

Val Asp Tyr Phe Pro Glu Tyr Asp Gly Pro Gln Arg Asp Ala Gln Ala
    290              295              300

Ala Arg Glu Phe Ile Leu Lys Met Phe Val Asp Leu Asn Pro Asp Ser
305              310              315              320

Asp Lys Ile Ile Tyr Ser His Phe Thr Cys Ala Thr Asp Thr Glu Asn
             325              330              335

Ile Arg Phe Val Phe Ala Ala Val Lys Asp Thr Ile Leu Gln Leu Asn
             340              345              350

Leu Arg Gly Cys Gly Leu Tyr
    355
```

```
<210> SEQ ID NO 64
<211> LENGTH: 359
<212> TYPE: PRT
<213> ORGANISM: Homo sapiens
<220> FEATURE:
<223> OTHER INFORMATION: G\'ce\'b1q/z

<400> SEQUENCE: 64

Met Thr Leu Glu Ser Ile Met Ala Cys Cys Leu Ser Glu Glu Ala Lys
1               5               10               15

Glu Ala Arg Arg Ile Asn Asp Glu Ile Glu Arg Gln Leu Arg Arg Asp
             20               25               30

Lys Arg Asp Ala Arg Arg Glu Leu Lys Leu Leu Leu Gly Thr Gly
             35               40               45

Glu Ser Gly Lys Ser Thr Phe Ile Lys Gln Met Arg Ile Ile His Gly
    50               55               60

Ser Gly Tyr Ser Asp Glu Asp Lys Arg Gly Phe Thr Lys Leu Val Tyr
65               70               75               80

Gln Asn Ile Phe Thr Ala Met Gln Ala Met Ile Arg Ala Met Asp Thr
             85               90               95

Leu Lys Ile Pro Tyr Lys Tyr Glu His Asn Lys Ala His Ala Gln Leu
             100              105              110

Val Arg Glu Val Asp Val Glu Lys Val Ser Ala Phe Glu Asn Pro Tyr
```

-continued

```
        115              120              125

Val Asp Ala Ile Lys Ser Leu Trp Asn Asp Pro Gly Ile Gln Glu Cys
    130              135              140

Tyr Asp Arg Arg Arg Glu Tyr Gln Leu Ser Asp Ser Thr Lys Tyr Tyr
145              150              155              160

Leu Asn Asp Leu Asp Arg Val Ala Asp Pro Ala Tyr Leu Pro Thr Gln
                165              170              175

Gln Asp Val Leu Arg Val Arg Val Pro Thr Thr Gly Ile Ile Glu Tyr
            180              185              190

Pro Phe Asp Leu Gln Ser Val Ile Phe Arg Met Val Asp Val Gly Gly
            195              200              205

Gln Arg Ser Glu Arg Arg Lys Trp Ile His Cys Phe Glu Asn Val Thr
    210              215              220

Ser Ile Met Phe Leu Val Ala Leu Ser Glu Tyr Asp Gln Val Leu Val
225              230              235              240

Glu Ser Asp Asn Glu Asn Arg Met Glu Glu Ser Lys Ala Leu Phe Arg
            245              250              255

Thr Ile Ile Thr Tyr Pro Trp Phe Gln Asn Ser Ser Val Ile Leu Phe
            260              265              270

Leu Asn Lys Lys Asp Leu Leu Glu Glu Lys Ile Met Tyr Ser His Leu
    275              280              285

Val Asp Tyr Phe Pro Glu Tyr Asp Gly Pro Gln Arg Asp Ala Gln Ala
    290              295              300

Ala Arg Glu Phe Ile Leu Lys Met Phe Val Asp Leu Asn Pro Asp Ser
305              310              315              320

Asp Lys Ile Ile Tyr Ser His Phe Thr Cys Ala Thr Asp Thr Glu Asn
            325              330              335

Ile Arg Phe Val Phe Ala Ala Val Lys Asp Thr Ile Leu Gln Leu Asn
            340              345              350

Leu Lys Tyr Ile Gly Leu Cys
        355
```

```
<210> SEQ ID NO 65
<211> LENGTH: 359
<212> TYPE: PRT
<213> ORGANISM: Homo sapiens
<220> FEATURE:
<223> OTHER INFORMATION: G\'ce\'b1q

<400> SEQUENCE: 65

Met Thr Leu Glu Ser Ile Met Ala Cys Cys Leu Ser Glu Glu Ala Lys
1               5               10               15

Glu Ala Arg Arg Ile Asn Asp Glu Ile Glu Arg Gln Leu Arg Arg Asp
            20               25               30

Lys Arg Asp Ala Arg Arg Glu Leu Lys Leu Leu Leu Gly Thr Gly
        35               40               45

Glu Ser Gly Lys Ser Thr Phe Ile Lys Gln Met Arg Ile Ile His Gly
    50               55               60

Ser Gly Tyr Ser Asp Glu Asp Lys Arg Gly Phe Thr Lys Leu Val Tyr
65               70               75               80

Gln Asn Ile Phe Thr Ala Met Gln Ala Met Ile Arg Ala Met Asp Thr
            85               90               95

Leu Lys Ile Pro Tyr Lys Tyr Glu His Asn Lys Ala His Ala Gln Leu
            100              105              110

Val Arg Glu Val Asp Val Glu Lys Val Ser Ala Phe Glu Asn Pro Tyr
```

-continued

```
                115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
                195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
    275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
        355
```

```
<210> SEQ ID NO 66
<211> LENGTH: 359
<212> TYPE: PRT
<213> ORGANISM: Homo sapiens
<220> FEATURE:
<223> OTHER INFORMATION: G\'ce\'b1q/14

<400> SEQUENCE: 66

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Glu Asn Pro Tyr
```

-continued

```
              115                   120                   125

Val Asp Ala Ile Lys Ser Leu Trp Asn Asp Pro Gly Ile Gln Glu Cys
    130                   135                   140

Tyr Asp Arg Arg Arg Glu Tyr Gln Leu Ser Asp Ser Thr Lys Tyr Tyr
145                   150                   155                   160

Leu Asn Asp Leu Asp Arg Val Ala Asp Pro Ala Tyr Leu Pro Thr Gln
                    165                   170                   175

Gln Asp Val Leu Arg Val Arg Val Pro Thr Thr Gly Ile Ile Glu Tyr
                180                   185                   190

Pro Phe Asp Leu Gln Ser Val Ile Phe Arg Met Val Asp Val Gly Gly
                195                   200                   205

Gln Arg Ser Glu Arg Arg Lys Trp Ile His Cys Phe Glu Asn Val Thr
    210                   215                   220

Ser Ile Met Phe Leu Val Ala Leu Ser Glu Tyr Asp Gln Val Leu Val
225                   230                   235                   240

Glu Ser Asp Asn Glu Asn Arg Met Glu Glu Ser Lys Ala Leu Phe Arg
                    245                   250                   255

Thr Ile Ile Thr Tyr Pro Trp Phe Gln Asn Ser Ser Val Ile Leu Phe
                260                   265                   270

Leu Asn Lys Lys Asp Leu Leu Glu Glu Lys Ile Met Tyr Ser His Leu
                275                   280                   285

Val Asp Tyr Phe Pro Glu Tyr Asp Gly Pro Gln Arg Asp Ala Gln Ala
    290                   295                   300

Ala Arg Glu Phe Ile Leu Lys Met Phe Val Asp Leu Asn Pro Asp Ser
305                   310                   315                   320

Asp Lys Ile Ile Tyr Ser His Phe Thr Cys Ala Thr Asp Thr Glu Asn
                    325                   330                   335

Ile Arg Phe Val Phe Ala Ala Val Lys Asp Thr Ile Leu Gln Leu Asn
                340                   345                   350

Leu Arg Glu Phe Asn Leu Val
        355
```

```
<210> SEQ ID NO 67
<211> LENGTH: 359
<212> TYPE: PRT
<213> ORGANISM: Homo sapiens
<220> FEATURE:
<223> OTHER INFORMATION: G\'ce\'b1q/16

<400> SEQUENCE: 67

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Leu Gly Thr Gly
            35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
```

```
            115              120              125

Val Asp Ala Ile Lys Ser Leu Trp Asn Asp Pro Gly Ile Gln Glu Cys
    130              135              140

Tyr Asp Arg Arg Arg Glu Tyr Gln Leu Ser Asp Ser Thr Lys Tyr Tyr
145              150              155              160

Leu Asn Asp Leu Asp Arg Val Ala Asp Pro Ala Tyr Leu Pro Thr Gln
                 165              170              175

Gln Asp Val Leu Arg Val Arg Val Pro Thr Thr Gly Ile Ile Glu Tyr
             180              185              190

Pro Phe Asp Leu Gln Ser Val Ile Phe Arg Met Val Asp Val Gly Gly
             195              200              205

Gln Arg Ser Glu Arg Arg Lys Trp Ile His Cys Phe Glu Asn Val Thr
    210              215              220

Ser Ile Met Phe Leu Val Ala Leu Ser Glu Tyr Asp Gln Val Leu Val
225              230              235              240

Glu Ser Asp Asn Glu Asn Arg Met Glu Glu Ser Lys Ala Leu Phe Arg
             245              250              255

Thr Ile Ile Thr Tyr Pro Trp Phe Gln Asn Ser Ser Val Ile Leu Phe
             260              265              270

Leu Asn Lys Lys Asp Leu Leu Glu Glu Lys Ile Met Tyr Ser His Leu
             275              280              285

Val Asp Tyr Phe Pro Glu Tyr Asp Gly Pro Gln Arg Asp Ala Gln Ala
    290              295              300

Ala Arg Glu Phe Ile Leu Lys Met Phe Val Asp Leu Asn Pro Asp Ser
305              310              315              320

Asp Lys Ile Ile Tyr Ser His Phe Thr Cys Ala Thr Asp Thr Glu Asn
                 325              330              335

Ile Arg Phe Val Phe Ala Ala Val Lys Asp Thr Ile Leu Gln Leu Asn
             340              345              350

Leu Asp Glu Ile Asn Leu Leu
         355
```

```
<210> SEQ ID NO 68
<211> LENGTH: 359
<212> TYPE: PRT
<213> ORGANISM: Homo sapiens
<220> FEATURE:
<223> OTHER INFORMATION: G\'ce\'b1q/12

<400> SEQUENCE: 68

Met Thr Leu Glu Ser Ile Met Ala Cys Cys Leu Ser Glu Glu Ala Lys
1               5               10              15

Glu Ala Arg Arg Ile Asn Asp Glu Ile Glu Arg Gln Leu Arg Arg Asp
             20              25              30

Lys Arg Asp Ala Arg Arg Glu Leu Lys Leu Leu Leu Leu Gly Thr Gly
             35              40              45

Glu Ser Gly Lys Ser Thr Phe Ile Lys Gln Met Arg Ile Ile His Gly
    50              55              60

Ser Gly Tyr Ser Asp Glu Asp Lys Arg Gly Phe Thr Lys Leu Val Tyr
65              70              75              80

Gln Asn Ile Phe Thr Ala Met Gln Ala Met Ile Arg Ala Met Asp Thr
             85              90              95

Leu Lys Ile Pro Tyr Lys Tyr Glu His Asn Lys Ala His Ala Gln Leu
             100             105             110

Val Arg Glu Val Asp Val Glu Lys Val Ser Ala Phe Glu Asn Pro Tyr
```

-continued

```
                115               120               125

Val Asp Ala Ile Lys Ser Leu Trp Asn Asp Pro Gly Ile Gln Glu Cys
    130               135               140

Tyr Asp Arg Arg Arg Glu Tyr Gln Leu Ser Asp Ser Thr Lys Tyr Tyr
145               150               155               160

Leu Asn Asp Leu Asp Arg Val Ala Asp Pro Ala Tyr Leu Pro Thr Gln
                165               170               175

Gln Asp Val Leu Arg Val Arg Val Pro Thr Thr Gly Ile Ile Glu Tyr
                180               185               190

Pro Phe Asp Leu Gln Ser Val Ile Phe Arg Met Val Asp Val Gly Gly
                195               200               205

Gln Arg Ser Glu Arg Arg Lys Trp Ile His Cys Phe Glu Asn Val Thr
    210               215               220

Ser Ile Met Phe Leu Val Ala Leu Ser Glu Tyr Asp Gln Val Leu Val
225               230               235               240

Glu Ser Asp Asn Glu Asn Arg Met Glu Glu Ser Lys Ala Leu Phe Arg
                245               250               255

Thr Ile Ile Thr Tyr Pro Trp Phe Gln Asn Ser Ser Val Ile Leu Phe
                260               265               270

Leu Asn Lys Lys Asp Leu Leu Glu Glu Lys Ile Met Tyr Ser His Leu
    275               280               285

Val Asp Tyr Phe Pro Glu Tyr Asp Gly Pro Gln Arg Asp Ala Gln Ala
    290               295               300

Ala Arg Glu Phe Ile Leu Lys Met Phe Val Asp Leu Asn Pro Asp Ser
305               310               315               320

Asp Lys Ile Ile Tyr Ser His Phe Thr Cys Ala Thr Asp Thr Glu Asn
                325               330               335

Ile Arg Phe Val Phe Ala Ala Val Lys Asp Thr Ile Leu Gln Leu Asn
                340               345               350

Leu Lys Asp Ile Met Leu Gln
        355
```

```
<210> SEQ ID NO 69
<211> LENGTH: 359
<212> TYPE: PRT
<213> ORGANISM: Homo sapiens
<220> FEATURE:
<223> OTHER INFORMATION: G\'ce\'b1q/13

<400> SEQUENCE: 69

Met Thr Leu Glu Ser Ile Met Ala Cys Cys Leu Ser Glu Glu Ala Lys
1               5               10               15

Glu Ala Arg Arg Ile Asn Asp Glu Ile Glu Arg Gln Leu Arg Arg Asp
                20               25               30

Lys Arg Asp Ala Arg Arg Glu Leu Lys Leu Leu Leu Leu Gly Thr Gly
        35               40               45

Glu Ser Gly Lys Ser Thr Phe Ile Lys Gln Met Arg Ile Ile His Gly
    50               55               60

Ser Gly Tyr Ser Asp Glu Asp Lys Arg Gly Phe Thr Lys Leu Val Tyr
65               70               75               80

Gln Asn Ile Phe Thr Ala Met Gln Ala Met Ile Arg Ala Met Asp Thr
                85               90               95

Leu Lys Ile Pro Tyr Lys Tyr Glu His Asn Lys Ala His Ala Gln Leu
                100               105               110

Val Arg Glu Val Asp Val Glu Lys Val Ser Ala Phe Glu Asn Pro Tyr
```

```
                 115                 120                 125

Val Asp Ala Ile Lys Ser Leu Trp Asn Asp Pro Gly Ile Gln Glu Cys
        130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
                195                 200                 205

Gln Arg Ser Glu Arg Arg Lys Trp Ile His Cys Phe Glu Asn Val Thr
        210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
        340                 345                 350

Leu Lys Gln Leu Met Leu Gln
        355
```

<210> SEQ ID NO 70
<211> LENGTH: 374
<212> TYPE: PRT
<213> ORGANISM: Homo sapiens
<220> FEATURE:
<223> OTHER INFORMATION: G\'ce\'b1s (\'e2\u710 \'88\u8224 \'86C)

<400> SEQUENCE: 70

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
        50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
                100                 105                 110

Arg Val Asp Tyr Ile Leu Ser Val Met Asn Val Pro Asp Phe Asp Phe
```

```
            115                 120                 125
Pro Pro Glu Phe Tyr Glu His Ala Lys Ala Leu Trp Glu Asp Glu Gly
    130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
                180                 185                 190

Ile Phe Glu Thr Lys Phe Gln Val Asp Lys Val Asn Phe His Met Phe
                195                 200                 205

Asp Val Gly Gly Gln Arg Asp Glu Arg Arg Lys Trp Ile Gln Cys Phe
    210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
                260                 265                 270

Val Ile Leu Phe Leu Asn Lys Gln Asp Leu Leu Ala Glu Lys Val Leu
                275                 280                 285

Ala Gly Lys Ser Lys Ile Glu Asp Tyr Phe Pro Glu Phe Ala Arg Tyr
    290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                325                 330                 335

Ala Ser Gly Asp Gly Arg His Tyr Cys Tyr Pro His Phe Thr Cys Ala
                340                 345                 350

Val Asp Thr Glu Asn Ile Arg Arg Val Phe Asn Asp Cys Arg Asp Ile
                355                 360                 365

Ile Gln Arg Met His Leu
    370

<210> SEQ ID NO 71
<211> LENGTH: 380
<212> TYPE: PRT
<213> ORGANISM: Homo sapiens
<220> FEATURE:
<223> OTHER INFORMATION: G\'ce\'b1s

<400> SEQUENCE: 71

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
```

```
                100             105             110
Arg Val Asp Tyr Ile Leu Ser Val Met Asn Val Pro Asp Phe Asp Phe
            115             120             125

Pro Pro Glu Phe Tyr Glu His Ala Lys Ala Leu Trp Glu Asp Glu Gly
        130             135             140

Val Arg Ala Cys Tyr Glu Arg Ser Asn Glu Tyr Gln Leu Ile Asp Cys
145             150             155             160

Ala Gln Tyr Phe Leu Asp Lys Ile Asp Val Ile Lys Gln Ala Asp Tyr
                165             170             175

Val Pro Ser Asp Gln Asp Leu Leu Arg Cys Arg Val Leu Thr Ser Gly
            180             185             190

Ile Phe Glu Thr Lys Phe Gln Val Asp Lys Val Asn Phe His Met Phe
            195             200             205

Asp Val Gly Gly Gln Arg Asp Glu Arg Arg Lys Trp Ile Gln Cys Phe
        210             215             220

Asn Asp Val Thr Ala Ile Ile Phe Val Val Ala Ser Ser Ser Tyr Asn
225             230             235             240

Met Val Ile Arg Glu Asp Asn Gln Thr Asn Arg Leu Gln Glu Ala Leu
            245             250             255

Asn Leu Phe Lys Ser Ile Trp Asn Asn Arg Trp Leu Arg Thr Ile Ser
            260             265             270

Val Ile Leu Phe Leu Asn Lys Gln Asp Leu Leu Ala Glu Lys Val Leu
            275             280             285

Ala Gly Lys Ser Lys Ile Glu Asp Tyr Phe Pro Glu Phe Ala Arg Tyr
        290             295             300

Thr Thr Pro Glu Asp Ala Thr Pro Glu Pro Gly Glu Asp Pro Arg Val
305             310             315             320

Thr Arg Ala Lys Tyr Phe Ile Arg Asp Glu Phe Leu Arg Ile Ser Thr
            325             330             335

Ala Ser Gly Asp Gly Arg His Tyr Cys Tyr Pro His Phe Thr Cys Ala
            340             345             350

Val Asp Thr Glu Asn Ile Arg Arg Val Phe Asn Asp Cys Arg Asp Ile
        355             360             365

Ile Gln Arg Met His Leu Arg Gln Tyr Glu Leu Leu
    370             375             380
```

```
<210> SEQ ID NO 72
<211> LENGTH: 380
<212> TYPE: PRT
<213> ORGANISM: Homo sapiens
<220> FEATURE:
<223> OTHER INFORMATION: G\'ce\'b1s/i1

<400> SEQUENCE: 72

Met Gly Cys Leu Gly Asn Ser Lys Thr Glu Asp Gln Arg Asn Glu Glu
1               5               10              15

Lys Ala Gln Arg Glu Ala Asn Lys Lys Ile Glu Lys Gln Leu Gln Lys
            20              25              30

Asp Lys Gln Val Tyr Arg Ala Thr His Arg Leu Leu Leu Leu Gly Ala
        35              40              45

Gly Glu Ser Gly Lys Ser Thr Ile Val Lys Gln Met Arg Ile Leu His
        50              55              60

Val Asn Gly Phe Asn Gly Asp Ser Glu Lys Ala Thr Lys Val Gln Asp
65              70              75              80

Ile Lys Asn Asn Leu Lys Glu Ala Ile Glu Thr Ile Val Ala Ala Met
```

-continued

```
                85                    90                    95
Ser Asn Leu Val Pro Pro Val Glu Leu Ala Asn Pro Glu Asn Gln Phe
            100                   105                   110

Arg Val Asp Tyr Ile Leu Ser Val Met Asn Val Pro Asp Phe Asp Phe
            115                   120                   125

Pro Pro Glu Phe Tyr Glu His Ala Lys Ala Leu Trp Glu Asp Glu Gly
            130                   135                   140

Val Arg Ala Cys Tyr Glu Arg Ser Asn Glu Tyr Gln Leu Ile Asp Cys
145                   150                   155                   160

Ala Gln Tyr Phe Leu Asp Lys Ile Asp Val Ile Lys Gln Ala Asp Tyr
                165                   170                   175

Val Pro Ser Asp Gln Asp Leu Leu Arg Cys Arg Val Leu Thr Ser Gly
                180                   185                   190

Ile Phe Glu Thr Lys Phe Gln Val Asp Lys Val Asn Phe His Met Phe
                195                   200                   205

Asp Val Gly Gly Gln Arg Asp Glu Arg Arg Lys Trp Ile Gln Cys Phe
            210                   215                   220

Asn Asp Val Thr Ala Ile Ile Phe Val Val Ala Ser Ser Ser Tyr Asn
225                   230                   235                   240

Met Val Ile Arg Glu Asp Asn Gln Thr Asn Arg Leu Gln Glu Ala Leu
                245                   250                   255

Asn Leu Phe Lys Ser Ile Trp Asn Asn Arg Trp Leu Arg Thr Ile Ser
                260                   265                   270

Val Ile Leu Phe Leu Asn Lys Gln Asp Leu Leu Ala Glu Lys Val Leu
                275                   280                   285

Ala Gly Lys Ser Lys Ile Glu Asp Tyr Phe Pro Glu Phe Ala Arg Tyr
            290                   295                   300

Thr Thr Pro Glu Asp Ala Thr Pro Glu Pro Gly Glu Asp Pro Arg Val
305                   310                   315                   320

Thr Arg Ala Lys Tyr Phe Ile Arg Asp Glu Phe Leu Arg Ile Ser Thr
                325                   330                   335

Ala Ser Gly Asp Gly Arg His Tyr Cys Tyr Pro His Phe Thr Cys Ala
                340                   345                   350

Val Asp Thr Glu Asn Ile Arg Arg Val Phe Asn Asp Cys Arg Asp Ile
                355                   360                   365

Ile Gln Arg Met His Leu Lys Asp Cys Gly Leu Phe
            370                   375                   380

<210> SEQ ID NO 73
<211> LENGTH: 380
<212> TYPE: PRT
<213> ORGANISM: Homo sapiens
<220> FEATURE:
<223> OTHER INFORMATION: G\'ce\'b1s/i3

<400> SEQUENCE: 73

Met Gly Cys Leu Gly Asn Ser Lys Thr Glu Asp Gln Arg Asn Glu Glu
1               5                   10                   15

Lys Ala Gln Arg Glu Ala Asn Lys Lys Ile Glu Lys Gln Leu Gln Lys
            20                   25                   30

Asp Lys Gln Val Tyr Arg Ala Thr His Arg Leu Leu Leu Leu Gly Ala
            35                   40                   45

Gly Glu Ser Gly Lys Ser Thr Ile Val Lys Gln Met Arg Ile Leu His
        50                   55                   60

Val Asn Gly Phe Asn Gly Asp Ser Glu Lys Ala Thr Lys Val Gln Asp
```

-continued

```
65              70              75              80

Ile Lys Asn Asn Leu Lys Glu Ala Ile Glu Thr Ile Val Ala Ala Met
                85              90              95

Ser Asn Leu Val Pro Pro Val Glu Leu Ala Asn Pro Glu Asn Gln Phe
               100             105             110

Arg Val Asp Tyr Ile Leu Ser Val Met Asn Val Pro Asp Phe Asp Phe
               115             120             125

Pro Pro Glu Phe Tyr Glu His Ala Lys Ala Leu Trp Glu Asp Glu Gly
       130             135             140

Val Arg Ala Cys Tyr Glu Arg Ser Asn Glu Tyr Gln Leu Ile Asp Cys
145             150             155             160

Ala Gln Tyr Phe Leu Asp Lys Ile Asp Val Ile Lys Gln Ala Asp Tyr
               165             170             175

Val Pro Ser Asp Gln Asp Leu Leu Arg Cys Arg Val Leu Thr Ser Gly
               180             185             190

Ile Phe Glu Thr Lys Phe Gln Val Asp Lys Val Asn Phe His Met Phe
               195             200             205

Asp Val Gly Gly Gln Arg Asp Glu Arg Arg Lys Trp Ile Gln Cys Phe
       210             215             220

Asn Asp Val Thr Ala Ile Ile Phe Val Val Ala Ser Ser Ser Tyr Asn
225             230             235             240

Met Val Ile Arg Glu Asp Asn Gln Thr Asn Arg Leu Gln Glu Ala Leu
               245             250             255

Asn Leu Phe Lys Ser Ile Trp Asn Asn Arg Trp Leu Arg Thr Ile Ser
               260             265             270

Val Ile Leu Phe Leu Asn Lys Gln Asp Leu Leu Ala Glu Lys Val Leu
               275             280             285

Ala Gly Lys Ser Lys Ile Glu Asp Tyr Phe Pro Glu Phe Ala Arg Tyr
       290             295             300

Thr Thr Pro Glu Asp Ala Thr Pro Glu Pro Gly Glu Asp Pro Arg Val
305             310             315             320

Thr Arg Ala Lys Tyr Phe Ile Arg Asp Glu Phe Leu Arg Ile Ser Thr
               325             330             335

Ala Ser Gly Asp Gly Arg His Tyr Cys Tyr Pro His Phe Thr Cys Ala
       340             345             350

Val Asp Thr Glu Asn Ile Arg Arg Val Phe Asn Asp Cys Arg Asp Ile
       355             360             365

Ile Gln Arg Met His Leu Lys Glu Cys Gly Leu Tyr
   370             375             380
```

```
<210> SEQ ID NO 74
<211> LENGTH: 380
<212> TYPE: PRT
<213> ORGANISM: Homo sapiens
<220> FEATURE:
<223> OTHER INFORMATION: G\'ce\'b1s/o

<400> SEQUENCE: 74

Met Gly Cys Leu Gly Asn Ser Lys Thr Glu Asp Gln Arg Asn Glu Glu
1               5               10              15

Lys Ala Gln Arg Glu Ala Asn Lys Lys Ile Glu Lys Gln Leu Gln Lys
               20              25              30

Asp Lys Gln Val Tyr Arg Ala Thr His Arg Leu Leu Leu Leu Gly Ala
       35              40              45

Gly Glu Ser Gly Lys Ser Thr Ile Val Lys Gln Met Arg Ile Leu His
```

-continued

```
        50                      55                      60

Val Asn Gly Phe Asn Gly Asp Ser Glu Lys Ala Thr Lys Val Gln Asp
65                      70                      75                      80

Ile Lys Asn Asn Leu Lys Glu Ala Ile Glu Thr Ile Val Ala Ala Met
                85                      90                      95

Ser Asn Leu Val Pro Pro Val Glu Leu Ala Asn Pro Glu Asn Gln Phe
            100                     105                     110

Arg Val Asp Tyr Ile Leu Ser Val Met Asn Val Pro Asp Phe Asp Phe
            115                     120                     125

Pro Pro Glu Phe Tyr Glu His Ala Lys Ala Leu Trp Glu Asp Glu Gly
        130                     135                     140

Val Arg Ala Cys Tyr Glu Arg Ser Asn Glu Tyr Gln Leu Ile Asp Cys
145                     150                     155                     160

Ala Gln Tyr Phe Leu Asp Lys Ile Asp Val Ile Lys Gln Ala Asp Tyr
                165                     170                     175

Val Pro Ser Asp Gln Asp Leu Leu Arg Cys Arg Val Leu Thr Ser Gly
            180                     185                     190

Ile Phe Glu Thr Lys Phe Gln Val Asp Lys Val Asn Phe His Met Phe
            195                     200                     205

Asp Val Gly Gly Gln Arg Asp Glu Arg Arg Lys Trp Ile Gln Cys Phe
        210                     215                     220

Asn Asp Val Thr Ala Ile Ile Phe Val Val Ala Ser Ser Ser Tyr Asn
225                     230                     235                     240

Met Val Ile Arg Glu Asp Asn Gln Thr Asn Arg Leu Gln Glu Ala Leu
                245                     250                     255

Asn Leu Phe Lys Ser Ile Trp Asn Asn Arg Trp Leu Arg Thr Ile Ser
            260                     265                     270

Val Ile Leu Phe Leu Asn Lys Gln Asp Leu Leu Ala Glu Lys Val Leu
            275                     280                     285

Ala Gly Lys Ser Lys Ile Glu Asp Tyr Phe Pro Glu Phe Ala Arg Tyr
        290                     295                     300

Thr Thr Pro Glu Asp Ala Thr Pro Glu Pro Gly Glu Asp Pro Arg Val
305                     310                     315                     320

Thr Arg Ala Lys Tyr Phe Ile Arg Asp Glu Phe Leu Arg Ile Ser Thr
                325                     330                     335

Ala Ser Gly Asp Gly Arg His Tyr Cys Tyr Pro His Phe Thr Cys Ala
            340                     345                     350

Val Asp Thr Glu Asn Ile Arg Arg Val Phe Asn Asp Cys Arg Asp Ile
            355                     360                     365

Ile Gln Arg Met His Leu Arg Gly Cys Gly Leu Tyr
    370                     375                     380
```

<210> SEQ ID NO 75
<211> LENGTH: 380
<212> TYPE: PRT
<213> ORGANISM: Homo sapiens
<220> FEATURE:
<223> OTHER INFORMATION: G\'ce\'b1s/z

<400> SEQUENCE: 75

```
Met Gly Cys Leu Gly Asn Ser Lys Thr Glu Asp Gln Arg Asn Glu Glu
1                       5                       10                      15

Lys Ala Gln Arg Glu Ala Asn Lys Lys Ile Glu Lys Gln Leu Gln Lys
                20                      25                      30

Asp Lys Gln Val Tyr Arg Ala Thr His Arg Leu Leu Leu Leu Gly Ala
```

-continued

```
          35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
            115                 120                 125

Pro Pro Glu Phe Tyr Glu His Ala Lys Ala Leu Trp Glu Asp Glu Gly
        130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
            165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
            195                 200                 205

Asp Val Gly Gly Gln Arg Asp Glu Arg Arg Lys Trp Ile Gln Cys Phe
        210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
            245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
            275                 280                 285

Ala Gly Lys Ser Lys Ile Glu Asp Tyr Phe Pro Glu Phe Ala Arg Tyr
        290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
            325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
            355                 360                 365

Ile Gln Arg Met His Leu Lys Tyr Ile Gly Leu Cys
        370                 375                 380

<210> SEQ ID NO 76
<211> LENGTH: 380
<212> TYPE: PRT
<213> ORGANISM: Homo sapiens
<220> FEATURE:
<223> OTHER INFORMATION: G\'ce\'b1s/q

<400> SEQUENCE: 76

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
```

-continued

```
              20              25              30

Asp Lys Gln Val Tyr Arg Ala Thr His Arg Leu Leu Leu Leu Gly Ala
        35              40              45

Gly Glu Ser Gly Lys Ser Thr Ile Val Lys Gln Met Arg Ile Leu His
    50              55              60

Val Asn Gly Phe Asn Gly Asp Ser Glu Lys Ala Thr Lys Val Gln Asp
65              70              75              80

Ile Lys Asn Asn Leu Lys Glu Ala Ile Glu Thr Ile Val Ala Ala Met
            85              90              95

Ser Asn Leu Val Pro Pro Val Glu Leu Ala Asn Pro Glu Asn Gln Phe
            100             105             110

Arg Val Asp Tyr Ile Leu Ser Val Met Asn Val Pro Asp Phe Asp Phe
            115             120             125

Pro Pro Glu Phe Tyr Glu His Ala Lys Ala Leu Trp Glu Asp Glu Gly
            130             135             140

Val Arg Ala Cys Tyr Glu Arg Ser Asn Glu Tyr Gln Leu Ile Asp Cys
145             150             155             160

Ala Gln Tyr Phe Leu Asp Lys Ile Asp Val Ile Lys Gln Ala Asp Tyr
                165             170             175

Val Pro Ser Asp Gln Asp Leu Leu Arg Cys Arg Val Leu Thr Ser Gly
            180             185             190

Ile Phe Glu Thr Lys Phe Gln Val Asp Lys Val Asn Phe His Met Phe
            195             200             205

Asp Val Gly Gly Gln Arg Asp Glu Arg Arg Lys Trp Ile Gln Cys Phe
    210             215             220

Asn Asp Val Thr Ala Ile Ile Phe Val Val Ala Ser Ser Ser Tyr Asn
225             230             235             240

Met Val Ile Arg Glu Asp Asn Gln Thr Asn Arg Leu Gln Glu Ala Leu
            245             250             255

Asn Leu Phe Lys Ser Ile Trp Asn Asn Arg Trp Leu Arg Thr Ile Ser
            260             265             270

Val Ile Leu Phe Leu Asn Lys Gln Asp Leu Leu Ala Glu Lys Val Leu
            275             280             285

Ala Gly Lys Ser Lys Ile Glu Asp Tyr Phe Pro Glu Phe Ala Arg Tyr
    290             295             300

Thr Thr Pro Glu Asp Ala Thr Pro Glu Pro Gly Glu Asp Pro Arg Val
305             310             315             320

Thr Arg Ala Lys Tyr Phe Ile Arg Asp Glu Phe Leu Arg Ile Ser Thr
            325             330             335

Ala Ser Gly Asp Gly Arg His Tyr Cys Tyr Pro His Phe Thr Cys Ala
            340             345             350

Val Asp Thr Glu Asn Ile Arg Arg Val Phe Asn Asp Cys Arg Asp Ile
            355             360             365

Ile Gln Arg Met His Leu Lys Glu Tyr Asn Leu Val
    370             375             380
```

```
<210> SEQ ID NO 77
<211> LENGTH: 380
<212> TYPE: PRT
<213> ORGANISM: Homo sapiens
<220> FEATURE:
<223> OTHER INFORMATION: G\'ce\'b1s/14

<400> SEQUENCE: 77

Met Gly Cys Leu Gly Asn Ser Lys Thr Glu Asp Gln Arg Asn Glu Glu
```

-continued

```
1                  5                  10                 15

Lys Ala Gln Arg Glu Ala Asn Lys Lys Ile Glu Lys Gln Leu Gln Lys
             20                  25                  30

Asp Lys Gln Val Tyr Arg Ala Thr His Arg Leu Leu Leu Leu Gly Ala
             35                  40                  45

Gly Glu Ser Gly Lys Ser Thr Ile Val Lys Gln Met Arg Ile Leu His
             50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
             85                  90                  95

Ser Asn Leu Val Pro Pro Val Glu Leu Ala Asn Pro Glu Asn Gln Phe
             100                 105                 110

Arg Val Asp Tyr Ile Leu Ser Val Met Asn Val Pro Asp Phe Asp Phe
             115                 120                 125

Pro Pro Glu Phe Tyr Glu His Ala Lys Ala Leu Trp Glu Asp Glu Gly
             130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
             165                 170                 175

Val Pro Ser Asp Gln Asp Leu Leu Arg Cys Arg Val Leu Thr Ser Gly
             180                 185                 190

Ile Phe Glu Thr Lys Phe Gln Val Asp Lys Val Asn Phe His Met Phe
             195                 200                 205

Asp Val Gly Gly Gln Arg Asp Glu Arg Arg Lys Trp Ile Gln Cys Phe
             210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
             245                 250                 255

Asn Leu Phe Lys Ser Ile Trp Asn Asn Arg Trp Leu Arg Thr Ile Ser
             260                 265                 270

Val Ile Leu Phe Leu Asn Lys Gln Asp Leu Leu Ala Glu Lys Val Leu
             275                 280                 285

Ala Gly Lys Ser Lys Ile Glu Asp Tyr Phe Pro Glu Phe Ala Arg Tyr
             290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
             325                 330                 335

Ala Ser Gly Asp Gly Arg His Tyr Cys Tyr Pro His Phe Thr Cys Ala
             340                 345                 350

Val Asp Thr Glu Asn Ile Arg Arg Val Phe Asn Asp Cys Arg Asp Ile
             355                 360                 365

Ile Gln Arg Met His Leu Arg Glu Phe Asn Leu Val
             370                 375                 380
```

<210> SEQ ID NO 78
<211> LENGTH: 380
<212> TYPE: PRT
<213> ORGANISM: Homo sapiens
<220> FEATURE:
<223> OTHER INFORMATION: G\'ce\'b1s/16

```
<400> SEQUENCE: 78

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
        115                 120                 125

Pro Pro Glu Phe Tyr Glu His Ala Lys Ala Leu Trp Glu Asp Glu Gly
    130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
            195                 200                 205

Asp Val Gly Gly Gln Arg Asp Glu Arg Arg Lys Trp Ile Gln Cys Phe
    210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
            245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
            275                 280                 285

Ala Gly Lys Ser Lys Ile Glu Asp Tyr Phe Pro Glu Phe Ala Arg Tyr
    290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
            325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
            355                 360                 365

Ile Gln Arg Met His Leu Asp Glu Ile Asn Leu Leu
    370                 375                 380

<210> SEQ ID NO 79
<211> LENGTH: 380
<212> TYPE: PRT
<213> ORGANISM: Homo sapiens
```

```
<220> FEATURE:
<223> OTHER INFORMATION: G\'ce\'b1s/12

<400> SEQUENCE: 79

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
        115                 120                 125

Pro Pro Glu Phe Tyr Glu His Ala Lys Ala Leu Trp Glu Asp Glu Gly
        130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
            195                 200                 205

Asp Val Gly Gly Gln Arg Asp Glu Arg Arg Lys Trp Ile Gln Cys Phe
        210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
            245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
            275                 280                 285

Ala Gly Lys Ser Lys Ile Glu Asp Tyr Phe Pro Glu Phe Ala Arg Tyr
        290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
            325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
            355                 360                 365

Ile Gln Arg Met His Leu Lys Asp Ile Met Leu Gln
    370                 375                 380

<210> SEQ ID NO 80
```

```
<211> LENGTH: 380
<212> TYPE: PRT
<213> ORGANISM: Homo sapiens
<220> FEATURE:
<223> OTHER INFORMATION: G\'ce\'b1s/13

<400> SEQUENCE: 80

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
                100                 105                 110

Arg Val Asp Tyr Ile Leu Ser Val Met Asn Val Pro Asp Phe Asp Phe
            115                 120                 125

Pro Pro Glu Phe Tyr Glu His Ala Lys Ala Leu Trp Glu Asp Glu Gly
        130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
            195                 200                 205

Asp Val Gly Gly Gln Arg Asp Glu Arg Arg Lys Trp Ile Gln Cys Phe
        210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
                260                 265                 270

Val Ile Leu Phe Leu Asn Lys Gln Asp Leu Leu Ala Glu Lys Val Leu
            275                 280                 285

Ala Gly Lys Ser Lys Ile Glu Asp Tyr Phe Pro Glu Phe Ala Arg Tyr
        290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
            355                 360                 365

Ile Gln Arg Met His Leu Lys Gln Leu Met Leu Gln
        370                 375                 380
```

-continued

```
<210> SEQ ID NO 81
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/s

<400> SEQUENCE: 81

Arg Gln Tyr Glu Leu Leu
1               5

<210> SEQ ID NO 82
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/olf, G\'ce\'b1s/olf

<400> SEQUENCE: 82

Lys Gln Tyr Glu Leu Leu
1               5

<210> SEQ ID NO 83
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/i1, G\'ce\'b1s/i1

<400> SEQUENCE: 83

Lys Asp Cys Gly Leu Phe
1               5

<210> SEQ ID NO 84
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/i3, G\'ce\'b1s/i3

<400> SEQUENCE: 84

Lys Glu Cys Gly Leu Tyr
1               5

<210> SEQ ID NO 85
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/o, G\'ce\'b1s/o

<400> SEQUENCE: 85

Arg Gly Cys Gly Leu Tyr
1               5

<210> SEQ ID NO 86
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/z, G\'ce\'b1s/z
```

<400> SEQUENCE: 86

Lys Tyr Ile Gly Leu Cys
1               5

<210> SEQ ID NO 87
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/14, G\'ce\'b1s/14

<400> SEQUENCE: 87

Arg Glu Phe Asn Leu Val
1               5

<210> SEQ ID NO 88
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/16, G\'ce\'b1s/16

<400> SEQUENCE: 88

Asp Glu Ile Asn Leu Leu
1               5

<210> SEQ ID NO 89
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/12

<400> SEQUENCE: 89

Lys Asp Ile Met Leu Gln
1               5

<210> SEQ ID NO 90
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1q/13, G\'ce\'b1s/13

<400> SEQUENCE: 90

Lys Gln Leu Met Leu Gln
1               5

<210> SEQ ID NO 91
<211> LENGTH: 6
<212> TYPE: PRT
<213> ORGANISM: Homo sapiens
<220> FEATURE:
<223> OTHER INFORMATION: C-terminally substituted 6-amino acids of
      G\'ce\'b1s/q

<400> SEQUENCE: 91

Lys Glu Tyr Asn Leu Val
1               5

<210> SEQ ID NO 92
<211> LENGTH: 6

```
<212> TYPE: PRT
<213> ORGANISM: Homo sapiens
<220> FEATURE:
<223> OTHER INFORMATION: C-terminally substituted 6-amino acids of
      G\'ce\'b1s/12

<400> SEQUENCE: 92

Lys Asp Ile Met Leu Gln
1               5

<210> SEQ ID NO 93
<211> LENGTH: 651
<212> TYPE: PRT
<213> ORGANISM: Homo sapiens
<220> FEATURE:
<223> OTHER INFORMATION: amino acid sequence of the AP-TGF\'ce\'b1.

<400> SEQUENCE: 93

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Ala Val Val Ser Arg Ser Gly Ile Ile Pro
            35                  40                  45

Val Glu Glu Glu Asn Pro Asp Phe Trp Asn Arg Glu Ala Ala Glu Ala
        50                  55                  60

Leu Gly Ala Ala Lys Lys Leu Gln Pro Ala Gln Thr Ala Ala Lys Asn
65                  70                  75                  80

Leu Ile Ile Phe Leu Gly Asp Gly Met Gly Val Ser Thr Val Thr Ala
                85                  90                  95

Ala Arg Ile Leu Lys Gly Gln Lys Lys Asp Lys Leu Gly Pro Glu Ile
                100                 105                 110

Pro Leu Ala Met Asp Arg Phe Pro Tyr Val Ala Leu Ser Lys Thr Tyr
            115                 120                 125

Asn Val Asp Lys His Val Pro Asp Ser Gly Ala Thr Ala Thr Ala Tyr
        130                 135                 140

Leu Cys Gly Val Lys Gly Asn Phe Gln Thr Ile Gly Leu Ser Ala Ala
145                 150                 155                 160

Ala Arg Phe Asn Gln Cys Asn Thr Thr Arg Gly Asn Glu Val Ile Ser
                165                 170                 175

Val Met Asn Arg Ala Lys Lys Ala Gly Lys Ser Val Gly Val Val Thr
                180                 185                 190

Thr Thr Arg Val Gln His Ala Ser Pro Ala Gly Thr Tyr Ala His Thr
            195                 200                 205

Val Asn Arg Asn Trp Tyr Ser Asp Ala Asp Val Pro Ala Ser Ala Arg
        210                 215                 220

Gln Glu Gly Cys Gln Asp Ile Ala Thr Gln Leu Ile Ser Asn Met Asp
225                 230                 235                 240

Ile Asp Val Ile Leu Gly Gly Gly Arg Lys Tyr Met Phe Arg Met Gly
                245                 250                 255

Thr Pro Asp Pro Glu Tyr Pro Asp Asp Tyr Ser Gln Gly Gly Thr Arg
            260                 265                 270

Leu Asp Gly Lys Asn Leu Val Gln Glu Trp Leu Ala Lys Arg Gln Gly
            275                 280                 285

Ala Arg Tyr Val Trp Asn Arg Thr Glu Leu Met Gln Ala Ser Leu Asp
        290                 295                 300

Pro Ser Val Thr His Leu Met Gly Leu Phe Glu Pro Gly Asp Met Lys
```

-continued

```
305                310                315                320

Tyr Glu Ile His Arg Asp Ser Thr Leu Asp Pro Ser Leu Met Glu Met
                325                330                335

Thr Glu Ala Ala Leu Arg Leu Leu Ser Arg Asn Pro Arg Gly Phe Phe
                340                345                350

Leu Phe Val Glu Gly Gly Arg Ile Asp His Gly His His Glu Ser Arg
                355                360                365

Ala Tyr Arg Ala Leu Thr Glu Thr Ile Met Phe Asp Asp Ala Ile Glu
                370                375                380

Arg Ala Gly Gln Leu Thr Ser Glu Glu Asp Thr Leu Ser Leu Val Thr
385                390                395                400

Ala Asp His Ser His Val Phe Ser Phe Gly Gly Tyr Pro Leu Arg Gly
                405                410                415

Ser Ser Ile Phe Gly Leu Ala Pro Gly Lys Ala Arg Asp Arg Lys Ala
                420                425                430

Tyr Thr Val Leu Leu Tyr Gly Asn Gly Pro Gly Tyr Val Leu Lys Asp
                435                440                445

Gly Ala Arg Pro Asp Val Thr Glu Ser Glu Ser Gly Ser Pro Glu Tyr
                450                455                460

Arg Gln Gln Ser Ala Val Pro Leu Asp Glu Glu Thr His Ala Gly Glu
465                470                475                480

Asp Val Ala Val Phe Ala Arg Gly Pro Gln Ala His Leu Val His Gly
                485                490                495

Val Gln Glu Gln Thr Phe Ile Ala His Val Met Ala Phe Ala Ala Cys
                500                505                510

Leu Glu Pro Tyr Thr Ala Cys Asp Leu Ala Pro Pro Ala Gly Thr Thr
                515                520                525

Asp Ala Ala His Pro Gly Tyr His Asp Cys Pro Asp Ser His Thr Gln
                530                535                540

Phe Cys Phe His Gly Thr Cys Arg Phe Leu Val Gln Glu Asp Lys Pro
545                550                555                560

Ala Cys Val Cys His Ser Gly Tyr Val Gly Ala Arg Cys Glu His Ala
                565                570                575

Asp Leu Leu Ala Val Val Ala Ala Ser Gln Lys Lys Gln Ala Ile Thr
                580                585                590

Ala Leu Val Val Val Ser Ile Val Ala Leu Ala Val Leu Ile Ile Thr
                595                600                605

Cys Val Leu Ile His Cys Cys Gln Val Arg Lys His Cys Glu Trp Cys
                610                615                620

Arg Ala Leu Ile Cys Arg His Glu Lys Pro Ser Ala Leu Leu Lys Gly
625                630                635                640

Arg Thr Ala Cys Cys His Ser Glu Thr Val Val
                645                650
```

<210> SEQ ID NO 94
<211> LENGTH: 39
<212> TYPE: PRT
<213> ORGANISM: Homo sapiens
<220> FEATURE:
<223> OTHER INFORMATION: signal-sequence peptide and the cleaved
      fragment of human TGFA

<400> SEQUENCE: 94

```
Met Val Pro Ser Ala Gly Gln Leu Ala Leu Phe Ala Leu Gly Ile Val
1                5                10                15
```

-continued

Leu Ala Ala Cys Gln Ala Leu Glu Asn Ser Thr Ser Pro Leu Ser Ala
            20                  25                  30

Asp Pro Pro Val Ala Ala Ala
        35

<210> SEQ ID NO 95
<211> LENGTH: 489
<212> TYPE: PRT
<213> ORGANISM: Homo sapiens
<220> FEATURE:
<223> OTHER INFORMATION: alkaline phosphatase sequence derived from
      human ALPP

<400> SEQUENCE: 95

Gly Ile Ile Pro Val Glu Glu Glu Asn Pro Asp Phe Trp Asn Arg Glu
1               5                   10                  15

Ala Ala Glu Ala Leu Gly Ala Ala Lys Lys Leu Gln Pro Ala Gln Thr
            20                  25                  30

Ala Ala Lys Asn Leu Ile Ile Phe Leu Gly Asp Gly Met Gly Val Ser
        35                  40                  45

Thr Val Thr Ala Ala Arg Ile Leu Lys Gly Gln Lys Lys Asp Lys Leu
    50                  55                  60

Gly Pro Glu Ile Pro Leu Ala Met Asp Arg Phe Pro Tyr Val Ala Leu
65                  70                  75                  80

Ser Lys Thr Tyr Asn Val Asp Lys His Val Pro Asp Ser Gly Ala Thr
                85                  90                  95

Ala Thr Ala Tyr Leu Cys Gly Val Lys Gly Asn Phe Gln Thr Ile Gly
            100                 105                 110

Leu Ser Ala Ala Ala Arg Phe Asn Gln Cys Asn Thr Thr Arg Gly Asn
        115                 120                 125

Glu Val Ile Ser Val Met Asn Arg Ala Lys Lys Ala Gly Lys Ser Val
    130                 135                 140

Gly Val Val Thr Thr Thr Arg Val Gln His Ala Ser Pro Ala Gly Thr
145                 150                 155                 160

Tyr Ala His Thr Val Asn Arg Asn Trp Tyr Ser Asp Ala Asp Val Pro
                165                 170                 175

Ala Ser Ala Arg Gln Glu Gly Cys Gln Asp Ile Ala Thr Gln Leu Ile
            180                 185                 190

Ser Asn Met Asp Ile Asp Val Ile Leu Gly Gly Gly Arg Lys Tyr Met
        195                 200                 205

Phe Arg Met Gly Thr Pro Asp Pro Glu Tyr Pro Asp Asp Tyr Ser Gln
    210                 215                 220

Gly Gly Thr Arg Leu Asp Gly Lys Asn Leu Val Gln Glu Trp Leu Ala
225                 230                 235                 240

Lys Arg Gln Gly Ala Arg Tyr Val Trp Asn Arg Thr Glu Leu Met Gln
                245                 250                 255

Ala Ser Leu Asp Pro Ser Val Thr His Leu Met Gly Leu Phe Glu Pro
            260                 265                 270

Gly Asp Met Lys Tyr Glu Ile His Arg Asp Ser Thr Leu Asp Pro Ser
        275                 280                 285

Leu Met Glu Met Thr Glu Ala Ala Leu Arg Leu Leu Ser Arg Asn Pro
    290                 295                 300

Arg Gly Phe Phe Leu Phe Val Glu Gly Gly Arg Ile Asp His Gly His
305                 310                 315                 320

His Glu Ser Arg Ala Tyr Arg Ala Leu Thr Glu Thr Ile Met Phe Asp
                325                 330                 335

```
Asp Ala Ile Glu Arg Ala Gly Gln Leu Thr Ser Glu Glu Asp Thr Leu
        340                 345                 350

Ser Leu Val Thr Ala Asp His Ser His Val Phe Ser Phe Gly Gly Tyr
        355                 360                 365

Pro Leu Arg Gly Ser Ser Ile Phe Gly Leu Ala Pro Gly Lys Ala Arg
        370                 375                 380

Asp Arg Lys Ala Tyr Thr Val Leu Leu Tyr Gly Asn Gly Pro Gly Tyr
385                 390                 395                 400

Val Leu Lys Asp Gly Ala Arg Pro Asp Val Thr Glu Ser Glu Ser Gly
                405                 410                 415

Ser Pro Glu Tyr Arg Gln Gln Ser Ala Val Pro Leu Asp Glu Glu Thr
        420                 425                 430

His Ala Gly Glu Asp Val Ala Val Phe Ala Arg Gly Pro Gln Ala His
        435                 440                 445

Leu Val His Gly Val Gln Glu Gln Thr Phe Ile Ala His Val Met Ala
        450                 455                 460

Phe Ala Ala Cys Leu Glu Pro Tyr Thr Ala Cys Asp Leu Ala Pro Pro
465                 470                 475                 480

Ala Gly Thr Thr Asp Ala Ala His Pro
                485
```

```
<210> SEQ ID NO 96
<211> LENGTH: 48
<212> TYPE: PRT
<213> ORGANISM: Homo sapiens
<220> FEATURE:
<223> OTHER INFORMATION: mature, ectodomain-shed fragment of human TGFA

<400> SEQUENCE: 96

Gly Tyr His Asp Cys Pro Asp Ser His Thr Gln Phe Cys Phe His Gly
1                 5                  10                  15

Thr Cys Arg Phe Leu Val Gln Glu Asp Lys Pro Ala Cys Val Cys His
                20                 25                  30

Ser Gly Tyr Val Gly Ala Arg Cys Glu His Ala Asp Leu Leu Ala Val
        35                 40                  45
```

```
<210> SEQ ID NO 97
<211> LENGTH: 25
<212> TYPE: RNA
<213> ORGANISM: Homo sapiens
<220> FEATURE:
<223> OTHER INFORMATION: GNAQHSS104236

<400> SEQUENCE: 97
ggagagagug gcaagaguac guuua                                        25
```

```
<210> SEQ ID NO 98
<211> LENGTH: 25
<212> TYPE: RNA
<213> ORGANISM: Homo sapiens
<220> FEATURE:
<223> OTHER INFORMATION: GNAQHSS104237

<400> SEQUENCE: 98
cccuuugacu uacaaagugu cauuu                                        25
```

```
<210> SEQ ID NO 99
<211> LENGTH: 25
<212> TYPE: RNA
<213> ORGANISM: Homo sapiens
```

```
<220> FEATURE:
<223> OTHER INFORMATION: GNA11HSS178464

<400> SEQUENCE: 99
ccggcaucau cgaguacccu uucga                                        25

<210> SEQ ID NO 100
<211> LENGTH: 25
<212> TYPE: RNA
<213> ORGANISM: Homo sapiens
<220> FEATURE:
<223> OTHER INFORMATION: GNA11HSS104213

<400> SEQUENCE: 100
gcaucaguac gucagugcca ucaag                                        25

<210> SEQ ID NO 101
<211> LENGTH: 25
<212> TYPE: RNA
<213> ORGANISM: Homo sapiens
<220> FEATURE:
<223> OTHER INFORMATION: GNA12MSS204749

<400> SEQUENCE: 101
ccaucgucaa caacaagcuc uucuu                                        25

<210> SEQ ID NO 102
<211> LENGTH: 25
<212> TYPE: RNA
<213> ORGANISM: Homo sapiens
<220> FEATURE:
<223> OTHER INFORMATION: GNA13-HSS173827

<400> SEQUENCE: 102
cagaagcccu uauaccacca cuuca                                        25

<210> SEQ ID NO 103
<211> LENGTH: 25
<212> TYPE: RNA
<213> ORGANISM: Homo sapiens
<220> FEATURE:
<223> OTHER INFORMATION: GNA13-HSS116479

<400> SEQUENCE: 103
gcagcccaag gaauggugga aacaa                                        25

<210> SEQ ID NO 104
<211> LENGTH: 25
<212> TYPE: RNA
<213> ORGANISM: Homo sapiens
<220> FEATURE:
<223> OTHER INFORMATION: ADAM17-HSS186181

<400> SEQUENCE: 104
cagaaucgug uugacagcaa agaaa                                        25

<210> SEQ ID NO 105
<211> LENGTH: 21
<212> TYPE: DNA
<213> ORGANISM: Homo sapiens
<220> FEATURE:
<223> OTHER INFORMATION: GNAQ_1

<400> SEQUENCE: 105
accgaatgga ggaaagcaag g                                            21
```

237

238

-continued

```
<210> SEQ ID NO 106
<211> LENGTH: 25
<212> TYPE: DNA
<213> ORGANISM: Homo sapiens
<220> FEATURE:
<223> OTHER INFORMATION: GNAQ2

<400> SEQUENCE: 106
catctctctg gggtccatca tattc                                          25

<210> SEQ ID NO 107
<211> LENGTH: 20
<212> TYPE: DNA
<213> ORGANISM: Homo sapiens
<220> FEATURE:
<223> OTHER INFORMATION: GNA11_1

<400> SEQUENCE: 107
cagcgaatac gaccaagtcc                                                20

<210> SEQ ID NO 108
<211> LENGTH: 20
<212> TYPE: DNA
<213> ORGANISM: Homo sapiens
<220> FEATURE:
<223> OTHER INFORMATION: GNA11_2

<400> SEQUENCE: 108
accaggggta ggtgatgatg                                                20

<210> SEQ ID NO 109
<211> LENGTH: 19
<212> TYPE: DNA
<213> ORGANISM: Homo sapiens
<220> FEATURE:
<223> OTHER INFORMATION: GNA12_1

<400> SEQUENCE: 109
gagggattct ggcatcagg                                                 19

<210> SEQ ID NO 110
<211> LENGTH: 19
<212> TYPE: DNA
<213> ORGANISM: Homo sapiens
<220> FEATURE:
<223> OTHER INFORMATION: GNA12_2

<400> SEQUENCE: 110
cgatccggtc caagttgtc                                                 19

<210> SEQ ID NO 111
<211> LENGTH: 24
<212> TYPE: DNA
<213> ORGANISM: Homo sapiens
<220> FEATURE:
<223> OTHER INFORMATION: GNA13_1

<400> SEQUENCE: 111
cctggataac ttggataaac ttgg                                           24

<210> SEQ ID NO 112
<211> LENGTH: 19
<212> TYPE: DNA
<213> ORGANISM: Homo sapiens
<220> FEATURE:
<223> OTHER INFORMATION: GNA13_2
```

-continued

```
<400> SEQUENCE: 112
ttcatggatg cctttggtg                                              19

<210> SEQ ID NO 113
<211> LENGTH: 22
<212> TYPE: DNA
<213> ORGANISM: Homo sapiens
<220> FEATURE:
<223> OTHER INFORMATION: GAPDH_1

<400> SEQUENCE: 113
gccaaggtca tccatgacaa ct                                          22

<210> SEQ ID NO 114
<211> LENGTH: 20
<212> TYPE: DNA
<213> ORGANISM: Homo sapiens
<220> FEATURE:
<223> OTHER INFORMATION: GADPH_2

<400> SEQUENCE: 114
gaggggccat ccacagtctt                                             20
```

G12-SPECIFIC DESIGNER RECEPTOR EXCLUSIVELY ACTIVATED BY DESIGNER DRUGS

FIELD OF INVENTION

The present invention relates to a Designer Receptor Exclusively Activated by Designer Drugs (DREADD), and an amino acid sequence for determining coupling or no coupling between G-protein and G-protein coupled receptor (GPCR) mediated by a GPCR ligand in a cell based assay.

BACKGROUND

G-protein coupled receptors (GPCRs), one of the largest protein superfamilies, are key mediators linking extracellular ligands to downstream signals and are the most common targets for pharmaceutical drug development (Hauser et al., 2017; Hauser et al., 2018). Ligand binding induces conformational changes in GPCRs that then lead to intracellular binding by particular heterotrimeric G-protein complexes, each consisting of $G\alpha$, $G\beta$ and $G\gamma$ subunits, where distinct $G\alpha$ subunits specify both GPCR interactions and the transduction of particular downstream signaling events (Wettschureck and Offermanns, 2005). The human genome encodes 16 $G\alpha$ genes that are grouped into four subfamilies $G\alpha_s$, $G\alpha_{i/o}$, $G\alpha_{q/11}$ and $G\alpha_{12/13}$, that capture broad properties of downstream signaling (e.g., adenylate cyclase activation by $G\alpha_s$) (Wettschureck and Offermanns, 2005). In general, each of the hundreds of mammalian GPCRs couple with more than one G-protein giving each a distinct coupling profile (Harding et al., 2018), or signature, which evokes a unique cellular response. Determining these GPCR profiles is critical to understanding their biology and pharmacology.

Pharmaceutical interest in GPCRs has prompted many efforts during the last decades to determine both their ligands and signaling (Hauser et al., 2018). Among approximately 360 non-sensory GPCR genes encoded in the human genome, one-third are still labelled as orphans to reflect the fact that either ligands and/or signaling are unknown (Harding et al., 2018). Previous efforts to uncover signaling profiles have been laborious and not standardized, yet tended to identify only the subfamily or signaling outcome (e.g. $Ca^{2+}$, cAMP, inositol phosphate, Rho activation), rather than the specific $G\alpha$ subunit binding event (Thomsen et al., 2005). Although this has led a collection of data on GPCR ligands and signaling exemplified in the IUPHAR/BPS Guide to Pharmacology (GtoPdb) (Harding et al., 2018), these databases have issues with mixed quality of G-protein coupling data as well as lack of "negative" coupling information. Certain G-proteins are still comparatively understudied in terms of their GPCR partners, particularly $G_{12/13}$, which signal principally through Rho GTPases. Moreover, for the majority of well-studied receptors, only the primary (i.e. the most prominent) coupling is known, with secondary couplings known only for a minority. Yet, this G-protein coupling information is limited to binary (primary coupling and not stated) or tertiary (primary, secondary couplings and not stated) scoring and fails to provide quantitative data sufficient to achieve successful bioinformatic analyses including GPCR residues involving G-protein coupling selectivity.

Efforts to predict coupling on the basis of sequence features have been made to complement the absence of a complete picture of G-protein signaling, especially for $G_{12/13}$ coupling as well as orphan GPCRs (Sgourakis et al., 2005b; Yabuki et al., 2005). In case of $G_{12/13}$, owing to limited availability of signaling assays, coupling information on this class of G-proteins is incomplete. In addition, for orphan GPCRs, which lack pharmacological compounds to activate receptors, an accurate signaling prediction is desired to investigate not only coupling information, but also ligand identification to be investigated. Although many methods have been employed, previous researches generally sought to identify broad sequence properties at particular sites on the sequences that are indicative of a particular coupling subgroup. These methods have met with mixed success, and usually following poorer performances for $G_{12/13}$ coupling prediction.

Despite many advances in the understanding of GPCRs, the mechanisms by which they specifically signal through G-proteins remain poorly understood.

Thus, there are still needs in the field of GPCR signalling to provide an improved method for determining a coupling probability between a G-protein and a G-protein coupled receptor (GPCR), an improved method for designing a G-protein coupled receptor (GPCR) with a predetermined G-protein coupling profile, and an alternative method for determining dissociation of a $G\alpha$ subunit from $G\beta\gamma$ subunits of a G-protein in view of GPCR ligand induced interaction.

In particular for pharmaceutical drug development, there also exists a need in providing a GPCR, which is designed to be exclusively activated by a designer drug (Designer Receptor Exclusively Activated by Designer Drugs (DREADD)). In addition, there exists a need in providing an optimized amino acid sequence for determining coupling or no coupling between G-protein and G-protein coupled receptor (GPCR), preferably a DREADD, mediated by a GPCR ligand in a cell based assay.

SUMMARY OF INVENTION

The aforementioned needs are met in part or all by means of the claimed inventive subject matter. Preferred embodiments are in particular described in the dependent claims, the detailed description, the sequence listing and/or the accompanying figures. The inventive aspects may comprise—in case it is reasonable for a person skilled in the art—any possible combination of the different preferred inventive embodiments as set out hereinafter including the detailed description, the experimental section, the sequence listing and/or the accompanied figures.

Accordingly, a first aspect of the invention relates to a computer-implemented method for determining a probability of coupling or no coupling between a G-protein and a G-protein coupled receptor (GPCR). In other words, the first aspect of the invention acts as a predictor for GPCR/G-protein couplings or no couplings. Therefore, the inventive method of the first aspect is synonymously referred to as (inventive) predictor, if not otherwise stated. The inventive predictor can be used for a host of biological and pharmaceutical applications.

The inventive predictor is improved over the prior art predictor of Sgourakis et al., 2005b; Yabuki et al., 2005, as it can—in addition to predicting the GPCR/G-protein coupling probability—also predict the no coupling propability. Furthermore, the inventive predictor shows an increased sensitivity of predicting the GPCR/G-protein coupling, in particular GPCR/G-protein coupling selectivity.

The method/predictor of the first inventive aspect comprises or consists of the following steps:

Method Step A:

a. Providing amino acid sequence data and/or three dimensional (3D) structural data of i. one or more G-proteins and one or more GPCRs known to couple as a G-protein/GPCR complex and ii. one or more G-proteins and one or more GPCRs known to not couple as a G-protein/GPCR complex.

In other words, acid sequence data and/or three dimensional (3D) structural data, preferably acid sequence data and optionally three dimensional (3D) structural data of the one or more G-proteins and GPCRs according to i) and ii) are grouped into coupled and uncoupled G-protein/GPCR complexes.

According to a preferred embodiment of the method step a) the amino acid sequence data and/or 3D structural data of the G-protein is provided for at least part of one or more of G-protein sub-families $G_s$, $G_{i/o}$, $G_{q/11}$, and $G_{12/13}$, preferably at least part of the α subunit of one or more of G-protein sub-families $G_s$, $G_{i/o}$, $G_{q/11}$, and $G_{12/13}$. The provision of data for G-protein sub-families, in particular the α subunit of one or more of G-protein sub-families $G_s$, $G_{i/o}$, $G_{q/11}$, and $G_{12/13}$ allows more precise prediction for G-protein sub-families. In addition or alternatively, the the amino acid sequence data and/or 3D structural data of the GPCR is preferably at least provided for part of the amino acid sequence data and/or 3D structural data of Class A GPCRs, more preferably wherein the part of the Class A GPCRs comprises or consists of at least part of the amino acid sequence data and/or 3D structural data of i. one or more of the seven transmembrane bundle (7TM) features, such as transmembrane bundle 1 (TM1), transmembrane bundle 2 (TM2), transmembrane bundle 3 (TM3), transmembrane bundle 4 (TM4), transmembrane bundle 5 (TM5), transmembrane bundle 6 (TM6), and transmembrane bundle 7 (TM7), more preferably TM3, TM5, and TM6, and/or ii. one or more of extra 7TM features, such as N-terminal, one or more extracellular loops (ECL), one or more intracellular loops (ICL), and/or C-terminal region, more preferably intracellular loop 3 (ICL3), and C-terminal region.

The above amino acid sequence data and/or 3D structural data of the seven transmembrane bundle (7TM) or extra 7TM of GPCRs are relevant for interactions with the G-protein.

According to a further preferred embodiment of the present invention, the amino acid sequence data and/or three dimensional (3D) structural data for of step a) comprises i) at least for one given G-protein data set a set of data of two or more respective coupling GPCRs and/or two or more respective uncoupling GPCRs and/or ii) at least for one given GPCR data set a set of data of two or more respective coupling G-proteins and/or two or more respective uncoupling G-proteins. In other words, the preferred embodiment provides not only primary, but also secondary, tertiary etc. coupling G-protein/GPCR data. Such data provision increases the sensitivity of the inventive predictor.

Method Step B:

b. Statistically aligning the amino acid sequence and/or the 3D structural data of the G-protein with the GPCR of the respective coupled or uncoupled G-protein/GPCR complex provided in step a) in order to determine one or more amino acid residues and/or one or more structural composition features found to be statistically significantly associated with a coupled G-protein/GPCR complex or with an uncoupled G-protein/GPCR complex, and statistically assigning a coupling or uncoupling probability to the determined amino acid residues and/or structural composition features.

In other words, the significantly aligned one or more amino acid residues and/or one or more structural composition features are grouped into coupled or uncoupled G-protein/GPCR complex groups.

As the statistically determined amino acid residues and/or structural composition features are statistically significantly associated with a coupled G-protein/GPCR complex or with an uncoupled G-protein/GPCR complex, amino acid residues and/or structural composition features not statistically significantly associated with a coupled G-protein/GPCR complex or with an uncoupled G-protein/GPCR complex are in general not used for statistically assigning the coupling or uncoupling probability. Furthermore, the assignment of the coupling or uncoupling probability in generally depends on the p-value; a p-value of greater or equal 0.5 assigns a coupling probability and a p-value of less than 0.5 assigns a uncoupling probability for the respectively determined amino acid residues and/or structural composition features.

According to a preferred embodiment, the statistical alignment and assignment of coupling or uncoupling probability according to step b) uses a Hidden Markov Model (HMM) profile, which in particular allows more sequences to be significantly identified.

Method Step C:

c. Training a machine learning classifier using the coupling or uncoupling probabilities assigned to the one or more amino acid residues and/or one or more structural composition features of step b) in order to create a predictor for determining a probability of coupling or no coupling between a G-protein and a G-protein coupled receptor (GPCR).

In other words, the assigned coupling or uncoupling probabilities of method step b) are classified in step c) by comparing the probabilities in relation to each other.

As an example, a logistic regression is used in the machine learning prediction of step c).

According to a preferred embodiment, the training step c) comprises a step of comparing the statistical alignment and probability of coupling or uncoupling and assigning weight for coupling or uncoupling to the respective significant coupling and/or uncoupling amino acid residues and/or structural composition features, more preferably in relation with a respective coupled or uncoupled G-protein/GPCR complex. The advantage of assigning respective weights to the probabilities results in an increased selectivity of predicting coupling or uncoupling of query G-proteins or query GPCRs with corresponding coupling partners.

Method Step D:

d. Providing an amino acid sequence and/or 3D structural data of a query GPCR and applying the trained machine learning predictor of step c) in order to determine a probability that the query GPCR couples or uncouples to a predetermined G-protein.

In other words, method step D relates to input data for the machine learning predictor of step c) comprising a query GPCR (synonym: GPCR of interest) and predicting in relation to the classification of probabilities a G-protein/GPCR profile, which means that the query GPCR couples or uncouples with a certain probability to the predetermined G-proteins.

Method Step E:

e. Providing an amino acid sequence and/or 3D structural data of a query G-protein and applying the trained machine learning predictor of step c) in order to determine a probability that the query G-protein couples or uncouples to a predetermined GPCR.

In addition to method step D or alternative thereto, the inventive method relates to input data for the machine learning predictor of step c) comprising a query G-protein (synonym: G-protein of interest) and predicting in relation to the classification of probabilities a G-protein/GPCR profile, which means that the query GPCR couples or uncouples with a certain probability to the predetermined GPCR.

The inventive predictor can comprise—in case it is reasonable for a person skilled in the art—any possible feature combination of the different inventive embodiments including preferred and alternative features. Moreover, the embodiments of the inventive predictor can comprise—in case it is reasonable for a person skilled in the art—any possible feature combination with singular or combined features of embodiments disclosed in the detailed description, the experimental section, sequence listing and/or figures.

According to the second aspect of the present invention, a computer-implemented method for designing a G-protein coupled receptor (GPCR) with a predetermined G-protein coupling profile is provided. In other words, the second aspect of the invention acts as a designer for GPCR/G-protein couplings or no couplings. Therefore, the inventive method of the second aspect is synonymously referred to as (inventive) designer, if not otherwise stated. The inventive designer can be used for a host of biological and pharmaceutical applications.

The inventive designer is improved over the prior art predictor of Sgourakis et al., 2005b; Yabuki et al., 2005, as it can optimize the designed GPCR sequence in view of a predetermined G-protein/GPCR coupling profile and, thus, shows an increased sensitivity of designing a GPCR having a predetermined G-protein/GPCR coupling profile.

The method/designer of the second inventive aspect comprises or consists of the method steps a) to d) already discussed with respect to embodiments of the first aspect of the present invention, namely the predictor. All inventive embodiments including preferred features and feature combinations disclosed with respect to the first aspect of the present invention are also applicable to embodiments and preferred embodiments of the second aspect of the invention, namely the designer.

In addition thereto, the method/designer of the second inventive aspect method step d) further comprises designing a GPCR with a predetermined G-protein coupling profile by amending the amino acid sequence and/or the 3D structural data of the query GPCR in order to optimize the probability that the GPCR couples to the predetermined G-protein and optionally to optimize the probability to not couple to other G-proteins.

In other words, the amino acid sequence and/or a 3D structural feature data of the query GPCR is optimized for a predetermined GPCR/G-protein coupling profile using the machine learning classifier of step c). According to a preferred embodiment the query GPCR is optimized for a predetermined GPCR/G-protein coupling profile of G-protein subfamilies in order to increase the sensitivity.

According to a further preferred embodiment, the inventive designer is used to design a Designer Receptor Exclusively Activated by Designer Drugs (DREADD).

The designer of the second aspect of the present invention can comprise—in case it is reasonable for a person skilled in the art—any possible feature combination of the different inventive embodiments.

According to a third aspect of the present invention, a computational data processing system is provided comprising data processing system having one or more processors coupled to a memory, having inputting and having outputting means. The data processing system of the third inventive aspect is configured to a. determine a probability of coupling or no coupling between a G-protein and a G-protein coupled receptor (GPCR) according to any one of the feature combinations of the inventive predictor of the first aspect of the present invention, or b. design a G-protein coupled receptor (GPCR) with a predetermined G-protein coupling profile according to any one of the feature combinations of the inventive designer of the second aspect of the present invention.

In general, the inventive system can at least in part be installed on a local server or on a webserver, in particular a cloud based webserver. An end user may use this inventive system via a suitable browser or software application to be downloadable on an end user device or another device connectable to the end user device.

The inventive data communication system can comprise—in case it is reasonable for a person skilled in the art—any possible feature combination of the different inventive embodiments including preferred and alternative features of the inventive predictor and inventive designer of the first and second inventive aspects, respectively. Moreover, the inventive embodiments can comprise—in case it is reasonable for a person skilled in the art—any possible feature combination with singular or combined features of embodiments disclosed in the detailed description, the experimental section, sequence listing and/or figures.

According to a fourth aspect of the present invention, the inventive predictor, the inventive designer and/or the inventive data processing system can be used together with one or more further data sets relating to the same or other GPCR signaling pathways selected from the group consisting of genomic sequencing, transcriptomics, proteomics, and/or metabolomics in quantification of GPCR downstream signaling in normal and/or pathological conditions.

The use of the fourth aspect of the present invention can comprise—in case it is reasonable for a person skilled in the art—any possible feature combination of the different inventive embodiments including preferred and alternative features of the inventive predictor, the inventive designer and the inventive data processing system of the first, second and third inventive aspects, respectively. Moreover, the inventive embodiments can comprise—in case it is reasonable for a person skilled in the art—any possible feature combination with singular or combined features of embodiments disclosed in the detailed description, the experimental section, sequence listing and/or figures.

According to a fifth aspect of the present invention, a Designer Receptor Exclusively Activated by Designer Drugs (DREADD) is provided, wherein the DREADD is a G-protein coupled receptor (GPCR). The DREADD may be obtainable by the inventive designer method according to the second aspect of the present invention. Such a designed DREADD is in particular relevant, as it can be designed for optimized G-protein sub-family coupling profile, preferably comprising a $G_{12}$-specific/GPCR coupling profile. According to one preferred embodiment the DREADD is a $G_{12}$-specific GPCR responding to a ligand and comprises or consists of an amino acid sequence according to SEQ ID Nos: 2, 3, or 4 or an amino acid sequence having at least 90, 91, 92, 93, 94, 95, 96, 97, 98, 99% sequence identity to SEQ ID Nos: 2, 3, or 4. The inventive DREADDs may be used also in other aspects of the present invention, such as in assays used for biologic and pharmaceutical developments, in particular the inventive assays as set out below in the sixth aspect of the present invention. The inventive DREADDs are in particular preferred when profiling a $G_{12}$ coupling to a GPCR.

The DREADD of the fifth aspect of the present invention can comprise—in case it is reasonable for a person skilled in the art—any possible feature combination of the different inventive embodiments including preferred and alternative features of the inventive predictor, the inventive designer and the inventive data processing system of the first, second and third inventive aspects, respectively. Moreover, the inventive embodiments can comprise—in case it is reasonable for a person skilled in the art—any possible feature combination with singular or combined features of embodiments disclosed in the detailed description, the experimental section, sequence listing and/or figures.

According to a sixth aspect of the present invention, a method for determining coupling or no coupling between G-protein and G-protein coupled receptor (GPCR) mediated by a GPCR ligand in a cell is provided. In other words, a cell or membrane based assay for determining a G-protein/GPCR coupling profile is provided. Therefore, the inventive method of the sixth aspect may synonymously be referred to as inventive assays. The inventive assay is characterized in that it uses a split luciferase complement system (NanoBiT). The NanoBiT system itself (a pair of large fragment of split luciferase (LgBiT) sequences and small fragment of split luciferase (SmBiT) sequences along with a 15-amino acid linker) was established by Promega (Dixon et al. ACS chemical biology 11, 400-408 (2016). PMID 26569370) and comprises the following sequences:

the large fragment of split luciferase (LgBiT) consists of an amino acid sequence according to SEQ ID No: 49
the small fragment of split luciferase (SmBiT) consists of an amino acid sequence according to SEQ ID No: 50
the flexible linker consists of an amino acid sequence according to SEQ ID No: 51

According to the present invention, in particular the inventive assays, the inventors generated LgBiT- or SmBiT-fused chimeric proteins as set out in more detail below and showed that these engineered chimeric proteins are useful for analyzing G protein activation in cells (and also in membrane preparation) and thereby determining coupling or no coupling between G-protein and G-protein coupled receptor (GPCR).

The inventive cell assay comprises or consists of the following assay method steps:

Assay Method Step A:

a. Providing a dissociation cell assay of a Gα subunit from Gβγ subunits of a chimeric G-protein comprising the GPCR, wherein the chimeric G-protein is expressed in the cell comprising a large fragment of split luciferase (LgBiT), preferably inserted with a flexible linker amino acid sequence into the helical domain, more preferably between the αA and αB helices or αB and αC, of the Gα subunit of the chimeric G-protein and a small fragment of the split luciferase (SmBiT), preferably fused with a flexible linker amino acid sequence to an N-terminal region of the Gβ and/or Gγ subunit of the chimeric G-protein.

According to a preferred embodiment of the dissociation cell assay the chimeric G-protein subunits comprise or consist of the following sequences:

the Gα subunit of the chimeric G-protein comprises or consists of an amino acid sequence according to any one of SEQ ID Nos: 5 to 15 and 33 to 41 or an amino acid sequence having at least 90, 91, 92, 93, 94, 95, 96, 97, 98, 99% sequence identity to any one of SEQ ID Nos: 5 to 15 and 33 to 41, and/or the Gβ subunit of the chimeric G-protein comprises or consists of an amino acid sequence according to any one of SEQ ID Nos: 16 to 20, and 42 or an amino acid sequence having at least 90, 91, 92, 93, 94, 95, 96, 97, 98, 99% sequence identity to any one of SEQ ID Nos: 16 to 20, and 42, and/or the Gγ subunit of the chimeric G-protein comprises or consists of an amino acid sequence according to any one of SEQ ID Nos: 21 to 32, 43 and 44 or an amino acid sequence having at least 90, 91, 92, 93, 94, 95, 96, 97, 98, 99% sequence identity to any one of SEQ ID Nos: 21 to 32, 43 and 44.

Or Assay Method Step B:

b. Providing a Ras homolog gene family, member A (RhoA) GTPase activation cell assay comprising chimeric RhoA GTPase and a chimeric PKC-related serine/threonine-protein kinase N1 (PKN1), wherein the chimeric RhoA GTPase is expressed in the cell comprising a large fragment of split luciferase (LgBiT), preferably fused with a flexible linker amino acid sequence to the N-terminal region of the chimeric RhoA GTPase, and wherein the PKN1 is expressed in the cell comprising a small fragment of the split luciferase (SmBiT), preferably fused with a flexible linker amino acid sequence to the N-terminal region.

The RhoA GTPase activation cell assay is in particular advantageous when determining the $G_{12/13}$ G-protein subunit with GPCR. According to a further preferred embodiment of the RhoA GTPase activation cell assay the chimeric RhoA GTPase and/or chimeric PKN1 comprise or consist of the following sequences:

the chimeric RhoA GTPase comprises or consists of an amino acid sequence according to SEQ ID No: 55 or an amino acid sequence having at least 90, 91, 92, 93, 94, 95, 96, 97, 98, 99% sequence identity to SEQ ID No: 55, and/or the chimeric PKC-related serine/threonine-protein kinase N1 (PKN1) comprises or consists of an amino acid sequence according to SEQ ID No: 56 or an amino acid sequence having at least 90, 91, 92, 93, 94, 95, 96, 97, 98, 99% sequence identity to SEQ ID No: 56.

Or Assay Method Step C:

c. Providing inositole triphosphate (IP3) accumulation cell assay comprising a chimeric inositole triphosphate receptor (IP3R), wherein the chimeric IP3R is expressed in the cell comprising a large fragment of split luciferase (LgBiT), preferably fused with a flexible linker amino acid sequence to the N-terminal region of the IP3R and comprising a small fragment of the split luciferase (SmBiT) spaced from the LgBiT, preferably fused with a flexible linker amino acid sequence to the C-terminal region of the IP3R.

According to a preferred embodiment of the IP3 accumulation cell assay the chimeric IP3R, preferably IP3R2 comprises or consists of the following sequence:

the chimeric inositole triphosphate receptor (IP3R) is based on the inositol triphosphate receptor 2 (IP3R2) and preferably comprises or consists of an amino acid sequence according to SEQ ID No: 57 or an amino acid sequence having at least 90, 91, 92, 93, 94, 95, 96, 97, 98, 99% sequence identity to SEQ ID No: 57, and/or OR Assay Method Step D:

d. Providing Gq and 1-phosphatidylinositol-4,5-bisphosphate phospholipase Cbeta (PLCβ) interaction cell assay comprising a chimeric Gα subunit from the Gαq family and a chimeric PLCβ, wherein the chimeric Gαq subunit is expressed in the cell comprising a large fragment of split luciferase (LgBiT), preferably inserted with flexible linker amino acid sequences into the helical domain, more preferably between the αA and αB or αB and αC helices, of the Gαq subunit of the chimeric G-protein, and wherein the chimeric PLCβ is expressed in the cell comprising a small fragment of the split luciferase (SmBiT), preferably fused with a flexible linker amino acid sequence to the N-terminal region.

The Gq-PLCβ interaction assay is in particular advantageous when determining the Gq/11 G-protein subunit with GPCR. According to another preferred embodiment of the Gq-PLCβ interaction cell assay the chimeric Gαq subunit and/or chimeric PLCβ comprise or consist of the following sequences:

the chimeric Gα subunit comprises or consists of an amino acid sequence according to SEQ ID No: 10-13 and 38-41 or an amino acid sequence having at least 90, 91, 92, 93, 94, 95, 96, 97, 98, 99% sequence identity to SEQ ID No: 10-13 and 38-41, and/or the chimeric PLCβ comprises or consists of an amino acid sequence according to SEQ ID No: 45-48 or an amino acid sequence having at least 90, 91, 92, 93, 94, 95, 96, 97, 98, 99% sequence identity to SEQ ID No: 45-48.

And

Assay Method Step E:

e. Contacting the cell of assay method step a), b), c) or d) with a luciferase substrate.

In other words, the cells comprised in the respective assays of method steps a), b) or c) are loaded with a suitable amount of luciferase. As preferred embodiment, the luciferase substrate is coelenterazine (CTZ) or a comparable luciferase substrate.

The associated chimeric G-protein subunits of the inventive G-protein dissociation assay (Assay Method Step A) form a bioluminescence active construct in presence of a luciferase substrate.

The dissociated chimeric RoA GTPase and chimeric PKN1 of the inventive RhoA GTPase activation assay (Assay Method Step B) are bioluminescence inactive in presence of a luciferase substrate.

The chimeric IP3R of the inventive IP3 accumulation cell assay (Assay Method Step C) is as such bioluminescence inactive in presence of a luciferase substrate.

The associated chimeric Gαq subunit and the chimeric PLCβ protein of the inventive Gq-PLCβ interaction assay form a bioluminescence active construct.

And Assay Method Step F:

f. Contacting the cell of step e) with a ligand of the GPCR.

In other words, the cells of the inventive assays are incubated with a suitable ligand for each assay in order to activate the signaling pathway of the respective GPCR.

In case a suitable GPCR ligand binds to the GPCR of the inventive G-protein dissociation assay, coupling of the GPCR with the Gα subunit of the chimeric G-protein is mediated and dissociation of the Gα subunit from Gβγ subunits of the chimeric G-protein is initiated. Upon dissociation of the Gα subunit from Gβγ subunits of the chimeric G-protein guanosine diphosphate (GDP) is released from the Gα subunit and guanosine triphosphate (GTP) is bound to the Gα subunit. The dissociated chimeric G-protein is bioluminescence inactive (see also FIG. 11A). In case a suitable GPCR ligand binds to the GPCR of the inventive RhoA GTPase activation cell assay, activation of RhoGTPase nucleotide exchange factors (RhoGEFs) is mediated. Upon activation of the RhoGEFs GDP is released from the chimeric RhoA GTPase and GTP is bound thereto. This exchange facilitates the coupling of the chimeric RhoA GTPase and the chimeric PKN1. Upon coupling of the chimeric RhoA GTPase and the chimeric PKN1 the LgBiT and SmBiT form a bioluminescent active construct (see also FIG. 13A).

In case a suitable GPCR ligand binds to the GPCR of an IP3R activation cell assay, 1-phosphatidylinositol-4,5-bisphosphate phosphodiesterase beta (PLCβ) is activated mediating the coupling of IP3 with IP3R, preferably IP3R2. Upon coupling, the SmBiT and LgBiT fragments associate to form a bioluminescence active construct (see also FIG. 14D).

In case a suitable GPCR ligand binds to the GPCR of an Gq-PLCβ interaction cell assay, a chimeric Gα subunit from the Gαq family interacts with the chimeric 1-phosphatidylinositol-4,5-bisphosphate phosphodiesterase beta (PLCβ). Upon binding, the SmBiT and LgBiT fragments associate to form a bioluminescence active construct (see also FIG. 16P).

And Assay Method Step G:

g. Measuring a bioluminescence signal of the cell of step f) and optionally the cell of step e).

The biolouminescence signal is measured in step f) of the inventive assays, wherein the bioluminescence signal corresponds to the formation of associated LgBiT and SmBiT fragments. Optionally the background fluorescence in step e) is additionally measured. Alternatively, reference fluorescence data may be provided in order to carry out step h).

And Assay Method Step H:

h. determining coupling or no coupling between G-protein and G-protein coupled receptor (GPCR) as a function of the measured bioluminescence signal in step f).

In other words, the higher the delta of signals measured in steps e) and f), the higher the probability of coupling. A threshold value may be used. Alternatively, the bioluminescence signal measured in step f) may be compared to an external reference signal value.

The inventive cell assays can comprise—in case it is reasonable for a person skilled in the art—any possible feature combination of the different inventive embodiments including preferred and alternative features. Moreover, the embodiments of the inventive cell assays can comprise—in case it is reasonable for a person skilled in the art—any possible feature combination with singular or combined features of embodiments disclosed in the detailed description, the experimental section, sequence listing and/or figures.

According to a seventh aspect of the present invention an amino acid sequence for determining coupling or no coupling between G-protein and G-protein coupled receptor (GPCR) mediated by a GPCR ligand in a cell based assay is provided, characterized in that the amino acid sequence is selected from a Gα subunit of the chimeric G-protein, which comprises or consists of an amino acid sequence according to any one of SEQ ID Nos: 5 to 15 and 33 to 41 or an amino acid sequence having at least 90, 91, 92, 93, 94, 95, 96, 97, 98, 99% sequence identity to any one of SEQ ID Nos: 5 to 15 and 33 to 41, and/or a Gβ subunit of the chimeric G-protein, which comprises or consists of an amino acid sequence according to any one of SEQ ID Nos: 16 to 20, and 42 or an amino acid sequence having at least 90, 91, 92, 93, 94, 95, 96, 97, 98, 99% sequence identity to any one of SEQ ID Nos: 16 to 20, and 42, and/or a Gγ subunit of the chimeric G-protein, which comprises or consists of an amino acid sequence according to any one of SEQ ID Nos: 21 to 32, 43 and 44 or an amino acid sequence having at least 90, 91, 92, 93, 94, 95, 96, 97, 98, 99% sequence identity to any one of SEQ ID Nos: 21 to 32, 43 and 44, and/or a chimeric RhoA GTPase, which comprises or consists of an amino acid sequence according to SEQ ID No: 55 or an amino acid sequence having at least 90, 91, 92, 93, 94, 95, 96, 97, 98, 99% sequence identity to SEQ ID No: 55, and/or a chimeric PKC-related serine/threonine-protein kinase N1 (PKN1), which comprises or consists of an amino acid sequence according to SEQ ID No: 56 or an amino acid sequence having at least 90, 91, 92, 93, 94, 95, 96, 97, 98, 99% sequence identity to SEQ ID No: 56, and/or a chimeric inositole triphosphate receptor (IP3R), which is based on the inositol triphosphate receptor 2 (IP3R2) and comprises or consists of an amino acid sequence according to SEQ ID No: 57 or an amino acid sequence having at least 90, 91, 92, 93, 94, 95, 96, 97, 98, 99% sequence identity to SEQ ID No: 57 and/or the chimeric 1-phosphatidylinositol-4,5-bisphosphate phospholipase Cbeta PLCβ, which comprises or consists of an amino acid sequence according to SEQ ID Nos: 45 to 48 or an amino acid sequence having at least 90, 91, 92, 93, 94, 95, 96, 97, 98, 99% sequence identity to SEQ ID Nos: 45 to 48.

Further aspects of the present invention relate to an inventive TGFα shedding assay, Active RhoA pulldown assay, $Ca^{2+}$ mobilization assay.

BRIEF DESCRIPTION OF DRAWINGS

Further aspects, characteristics and advantages of the invention will ensue from the following description of the embodiments with reference to the accompanying drawings, wherein FIG. 1 relates to chimeric G-protein-based TGFα shedding assay to probe interaction between an active GPCR and a C-terminal tail of a Gα subunit, wherein (A) represents a schematic description of the mechanism of the TGFα shedding assay.

(B) represents graphs of blunted TGFα shedding response in the HEK293 cells devoid of the $G_{q/11}$ and the $G_{12/13}$ subfamilies.

(C) represents schematic description of the chimeric G-protein-based TGFα shedding assay in $\Delta G_q/\Delta G_{12}$ cells.

(D) represents an overview on representative data for the chimeric G-protein-based assay.

Figure 2:
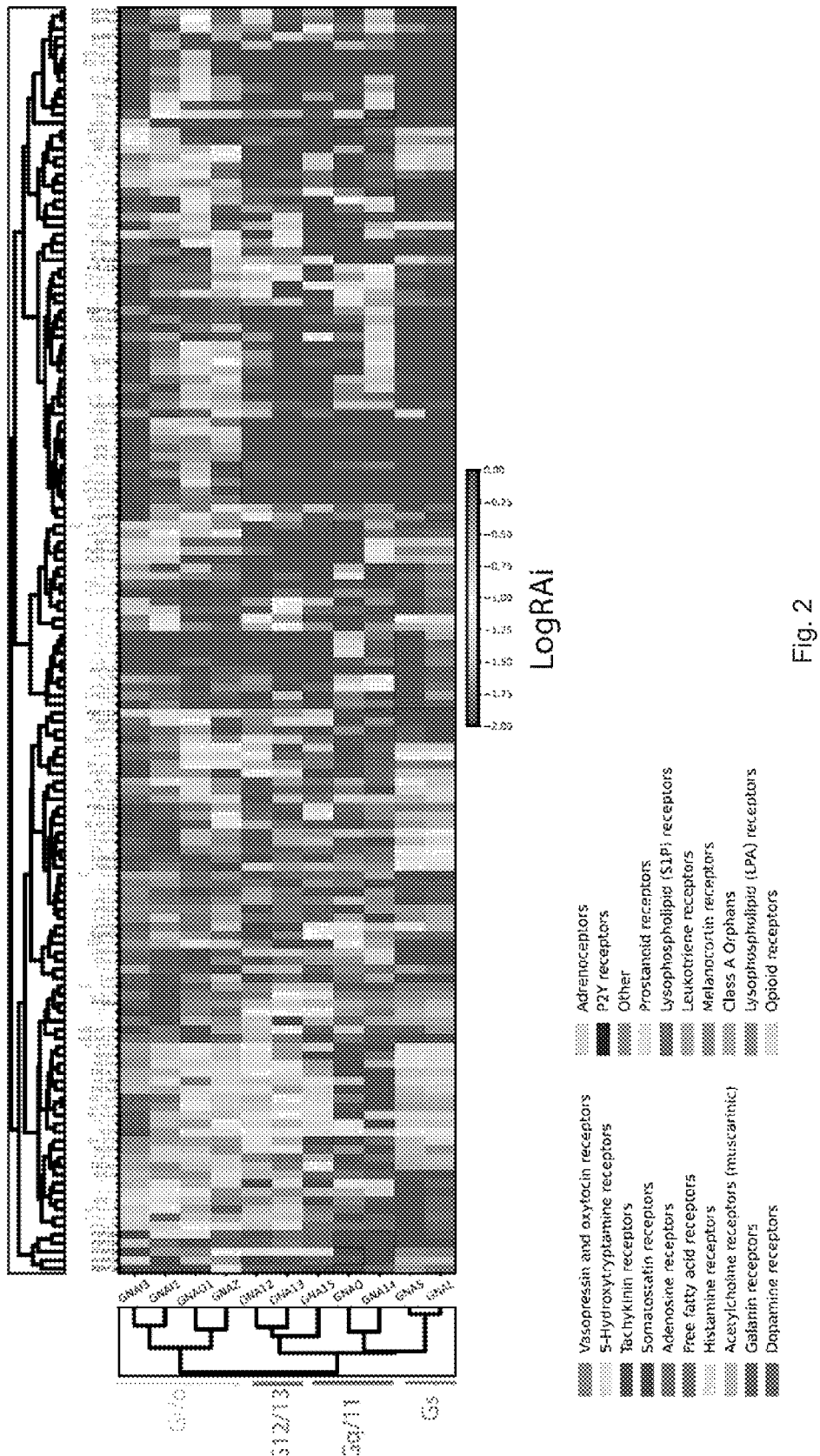

FIG. 2 represents signatures of G-protein coupling determined by the chimeric G-protein-based assay.

Figure 3:
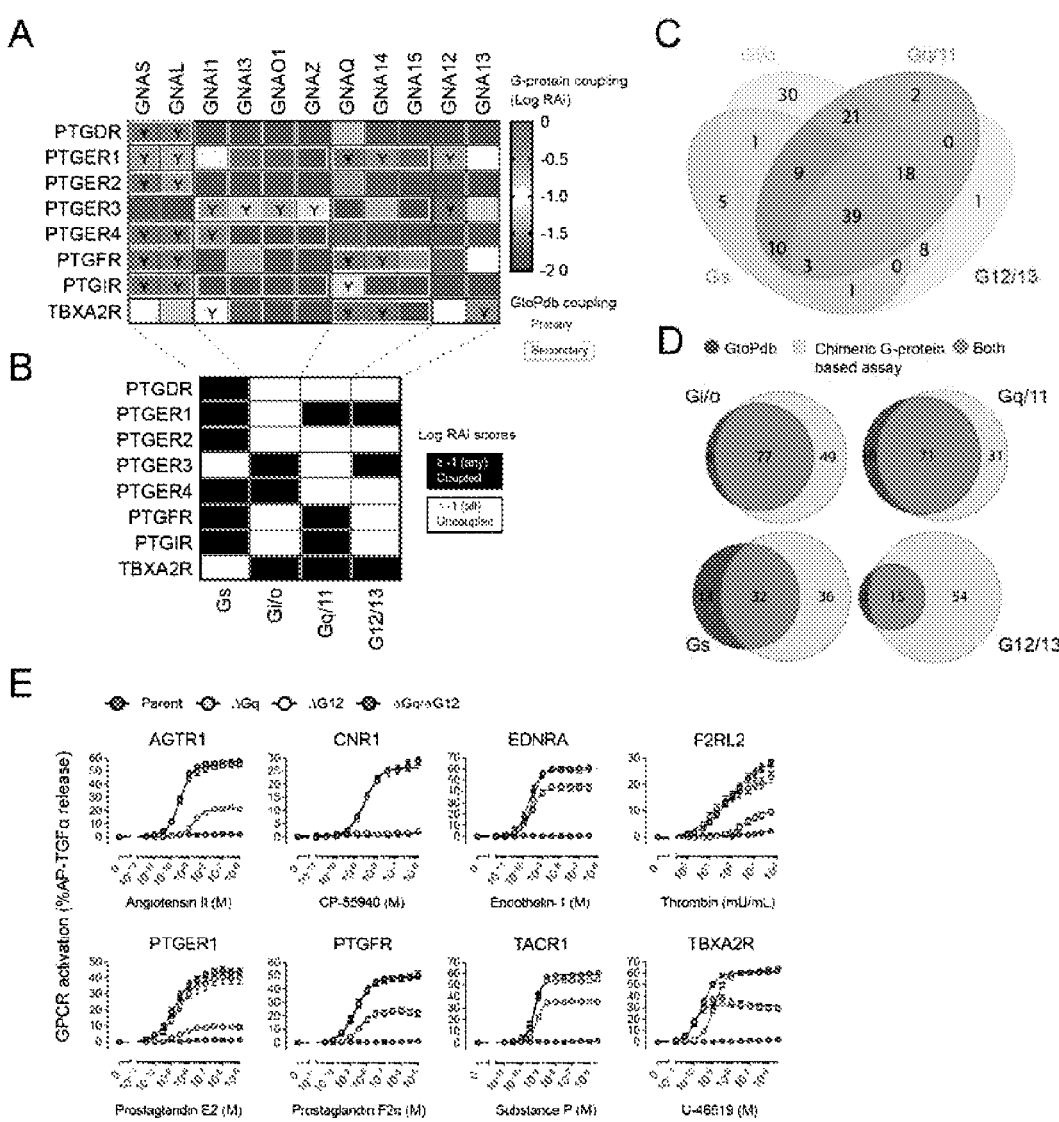

FIG. 3 relates to a comparison between dataset of the chimeric G-protein-based assay and GtoPdb and validation of $G_{12/13}$ signaling for the newly characterized GPCRs, wherein (A) represents a schematic classification of the LogRAi scores and its comparison with GtoPdb.

(B) represents a schematic view on combined binary coupling/non-coupling data for each of the four G-protein subfamilies.

(C) represents Venn diagrams with the numbers of receptors coupled to each G-protein subfamily in the chimeric G-protein-based assay (LogRAi≥−1).

(D) represents Venn diagrams of receptor couplings to the four G-protein families according to the chimeric G-protein-based assay (LogRAi≥−1) and GtoPdb.

(E) represents GPCRs that were identified as being coupled with $G_{12/13}$ by the chimeric G-protein-based assay were examined for their ability to engage and activate native, endogenous $G_{12/13}$ in HEK293 cells.

FIG. 4 relates to development of G-protein coupling predictor, wherein (A) represents a schematic workflow of the procedure: features are extracted from sub-alignments of coupled and uncoupled receptors to a particular G-protein; features are used to generate a training matrix which is employed to train a logistic regression model through a 5-fold cross validation procedure.

(B) represents a schematic overview on the final model tested on reported couplings not previously seen during training and compared to PredCouple.

(C) represents graphs on highly confident predicted couplings (coupling probability >0.9) for 61 Class A GPCRs lacking information about transduction from both GtoPdb or the chimeric G-protein-based TGFα shedding assay (black) vs. receptors with experimental coupling information (gray).

Figure 5:
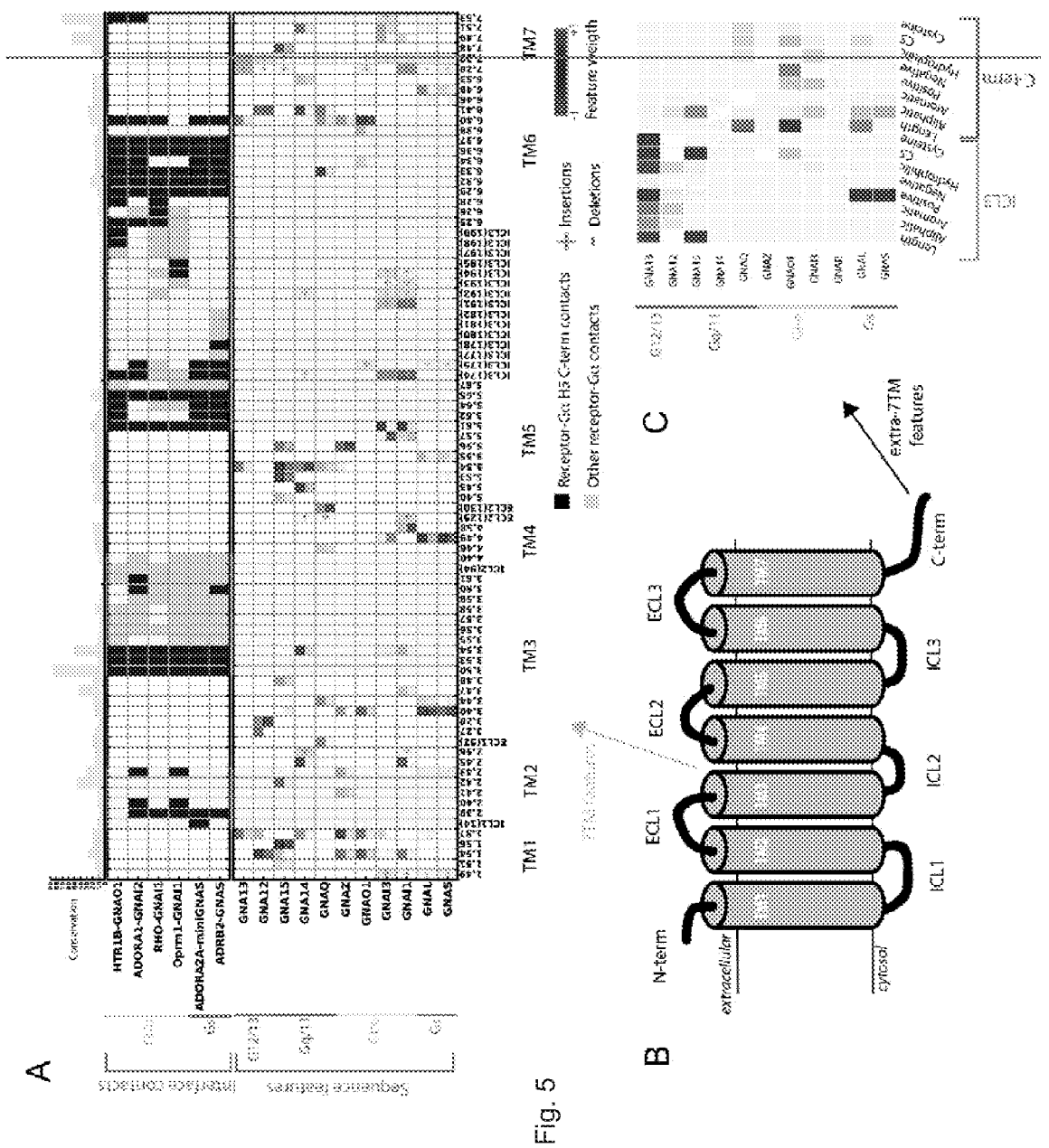

FIG. 5 relates to featured residues in GPCRs involved in G-protein coupling selectivity, wherein (A) represents a schematic overview on comparison of significant coupling features weights for the 11 G-proteins (bottom), interface contacts of 6 available GPCR-G-protein complexes (central) and 7TM domain position conservation (top).

(B) represents a schematic overview of the 7TM topology indicating the regions contributing to the features.

(C) represents a schematic overview on significant coupling feature weights for the 11 G-proteins (same color codes as in A) of extra-7TM features of ICL3 and C-term, including length and amino-acid composition.

Figure 6:
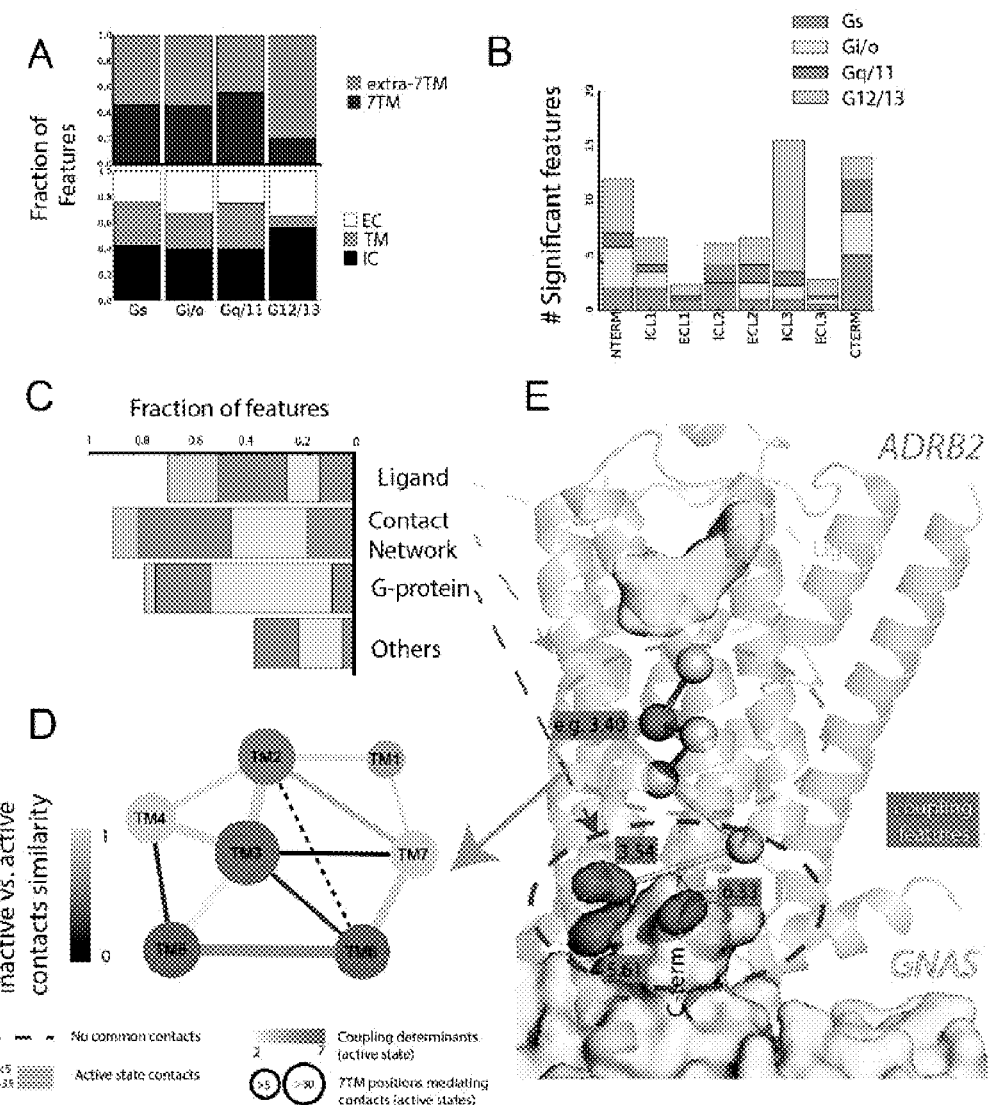

FIG. 6 relates to a functional analysis of residues linked to coupling selectivity, wherein (A) Upper panel represents: distribution of coupling feature fractions for intra- and extra-7TM portions. Lower panel represents: distribution of the coupling feature fractions within transmembrane sectors (i.e. extracellular—EC, transmembrane—TM, intracellular—IC).

(B) represents a graph on distribution of the fractions of coupling significant features outside of the 7TM bundle.

(C) represents a graph on distribution of coupling feature fractions (relative to the total number of positions of the same class) within functional sites (i.e. mediating either ligand/G-protein binding or intra-molecular contacts).

(D) represents a graph on intra-molecular contacts within 7TM helices.

(E) represents a three dimensional schematic view of the ADRB2-GNAS complex (PDB: 3SN6) with side chains of coupling features at G-protein-binding sites depicted as red surfaces.

Figure 7:
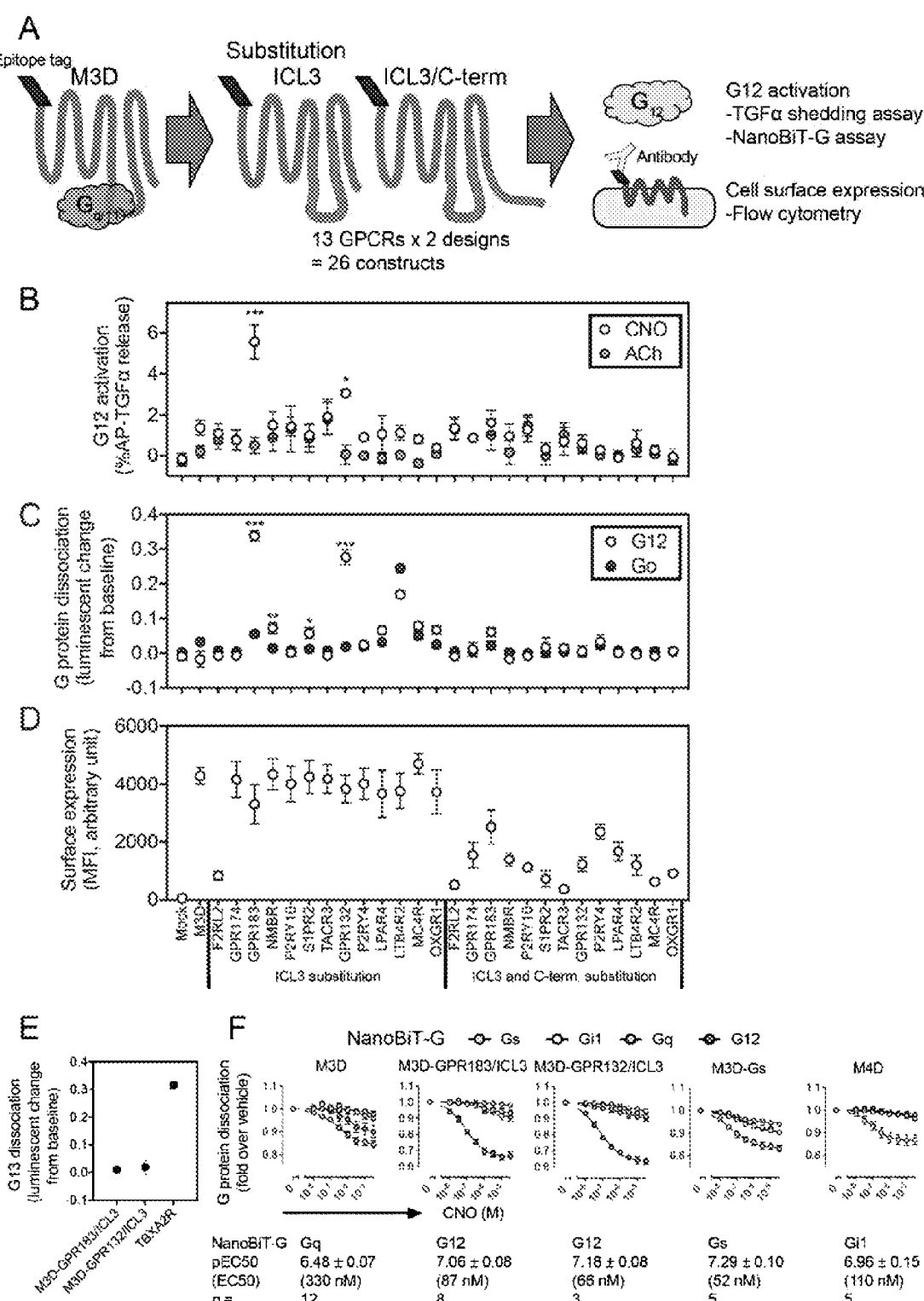

FIG. 7 relates to the generation of $G_{12}$-coupled designer GPCRs, wherein (A) represents a schematic view of generating and assessing ICL3- or ICL3/C-terminus-swapped constructs from $G_{q/11}$-coupled M3D.

(B-D) represent screening graphs of M3D-derived chimeric constructs.

(E) represents graphs on lack of $G_{13}$ activation by the new DREADD constructs.

(F) represents graphs on concentration-response curves for G-protein activation by DREADD constructs.

Figure 8:
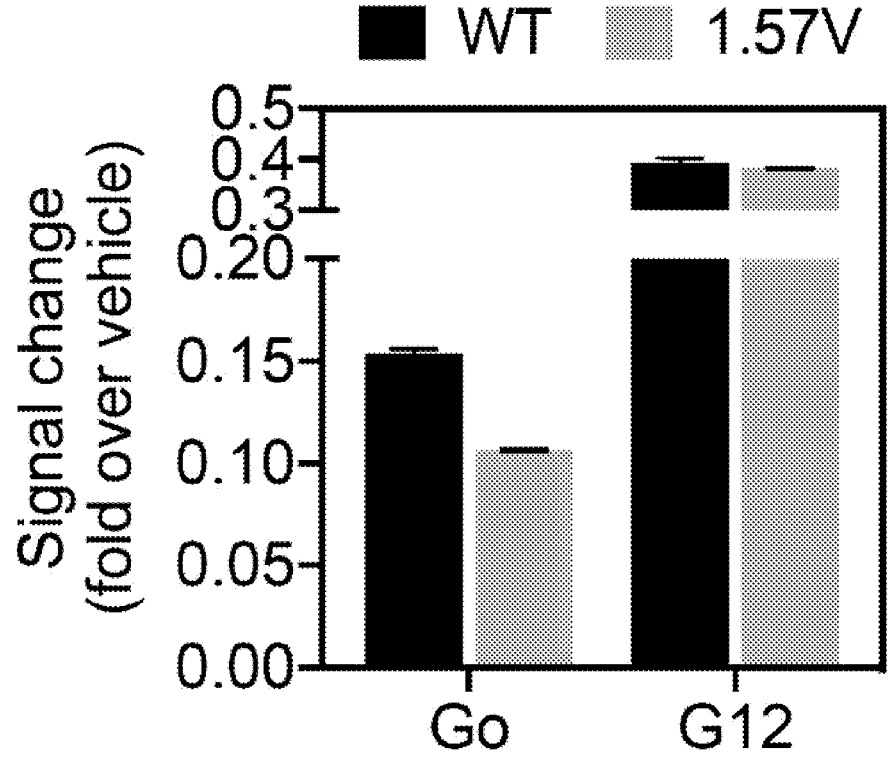

FIG. 8 relates to point mutation to enhance G-protein-coupling selectivity.

Figure 9:
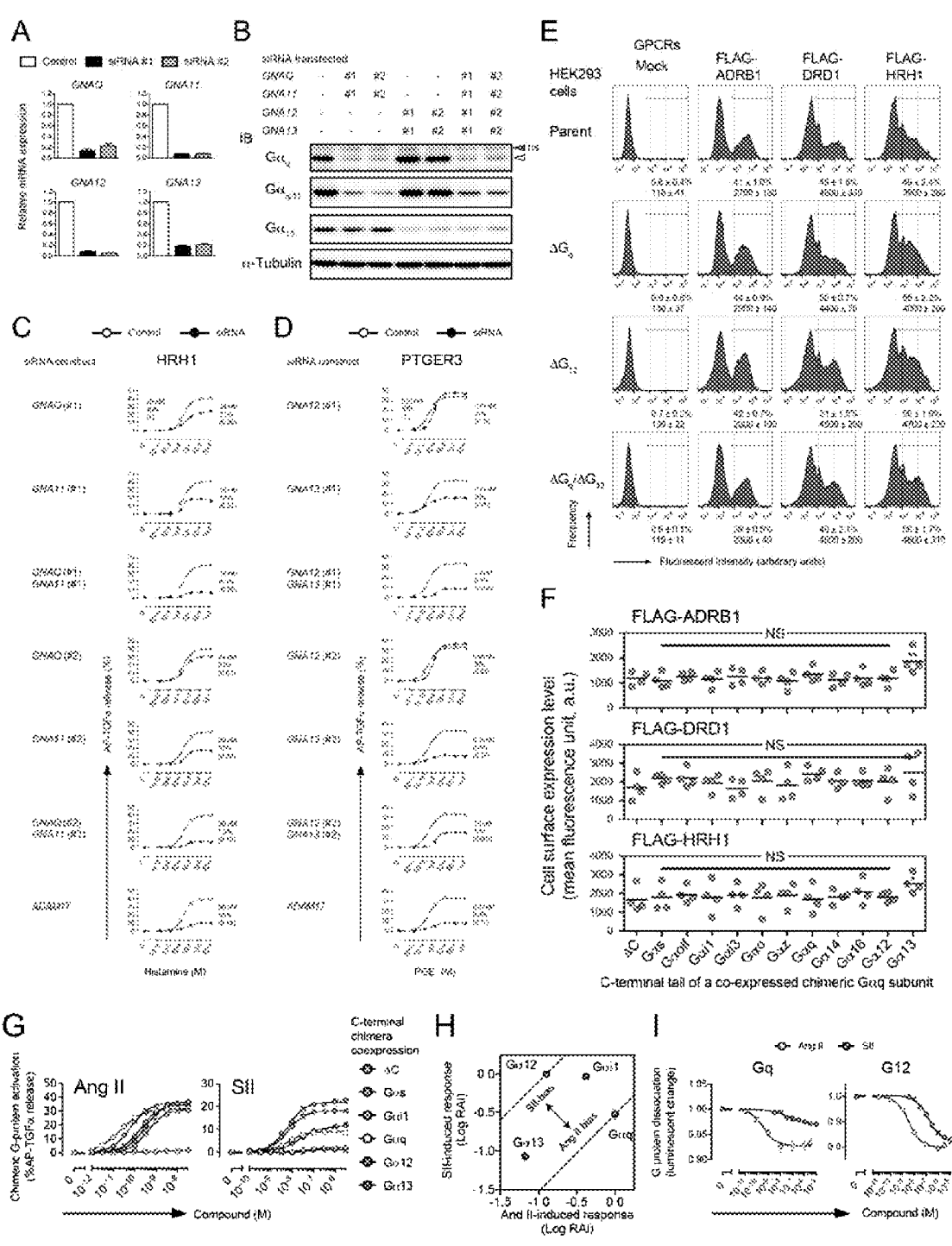

FIG. 9 relates to validation of the TGF$\alpha$ shedding assay, wherein (A) represents graphs on siRNA-mediated knockdown of mRNA expression.

(B) represents an overview siRNA-mediated knockdown at protein expression levels.

(C) represents graphs on knockdown of $G_{q/11}$ attenuates AP-TGF$\alpha$ release induced by $G_{q/11}$-coupled HRH1.

(D) represents graphs Knockdown of $G_{12/13}$ attenuates AP-TGF$\alpha$ release induced by $G_{12/13}$-coupled PTGER3.

(E) represents graphs on parental, $\Delta G_q$, $\Delta G_{12}$ and $\Delta G_q/\Delta G_{12}$ HEK293 cells were transiently transfected with a plasmid encoding N-terminally FLAG epitope-tagged GPCR (HRH1, ADRB1 or DRD1) or an empty plasmid (Mock).

(F) represents cell surface expression levels dependent on C-terminal region of a co-expressed chimeric $G\alpha_q$ subunit.

(G) represents graphs on concentration-response curves of AGTR1 for the endogenous ligand (Angiotensin II, AngII) and a biased agonist ([Sar$^1$-Ile$^4$-Ile$^8$] AngII, SII). G-protein signaling activity was assessed by the chimeric-G-protein-based assay.

(H) represents ligand bias plots.

(I) represents graphs on validation of SII bias toward $G_{12}$ by the NanoBiT-G-protein dissociation assay.

Figure 10:
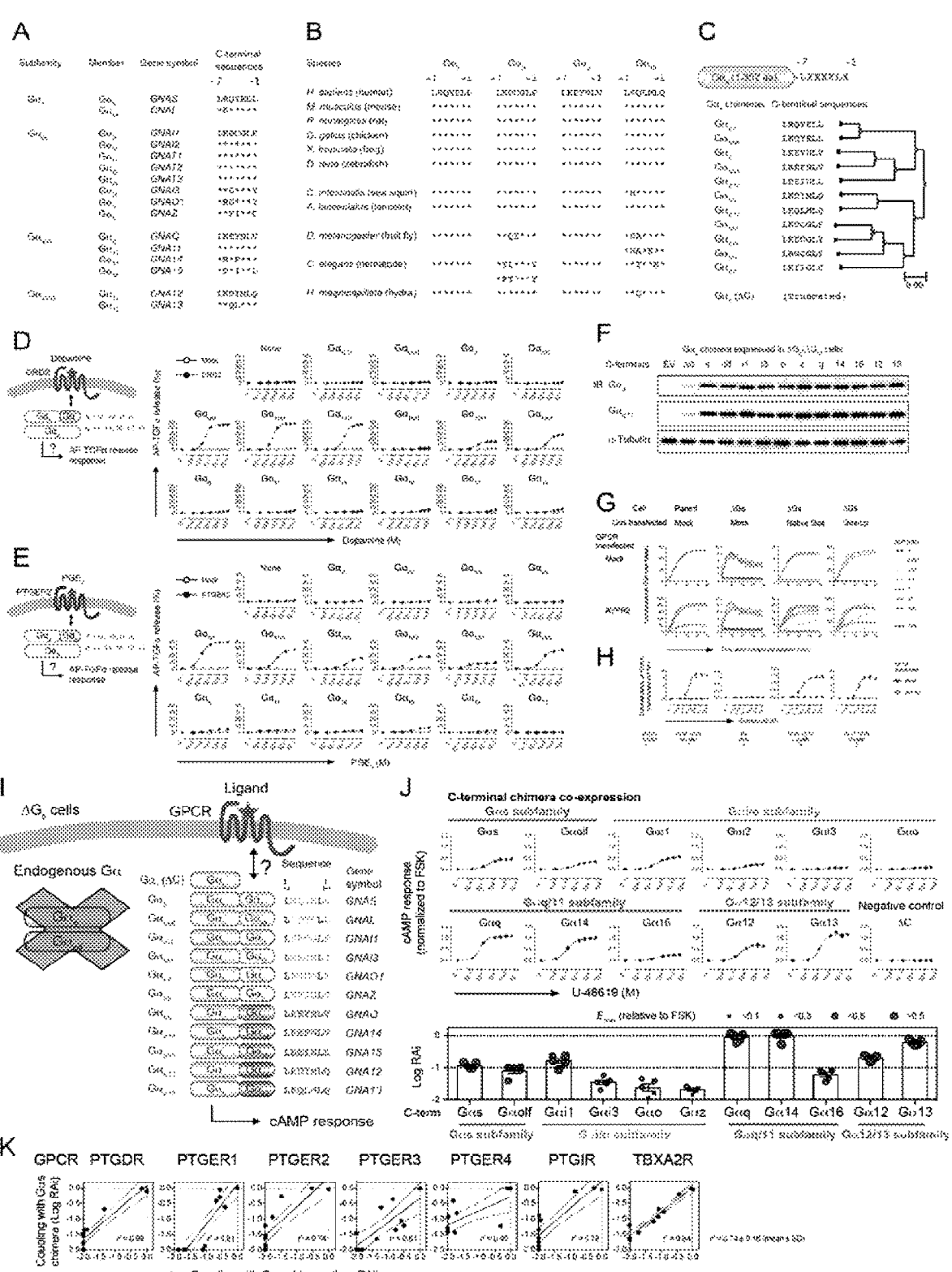

FIG. 10 relates to chimeric G$\alpha$ subunits and their activity for TGF$\alpha$ shedding and cAMP responses, wherein (A) represents an overview on seven C-terminal sequences (CGN numbering (Flock et al., 2015) of G.H5.20-G.H5.26) of G$\alpha$ subunits among the 16 human G$\alpha$ subunits.

(B) represents an overview on evolutionally conservation the seven C-terminal sequences of representative G$\alpha$ subunits from the four G-protein subfamilies.

(C) represents an overview on Chimeric G-proteins used in this study.

(D) represents graphs Capacity of G$\alpha$ subunits to induce TGF$\alpha$ shedding response.

(E) represents graphs Capacity of G$\alpha$ subunits to induce TGF$\alpha$ shedding response.

(F) represents an overview Protein expression levels of chimeric G$\alpha_q$ subunits.

(G) represents graphs on kinetics of cAMP level upon $G_s$-coupled receptor stimulation.

(H) represents graphs on concentration-response curves.

(I) represents an overview on chimeric G-protein-based cAMP assay in $\Delta G_s$ cells.

(J) represents graphs on representative data for the chimeric G-protein-based cAMP assay.

(K) represents graphs on comparison of the chimeric G-protein backbones in coupling profiles.

Figure 11:
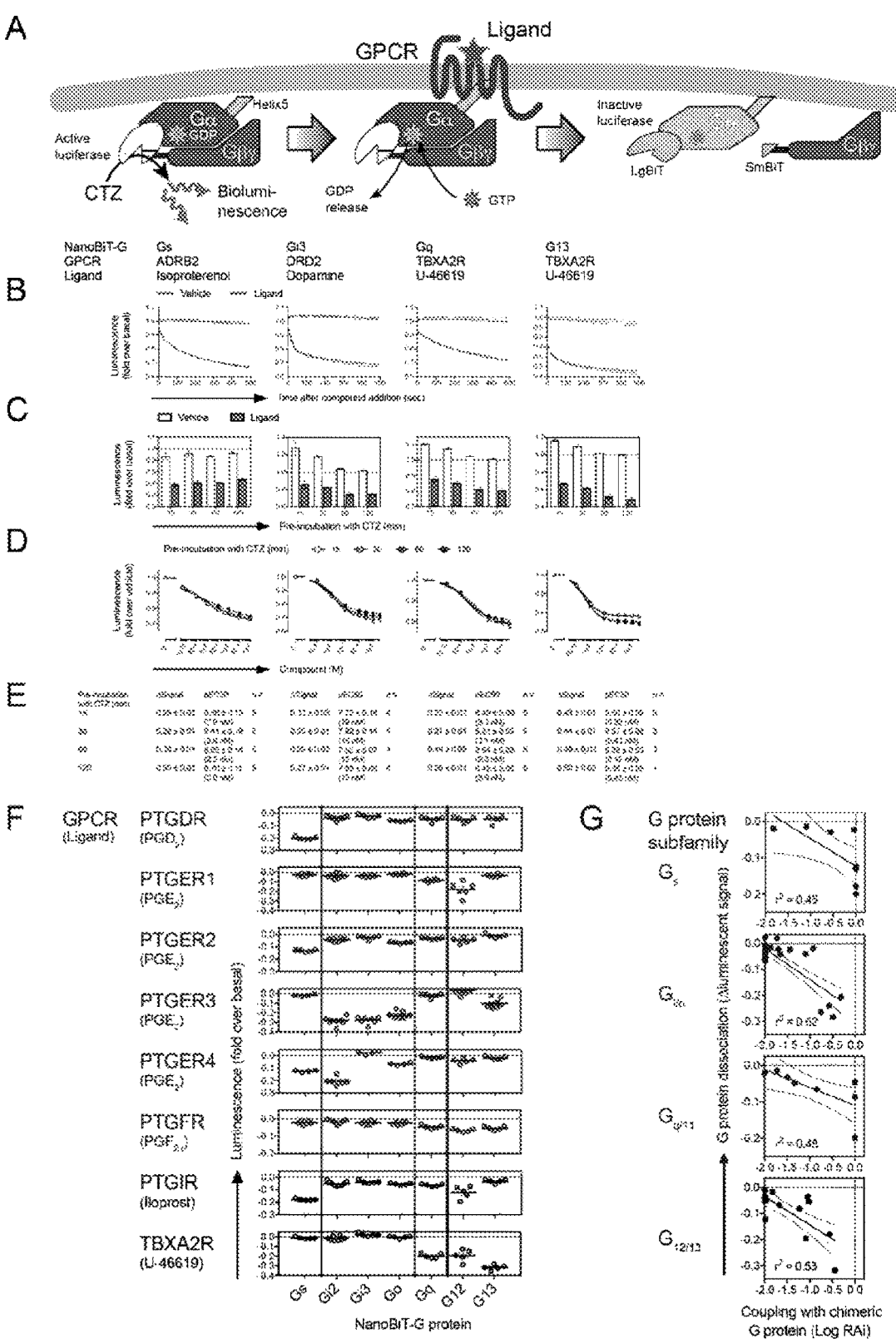

FIG. 11 relates to development and validation of the NanoBiT-G-protein dissociation assay, wherein (A) represents a schematic view of the NanoBiT-G-protein assay.

(B) represents a graph on luminescent kinetics of Nano-BiT-G-proteins after GPCR ligand stimulation.

(C-E) represent graphs on the effect of preincubation time with CTZ (F) represents graphs on validation of the NanoBiT-G-proteins by using prostanoid receptors.

(G) represents graphs on comparison of coupling profiling between the chimeric G-protein-based TGF$\alpha$ shedding assay and NanoBiT-G-protein assay.

Figure 12:
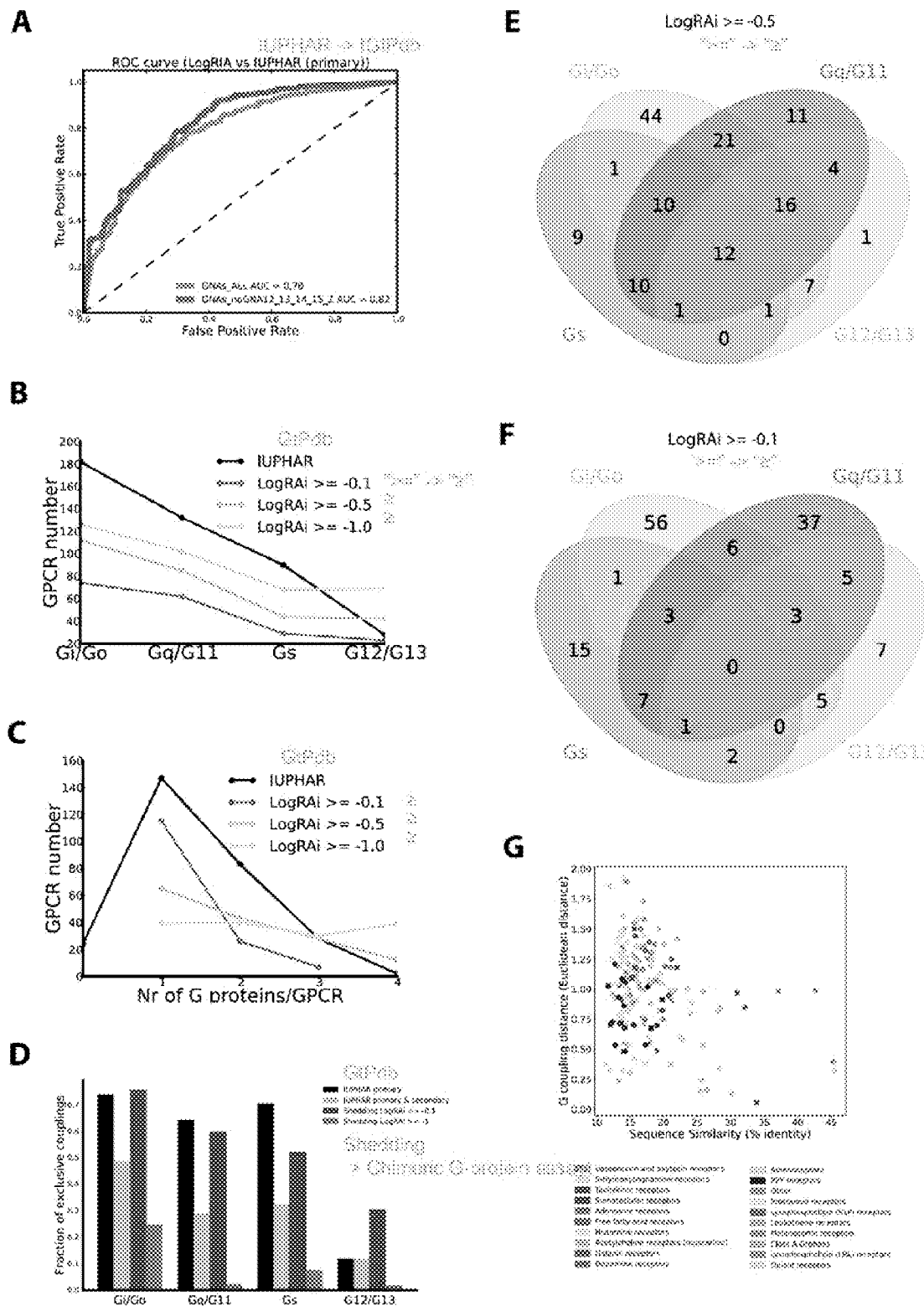

FIG. 12 relates to analysis of the chimeric G-protein-based assay dataset and comparison with GtoPdb, wherein (A) represents a graph on Roc curve comparing the chimeric G-protein-based TGF$\alpha$ shedding assay couplings with GtoPdb couplings.

(B) represents a graph on number of GPCRs coupled to G-proteins of the four families at different LogRAi thresholds in the chimeric G-protein-based TGF$\alpha$ shedding assay as well as in GtoPdb.

(C) represents a graph on distribution of the number of reported bindings (of any of the four G-protein families) for each receptor at different LogRAi thresholds in the chimeric G-protein-based TGF$\alpha$ shedding assay as well as in GtoPdb.

(D-F) represent an overview on fractions of specific couplings.

(G) represents a graph on comparison of receptor sequence and coupling profile similarities.

Figure 13:
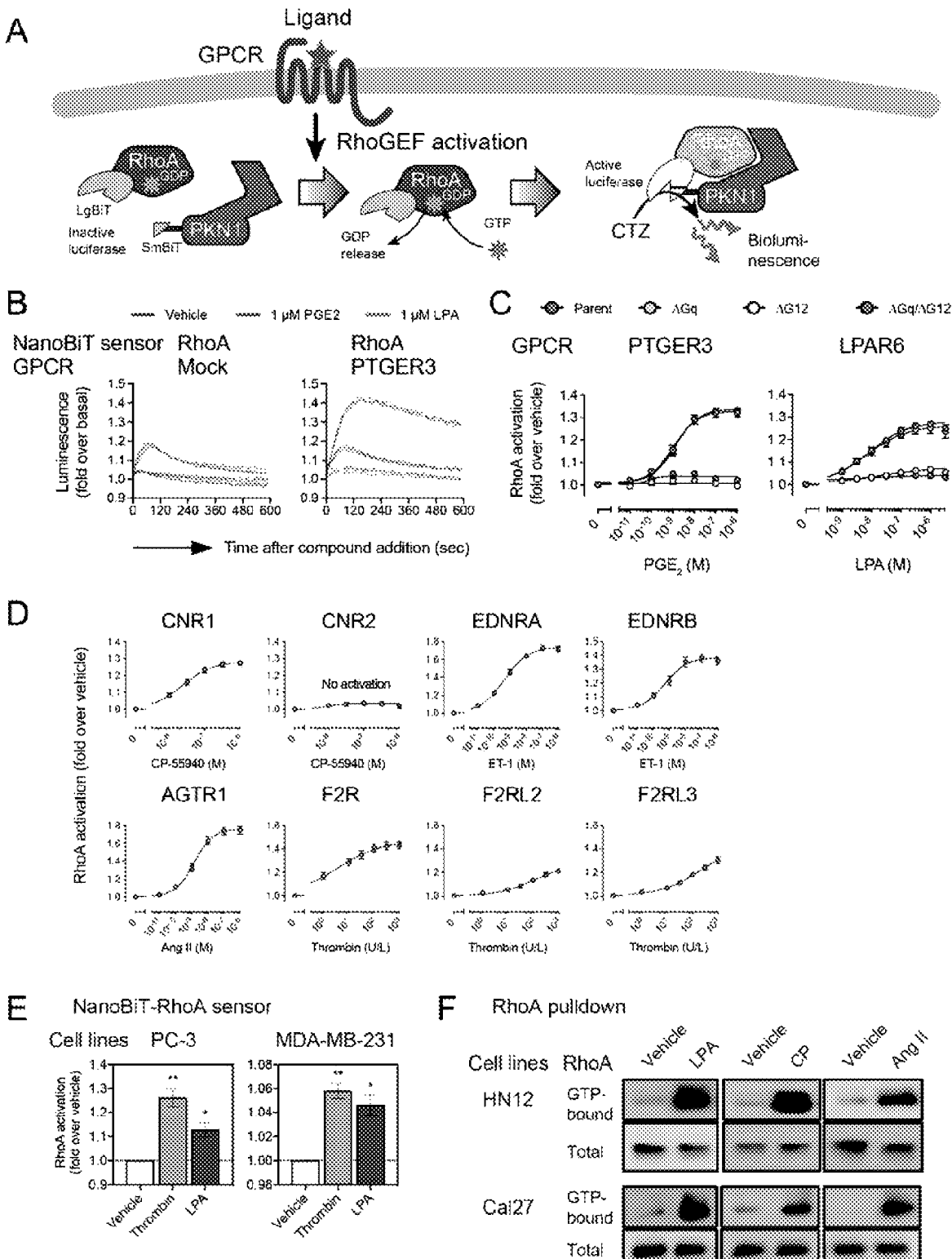

FIG. 13 relates to validation of RhoA activation by the newly identified $G_{12/13}$-coupled GPCRs, wherein (A) represents a schematic view of the NanoBiT-RhoA sensor.

(B) represents graphs on luminescent kinetics of the NanoBiT-RhoA sensor after GPCR ligand stimulation.

(C) represents graphs on validation of $G_{12/13}$-mediated signal of the NanoBiT-RhoA sensor.

(D) represents graphs on NanoBiT-RhoA activation by selected GPCRs.

(E) represents graphs on NanoBiT-RhoA activation through endogenously expressed GPCRs.

(F) represents an overview on RhoA pulldown assay to detect $G_{12/13}$ activation by endogenously expressed GPCRs.

Figure 14:
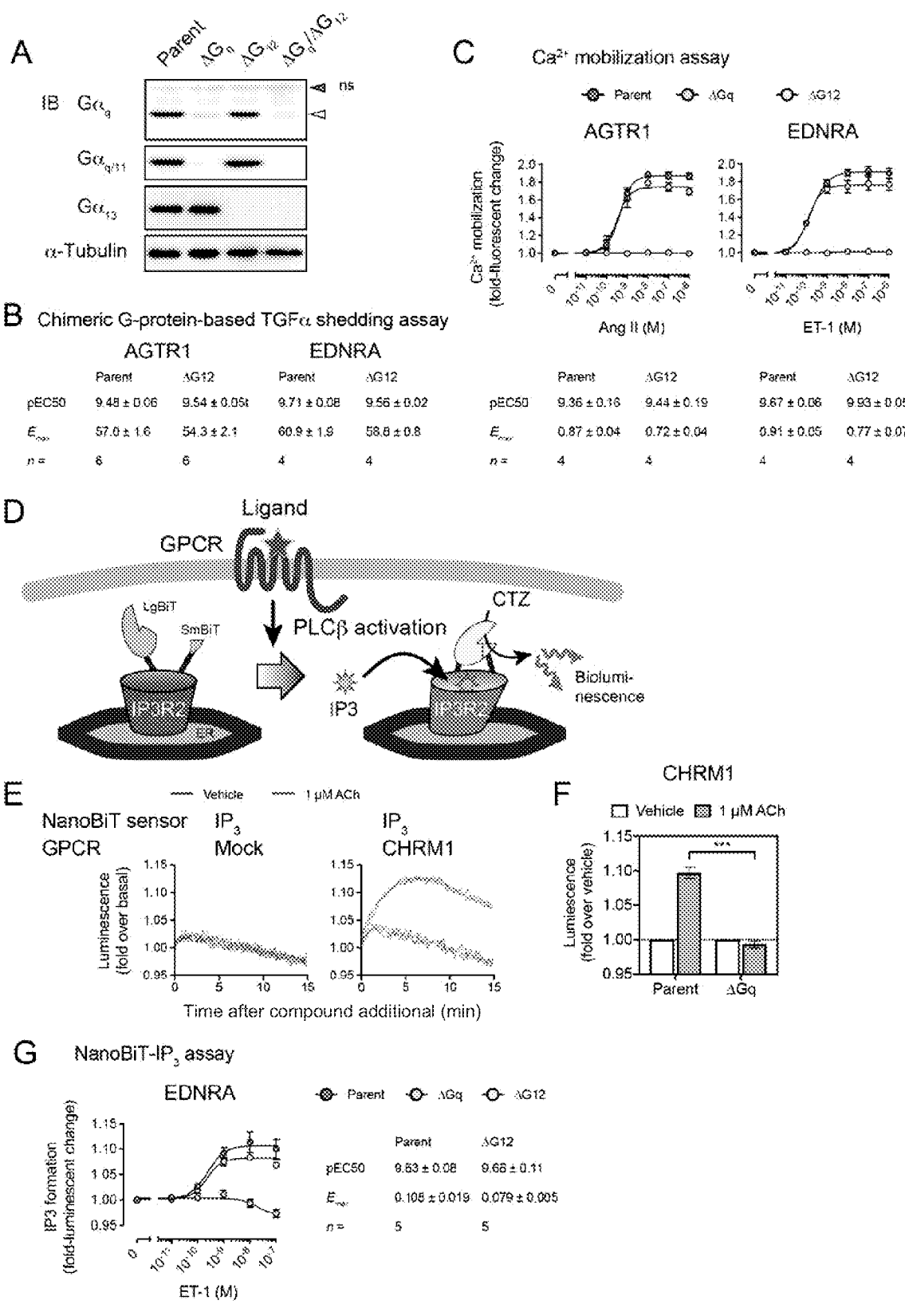

FIG. 14 relates to $G_{q/11}$ signaling in the absence of $G_{12/13}$ for GPCRs coupled with $G_{q/11}$, and $G_{12/13}$, wherein (A) represents an overview on protein expression levels of G$\alpha$ subunits.

(B) represents an overview on parameters obtained from concentration-response curves of the chimeric G-protein-based TGF$\alpha$ shedding assay.

(C) represents graphs on Ca$^{2+}$ mobilization assay.

(D) represents a schematic overview of the NanoBiT-IP$_3$ sensor.

(E) represents graphs on luminescent kinetics of the NanoBiT-IP$_3$ sensor after GPCR ligand stimulation.

(F) represents a graph on validation of $G_{q/11}$-mediated signal of the NanoBiT-IP$_3$ sensor.

(G) represents a graph on measurement of IP$_3$ formation in EDNRA.

Figure 15:
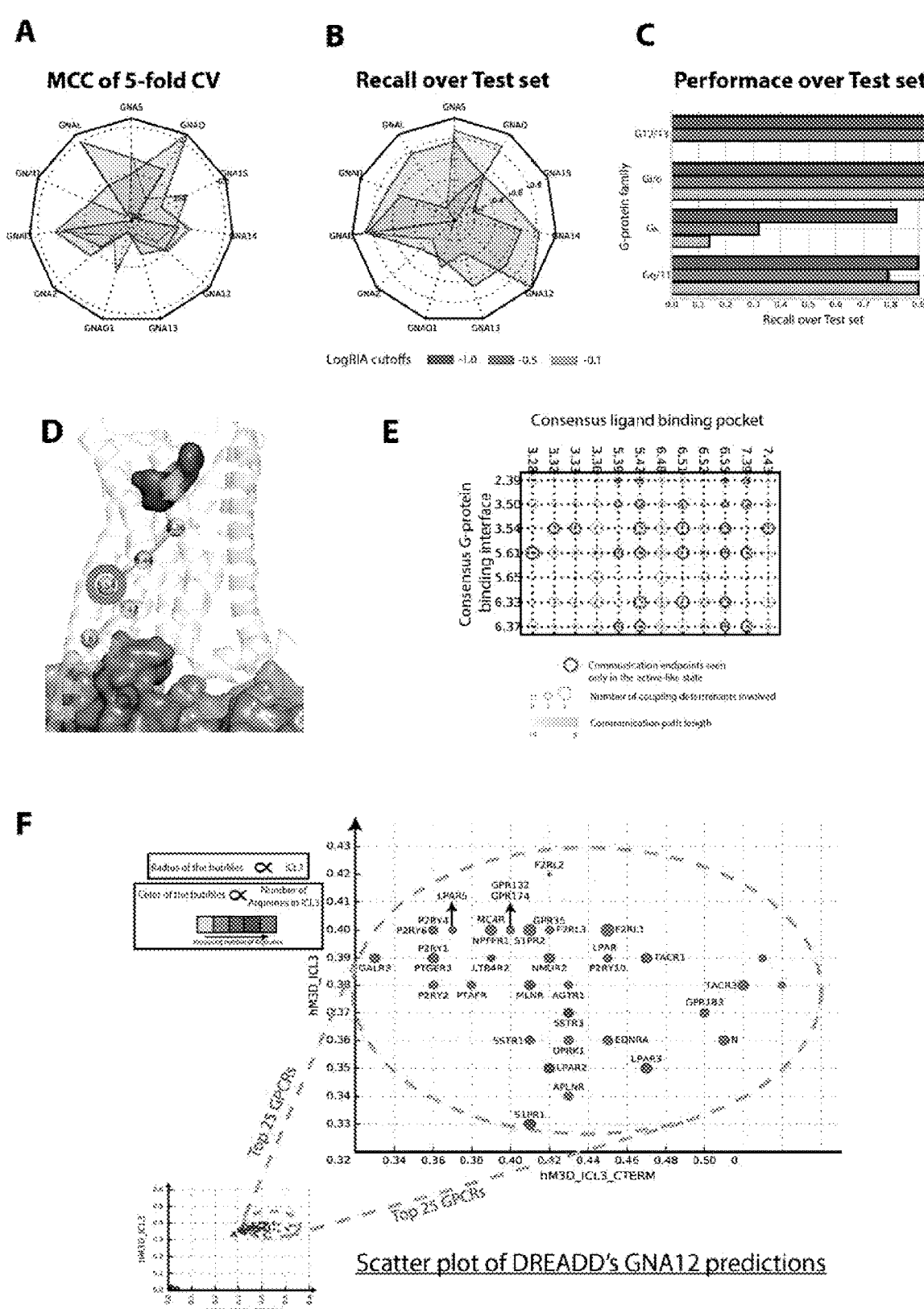

FIG. 15 relates to predictor performances, shortest path from contact network analysis, DREADD predictions scatter plot, wherein (A) represents a radial plot representing Matthew correlation coefficient (MCC) of 5-fold cross validation (averaged over 10 runs).

(B) represents a radial plot representing Recall (Sensitivity) of the best performing predictors over the Test set.

(C) represents a bar plot representing the recall (sensitivity) of the best performing predictors, trained at different LogRAi cutoffs, over the test set.

(D) represents an overview on example of a shortest communication pathway, depicted on 3D cartoons of the ADRB2-GNAS complex (PDB ID: 3SN6), linking the ligand and G-protein consensus binding pocket pockets.

(E) represents a connectivity matrix displaying shortest paths (as intersecting circles) linking residues forming the ligand and G-protein consensus binding pockets (i.e. shown to form such interfaces in at least 50% of the considered structures).

(F) represents a scatter plot of the relative coupling probabilities of chimeric sequences obtained by swapping on the hM3D backbone sequence the sequence stretches corresponding to the ICL3 alone (y-axis) or in combination with the C-term (x-axis) from the 148 receptors of the chimeric G-protein-based TGFα shedding assay.

Figure 16:
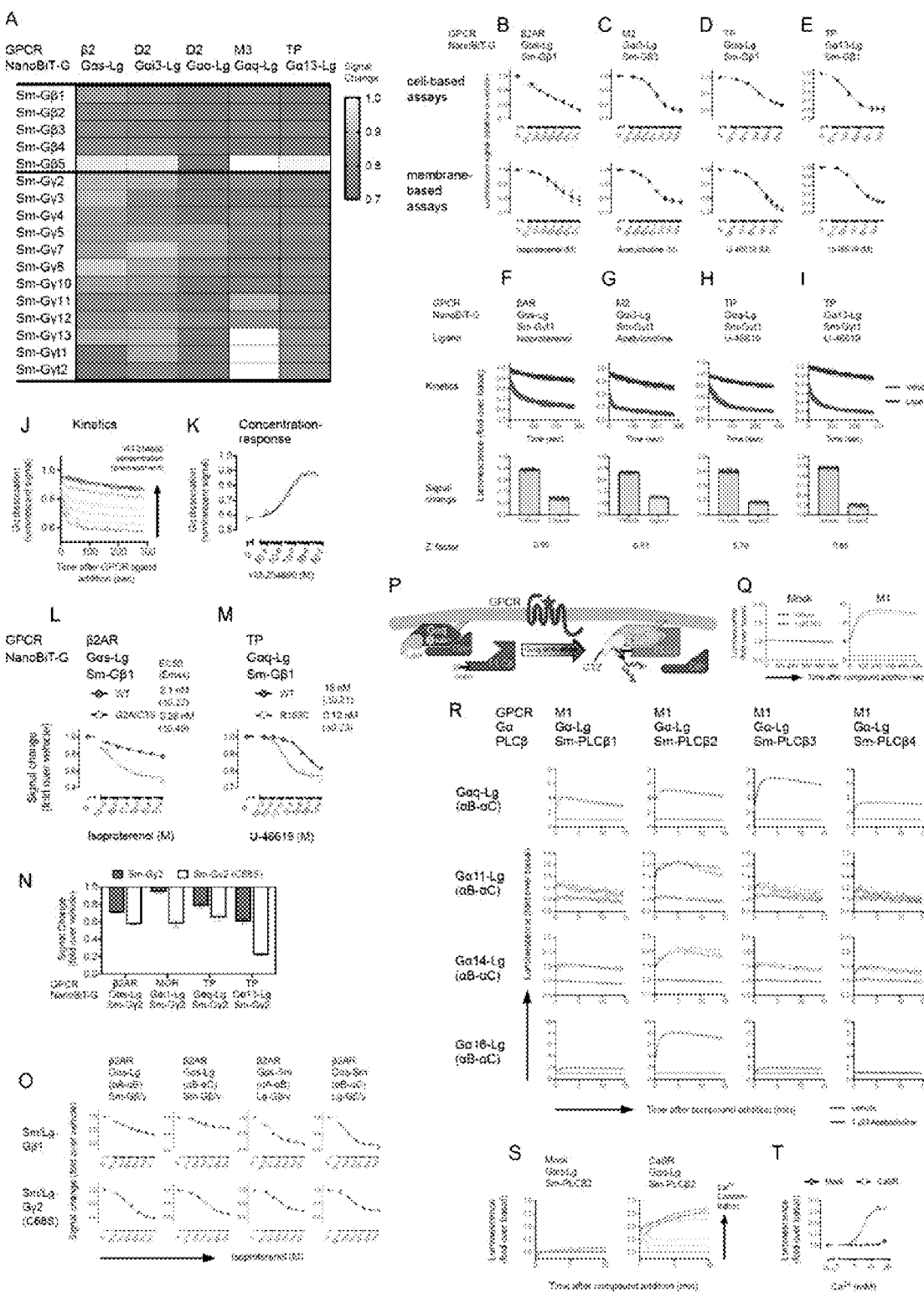

FIG. 16 relates to validation and application of the NanoBiT-G-proteins, wherein (A) represents a heatmap representing G-protein dissociation profiles across Gβ and Gγ subtypes.

(B-E) represents membrane-based NanoBiT-G-protein dissociation assay.

(F-I) represents robustness of the NanoBiT-G-protein dissociation assay.

(J-K) represents assessment of G-protein inhibitor.

(L-N) represents enhanced sensitivity of the NanoBiT-G-protein dissociation assay.

(O) represents assessment of NanoBiT-G-protein constructs.

(P) represents schematic view e to assess NanoBiT-G-protein activation by its interaction with PLCβ (NanoBiT-$G_q$/PLC assay).

(Q) represents graphs on luminescent kinetics of NanoBiT-$G_q$/PLC assay after GPCR ligand stimulation.

(R) represents combinations of the $Gα_q$ family members and PLCβ subtypes.

(S-T) represents detection of CaSR activation by $Ca^{2+}$.

DETAILED DESCRIPTION OF EMBODIMENTS

Following the general description of the inventive aspects in the summary of the invention, detailed aspects of the inventive embodiments are discussed below in detail. Combination of a singular feature of different feature combinations of the detailed description may be inventively combined with other general features or feature combinations as set out in the summary of the invention.

$G_{q/11}$- and $G_{12/13}$-Dependent TGFα Shedding Responses

To evaluate G-protein coupling, the inventors exploited a TGFα shedding assay (FIG. 1A), which they showed previously to be a robust, high-throughput means to measure accumulated GPCR signals (Inoue et al., 2012). In the assay, they detect ADAM17-induced ectodomain shedding of alkaline phosphatase-fused TGFα (AP-TGFα) and subsequent release into conditioned media. The inventors previously observed that $G_{q/11}$- or $G_{12/13}$-coupled receptors induce this process (Inoue et al., 2012), which they first tested using a panel of HEK293 cells lacking one or both of the $G_{q/11}$ and the $G_{12/13}$ subfamilies (hereafter denoted as $ΔG_q$, $ΔG_{12}$ and $ΔG_q/ΔG_{12}$; FIG. 1A) (Devost et al., 2017; Schrage et al., 2015). The inventors tested GPCRs (FIG. 1B) that are reported to couple with either $G_{q/11}$, (CHRM1 and HRH1 (Harding et al., 2018)) or $G_{12/13}$ (LPAR6 and PTGER3 (Kihara et al., 2014; Sugimoto and Narumiya, 2007)) or both (GALR2 and GHSR (Harding et al., 2018)). TGFα shedding responses of the $G_{q/11}$-coupled receptors and the $G_{12/13}$-coupled receptors were diminished in $ΔG_q$ and $ΔG_{12}$ cells, respectively, while the responses were retained in cells lacking uncoupled G-proteins. In the receptors coupling to both, the TGFα shedding responses remained in $ΔG_q$ and $ΔG_{12}$ cells. For all tested GPCRs, TGFα shedding responses were completely abolished in $ΔG_q/ΔG_{12}$ cells nor could $G_s$- or $G_{i/o}$-coupled receptors induce TGFα shedding responses. siRNA-mediated knockdown experiments in the parental HEK293 cells confirmed involvement of $G_{q/11}$ and $G_{12/13}$ in the TGFα shedding response (FIG. 9). Thus, this is clear evidence that the TGFα shedding assay selectively measures $G_{q/11}$ and/or $G_{12/13}$ signaling.

To exclude the possibility that the blunted AP-TGFα release signal was caused by loss of GPCR expression, the inventors compared surface expression levels of epitope-tagged GPCRs among parental, $ΔG_q$, $ΔG_{12}$ and $G_q/ΔG_{12}$ cells using a flow cytometry. All tested GPCRs (FLAG-ADRB1, FLAG-HRH1 and FLAG-DRD1) were equally expressed in the parental as well as the G-protein-KO cells (FIG. 10A).

Chimeric G-Protein-Based Signaling Assay

The inventors exploited the above assay system, and the previously identified importance of the Gα subunit C-terminus, to develop the inventive TGFα shedding assay to assess binding of G-proteins to any GPCR of interest (query GPCR). Specifically, they constructed chimeric Gα subunits where the native 6-amino acid C-termini of members from the $Gα_{q/11}$ and the $Gα_{12/13}$ families were substituted with those from other human Gα subunits (FIGS. 1C and FIGS. 10A-C and SEQ ID No. 58 to 92) and expressed them together with a test GPCR in the signaling-silenced $ΔG_q/ΔG_{12}$ cells (FIG. 1C). The resulting downstream signals measured by the TGFα shedding assay should thus reflect the true binding events between any GPCR and its G-protein counterparts (FIG. 1D).

The inventors tested a series of chimeric Gα subunits for their ability to induce the TGFα shedding response. Specifically, they constructed chimeric Gα subunits with the same C-terminal tail, but a different backbone (FIGS. 10D-E), using members of the $G_{q/11}$ ($Gα_q$, $Gα_{11}$, $Gα_{14}$ and $Gα_{16}$ subunits) and the $G_{12/13}$ ($Gα_{12}$ and $Gα_{13}$ subunits) subfamilies. They expressed each chimeric Gα subunits (C-terminal $Gα_{i1}$ or $Gα_s$ chimeras) together with a test/query GPCR ($G_{i/o}$-coupled DRD2 or $G_s$-coupled PTGER2, respectively) and stimulated the cells with an agonist. The inventors found that the $Gα_q$ backbone was the most efficacious in inducing TGFα shedding response (% AP-TGFα release response) for both receptors (FIGS. 10D-E); they thus chose this backbone for all subsequent experiments.

The inventors generated chimeric $Gα_q$ subunits for each of the 11 unique C-terminal hexapeptides, which cover all of the 16 human Gα subunits (FIGS. 1C, 10A-C; C-terminal 6-amino acids are identical for $Gα_{i1}$, $Gα_{i2}$, $Gα_{t1}$, $Gα_{t2}$ and $Gα_{t3}$; and for $Gα_q$ and $Gα_{11}$), and one negative control lacking the tail ($Gα_q$ ΔC). The 11 $Gα_q$ chimeras were equally expressed in $ΔG_q/ΔG_{12}$ cells (FIG. 10F). Transfected cells were harvested and seeded in a 96-well plate and stimulated with or without titrated concentrations of a GPCR ligand (typically, 12 points in total). AP-TGFα release signals over titrated concentrations were fitted with a sigmoidal concentration-response curve, from which $EC_{50}$ and $E_{max}$ (an amplitude of ligand-induced response) values were obtained. For each chimeric $G\alpha$ condition, an $E_{max}/EC_{50}$ value was normalized by the maximum $E_{max}/EC_{50}$ value among the 11 $G\alpha$ chimeras (e.g., $G\alpha_q$ C-terminus for TBXA2R; FIG. 1D). This gives a relative, dimensionless $E_{max}/EC_{50}$ value (relative intrinsic activity, RAi (Ehlert et al., 1999)), which is a base-10 log-transformed (LogRAi) and used as coupling indices. With their pre-determined threshold criteria (see section EXPERIMENTAL MODEL AND SUBJECT DETAILS), LogRAi ranged from −2 to 0 (100-fold in linear range). The assay produced robust, reproducible results as evidenced by well clustered plots across independent experiments (FIG. 1D). By using a similar approach (restoration of a chimeric $G\alpha$ subunit in G-protein-KO cells), they performed a $G_s$-based cAMP assay and confirmed that LogRAi values obtained from the $G\alpha_s$ backbone and the $G\alpha_q$ backbone were well correlated in prostanoid receptors (FIGS. 10I-K; $r^2$=0.74±0.16, n=7), which show distinct G-protein-coupling profiles (Sugimoto and Narumiya, 2007; Woodward et al., 2011).

As above, the inventors measured cell surface expression of GPCRs by flow cytometry to exclude GPCR expression level effects (FIG. 9F). Except for a modest increase in the conditions with the chimeric $G\alpha_{q/13}$ co-expression, expression levels of N-terminal FLAG epitope-tagged GPCRs (FLAG-ADRB1 and FLAG-HRH1) were almost equal among cells co-expressing any of the G□ chimeras.

The NanoBiT-G-Protein Dissociation Assay

To complement the inventive chimeric G-protein-based TGF$\alpha$ shedding assay, the inventors made an additional inventive assay in which dissociation of the $G\alpha$ subunit from the $G\beta\gamma$ subunits, a critical process of G-protein activation, is measured via a luciferase complementation system. Bioluminescence Resonance Energy Transfer (BRET) between a Renilla luciferase-inserted $G\alpha$ subunit and a GFP10-fused $G\beta$ or $G\gamma$ subunit was previously developed to measure $G\alpha$-$G\beta\gamma$ dissociation (Gales et al., 2005). Here, they replaced the BRET pair with a split luciferase (NanoLuc Binary Technology; NanoBiT) (Dixon et al., 2016). Specifically, they inserted a large fragment (LgBiT) of the NanoBiT into the helical domain (between the $\alpha$A and $\alpha$B helices) of a $G\alpha$ subunit (G$\alpha$-Lg) and fused a small fragment (SmBiT) to the N-termini of $G\beta$ or $G\gamma$ subunits (Sm-$G\beta$ or Sm-$G\gamma$) (see also SEQ ID. Nos: 5 to 51). The inventors confirmed that $G\alpha_s$-Lg retained a $G_s$ signaling function by measuring adenyl cyclase-activating activity upon a $G_s$-coupled receptor stimulation (FIGS. 10G-H). They generated a series of G$\alpha$-Lg, Sm-$G\beta$ and Sm-$G\gamma$ subunits and optimized a combination. When expressed together in cells, these constructs form a heteromer with an enzymatically active luciferase, whose activity is measurable upon loading with coelenterazine (CTZ), a substrate of the luciferase (FIG. 11A). GPCR ligand stimulation triggers dissociation of G$\alpha$-Lg from Sm-$G\beta$/$G\gamma$ making the real-time dissociation response detectable (FIG. 11B). The inventive NanoBiT-G-protein assay demonstrated highly reproducible dissociation signals across independent experiments and was minimally affected by preincubation time with CTZ (FIG. 11F). Comparison of NanoBiT-G-protein dissociation signals with the chimeric G-protein-based assay for eight prostanoid receptors showed a moderately strong correlation ($r^2$≥0.5) across all of the four G-protein subfamilies (FIGS. 11F-G).

Ligand Biased G-Protein Signaling

Since the chimeric G-protein-based assay recognizes a ligand-activated conformation of a GPCR, the inventors assessed whether it could also detect ligand bias among different G protein subfamilies. An angiotensin II (Ang II) analog, [Sar[1], Ile[4,6]]-Angiotensin II (SII), was shown to induce $G_{i/o}$ over $G_{q/11}$ as compared with Ang II in cells expressing AGTR1 (Sauliere et al., 2012). They performed the assay using Ang II and SII (FIG. 9G) and calculated coupling scores for Ang II-induced LogRAi and SII-induced LogRAi (FIG. 9H). If SII behaves as a balanced agonist across G-proteins, LogRAi plots obtained from Ang II and SII would be linearly aligned. their results recapitulated the Gr-bias of SII (Sauliere et al., 2012), and further showed that SII was biased toward $G_{12}$ over $G_q$ as compared with the reference ligand (Ang II). These findings were backed up by the NanoBiT-G-protein assay (FIG. 9I).

Hundreds of Known and New Couplings

Using the inventive chimeric G-protein-based assay, the inventors profiled coupling across 148 human GPCRs (FIG. 2), which represent ~80% of liganded Class A GPCRs. Whenever possible, they used endogenous ligands; when ligands were unstable (e.g., thromboxane A2 for TBXA2R) and/or endogenous ligands were not yet identified, they chose available synthetic ligands (U-46619 for TBXA2R and MDL29951 for GPR17).

The inventors compared coupling data from the inventive chimeric G-protein-based assay with that of GtoPdb. For each of the four G-protein subfamilies, they defined positive coupling if any member of the subfamily scored LogRAi≥−1 and negative coupling if all of the members scored LogRAi<−1 (FIGS. 3A-B). ROC analysis gives AUC=0.78 (FIG. 12A) when considering high-confidence known coupling data and suggested a threshold of LogRAi≥−1.0 (optimizing TPR while minimizing FPR; see section EXPERIMENTAL MODEL AND SUBJECT DETAILS below) for defining true couplings. The assay also showed other broad similarities to GtoPdb, including $G_{i/o}$ being the most common, and $G_{12/13}$ the least (FIGS. 3C-D). They also recapitulated that the majority of receptors coupled to only one G-protein, which does not change greatly with altered Log-RAi thresholds (FIG. 12C), though as expected there is greater coupling promiscuity at lower values. In addition, both GtoPdb and the inventors data (at various LogRAi stringencies) suggests $G_{i/o}$ subunits to be the most specific, always displaying the highest fraction of exclusively bound receptors, with $G_{12/13}$ being the most promiscuous (FIGS. 3C, 12B, D). A total of 39 promiscuous receptors are reported to couple to members of all four G-protein families (FIG. 4C), however promiscuity decreases as a function of the LogRAi threshold (FIGS. 12E, F). Overall, the dataset shows an excellent agreement with known couplings (FIG. 3D), with more than 88% of reported couplings reproduced for three classes (i.e. $G_{i/o}$, $G_{q/11}$ and $G_{12/13}$).

The inventors found no correlation between sequence and coupling similarities, either performing pairwise comparisons on the whole set or intra-family (FIGS. 2 and 12G). Moreover, both extremes are evident: receptor pairs with low sequence similarity can have similar couplings and close homologs from the same family can show large differences (see prostanoid receptors; FIGS. 3A, B). The inventors' exploration of 11 distinct G-proteins also reveals key differences among G-protein sub-families in terms of their coupling preferences, which essentially reflects sequence similarity of the last 6 C-terminal amino acids (FIGS. 2 and 10C). For instance, several receptor families show overall coupling preferences for specific classes, like Opioid and Dopamine receptors for $G_{i/o}$, or Prostanoid and Adrenoceptors for $G_s$; in contrast others show more coupling promiscuity, like Endothelin, Ghrelin and Proteinase-activated receptors (FIG. 2). The great utility of the inventors' dataset is immediately clear. There are entire groups of poorly annotated (in GtoPdb) receptors that are well represented in the inventors' dataset, including ten GPCRs protease-activated receptors and P2Y receptors (P2RY10 and P2RY12), where the latter is a major target of antiplatelet agents, with roles in platelet aggregation (Dorsam and Kunapuli, 2004) and bleeding disorders (Patel et al., 2014). While P2RY10 displays specificity for both $G_{i/o}$ and $G_{12/13}$ subfamily members, the inventors find P2RY12 to be specific for $G_{i/o}$. Elsewhere, GPR132, recently emerged as a mediator of breast carcinoma metastasis (Chen et al., 2017), shows a previously unreported coupling promiscuity.

In general, more than half of the couplings detected (160/292, 55%) have not previously been reported (FIG. 3D). As expected, the biggest proportion of new couplings are $G_{12/13}$ where the inventors' data makes up 57% of all known couplings of this type (15 out of 26 reported $G_{12/G13}$ couplings in GtoPdb, which also considers non-Class A GPCRs). To validate that newly identified $G_{12/13}$ couplings indeed reflect capability of endogenous $G_{12/13}$ activation, and not artifacts of chimeric $G\alpha$ subunit overexpression, they assessed TGF$\alpha$ shedding responses in $\Delta G_q$ cells (FIGS. 1A, B). The inventors tested eight GPCRs (AGTR1, CNR1, EDNRA, F2RL2, PTGER1, PTGFR, TACR1 and TBXA2R), in which $G_{12/13}$ coupling was not registered in GtoPdb, but was detected by the chimeric G-protein-based assay. The inventors found that all of them induced TGF$\alpha$ shedding responses in $\Delta G_q$ cells and that the signals were completely silenced in $\Delta G_q/\Delta G_{12}$ cells (FIG. 3E). To assess a more proximal signaling event to $G_{12/13}$ activation, they generated an inventive NanoBiT-RhoA sensor (FIGS. 13A-C; see section EXPERIMENTAL MODEL AND SUBJECT DETAILS) and found that all of tested GPCRs that were newly identified as $G_{12/13}$-coupled receptors (FIG. 3E), when overexpressed in HEK293 cells, induced RhoA activation (FIG. 13D). The inventors also found that thrombin also activated RhoA, presumably by activating its receptors (F2L, F2RL2 and/or F2RL3) that were endogenously expressed in PC-3 and MDA-MB-231 cells (FIG. 13E). In HN12 cells and Cal27 cells, a RhoA pulldown assay showed that CP-55940 (CP; likely via CNR1, but not CNR2; FIG. 13E) and Ang II induced activation of RhoA (FIG. 13F). Together, these data demonstrate that the $G_{12/13}$-coupled receptors identified by the chimeric G-protein-based assay induce RhoA activation in overexpressed HEK293 cells and/or endogenously expressed cell lines.

To test whether apparent unchanged TGF$\alpha$ shedding responses in $\Delta G_{12}$ cells as compared with those in the parental cells (AGTR1 and EDNRA) arose from enhanced or compensated $G_q$-signaling in $\Delta G_{12}$ cells, the inventors analyzed G-protein expressions and performed a $Ca^{2+}$ mobilization assay and a NanoBiT-IP$_3$ assay (FIG. 14; see section EXPERIMENTAL MODEL AND SUBJECT DETAILS), both of which selectively measured $G_q$-signaling (FIGS. 14C, F). Expression levels of $G\alpha_q$ and $G\alpha_{11}$ were unchanged in $\Delta G_{12}$ cells, nor was that of $G\alpha_{13}$ in $\Delta G_q$ cells (FIG. 14A). Both $Ca^{2+}$ and IP$_3$ responses in $\Delta G_{12}$ cells were comparable to those in the parental cells (FIG. 14C, G). Thus, TGF$\alpha$ shedding responses in $\Delta G_{12}$ and $\Delta G_q$ cells are an accurate reflection of $G_{q/11}$- and $G_{12/13}$ signaling.

Sequence Features Indicative of Coupling Specificity

The inventors used a statistical model to identify sequence features associated with each of the eleven couplings determined above (all details given in section EXPERIMENTAL MODEL AND SUBJECT DETAILS). Briefly, the inventors used sequence alignments for each coupling group to define residues and more general compositional features (e.g. C-terminal or IC3 length, charge distributions, etc.) found to be statistically associated to coupling for each G-protein.

These were used to train and test a machine learning (Logistic regression) predictor (FIG. 4A) and identify the features most predictive for each G-protein.

Figures 4A, 4B:
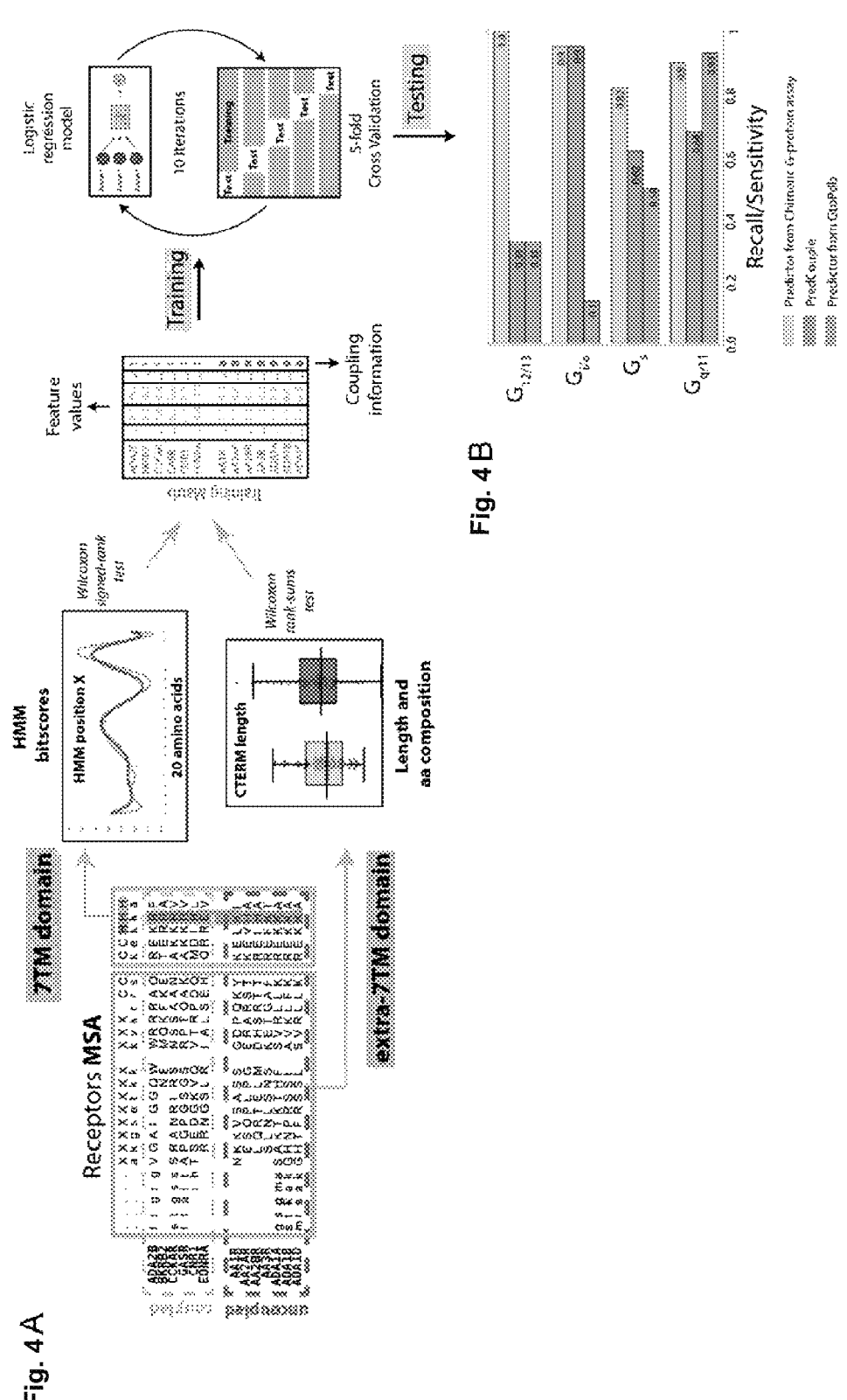
Figure 4C:
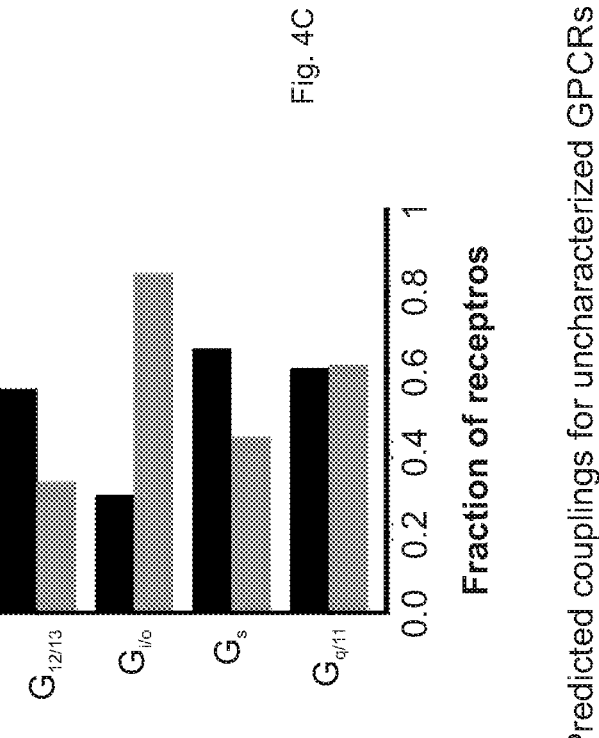

The inventive predictor performs better than another available coupling prediction approach (PredCouple) (Sgourakis et al., 2005a) in predicting known couplings not used during training for all coupling groups, but particularly for $G_{12/13}$, which is expected since few data were available to train such predictors previously (FIG. 4B). Note that same predictor trained only with known couplings from GtoPdb (Harding et al., 2018) performed worse (FIG. 4B) as might be expected. Using a stricter LogRAi cutoff to define coupling groups, led to a general decrease in performance during the testing phase, except for $G_{i/o}$ (FIGS. 15A-C). The poorer performance, for the $G_s$ subfamily, which also shows a poorer overlap between the chimeric G-protein-based assay and GtoPdb (FIG. 3D), is probably a consequence of the fact that the chimeric system does not capture all sequence determinants emerging for $G_s$. Nevertheless, this tool can be exploited to illuminate the transduction mechanisms of less characterized receptors. Indeed, for the 61 receptors (21% of 286 Class A GPCRs) lacking coupling information from either GtoPdb or the chimeric G-protein-based assay, the inventors predict a prevalence of $G_s$ followed by $G_{q/11}$ and $G_{12/13}$ couplings, the latter contrasting with the smallest fraction among experimental couplings (FIG. 4C). For example, P2RY8 is readily predicted to be coupled to $G_{12/13}$, being consistent with a report of mutual exclusive mutations in lymphomas between the P2RY8 and the GNA13 genes, which implies a putative functional link (Muppidi et al., 2014).

The inventive model identified different combinations of sequence features important for each coupling group (FIG. 5). After training, different weights are assigned to each feature in the logistic function to achieve optimal prediction performances, thus highlighting the most relevant determinants for each coupling (FIG. 5; see section EXPERIMENTAL MODEL AND SUBJECT DETAILS). Significant features are more abundant at the cytosolic side of the receptor (FIGS. 6A, B) including many at the known G-protein binding interface (e.g. TM3, TM5, TM6 and ICL3), but also within the core of the structure, mainly contributing to a contact network and could thus mediate specific conformational differences required to accommodate a particular G-protein (FIG. 6).

Surprisingly, only a few significant positions (12 of 51 or 23%) overlap with residues lying directly at known GPCR/G-protein interfaces (FIGS. 5A and 6C). These include ICL3, TM5 and TM6 positions associated with $G_{i/o}$ missing from $G_s$ (e.g. 5.61, ICL3:174, 191-194) that are likely responsible for specificity. Several other positions (11, 21%) are immediately adjacent to direct contacts, suggesting they could nevertheless affect these interfaces. This is logical as some of the contacting positions are typically highly conserved across GPCRs (e.g. the DRY or NPxxY motifs). Overall, the majority (or 90%) of significant positions within the 7TM bundle mediate intra- or inter-protein contacts with either G-proteins or ligands. The majority of significant positions (29, 57% of the total) appear to mediate active-like state specific intramolecular contacts, which the inventors uncovered by comparing functional state specific contact networks (i.e. active-like and inactive-like) from three-dimensional (3D) structures (FIGS. 6C-E; see section EXPERIMENTAL MODEL AND SUBJECT DETAILS below). Helices TM3, TM5 and TM6 undergo major rewiring of their intramolecular contacts upon receptor activation and display the highest content of significant coupling features in the active-like network (FIG. 6D). This further stresses their role as master regulators of receptor activation and G-protein recognition (Koehl et al., 2018). Residues previously described as universal mediators of receptor activation participate to this network as either endpoints (6.37) or mediators (3.46 and 7.53) of the shortest paths linking the ligand and G-protein binding pockets (FIGS. 15D, E; see section EXPERIMENTAL MODELAND SUBJECT DETAILS below).

Several other features lie within regions outside the 7TM bundle, particularly in the ICL3 or C-terminal regions (FIGS. 5C and 6A, B), that are not usually visible in experimental structures (with the exception of ICL3 in some $G_{i/o}$ complexes), but which nevertheless play critical roles in signaling (Venkatakrishnan et al., 2014). There is broadly an equal contribution of positions from within or outside of the 7TM bundle across all families, with a greater prevalence of the outside positions for the $G_{12/13}$ subfamily (FIGS. 6A, B).

Data Driven Design of a $G_{12}$-Specific DREADD

The prominent roles for ICL3, and to a lesser extent the C-terminus, for $G_{12/13}$-coupled receptors, where length and electrostatic charge are predicted to be important for coupling (FIGS. 5B, C), together with the lack of structure and tools for probing $G_{12/13}$ signaling prompted the inventors to develop a new chemogenetic receptor for studying $G_{12/13}$ coupling. DREADDs are engineered receptors that permit spatial and temporal control of G-protein signaling in vivo, being thus of great use in studying and manipulating signaling (Urban and Roth, 2015; Wess et al., 2013). DREADDs derived from the muscarinic acetylcholine (Ach) receptors are widely used in combination with clozapine-N-oxide (CNO), a synthetic, biologically inert ligand. To date, DREADDs coupling to $G_s$, $G_{i/o}$ and $G_{q/11}$ (M3D-$G_s$, M4D and M3D, respectively) have been developed (Armbruster et al., 2007; Guettier et al., 2009), but there is no yet a $G_{12/13}$-coupled DREADD available, which the inventors sought to design using their inventive predictor.

The design of M3D-$G_s$ involved a strategy of substituting both ICL2 and ICL3 of the $G_{q/11}$-coupled M3D with those of $G_s$-coupled β1AR (Guettier et al., 2009). In the inventors' analysis, a major feature contributing to $G_{12/13}$ coupling was ICL3, followed by the C-terminal tail (FIGS. 5C and 6B). The inventors thus explored whether these features would be sufficient to induce such signaling in M3D. The inventors first predicted the probability of $G_{12}$ coupling for M3D chimeras containing ICL3 swapped from all other GPCRs alone or in combination with C-terminal stretches (FIGS. 7 and 15F). Among all possible GPCR constructs (144 ICL3 swapped chimeras and 144 dual ICL3/C-terminus chimeras), the inventors selected the top 10 predictions of each chimera type (13 GPCRs in total by excluding overlaps and selecting representative constructs when multiple members from one GPCR were predicted) leading to 26 constructs (FIG. 7A). The inventors functionally screened $G_{12}$-coupling activity of the M3D-based chimeras using two assays. In the first, the chimera construct was expressed together with the AP-TGFα reporter (SEG ID No. 93 to 96) in $\Delta G_q$ HEK293 cells, in which $G_{12}$ signaling is selectively detectable (FIG. 7B). The inventors measured TGFα shedding response upon CNO or Ach stimulation. Among the 26 constructs screened, chimeras with the GPR183-derived ICL3 substitution (M3D-GPR183/ICL3) and the GPR132-derived ICL3 substitution (M3D-GPR132/ICL3) showed significant $G_{12}$ signaling (P values<0.05) (FIG. 7B). Ach did not induce detectable $G_{12}$ signaling in any of the tested constructs (FIG. 7B). In the second assay, the chimera construct was expressed together with NanoBiT-$G_{12}$ in the parental HEK293 cells and stimulated with CNO. As a negative-control counter experiment, the inventors used NanoBiT-$G_o$ since their preliminary experiment indicated a minor coupling of some chimeras to $G_o$. NanoBiT-$G_{12}$ screening identified four constructs (M3D-GPR183/ICL3, M3D-GPR132/ICL3, M3D-P2RY10/ICL3 and M3D-NMBR/ICL3) significantly (P<0.05) coupled to $G_{12}$ and not to $G_o$ (FIG. 7C). One construct (M3D-LTB4R2/ICL3) induced both $G_{12}$ and $G_o$ coupling with a higher $G_o$ dissociation signal. In both assays, double swapped ICL3/C-terminus chimeras showed negligible $G_{12}$ signaling, which was in part attributable to lower surface expression of these constructs (FIG. 7D).

The ©nventors then evaluated selectivity of G-protein coupling for the two candidate constructs using the NanoBiT-G-protein dissociation assay with titrated CNO concentrations. As controls, the inventors compared with previously established muscarinic DREADDs (M3D, M4D and M3D-$G_s$) (Armbruster et al., 2007; Guettier et al., 2009). They tested representative NanoBiT-G-proteins ($G_s$, $G_o$, $G_q$ and $G_{12}$) from the four subfamilies. The NanoBiT-G-protein assay correctly measured primary coupling of the three established DREADDs (M3D, M4D and M3D-$G_s$ for $G_q$, $G_o$ and $G_s$, respectively; FIG. 7E). M3D-GPR183/ICL3 and M3D-GPR132/ICL3 constructs showed robust $G_{12}$ dissociation signal while dissociations of the other G-proteins were much lower than those of $G_{12}$. None of the DREADD constructs induced significant NanoBiT-$G_{13}$ dissociation (FIG. 7E). The $EC_{50}$ values of CNO for each primary-coupling G-protein were in a subnanomolar range (0.1-1 μM) for all of the DREADDs (FIG. 7F). Thus, the constructs M3D-GPR183/ICL3 and M3D-GPR132/ICL3 are new $G_{12}$-selective DREADDs.

DISCUSSION

The extensive dataset provided according to the present invention greatly expands known GPCR/G-protein couplings and provides better resolution by considering all 11 specific human G-proteins rather than subfamilies. The inventive assays, resource and accompanying predictor (available at gpcr.russelllab.org) can be used for a host of biological and pharmaceutical applications. For example, the inventive TGFα shedding assay, applied to AGTR1, demonstrates the promise to develop sub-G-protein biased ligands (i.e. discriminating one G-protein signaling from another), which have recently attracted attention because of their potentials for therapeutic-signal-targeted medicine with reduced on-target side effects (Violin et al., 2014). Most importantly, the extensive dataset provides the first coupling information for many receptors (e.g. protease-activated or P2Y receptors), shows differences in G-proteins in the same family (e.g. prostanoid receptors) and, in particular, identifies dozens of receptors coupled to the previously understudied $G_{12/13}$ (Rho signaling).

The $G_{12/13}$ subfamily remains challenging to study owing to lack of well-established methods for assessing signaling. The inventive TGFα shedding assay combined with $\Delta G_q$ cells is an excellent platform for selective measurement of $G_{12/13}$ signaling with high robustness and throughput, and in the future will enable precise characterization of receptors and their ligands. Other assays developed in this invention (the chimeric G-protein-based TGFα shedding assay, the NanoBiT-G-protein dissociation assay and the NanoBiT-RhoA sensor) will also be useful for cross-validating results. $G_{12/13}$ signaling is also implicated in immune processes and various diseases (Herroeder et al., 2009; Suzuki et al., 2009), including receptors S1 PR2 and P2RY8 in B cell lymphoma (Muppidi et al., 2014; O'Hayre et al., 2016). Agonists for $G_{12/13}$-coupled receptors in lymphocytes can attenuate immune responses and antagonists could potentially boost them, both of which offer attractive possibilities for future therapies. A list of the expanded members of $G_{12/13}$-coupled receptors identified here will provide a basis for such drug development. Indeed, some of the inventors' newly identified $G_{12/13}$-coupled GPCRs (e.g., CNR1, FFAR1, GHSR, GPR35, HRH2, HTR2C) are already targets for agonists approved as therapeutics (Hauser et al., 2017), suggesting additional possibilities for drug repurposing. Transgenic mice expressing the inventors' new $G_{12}$-coupled DREADD could help to explore $G_{12}$ signaling and ultimately develop such therapies.

Integrating this large GPCR/G-protein dataset with information about protein sequence and structure has identified numerous insights into how receptors selectively interact with G-proteins. Several recent structures have provided insights into the complex landscape governing GPCR coupling specificity, which is complicated by multiple factors including conformational plasticity, kinetics, ligand biasing and G-protein pre-association (Capper and Wacker, 2018). While previous efforts successfully identified sequence and structural features that determine coupling selectivity in G-proteins (i.e. the barcode), a systematic identification of receptor determinants is still lacking. The present invention identifies several features that agree with what is already known. Generally, TM3, TM5 and TM6 have the greatest number of predicted coupling features, suggesting the importance of ICL2, TM5, ICL3 and TM6 in determining complementarity to the G-protein barcode.

One potential issue with the results presented according to the present invention is the use of inventive chimeric $G\alpha$ subunits, where only the 6 C-terminal amino acids are used to assess ligand-induced GPCR activation. This necessarily misses contributions of the remaining (backbone) region of the $G\alpha$ subunits. However, the good agreement with known couplings (FIG. 3D) suggests that these effects are not predominating. Moreover, relative contributions (or synergistic effects) of C-terminus and backbone to coupling selectivity seem to differ among GPCRs (FIG. 4A). Ultimately, an extensive G-protein coupling dataset considering native $\alpha$ subunit sequences will naturally provide a more complete view of coupling determinants.

One would expect naively that coupling determinants would only lie at the interface between G-proteins and receptors and that a few simple sequence changes would account for selectivity. Decades of sequence gazing have failed to find such simple explanations. Recent receptor/G-protein complexes suggest that additional features outside the interface, such as an internal network of polar contacts, induce a greater rigidity of TM6 and lead to a preference of $G_{i/o}$ over $G_s$. Many of the inventors' predicted sequence features away from the interface indeed participate in intramolecular contact networks linking ligand and G-protein binding sites. The inventors speculate that these features allow allosteric and dynamic control of a G-protein binding interface of GPCRs possibly by stabilizing a specific intermediate state of a receptor/G-protein complex. The inventors also find a general tendency for TM5, ICL3 and TM6 insertions in $G_{i/o}$-coupled, and deletions in $G_s$-coupled receptors, which broadly agrees with the notion that the bulkier side-chains of the $G_s$ G-protein C-terminus can only be accommodated by larger and more flexible crevices found in $G_s$-specific receptors (FIG. 7A).

The inventors predicted many G protein-coupling features to lie outside of the 7TM bundle. For example, ICL3 contains features for $G_{12/13}$ coupling, the importance of which is verified by the successful generation of ICL3-swapped DREADDs. $G_{12/13}$ is the receptor class where the inventors predict the smallest number of significant features overlapping with G-protein interface residues (FIGS. 5A and 6C) and the greatest fraction of features outside the 7TM bundle, particularly in ICL3 (FIG. 6A). Since the ICL3 is typically disordered (i.e. lacks a pre-defined structure), it is possible that the fewer specific couplings observed for $G_{12/13}$ receptors (FIG. 3C) are a consequence of the lack of well-defined contact points in the receptor structure. Since (non $G_{12/13}$) G protein/GPCR complex structures show limited, but nevertheless G-protein class specific, interactions between ICL3 and flanking amino acid residues (i.e. TM5/ICL3 for $G_s$ and ICL3/TM6 for $G_{i/o}$ complexes; FIG. 5A), the inventors speculate that $G_{12/13}$ receptors might also engage in ICL3 and Helix 5 in the $G\alpha$ subunit-specific interactions that are likely different from $G_s$ or $G_{i/o}$ (or that an ICL3-Helix 5 interaction occurs during an intermediate state).

The present invention has demonstrated the power of integrating a new, powerful assay with systematic data analysis to provide new insights in molecular mechanism. With the extensive analysis, the inventors devised both biological and computational tools that will advance understanding of how cells respond to extracellular signals. Integrating the inventive resources with other datasets, such as genomic sequencing, transcriptomics, proteomics, metabolomics, and/or by considering other members of GPCRs mediated pathways, will provide new means to quantify downstream signaling in normal and pathological conditions, and provide considerable possibilities for new therapies and personalized medicine.

DETAILED DESCRIPTION OF THE FIGURES

Figure 1:
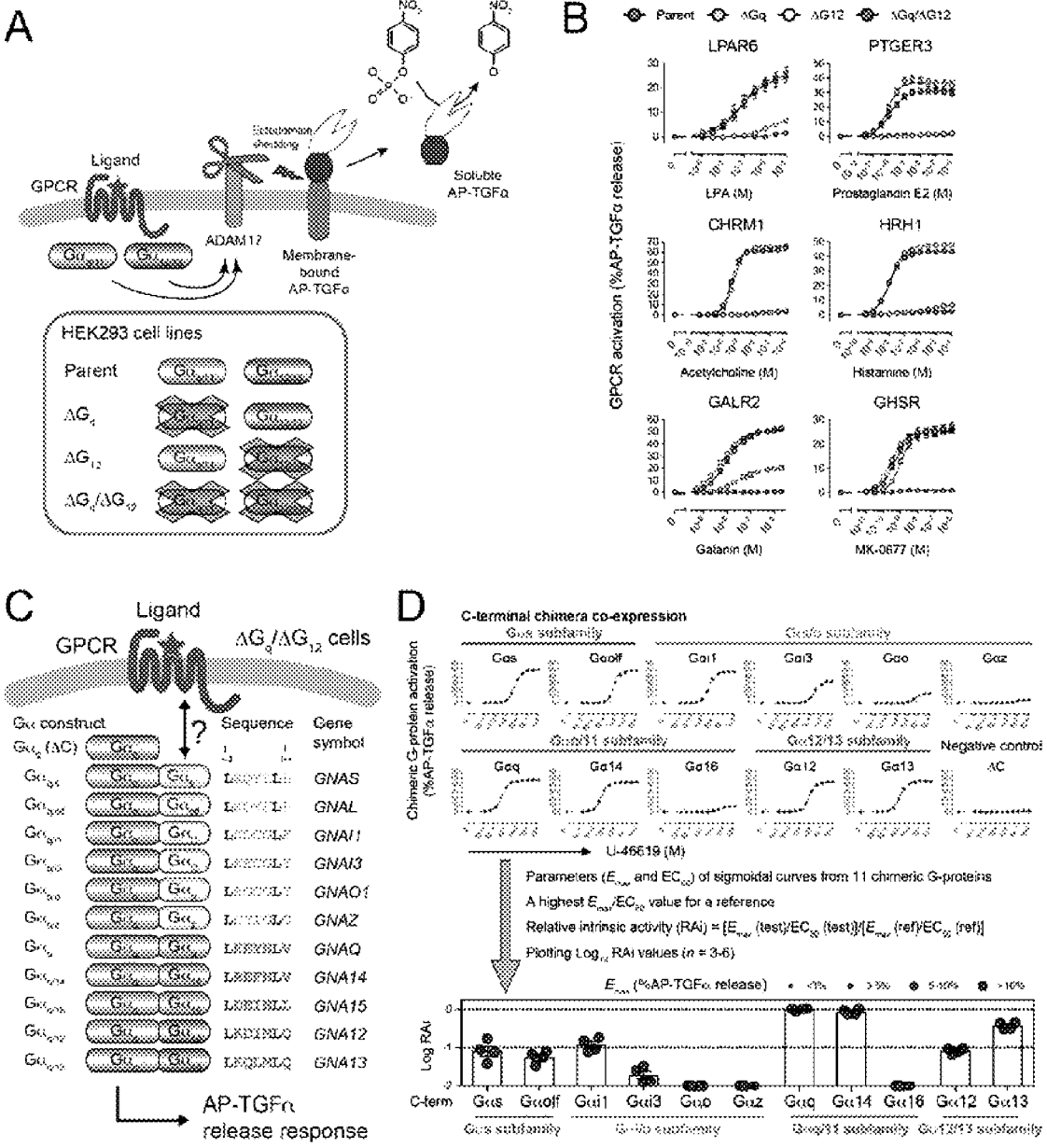

FIG. 1 relates to a Chimeric G-protein-based TGFα shedding assay to probe interaction between an active GPCR and a C-terminal tail of a $G\alpha$ subunit. FIG. 1(A) discloses a schematic description of the mechanism of the TGFα shedding assay. $G_{q/11}$- and/or $G_{12/13}$-coupled receptors induce activation of a membrane-bound metalloprotease ADAM17, which is endogenously expressed in HEK293 cells, and subsequent ectodomain shedding of the alkaline phosphatase-fused TGFα (AP-TGFα) construct. AP-TGFα release into conditioned media is quantified through a colorimetric reaction. Parental HEK293 cells and cells devoid of the $G\alpha_{q/11}$ subunits ($\Delta G_q$), the $G\alpha_{12/13}$ subunits ($\Delta G_{12}$) or the $G\alpha_{q/11/12/13}$ subunits ($\Delta G_q/\Delta G_{12}$) were used in the TGFα shedding assay.

FIG. 1 (B) discloses graphs of blunted TGFα shedding response in the HEK293 cells devoid of the $G_{q/11}$ and the $G_{12/13}$ subfamilies. GPCRs known to couple with $G_{12/13}$ (LPAR6 and PTGER3), $G_{q/11}$ (CHRM1 and HRH1) and both (GALR2 and GHSR) were examined for ligand-induced TGFα shedding responses in the parental HEK293 cells or the indicated G-protein-deficient cells. Symbols and error bars represent mean and SEM, respectively, of 3-6 independent experiments with each performed in triplicate.

FIG. 1(C) discloses a schematic description of the chimeric G-protein-based TGFα shedding assay in $\Delta G_q/\Delta G_{12}$ cells. A test GPCR is expressed together with one of 11 chimeric $G\alpha$ subunits harboring C-terminal 6-amino acid substitution in $\Delta G_q/\Delta G_{12}$ cells and restoration of ligand-induced AP-TGFα release response is measured. Note that there are 11 unique C-terminal sequences for the 16 human Gα subunits (the C-terminal 6-amino acid sequences of $G\alpha_{i1}$, $G\alpha_{i2}$, $G\alpha_{t1}$, $G\alpha_{t2}$ and $G\alpha_{t3}$ and those of $G\alpha_q$ and $G\alpha_{11}$ are identical; also see FIGS. 10A-C) and that the invariant leucine is encoded at the −7 position. The C-terminally truncated $G\alpha_q$ construct ($G\alpha_q$ (AC)) is used for a negative control.

FIG. 1 (D) discloses representative data for the chimeric G-protein-based assay. TBXA2R was expressed with one of the 11 $G\alpha_q$ constructs or the $G\alpha_q$ (AC) and treated with titrated concentration of a ligand (U-46619). AP-TGFα release responses were fitted to a sigmoidal concentration-response curve (upper panels). G-protein coupling is scored as logarithmic values of relative intrinsic activity (RAi), which is defined as an $E_{max}/EC_{50}$ value normalized by the highest value. Symbol size is proportional to $E_{max}$, which reflects fitting quality. During data processing, a concentration-response curve that failed to converge or has an $E_{max}$ value of less than 3% AP-TGFα release, or a RAi value of less than 0.01 were defined as LogRAi value of −2. Data for the concentration-response curves are from a representative experiment (mean±SD of triplicate measurements). Each LogRAi plot denotes single experiment and bars and error bars are mean±SEM (n=4).

FIG. 2 relates to signatures of G-protein coupling determined by the chimeric G-protein-based assay and discloses a heatmap of the LogRAi values for the 148 receptors of the chimeric G-protein-based assay. Cell colors range from blue (LogRAi=−2) to red (LogRAi=0). Receptors (columns) and G-proteins (rows) are rearranged according to the dendrogram of the full linkage clustering of the distance matrix calculated from the coupling profiles. Receptor gene symbols are colored according to family membership as reported in GtoPdb. Heatmap was generated through the scipy library (https://www.scipy.orq/).

FIG. 3 relates to a comparison between dataset of the chimeric G-protein-based assay and GtoPdb and validation of $G_{12/13}$ signaling for the newly characterized GPCRs.

FIG. 3 (A) discloses a schematic classification of the LogRAi scores and its comparison with GtoPdb. An example heatmap of LogRAi scores for the eight prostanoid receptors is shown, with a LogRAi cutoff of −1 to binary-classify the data into coupled (Y) or uncoupled classes. G-protein coupling from GtoPdb (subfamily levels) is overlaid.

FIG. 3 (B) discloses a schematic combined binary coupling/non-coupling data for each of the four G-protein subfamilies.

FIG. 3 (C) discloses Venn diagrams with the numbers of receptors coupled to each G-protein subfamily in the chimeric G-protein-based assay (LogRAi≥−1).

FIG. 3 (D) discloses Venn diagrams of receptor couplings to the four G-protein families according to the chimeric G-protein-based assay (LogRAi≥−1) and GtoPdb.

FIG. 3 (E) discloses GPCRs that were identified as being coupled with $G_{12/13}$ by the chimeric G-protein-based assay were examined for their ability to engage and activate native, endogenous $G_{12/13}$ in HEK293 cells. As indicated GPCR was expressed in the parental, $\Delta G_q$, $\Delta G_{12}$ and $\Delta G_q/\Delta G_{12}$ cells with the AP-TGFα reporter construct, but not with a chimeric Gα subunit, and its ligand-induced response was assessed. Note that in all of the tested GPCRs, AP-TGFα release response occurred in $\Delta G_q$ cells, but was completely silenced in $\Delta G_q/\Delta G_{12}$ cells, showing induction of $G_{12/13}$-dependent signaling. Symbols and error bars represent mean and SEM, respectively, of 3-6 independent experiments with each performed in triplicate.

FIG. 4 relates to the development of G-protein coupling predictor.

FIG. 4 (A) discloses a schematic workflow of the procedure: features are extracted from sub-alignments of coupled and uncoupled receptors to a particular G-protein; features are used to generate a training matrix which is employed to train a logistic regression model through a 5-fold cross validation procedure.

FIG. 4 (B) discloses a schematic overview on the final model tested on reported couplings not previously seen during training and compared to PredCouple.

FIG. 4 (C) discloses highly confident predicted couplings (coupling probability >0.9) for 61 Class A GPCRs lacking information about transduction from both GtoPdb or the chimeric G-protein-based TGFα shedding assay (black) vs. receptors with experimental coupling information (gray).

FIG. 5 relates to featured residues in GPCRs involved in G-protein coupling selectivity.

FIG. 5 (A) discloses a schematic overview on a comparison of significant coupling features weights for the 11 G-proteins (bottom), interface contacts of 6 available GPCR-G-protein complexes (central) and 7TM domain position conservation (top). On the bottom panel are all the features (columns) that are found to be statistically significant (P<0.05) for at least one coupling group (rows). Each cell is colored based on coefficient of the given feature in the decision function of the corresponding coupling group (i.e. weight), with negative and positive values colored red and green respectively. Coupling features at 7TM domain with significantly different amino acid distributions are characterized by two values, representing the weights of the bitscores obtained from the coupled (top sub-cell) and not coupled (bottom sub-cell) HMMs for each G-protein. Insertions (i.e. positions present only in the coupled subset) or deletions (i.e. positions present only in the uncoupled subset) are indicated with a gray "+" and "−". Black/grey boxes in the center show contacts mediated by the last 6 a.a. of α5 C-term (black) and contacts mediated by other positions of Gα subunit (grey). Top bars shows conservation profiles for PFAM 7tm_1 positions obtained by calculating the information content from HMM positions bit scores (Wheeler et al., 2014).

FIG. 5 (B) discloses a schematic overview of the 7TM topology indicating the regions contributing to the features.

FIG. 5 (C) discloses a schematic overview on significant coupling feature weights for the 11 G-proteins (same color codes as in A) of extra-7TM features of ICL3 and C-term, including length and amino-acid composition.

FIG. 6 relates to functional analysis of residues linked to coupling selectivity.

FIG. 6 (A) discloses in the upper panel a distribution of coupling feature fractions for intra- and extra-7TM portions. The formers comprise the 7TM helical bundle only, while the latters the N- and C-terminals, ECLs and ICLs; FIG. 6 (A) discloses in the lower panel a distribution of the coupling feature fractions within transmembrane sectors (i.e. extracellular—EC, transmembrane—TM, intracellu-ar—IC). Extra- and intra-cellular portions are defined by ECL and ICL regions plus 5 helical positions preceding and following them.

FIG. 6 (B) discloses a distribution of the fractions of coupling significant features outside of the 7TM bundle.

FIG. 6 (C) discloses a distribution of coupling feature fractions (relative to the total number of positions of the same class) within functional sites (i.e. mediating either ligand/G-protein binding or intra-molecular contacts).

FIG. 6 (D) discloses a graph representing intra-molecular contacts within 7TM helices. Each helix is represented by a node, whose diameter is proportional to the number of helix positions mediating contacts in the contact network derived from active-like structures and whose color (red scale) is proportional to the number of significant coupling features present in the corresponding region. Edges represent contacts between 7TM helices, where width is proportional to the number of contacts in the active-like contact network, while color scale (gray) is proportional to the similarity degree (calculated as a Jaccard index) between contacts mediated in the active- and inactive-like contact networks.

FIG. 6 (E) discloses a three dimensional schematic view of the ADRB2-GNAS complex (PDB: 3SN6) (Rasmussen et al., 2011) with side chains of coupling features at G-protein-binding sites depicted as red surfaces. A representative coupling feature at intra-molecular contacts sites (i.e. position 3.40) is depicted as a red sphere mediating one of the shortest paths linking the ligand and G-protein binding pockets (wheat sticks and spheres). The ligand and GNAS (Gαs) are depicted as cyan and pale-yellow surfaces, respectively.

FIG. 7 relates to generation of $G_{12}$-coupled designer GPCRs.

FIG. 7 (A) discloses a schematic view of generating and assessing ICL3- or ICL3/C-terminus-swapped constructs from $G_{q/11}$-coupled M3D. Based on the predictor scoring (FIG. 15F), the inventors selected 13 GPCRs and made 26 constructs.

FIGS. 7 (B-D) discloses screening graphs of M3D-derived chimeric constructs. $G_{12}$ signaling of the constructs assessed by the TGFα shedding assay in the $\Delta G_q$ cells treated with 10 μM clozapine N-oxide (CNO) or 10 μM acetylcholine (ACh) (B). Activation of $G_{12}$ and Go was measured by the NanoBiT-G-protein dissociation assay with 10 μM CNO (C). $G\alpha_{12}$-Lg or $G\alpha_o$-Lg was co-expressed with Sm-Gγt1. Changes in decreased luminescent signals are inversely plotted in the y-axis. (C). Surface expression of the M3D-derived chimeric constructs was assessed by a flow cytometry using an anti-FLAG epitope-antibody, followed by a fluorescently labeled secondary antibody (D). Symbols and error bars represent mean and SEM, respectively, of 4-8 independent experiments with each performed in duplicate or triplicate. *, P<0.05; , P<0.01; *, P<0.001 (two-way ANOVA, followed by Sidak's multiple comparison tests).

FIG. 7 (E) disclose graphs on lack of $G_{13}$ activation by the new DREADD constructs. Dissociation signals of the Nano-BiT-$G_{13}$ protein were assessed by using 10 μM CNO (M3D-GPR183/ICL3 and M3D-GPR132/ICL3) and 1 μM U-46619 (TBXA2R). Symbols and error bars represent mean and SEM, respectively, of 3-11 independent experiments with each performed in duplicate.

FIG. 7 (F) disclose graphs on concentration-response curves for G-protein activation by DREADD constructs. Previously established DREADDs ($G_q$m-coupled M3D, $G_{i/o}$-coupled M4D and $G_s$-coupled M3D-$G_s$) and the newly generated DREADDs (M3D-GPR183/ICL3 and M3D-GPR132/ICL3) were profiled for their G-protein coupling using representative members ($G_s$, $G_{i1}$, $G_q$ and $G_{13}$) of the 4 G-protein subfamilies. Symbols and error bars represent mean and SEM, respectively, of 3-12 independent experiments with each performed in duplicate. For each DREADD, parameters for the most efficaciously coupled G-protein are shown in bottom of the panel.

FIG. 8 relates to point mutation to enhance G-protein-coupling selectivity. G-protein activation by M3D-GPR183/ICL3 (WT) and a single amino-acid substitution at the position 1.57 with valine (1.57V) was measured by the NanoBiT-G-protein dissociation assay. $G\alpha_{12}$-Lg or $G\alpha_o$-Lg was co-expressed with Sm-Gγ$_{t1}$. Changes in decreased luminescent signals are inversely plotted in the y-axis. Note that in the 1.57V construct $G_o$ activation was decreased while $G_{12}$ activation was unchanged. The inventors found that the ICL3 substitution and/or the 1.57V mutation (position 103 in the FLAG-tagged DREADD; 93 in the original human M3 receptor) of the inventive DREADD constructs specifically binding $G_{12}$ subunit significantly increase selectivity.

Furthermore, for the inventive DREADD constructs, point mutations may additionally be present at Y(3.33)C and A(5.46)G, which refer to amino acid positions 149 (Y) and 239 (A), respectively, in the original human M3 receptor (Gene symbol CHRM3, disclosed in PNAS 2007, Pubmed ID 17360345). When referring to position numbers based on inventive DREADD constructs (with the 10-amino acid FLAG tag at N-terminus), they will be positions 159 (Y) and 249 (A).

FIG. 9 relates to validation of the TGFα shedding assay.

FIG. 9(A) discloses graphs on siRNA-mediated knock-down of mRNA expression. HEK293 cells transfected with a siRNA construct specific to each gene (two targeting constructs per gene) were analyzed for mRNA expression by quantitative real-time PCR. The GNAQ, the GNA11, the GNA12 and the GNA13 genes encode $G\alpha_q$, $G\alpha_{11}$, $G\alpha_{12}$ and $G\alpha_{13}$ subunits, respectively. mRNA levels are shown as relative values to that in control siRNA-transected cells. Bars and error bars represent mean and SEM, respectively (n=3).

FIG. 9(B) discloses an overview siRNA-mediated knock-down at protein expression levels. Lysates from HEK293 cells transfected with a mixture of the indicated siRNA constructs were subjected to immunoblot analyses using antibodies specific to $G\alpha_q$ (an open arrowhead), $G\alpha_{q/11}$, $G\alpha_{13}$ or α-tubulin. Note that owing to a lack of a sensitive, validated antibody against $G\alpha_{12}$, immunoblot for $G\alpha_{12}$ was not assessed. ns, non-specific immunoreactive band (a filled arrowhead).

FIG. 9(C) discloses graphs on knockdown of $G_{q/11}$, attenuates AP-TGFα release induced by $G_{q/11}$-coupled HRH1. HEK293 cells transfected with a siRNA construct (filled symbols) and an HRH1-encoding plasmid were subjected to the TGFα shedding assay. Note that the data for the control siRNA (open symbols) are identical in all of the panels. The ADAM17 gene encode a membrane protease that cleaves the AP-TGFα reporter protein (Inoue et al., 2012). Numbers to the right of each plot indicate EC$_{50}$, E$_{max}$ and RAi values obtained from sigmoidal concentration-response curves. Symbols and error bars are mean and SD (three replicate wells per one point), respectively, from a representative experiment of at least two independent experiments with similar results.

FIG. 9(D) discloses graphs on knockdown of $G_{12/13}$ attenuates AP-TGFα release induced by $G_{12/13}$-coupled PTGER3. Details as for (B), but using another PTGER3 and the corresponding ligand, prostaglandin E$_2$ (PGE$_2$).

FIG. 9(E) discloses graphs on parental, $\Delta G_q$, $\Delta G_{12}$ and $\Delta G_q/\Delta G_{12}$ HEK293 cells were transiently transfected with a plasmid encoding N-terminally FLAG epitope-tagged GPCR (HRH1, ADRB1 or DRD1) or an empty plasmid (Mock). The transfected cells were stained fluorescently labeled with anti-FLAG tag antibody, followed by a secondary antibody conjugated with a fluorophore, and subjected to flow cytometry analysis. Data are shown in histograms and numbers at bottom of each panel indicate mean and SD (four biological replicates per one condition), respectively, of fluorescently positive percentage and mean fluorescent intensity (MFI) from a representative experiment of two independent experiments with similar results. Note that due to transient transfection, there are two peaks showing a highly expressing cell pool and poorly expressing one.

FIG. 9(F) discloses Cell surface expression levels dependent on C-terminal region of a co-expressed chimeric $G\alpha_q$ subunit. In $\Delta G_q/\Delta G_{12}$ HEK293 cells, chimeric $G\alpha$ subunits were individually transfected with a plasmid encoding an N-terminally FLAG epitope-tagged GPCR (HRH1, ADRB1 or DRD1). The transfected cells were stained fluorescently labeled with anti-FLAG tag antibody, followed by a secondary antibody conjugated with a fluorophore, and subjected to flow cytometry analysis. Plots in the panels denote independent experiments and bars represent mean values (n=4 or 5). MFI values that significantly differ from the control ($G\alpha_q$ ($\Delta C$)) are denoted by asterisks: *P<0.05 (one-way ANOVA with Dunnett's post hoc test). NS denotes not significantly different from control.

FIG. 9(G) discloses graphs on concentration-response curves of AGTR1 for the endogenous ligand (Angiotensin II, AngII) and a biased agonist ([Sar$^1$-Ile$^4$-Ile$^8$] AngII, SII). G-protein signaling activity was assessed by the chimeric-G-protein-based assay. Symbols and error bars are mean and SEM, respectively, of eight independent experiments with each performed triplicate.

FIG. 9(H) discloses ligand bias plots. For each chimeric-G-protein coupling, LogRAi values were plotted. If SII behaves as a balanced ligand, plots would be linearly aligned. Dotted lines (slope=1) were drawn crossing C-terminal $G\alpha_q$ or $G\alpha_{12}$ chimera, indicating that SII is more biased towards $G_{12}$ than $G_q$. Note that activation of $G\alpha_s$ by SII was minimum and thus not included in the plot. Symbols and error bars are mean and SEM, respectively, of eight independent experiments.

FIG. 9 (I) discloses graphs on validation of SII bias toward $G_{12}$ by the NanoBiT-G-protein dissociation assay. NanoBiT-G-proteins ($G_q$ and $G_{12}$) were expressed with AGTR1 and ligand-induced G-protein-dissociation signal was measured. Symbols and error bars are mean and SEM, respectively, of six independent experiments.

FIG. 10 relates to chimeric $G\alpha$ subunits and their activity for TGF$\alpha$ shedding and cAMP responses.

FIG. 10 (A) discloses overview on seven C-terminal sequences (CGN numbering (Flock et al., 2015) of G.H5.20-G.H5.26) of $G\alpha$ subunits among the 16 human $G\alpha$ subunits. Asterisks indicate identical amino acids to one above. Note that there are 11 distinct sequences and that the −7 position (G.H5.20) is a completely conserved leucine.

FIG. 10 (B) discloses an overview on evolutionally conservation the seven C-terminal sequences of representative $G\alpha$ subunits from the four G-protein subfamilies.

FIG. 10 (C) discloses an overview on chimeric G-proteins used in this study. The inventors used human $G\alpha_q$-based chimera with a substitution of six C-terminal amino acids. In the negative-control $G\alpha_q$, the seven C-terminal amino acids are truncated.

FIG. 10 (D) discloses graphs on capacity of $G\alpha$ subunits to induce TGF$\alpha$ shedding response. Scheme of the experiment is shown in left. $G_{i/o}$-coupled DRD2 was co-expressed with an indicated chimeric $G\alpha$ subunit or a native, full-length $G\alpha$ subunit in $\Delta G_q/\Delta G_{12}$ cells and subjected to the TGF$\alpha$ shedding assay by using dopamine. Note that the $G\alpha_{q/i1}$ chimera induced the most potent response and the other negative control conditions ($G\alpha_{i1}$, $G\alpha_q$ or an empty vector transfection (Mock)) did not induce the signal. Symbols and error bars are mean and SD (three wells per one point), respectively, from a representative experiment of at least two independent experiments with similar results.

FIG. 10 (E) discloses graphs on capacity of $G\alpha$ subunits to induce TGF$\alpha$ shedding response. Scheme of the experiment is shown in left. The experimental design is the same as DRD2, except for usage of $G_s$-coupled PTGER2, C-terminal $G\alpha_s$ chimeras and prostaglandin E$_2$ (PGE$_2$). Note that the $G\alpha_{q/s}$ chimera induced the most potent response and the other negative control conditions ($G\alpha_s$ long isoform ($G\alpha_{sL}$), $G\alpha_s$ short isoform ($G\alpha_s$s), $G\alpha_q$ or an empty vector transfection (Mock)) did not induce the signal. Symbols and error bars are mean and SD (three replicate wells per one point), respectively, from a representative experiment of at least two independent experiments with similar results.

FIG. 10 (F) discloses overview on protein expression levels of chimeric $G\alpha_q$ subunits. Lysates from $\Delta G_q/\Delta G_{12}$ cells transfected with a plasmid encoding an indicated chimeric $G\alpha_q$ subunit were subjected to immunoblot analyses using antibodies specific to $G\alpha_q$, $G\alpha_{q/11}$ or $\alpha$-tubulin. Note that expression levels of the chimeric $G\alpha_q$ subunits were almost equal except for the C-terminally truncated $G\alpha_q$(AC), which was previously shown to undergo spontaneous activation (Denker et al., 1992), and thereby likely to be unstable in cells owing to its tendency to separate from $G\beta\gamma$ subunits.

FIG. 10 (G) discloses graphs on kinetics of cAMP level upon $G_s$-coupled receptor stimulation. HEK293 cells devoid of the $G_s$ subfamily (AGs, lacking $G\alpha_s$ and $G\alpha_{olf}$) (Stallaert et al., 2017) transiently expressing a cAMP biosensor (Glo-22F), a $G_s$-coupled receptor (AVPR2 or mock transfection) and a $G\alpha_s$ construct (native $G\alpha_s$, $G\alpha_s$-Lg or mock transfection) were loaded with D-luciferin. The cells were stimulated with an increasing concentration of arginine-vasopressin, an AVPR2 ligand, or Forskolin (FSK, 10 μM), an adenylyl cyclase activator, and luminescent signals were measured for 20 min. luminescent signals were normalized to initial counts and relative values are plotted. Each line indicates a kinetics from a single well and data are from a representative experiment of at least three independent experiments with similar results. Note that owing to preference of Forskolin to a $G\alpha_s$-bound adenylyl cyclase (Insel and Ostrom, 2003), Forskolin-induced cAMP response was attenuated in the $\Delta G_s$ cells. Also note that in native $G\alpha_s$-expressing cells, owing to higher initial luminescent counts reflecting constitutive $G_s$ activity, amplitude of fold change is smaller than the other conditions.

FIG. 10 (H) discloses graphs on concentration-response curves. Fold-change luminescent signals at 10 min after ligand addition in A were normalized to Forskolin response and fitted to a sigmoidal curve. Symbols and error bars are mean and SEM, respectively (n=3 or 4). Pharmacological parameters are shown at the bottom (mean±SEM). Mean pEC$_{50}$ values were anti-logarithmically transformed and expressed as μM values in parenthesis.

FIG. 10 (I) discloses overview on chimeric G-protein-based cAMP assay in $\Delta G_s$ cells. A test GPCR is expressed together with one of 11 chimeric $G\alpha_s$ subunits harboring C-terminal 6-amino acid substitution in $\Delta G_s$ cells and restoration of ligand-induced cAMP response is measured by a luminescent cAMP biosensor. The C-terminally truncated $G\alpha_s$ construct ($G\alpha_s$ ($\Delta C$)) is used for a negative control.

FIG. 10 (J) discloses graphs on representative data for the chimeric G-protein-based cAMP assay. TBXA2R was expressed with one of the 11 $G\alpha_s$ constructs or the $G\alpha_s$ ($\Delta C$) and treated with titrated concentration of a ligand (U-46619). Ligand-induced cAMP responses normalized to forskolin (10 μM)-induced response were fitted to a sigmoidal concentration-response curve (upper panels). G-protein coupling is scored as logarithm of RAi values. Symbol size is proportional to $E_{max}$, which reflects fitting quality. Data for the concentration-response curves are from a representative experiment (mean±SD of triplicate measurements). Each LogRAi plot denotes single experiment (n=5).

FIG. 10 (K) discloses graphs on comparison of the chimeric G-protein backbones in coupling profiles. Log RAi values obtained from the chimeric $G_q$-based TGFα shedding assay are plotted against the chimeric $G_s$-based cAMP assay for seven prostanoid receptors. Considered were only mean values for the plots. Note that PTGFR showed poor responses in the cAMP assay and thus not used for the comparison. Linear regression analysis was performed and 90% confidence bands of the best-fit line were shown. Mean±SD of $r^2$ values from the seven prostanoid receptors is shown at the bottom.

FIG. 11 relates to the development and validation of the NanoBiT-G-protein dissociation assay.

FIG. 11 (A) discloses schematic view of the NanoBiT-G-protein assay. Components of the NanoBiT-G-protein (typically, LgBiT-inserted Gα subunit, SmBiT-fused $G_1$ subunit and native Gγ₂ subunit and a test GPCR are transiently expressed in HEK293 cells. By loading with coelenterazine (CTZ), a substrate for the NanoBiT luciferase, the NanoBiT-G-protein emits bioluminescence. Stimulation with a GPCR ligand triggers exchange of a guanine nucleotide (GDP release and GTP incorporation) of the NanoBiT-G-protein and induces dissociation of Gα-Lg from Sm-Gβγ, thereby reducing bioluminescence signals. Note that both Gα and Gβγ subunits are lipidated (not shown) and localized to membrane.

FIG. 11 (B) Graph on luminescent kinetics of NanoBiT-G-proteins after GPCR ligand stimulation. Representative members ($G_s$, $G_{i3}$, $G_q$ and $G_{13}$) from the four G-protein subfamilies were co-expressed with a corresponding coupling GPCR and stimulated with its ligand (10 μM isoproterenol, 10 μM dopamine or 1 μM U-46119) or vehicle. After ligand addition, a microplate was measured at 10-see interval for 10 min. Each line indicates a luminescent trace of one well, normalized to an initial count, from a representative experiment of at least three independent experiments with similar results. Note that due to a time lag between manual ligand addition and beginning of measurement, NanoBiT-$G_{13}$ shows already dissociated signal from the initial reading.

FIGS. 11 (C-E) discloses graphs on the effect of preincubation time with CTZ. Cells expressing the indicated combination of the NanoBiT-G-protein and the test GPCR were loaded with CTZ for 15-120 min before measurements (baseline and ligand stimulation). Luminescent signals after 3-5 min ligand addition (10 μM isoproterenol, 10 μM dopamine or 1 μM U-46119) or vehicle treatment were normalized to the baseline signals (FIG. 11C). Bars and error bars represent mean and SEM of indicated numbers of independent experiments in FIG. 11E. Changes in the luminescent signals across titrated ligand concentrations were further normalized to that of vehicle treatment and expressed as concentration-response curves (FIG. 11D). Symbols and error bars represent mean and SEM of indicated numbers of independent experiments in FIG. 11E. Parameters (signal changes and $pEC_{50}$ values) were calculated from the sigmoidal curves (FIG. 11E). Data are expressed as mean±SEM of indicated numbers of independent experiments. Mean $pEC_{50}$ values were anti-logarithmically transformed and expressed as nM values.

FIG. 11 (F) discloses graphs on validation of the NanoBiT-G-proteins by using prostanoid receptors. Seven NanoBiT-G-protein ($G_s$, $G_{i2}$, $G_{i3}$, $G_o$, $G_q$, $G_{12}$ and $G_{13}$) were profiled for the eight prostanoid receptors with their ligands shown in parentheses. Each dot represent data from independent experiments and lines and error bars indicate mean and SEM (n=5-9).

FIG. 11 (G) discloses graphs on comparison of coupling profiling between the chimeric G-protein-based TGFα shedding assay and NanoBiT-G-protein assay. Log RAi values obtained from the chimeric G-protein-based assay are plotted against G-protein dissociation signals from the NanoBiT-G-protein assay for the eight prostanoid receptors. Considered were only mean values for the plots. The $G_i$ family contains data for three members ($G\alpha_{q/i1}$d, $G\alpha_{q/i3}$ and $G\alpha_{q/o}$ chimeras; NanoBiT-$G_{i2}$, NanoBiT-$G_{i3}$ and NanoBiT-$G_o$, respectively) and the $G_{12}$ family includes data for two members ($G\alpha_{q/i2}$ and $G\alpha_{q/i3}$ chimeras; NanoBiT-$G_{12}$ and NanoBiT-$G_{13}$, respectively). PTGER3-$G_{12}$ data were excluded owing to the increased luminescent signal. Linear regression analysis was performed and 95% confident intervals were shown.

FIG. 12 relates to analysis of the chimeric G-protein-based assay dataset and comparison with GtoPdb.

FIG. 12 (A) discloses a graph on Roc curve comparing the chimeric G-protein-based TGFα shedding assay couplings with GtoPdb couplings: roc curves were generated considering only GtoPdb best characterized primary couplings (i.e. reported in at least 3 publications) as binary classifier and TGFα□shedding assay values as scores. Roc curves were calculated either considering coupling values for all the G-proteins in the chimeric G-protein-based TGFα shedding assay (gray) or by excluding poorly characterized couplings (i.e. GNA12, GNA13, GNA14, GNA15, GNAZ; red curve).

FIG. 12 (B) discloses graph on number of GPCRs coupled to G-proteins of the four families at different LogRAi thresholds in the chimeric G-protein-based TGFα shedding assay as well as in GtoPdb.

FIG. 12 (C) discloses graph on distribution of the number of reported bindings (of any of the four G-protein families) for each receptor at different LogRAi thresholds in the chimeric G-protein-based TGFα shedding assay as well as in GtoPdb.

Figures (D-F) disclose overview on fractions of specific couplings, i.e. receptors binding to members of only one G-protein family, in the chimeric G-protein-based TGFα shedding assay (dark red and orange bars for LogRAi≥−0.1 and −1 couplings) and GtoPdb (black and grey bars for primary only and primary & secondary couplings); Venn diagrams with the numbers of receptors coupled to each G-protein family in the chimeric G-protein-based TGFα shedding assay at higher LogRAi stringencies ≥−0.5 (E) and ≥−0.1 (F).

FIG. 12 (G) discloses graph on comparison of receptor sequence and coupling profile similarities: the inventors calculated receptor pairwise sequence similarity by outputting distance matrices from ClustalO (Sievers et al., 2011). The inventors compared receptor pairwise coupling similarity by calculating the distance matrix of coupling profiles (i.e. vectors containing LogRAi values for 11 G-proteins) through the pdist function from scipy (https://www.scipy.org/).

FIG. 13 relates to validation of RhoA activation by the newly identified $G_{12/13}$-coupled GPCRs.

FIG. 13 (A) discloses a schematoc overview of the NanoBiT-RhoA sensor. The two fragments (LgBiT and SmBiT) of the NanoBiT luciferase are N-terminally fused to RhoA and its effector PKN1, respectively. Upon activation by exchanging GDP to GTP, GTP-bound RhoA interacts with PKN1, thereby increasing luminescent signals being measurable upon loading with CTZ.

FIG. 13 (B) discloses graphs on luminescent kinetics of the NanoBiT-RhoA sensor after GPCR ligand stimulation. HEK293 cells expressing the sensor alone (Mock) or with a test GPCR (PTGER3) were stimulated with its ligand (prostaglandin $E_2$, $PGE_2$), lysophosphatidic acid (LPA) or vehicle. After ligand addition, a microplate was measured at 10-sec interval for 10 min. Each line indicates a luminescent trace of one well, normalized to an initial count, from a representative experiment of at least three independent experiments with similar results. Note that LPA stimulates LPA receptors endogenously expressed in HEK293 cells.

FIG. 13 (C) discloses graphs on validation of $G_{12/13}$-mediated signal of the NanoBiT-RhoA sensor. PTGER3 or LPAR6 was expressed with the NanoBiT-RhoA sensor in the parental, $\Delta G_q$, $\Delta G_{12}$ and $\Delta G_q/\Delta G_{12}$ HEK293 cells, and ligand-induced luminescent signals were measured. Symbols and error bars represent mean and SEM, respectively, of 4 (PTGER3) and 6 (LPAR6) independent experiments with each performed in duplicate. ***, P<0.001 (t-test).

FIG. 13 (D) discloses graphs on NanoBiT-RhoA activation by selected GPCRs. Test GPCRs including the newly identified $G_{12/13}$-coupled GPCRs (FIG. 3E) were expressed together with the NanoBiT-RhoA sensor in HEK293 cells and ligand-stimulated luminescent signals were measured. Note that CP-55940-induced RhoA activation occurred in cells expressing CNR1, but not CNR2. Symbols and error bars represent mean and SEM, respectively, of 5-7 independent experiments with each performed in single measurement or duplicate. *P<0.05, **P<0.05 as compared with vehicle treatment (one-way ANOVA with Dunnett's post hoc test).

FIG. 13 (E) discloses graphs on NanoBiT-RhoA activation through endogenously expressed GPCRs. PC-3 cells and MDA-MB-231 cells transiently expressing the NanoBiT-RhoA sensor alone were stimulated with vehicle, thrombin (1000 U L$^{-1}$) or LPA (1 μM), which is a potent inducer of RhoA activation in many cell types. Bars and error bars represent mean and SEM, respectively, of 3 independent experiments with each performed in triplicate. ***, P<0.001 (t-test).

FIG. 13 (F) discloses overview on RhoA pulldown assay to detect $G_{12/13}$ activation by endogenously expressed GPCRs. HN12 cells and Cal27 cells were serum-starved and treated with 5 μM LPA, 10 μM CP-55940, 1 μM Ang II or vehicle. Cell lysates were subjected to the pulldown assay using Rhotekin-beads and precipitated GTP-bound RhoA proteins as well as input RhoA proteins (Total) were assessed by immunoblot analysis. Images of immunoblot membranes are representatives of two experiments with similar results.

FIG. 14 relates to $G_{q/11}$ signaling in the absence of $G_{12/13}$ for GPCRs coupled with $G_{q/11}$ and $G_{12/13}$.

FIG. 14(A) discloses overview on protein expression levels of Gα subunits. Lysates from the parent, $\Delta G_q$, $\Delta G_{12}$ and $\Delta G_q/\Delta G_{12}$ cells were subjected to immunoblot analyses using antibodies specific to $G\alpha_q$ (an open arrowhead), $G\alpha_{q/11}$, $G\alpha_{13}$ or α-tubulin. Note that compensatory upregulation of Gα subunits in $\Delta G_q$ cells (for $G\alpha_{13}$) or $\Delta G_{12}$ (for $G\alpha_q$ or $G\alpha_{11}$) was not observed. Also, note that owing to a lack of a sensitive, validated antibody against $G\alpha_{12}$, immunoblot for $G\alpha_{12}$ was not assessed. ns, non-specific immunoreactive band (a filled arrowhead).

FIG. 14 (B) discloses overview on parameters obtained from concentration-response curves of the chimeric G-protein-based TGFα shedding assay (FIG. 3E above).

FIG. 14 (C) discloses graphs on Ca$^{2+}$ mobilization assay. The parent, $\Delta G_q$ and $\Delta G_{12}$ cells transiently expressing AGTR1 or EDNRA were loaded with a Ca$^{2+}$ fluorescent dye and ligand-induced Ca$^{2+}$ mobilization was assessed. Symbols and error bars represent mean and SEM of the indicated numbers of independent experiments with each performed in duplicate. Parameters obtained from the concentration-response curves are shown at the bottom.

FIG. 14 (D) discloses a schematic overview of the NanoBiT-IP$_3$ sensor. The two fragments (LgBiT and SmBiT) of the NanoBiT luciferase are N-terminally and C-terminally, respectively, fused to inositol-triphosphate (IP$_3$) receptor IP3R2. Upon activation of phospholipase Cβ and hydrolysis of phosphoinositides, released IP$_3$ induces conformational change in IP3R2 and increases luciferase activity.

FIG. 14 (E) discloses a graphs on luminescent kinetics of the NanoBiT-IP$_3$ sensor after GPCR ligand stimulation. HEK293 cells expressing the sensor alone (Mock) or with a test GPCR (CHRM1) were stimulated with its ligand (acetylcholine, ACh) or vehicle. After ligand addition, a microplate was measured at 10-see interval for 15 min. Each line indicates a luminescent trace of one well, normalized to an initial count, from a representative experiment of at least three independent experiments with similar results.

FIG. 14 (F) discloses a graph on validation of $G_{q/11}$-mediated signal of the NanoBiT-IP$_3$ sensor. The parental or ΔGq cells transiently expressing CHRM1 and the NanoBiT-IP$_3$ sensor were stimulated with vehicle or ACh, and ACh-induced luminescent signal change was normalized to that of vehicle treatment. Bar and error bars represent mean and SEM, respectively, of 5 (parent) or 4 ($\Delta G_q$) independent experiments with each performed in triplicate.

FIG. 14 (G) discloses graph on measurement of IP$_3$ formation in EDNRA. The parent, $\Delta G_q$ and $\Delta G_{12}$ cells transiently expressing EDNRA and the NanoBiT-IP$_3$ sensor were stimulated with a titrated ligand and ligand-induced luminescent signal was assessed. Symbols and error bars represent mean and SEM of the indicated numbers of independent experiments with each performed in duplicate. Parameters obtained from the concentration-response curves are shown at the bottom.

FIG. 15 relates to predictor performances, shortest path from contact network analysis, DREADD predictions scatter plot.

FIG. 15 (A) discloses a radial plot representing Matthew correlation coefficient (MCC) of 5-fold cross validation (averaged over 10 runs).

FIG. 15(B) discloses radial plot representing Recall (Sensitivity) of the best performing predictors over the Test set.

FIG. 15 (C) discloses bar plot representing the recall (sensitivity) of the best performing predictors, trained at different LogRAi cutoffs, over the test set.

FIG. 15 (D) discloses overview on example of a shortest communication pathway, depicted on 3D cartoons of the ADRB2-GNAS complex (PDB ID: 3SN6), linking the ligand and G-protein consensus binding pocket pockets.

FIG. 15 (E) discloses a connectivity matrix displaying shortest paths (as intersecting circles) linking residues forming the ligand and G-protein consensus binding pockets (i.e. shown to form such interfaces in at least 50% of the considered structures). Circle color indicates the path length and the diameter is proportional to the number of significant coupling features found at linking positions. Circle rims are red marked if the path is exclusively found on active-like GPCR structures.

FIG. 15 (F) discloses a scatter plot of the relative coupling probabilities of chimeric sequences obtained by swapping on the hM3D backbone sequence the sequence stretches corresponding to the ICL3 alone (y axis) or in combination with the C-term (x axis) from the 148 receptors of the chimeric G-protein-based TGFα shedding assay. The zoomed caption highlights the cluster of chimeric sequences (including GPR183 and GPR132) displaying an increase of coupling probability for GNA12 compared to the reference (i.e. hM3D).

FIG. 16 relates to alidation and application of the Nano-BiT-G-proteins.

FIG. 16(A) represents a heatmap comprising G-protein dissociation profiles across Gβ and Gγ subtypes. Gα-Lg along with coupling GPCR (y-axis) was co-expressed with an indicated subtype of Sm-Gβ or Sm-Gγ and stimulated with a ligand (10 μM isoproterenol for β2AR, 10 μM dopamine for D2, 10 μM acetylcholine for M3 and 1 μM U-46119 for TP). Changes in decreased luminescent signals are presented in a heatmap.

FIG. 16 (B-E) represent graphs on membrane-based NanoBiT-G-protein dissociation assay. Indicated combination of NanoBiT-G-protein and GPCR was expressed in HEK293 cells and used to cell-based assay (top panels) or membrane preparation by homogenizing cells and ultracentrifuge. The resulting membrane fraction was subjected to membrane-based assay (bottom panels).

FIG. 16 (F-I) represent graphs on robustness of the NanoBiT-G-protein dissociation assay. Indicated combination of NanoBiT-G-protein and GPCR was expressed in HEK293 cells and membrane fraction was prepared. In a 96-well plate assay, a half (48-wells) was stimulated with a ligand and the other half (48-well) was treated with vehicle. Kinetics data (top panels) and concentration responses after 3-5 min ligand addition (bottom panels) are shown. Note that in all of the four representative G-protein members, Z' factor exceeds 0.5, indicating that the NanoBiT-G-protein dissociation assay is robust.

FIG. 16 (J-K) represent graphs on assessment of G-protein inhibitor. TP, $Gα_q$-Lg and Sm-Gγ$_{t1}$, were expressed in HEK293 cells and membrane fraction was prepared. After dispensed in a 96-well plate, the samples were treated with titrated concentration of YM-254890, a Gq inhibitor, for 30 min. The samples were then stimulated with 1 μM U-46619. Kinetics data (J) and concentration responses after 3-5 min ligand addition (K) are shown.

FIG. 16 (L-N) represent graphs on enhanced sensitivity of the NanoBiT-G-protein dissociation assay. Indicated combination of NanoBiT-G-protein and GPCR was expressed in HEK293 cells and subjected to cell-based assays. Note that lipidation-defective Gα subunit (L), constitutively active Gα subunit (M) and lipidation-defective Gγ subunits (N) show larger $E_{max}$ (or signal change) and/or smaller $EC_{50}$ values, demonstrating that the NanoBiT-G-protein dissociation signal is more sensitive than the wild-type construct.

FIG. 16 (O) represent graphs on assessment of chimeric G-protein constructs. Indicated combination of NanoBiT-G-protein and GPCR was expressed in HEK293 cells and subjected to the NanoBiT-G-protein dissociation assay. Concentration responses after 3-5 min ligand addition are shown. Note that in Gα subunit, both insertion sites (αA-αB linker and αB-αC linker) as well as both fragments (LgBiT and SmBiT) were functional.

FIG. 16 (P) represent a schematic view to assess Nano-BiT-G-protein activation by its interaction with PLCβ (NanoBiT-G$_q$/PLC assay). $Gα_q$-Lg and Sm-PLCβ are expressed in cells together with G$_q$-coupled receptors. Ligand stimulation induces interaction between $Gα_q$ and PLCβ, thereby emitting bioluminescent signals.

FIG. 16 (Q) represents graphs on luminescent kinetics of NanoBiT-G$_q$/PLC assay after GPCR ligand stimulation. $Gα_q$-Lg (LgBiT insertion at the αB-αC linker) and Sm-PLCβ$_3$ are expressed in cells with or without (mock) M1. The cells were treated with 1 μM acetylcholine or vehicle. Each line indicates a luminescent trace of one well, normalized to an initial count, from a representative experiment of at least three independent experiments with similar results.

FIG. 16 (R) represents graphs on combinations of the $Gα_q$ family members and PLCβ subtypes. All of the 4 $Gα_q$ family members ($Gα_q$, $Gα_{11}$, $Gα_{14}$ and $Gα_{16}$; LgBiT insertion at the αB-αC linker) and the 4 PLCβ subtypes (PLCβ$_{1-4}$; SmBiT fusion at N-terminus) was tested. Note that the Sm-PLCβ2 construct shows high ligand-induced signal changes across the 4 $Gα_q$ family members.

FIG. 16 (S-T) represent graphs on detection of CaSR activation by Ca$^{2+}$. $Gα_q$-Lg (LgBiT insertion at the αB-αC linker) and Sm-PLCβ$_2$ are expressed in cells with or without (mock) CaSR. The cells were treated with titrated concentration of Ca$^{2+}$. Kinetics data (R) and concentration responses after 5-10 min ligand addition (S) are shown.

The present invention is explained further with the aid of the following non-limiting examples, illustrating the parameters of and compositions employed within the present invention. Unless stated otherwise, all data, in particular percentages, parts and ratios are by weight.

According to the present invention the individual features of the exemplary embodiments of the inventive aspects as disclosed in the summary, the detailed description or claims of the present application can respectively be separately combined with singular features or feature combinations of the exemplary embodiments herein below.

Experimental Model and Subject Details

Cells and Transfection

HEK293A cells (Female origin; Thermo Fisher Scientific) and their derivative G-protein-deficient HEK293 cells were maintained in Dulbecco's Modified Eagle Medium (DMEM 2, Nissui Pharmaceutical) supplemented with 10% fetal bovine serum (Gibco®, Thermo Fisher Scientific) and penicillin-streptomycin-glutamine (complete DMEM). Generation and characterization of the ΔGq HEK293 cells, in which null mutations were introduced into the GNAQ and the GNA11 genes by a CRISPR-Cas9 system (Schrage et al., 2015) and thus their functional products are lacking, the ΔG$_{12}$ HEK293 cells (lacking functional products of the GNA12 and the GNA13 genes), the ΔG$_q$/ΔG$_{12}$ HEK293 cells (lacking those of the GNAQ, the GNA11, GNA12 and the GNA13 genes) (Devost et al., 2017) and the ΔGs HEK293 cells (lacking those of the GNAS and the GNAL genes) (Stallaert et al., 2017) were described previously. The cells were regularly tested for mycoplasma contamination using a MycoAlert Mycoplasma Detection Kit (Lonza).

Transfection was performed by using a lipofection reagent, Lipofectamine® 2000 Reagent (Thermo Fisher Scientific), or polyethylenimine (PEI) solution (Polyethylenimine "Max", Polysciences). Typically, HEK293 cells were seeded in a 6-well culture plate at cell density of 2×10$^5$ cells ml$^{-1}$ in 2 ml of the complete DMEM and cultured for one day in a humidified 37° C. incubator with 5% $CO_2$. Seeding density for the $\Delta G_{12}$ cells and the $\Delta G_q/\Delta G_{12}$ cells were increased to $2.5 \times 10^5$ cells $ml^{-1}$ owing to slower growth of the cells than the parent HEK293 cells and the $\Delta G_q$ cells. For Lipofectamine® 2000 transfection, a transfection mixture was prepared by mixing plasmid solution diluted in 250 µl of Opti-MEM (Life Technologies) and Lipofectamine® 2000 solution (2.5 µl) in 250 µl of Opti-MEM. For PEI transfection, a transfection solution was mixed by combining plasmid solution diluted in 100 µl of Opti-MEM and 4 µl of 1 mg $ml^{-1}$ PEI solution in 100 µl of Opti-MEM. Both Lipofectamine® 2000 and the PEI transfection gave almost identical transfection efficiency in the inventors' culture condition. The transfected cells were further incubated for one day before subjected to an assay as described below.

MDA-MB-231 cells (female origin) and PC-3 cells (male origin) were maintained in in RPMI 1640 (Nissui Pharmaceutical) supplemented with 5% fetal bovine serum and penicillin-streptomycin-glutamine. MDA-MB-231 cells and PC-3 cells were seeded in a 10-cm culture dish at cell density of $2 \times 10^5$ cells $ml^{-1}$ in 10 ml of the media and cultured for one day in the incubator. Transfection was performed by using 20 µL of Lipofectamine® 2000 transfection reagent. The transfected cells were incubated for one day before subjected to the NanoBiT-RhoA assay as described below.

HN12 cells (female origin) and Cal27 cells (male origin), which were characterized as part of a head and neck cancer cell oncogenome effort (Martin et al., 2014) and obtained from this NIH cell collection, were maintained in DMEM supplemented with 10% FBS (Sigma-Aldrich).

Method Details

Plasmids

Only human GPCRs and human Gα subunits were used in this study. An open reading frame of each full-length GPCR was cloned into pCAGGS expression plasmid (a kind gift from Dr. Jun-ichi Miyazaki at Osaka University, Japan) or pcDNA3.1 expression plasmid. Except when otherwise specified, GPCR sequences were devoid of epitope tags. The GPCRs examined for this study (148 GPCRs) originated from a previous GPCR library (109 GPCRs) (Inoue et al., 2012) and an extended list of GPCR families (39 GPCRs). In their library, the inventors covered all of the members for selected GPCR families. The inventors note that there are 8 GPCRs (AGTR2, GPBAR1, GPER, GPR18, HTR5A, MC2R, NPBWR2 and PTGDR2) that were unresponsive in the chimeric G-protein-based TGFα shedding assay (data not shown) and thus were not included in the G-protein coupling dataset.

Full-length, untagged Gα subunits were cloned into the pCAGGS plasmid. Chimeric Gα subunits, in which the C-terminal 6 amino acids were substituted, were generated with PCR-amplified fragments using synthesized oligonucleotides encoding swapped C-terminal sequences. A C-terminally truncated $G\alpha_q$ subunit, which lacked 7 amino acids (note that the −7 position is identical among all of the Gα subunits), was used as a negative control for the chimeric-G-protein-based TGFα shedding assay. Inserted sequences were verified by Sanger sequencing (Fasmac). Codon-optimized AP-TGFα cloned into the pCAGGS plasmid was used in this study. Amino acid sequences for the AP-TGFα construct are listed in SEQ ID Nos. 93-96 and the amino acid sequences for the chimeric-G-proteins are listed in 58 to 92.

M3D and M4D (Armbruster et al., 2007) were generated by introducing the two mutations ($Y^{3.33}C$ and $A^{5.46}G$), which alter ligand specificity from ACh to CNO, in human CHRM3 (corresponding to Y149C and A239G) and CHRM4 (Y113C and A203G), respectively, by using an NEBuilder HiFi DNA Assembly system (New England Biolabs) and cloned into the pcDNA3.1 vector with N-terminal FLAG-epitope (DYKDDDDK) tag. ICL3-substituted M3D chimeras were constructed by the NEBuilder system with PCR-amplified fragments using synthesized oligonucleotides encoding swapped ICL3 sequences. Dual ICL3- and C-terminally-substituted M3D chimeras were generated by assembling PCR-amplified fragments with synthesized oligonucleotides for C-terminal sequences. The substituted ICL3 and C-terminus correspond to residues 778-1455 and 1633-1770 of the CHRM3 ORF. A coding sequence for M3D-$G_s$ (Guettier et al., 2009) was human codon-optimized and gene-synthesized by Genscript and inserted into pcDNA3.1 with the N-terminal FLAG-epitope tag. Throughout the study, the inventors used the same N-terminally FLAG-tagged DREADD constructs for functional assays and expression analysis. Amino acid sequences used for suitable DREADDs are shown in SEQ ID Nos. 1 to 4 and 52 to 54.

For NanoBiT-G-proteins (see SEQ ID Nos. 5 to 48), the large fragment (LgBiT) of the NanoBiT luciferase (See SEQ ID. No. 49) was inserted into the helical domain of human Gα subunit (Gα-Lg) flanked by 15-amino acid flexible linkers (see SEQ ID No. 51) and the small fragment (SmBiT) (see SEQ ID No. 50) was N-terminally fused to human Gβ subunit (Sm-GP) or human Gγ subunit (Sm-Gγ) with the 15-amino acid linker. A coding sequence for the Gα-Lg was human codon-optimized and gene-synthesized by Genscript and inserted into pcDNA3.1 plasmid. To construct a coding sequence for the Sm-Gβ and the Sm-Gγ oligonucleotides encoding the N-terminal SmBiT-linker (Fasmac) and PCR-amplified fragment of full-length Gβ ($G\beta_1$, $G\beta_3$ or $G\beta_5$) or Gγ ($G\gamma_2$ or $G\gamma_{t1}$) were assembled by using the NEBuilder system and cloned into the pCAGGS vector. Coding sequences for untagged $G\beta_1$ and $G\gamma_2$ were inserted into pcDNA3.1 vector. Coding sequences for RIC8A and RIC8B (isoform 2) were cloned into pCAGGS vector.

For generation of the inventive NanoBiT-RhoA sensor, the inventors replaced firefly luciferase fragments of previously described RhoA constructs (Leng et al., 2013) with the NanoBiT fragments. Specifically, LgBiT and SmBiT were N-terminally fused to human RhoA (residues 2-193) and the GTPase-binding domain (GBD) of human PKN1 (residues 13-112), a RhoA effector, respectively, with the 15-amino acid linker. A coding sequence for RhoA and PKN1-GBD was human codon-optimized and gene-synthesized by Genscript and inserted into the pCAGGS plasmid by following a similar method as described in the NanoBiT-G-protein construction. Amino acid sequences for the NanoBiT-RhoA constructs (Lg-RhoA and Sm-PKN1) are listed in SEQ ID Nos. 55 and 56.

Similarly, to construct the inventive NanoBIT-IP$_3$ sensor, the inventors exchanged firefly luciferase fragments of a previously described IP$_3$ construct (Ataei et al., 2013) with the NanoBiT fragments. Specifically, LgBiT and SmBiT were fused to N-terminus and C-terminus, respectively, of IP$_3$-binding core domain (IBC) of human type 2 IP$_3$ receptor (Gene symbol ITPR2; residues 225-604), flanked by the 15-amino acid linker. A coding sequence for ITPR2-IBC was human codon-optimized and gene-synthesized by Genscript, and inserted into the pCAGGS plasmid by following an above-described method. An amino acid sequence for the NanoBiT-IP$_3$ sensor (Lg-IP3R2-Sm) is listed in SEQ ID No. 57.

TGFα Shedding Assay

The TGFα shedding assay was performed as described previously (Inoue et al., 2012) with minor modifications. Plasmid transfection was performed in a 6-well plate with a mixture of 500 ng AP-TGFα-encoding plasmid, 200 ng GPCR-encoding plasmid with or without 100 ng Gα-encoding plasmid (per well, hereafter). After 1-day culture, the transfected cells were harvested by trypsinization, pelleted by centrifugation at 190 g for 5 min and washed once with Hank's Balanced Salt Solution (HBSS) containing 5 mM HEPES (pH 7.4). After centrifugation, the cells were resuspended in 6 ml of the HEPES-containing HBSS. The inventors note that trypsinization and following washing procedure resulted in higher signal-to-background TGFα shedding response as compared with harvesting cells without trypsin (EDTA only). The cell suspension was seeded in a 96-well culture plate (cell plate) at a volume of 90 μl (per well hereafter) and incubated for 30 min in a 5% CO$_2$ incubator at 37° C. The cells were treated with a GPCR ligand (10×, diluted in HBSS containing 5 mM HEPES (pH 7.4) and 0.01% (w/v) bovine serum albumin (BSA, fatty acid-free and protease-free grade; Serva)). After spinning the cell plates, conditioned media (80 μl) was transferred to an empty 96-well plate (conditioned media (CM) plate). AP reaction solution (10 mM p-nitrophenylphosphate (p-NPP), 120 mM Tris-HCl (pH 9.5), 40 mM NaCl, and 10 mM MgCl$_2$) was dispensed into the cell plates and the CM plates (80 μl). Absorbance at 405 nm (Ab$_{405}$) of the plates was measured, using a microplate reader (SpectraMax 340 PC384, Molecular Devices), before and after 1-h or 2-h incubation at room temperature. Ligand-induced AP-TGFα release was calculated as described previously. Unless otherwise noted, spontaneous AP-TGFα release signal, which varies from 8-30% of total AP-TGFα expression depending on transfected conditions, was subtracted from ligand-induced AP-TGFα release signal. Using the Prism 7 software (GraphPad Prism), the AP-TGFα release signals were fitted to a four-parameter sigmoidal concentration-response curve, from which EC$_{50}$ and E$_{max}$ values were obtained.

Calculation of G-Protein Coupling Score

The inventors used a factor known as the relative intrinsic activity (RAi) (Ehlert et al., 1999) to calculate scores for G-protein coupling. For each sigmoidal curve of chimeric Gα-expressed condition, the inventors divided a maximal response (E$_{max}$) by a potency (EC$_{50}$) and normalized an E$_{max}$/EC$_{50}$ value to a maximum value among 11 chimeric Gα curves. The resulting dimensionless, relative E$_{max}$/EC$_{50}$ (defined as RAi) parameter was then log (base 10) transformed to give Log RAi values used to quantify coupling. To minimize the occurrence of outliers arising from experimental variations especially for weak AP-TGFα release signal, the inventors set two thresholds. As a first threshold, a Gα chimera condition in which E$_{max}$ was smaller than 3% AP-TGFα release or a concentration-response curve did not converge, was regarded as RAi value of 0. As a second threshold, RAi value smaller than 0.01 was set as 0.01. Thus, a Log RAi values range from −2 to 0 and for the bioinformatics analyses, the inventors used mean values of Log RAi (n=3-6).

NanoBiT-G-Protein Dissociation Assay

Plasmid transfection was performed in a 6-well plate with a mixture of 100 ng Gα-Lg-encoding plasmid, 500 ng Sm-Gβ-encoding plasmid, 500 ng untagged Gγ$_2$-encoding plasmid, 200 ng GPCR-encoding plasmid with or without 100 ng RIC8-encoding plasmid (per well, hereafter). Unless otherwise stated, the combination of following plasmid mixtures was used: Gα$_s$-Lg, Sm-Gβ$_1$, Gγ$_2$ and RIC8B for NanoBiT-G$_s$; Gα$_{i1}$-Lg, Sm-Gβ$_5$ and Gγ$_2$ for NanoBiT-G$_{i1}$; Gα$_{i2}$-Lg, Sm-Gβ$_3$ and Gγ$_2$ for NanoBiT-G$_{i2}$; Gα$_{i3}$-Lg, Sm-Gβ$_3$ and Gγ$_2$ for NanoBiT-G$_{i3}$; Gα$_o$-Lg, Sm-Gβ$_1$ and Gγ$_2$ for NanoBiT-G$_o$; Gα$_q$-Lg, Sm-Gβ$_1$, Gγ$_2$ and RIC8A for NanoBiT-G$_q$; Gα$_{12}$-Lg, Sm-Gβ$_1$, Gγ$_2$ and RIC8A for NanoBiT-G$_{12}$; Gα$_{13}$-Lg, Sm-Gβ$_1$, Gγ$_2$ and RIC8A for NanoBiT-G$_{13}$. After 1-day culture, the transfected cells were harvested with 1 mL of 0.53 mM EDTA-containing Dulbecco's PBS (D-PBS), followed by addition of 2 mL the HEPES-containing HBSS. The cells were pelleted by centrifugation at 190 g for 5 min and resuspended in 2 mL of the 0.01% BSA- and 5 mM HEPES (pH 7.4)-containing HBSS (assay buffer). The cell suspension was seeded in a 96-well culture white plate (Greiner Bio-One) at a volume of 80 μl (per well hereafter) and loaded with 20 μl of 50 μM coelenterazine (Carbosynth) solution diluted in the assay buffer. After 2-h incubation with coelenterazine at room temperature, background luminescent signals were measured using a luminescent microplate reader (SpectraMax L, Molecular Devices). The inventors note that incubation time with coelenterazine can be shortened, but an effect of baseline drift should be taken into account (FIG. 14C-E). Test compound (6×, diluted in the assay buffer) was manually added to the cells (20 μl). Luminescent signals were measured 3-5 min after ligand addition and divided by the initial count. The ligand-induced signal ratio was normalized to that treated with vehicle. The consequent fold-change values were fitted to a four-parameter sigmoidal concentration-response described above.

NanoBiT-RhoA Assay

Plasmid transfection in HEK293 cells was performed by using a mixture of 100 ng Lg-RhoA plasmid, 500 ng Sm-PKN1 plasmid and 200 ng GPCR plasmid (per well in a 6-well plate). For transfection in MDA-MB-231 cells and PC-3 cells, 1.5 μg Lg-RhoA plasmid and 7.5 ag of Sm-PKN1 plasmid were used (per 10-cm dish). The transfected cells were harvested, seeded in a white 96-well plate and loaded with 10 μM CTZ in the same manner described in the NanoBiT-G-protein dissociation assay. After measuring an initial luminescent signal, test compounds were added to the cells. Then, 3-5 min later, luminescent signals were measured and fold-change values were plotted as described above.

NanoBiT-IP$_3$ Sensor Assay

Plasmid transfection was performed by using a mixture of 1 μg Lg-IP3R2-Sm plasmid and 200 ng GPCR plasmid (per well in a 6-well plate). The transfected cells were harvested, seeded in a white 96-well plate and loaded with 10 μM CTZ in the same manner described in the NanoBiT-G-protein dissociation assay. After measuring an initial luminescent signal, test compounds were added to the cells. Then, 5-10 min later, luminescent signals were measured and fold-change values were plotted as described above.

NanoBiT-Gq-PLCβ Interaction Assay

Plasmid transfection was performed by using a mixture of 100 ng Gα-Lg-encoding plasmid, 500 ng Sm-PLCβ-encoding plasmid, 500 ng untagged Gβ$_1$-encoding plasmid, 500 ng untagged Gγ$_2$-encoding plasmid, 200 ng GPCR-encoding plasmid and 100 ng RIC8A-encoding plasmid (per well in a 6-well plate, hereafter). The transfected cells were harvested, seeded in a white 96-well plate and loaded with 10 μM CTZ in the same manner described in the inventive NanoBiT-G-protein dissociation assay. After measuring an initial luminescent signal, test compounds were added to the cells. Then, 5-10 min later, luminescent signals were measured and fold-change values were plotted as described above.

siRNA Transfection

Stealth siRNA duplexes against mRNA encoding $G\alpha_q$, $G\alpha_{11}$, $G\alpha_{12}$, $G\alpha_{13}$ and TACE (gene symbols, GNAQ, GNA11, GNA12, GNA13 and ADAM17, respectively) and Stealth negative control were purchased from Life Technologies. Target sequences and manufacturer's catalog numbers are as follows: GNAQ (#1), 5'-GGAGAGAGUGGCAAGAGUACGUUUA-3', GNAQHSS104236; GNAQ (#2), 5'-CCCUUUGACUUA-CAAAGUGUCAUUU-3', GNAQHSS104237; GNA11 (#1), 5'-CCGGCAUCAUCGAGUACCCUUUCGA-3', GNA11HSS178464; GNA11 (#2), 5'-GCAUCAGUACGU-CAGUGCCAUCAAG-3', GNA11 HSS104213; GNA12 (#1), 5'-CCAAGGGAAUUGUGGAGCAUGACUU-3', GNA12-HSS178466; GNA12 (#2), 5'-CCAUCGU-CAACAACAAGCUCUUCUU-3', GNA12MSS204749; GNA13 (#1), 5'-CAGAAGCCCUUAUACCACCAC-UUCA-3', GNA13-HSS173827; GNA13 (#2), 5'-GCAGCCCAAGGAAUGGUGGAAACAA-3', GNA13-HSS116479; ADAM17, 5'-CAGAAUCGU-GUUGACAGCAAAGAAA-3', ADAM17-HSS186181. siRNA constructs for the GNA12 (#1), the GNA13 (#1) and the ADAM17 genes were described previously and validated (Inoue et al., 2012).

HEK293 cells were seeded in a 6-well culture plate at cell density of $1\times10^5$ cells ml$^{-1}$ in 2 ml of the complete DMEM and incubated for 1 day. Transfection of siRNA transfection was performed by using Lipofectamine® RNAiMAX (Thermo Fisher Scientific) according to the manufacturer instructions (final siRNA concentration of 10 nM and 2 µL (per well in a 6-well plate) of Lipofectamine® RNAiMAX). After 1-day incubation, media were replaced and transfection of plasmids encoding AP-TGFα and GPCR was performed as described above. The resulting cells were subjected to the TGFα shedding assay.

Quantitative Real-Time PCR Analysis

Total RNA from siRNA-transfected HEK293 cells was prepared using a GenElute Mammalian Total RNA Miniprep Kit (Sigma-Aldrich). Total RNA was reverse-transcribed using High-Capacity cDNA RT Kits (Applied Biosystems) according to manufacturer instructions. Real-time quantitative PCRs were performed with SYBR Premix Ex Taq (Takara Bio) and monitored by ABI Prism 7300 (Applied Biosystems). Standard plasmids ranging from $10^2$-$10^8$ copies per well were used to quantify the absolute number of transcripts of cDNA samples. The numbers of transcripts were normalized to the number of GAPDH in the same sample and expressed as relative values to that in control siRNA-transfected cells.

Primers were as follows:

```
GNAQ,
5'-ACCGAATGGAGGAAAGCAAGG-3'
and

5'-CATCTCTCTGGGGTCCATCATATTC-3';

GNA11,
5'-CAGCGAATACGACCAAGTCC-3'
and

5'-ACCAGGGGTAGGTGATGATG-3';
```

```
-continued

GNA12,
5'-GAGGGATTCTGGCATCAGG-3'
and

5'-CGATCCGGTCCAAGTTGTC-3';

GNA13,
5'-CCTGGATAACTTGGATAAACTTGG-3'
and

5'-TTCATGGATGCCTTTGGTG-3';

GAPDH,
5'-GCCAAGGTCATCCATGACAACT-3'
and

5'-GAGGGGCCATCCACAGTCTT-3'.
```

Western Blot

The parental HEK293 cells and a panel of the G-protein-KO HEK293 cells ($\Delta G_q$, $\Delta G_{12}$ and $\Delta G_q/\Delta G_{12}$ cells) in growth phase were harvested and approximately $1\times10^6$ cells were lysed in 500 µL of SDS-PAGE sample buffer (62.5 mM Tris-HCl (pH 6.8), 50 mM dithiothreitol, 2% SDS, 10% glycerol and 4 M urea) containing 1 mM EDTA and 1 mM phenylmethylsulfonyl fluoride. Cell lysates were homogenized with a hand-held ultrasonic homogenizer (Microtech) and proteins were denatured at 95° C. for 5 min. The lysates were loaded and separated on a 12.5% polyacrylamide SDS-gel. After electrophoresis, the gel was blotted to a nitrocellulose membrane. The blotted membrane was blocked with 5% skim milk-containing blotting buffer (10 mM Tris-HCl (pH 7.4), 190 mM NaCl and 0.05% Tween 20), immunoblot with primary (1 µg ml$^{-1}$) and secondary antibodies (1:2000 dilution). Primary antibodies used in this study were anti-$G\alpha_q$ antibody (goat polyclonal; Abcam, ab128060), anti-$G\alpha_{11}$ antibody (mouse monoclonal, clone D-6; Santa Cruz Biotechnologies, sc-390382), anti-$G\alpha_{13}$ antibody (rabbit monoclonal, clone EPR5436; Abcam, ab128900) and anti-α-tubulin antibody (mouse monoclonal, clone DM1A; Santa Cruz Biotechnologies, sc-32293). The inventors note that by using cell lysates overexpressing Gα subunits, the anti-$G\alpha_q$ antibody and the anti-$G\alpha_{13}$ antibody were validated to be specific, but the anti-$G\alpha_{11}$ antibody reacted with both $G\alpha_q$ and $G\alpha_{11}$ (data not shown), and thus the inventors labeled immuno-reactive bands as $G\alpha_{q/11}$. Secondary antibodies were conjugated with horseradish peroxidase (HRP) and were anti-goat IgG antibody (American Qualex, A201PS), anti-mouse IgG (GE Healthcare, NA9310) and anti-rabbit IgG (GE Healthcare, NA9340). Membrane were soaked with a commercial chemiluminescent reagent (ImmunoStar® Zeta, FujiFilm Wako Pure Chemicals) or in-house reagent (100 mM Tris-HCl (pH 8.5), 50 mg ml$^{-1}$ Luminol Sodium Salt HG (FujiFilm Wako Pure Chemicals), 0.2 mM p-Coumaric acid and 0.03% (v/v) of $H_2O_2$). and a chemiluminescence image was acquired with a LAS-4000 (FujiFilm) and analyzed with Multi Gauge ver. 3.0 (FujiFilm).

Flow Cytometry

Plasmid transfection was performed in a 12-well plate with volumes of 500 ng plasmid encoding N-terminally FLAG epitope-tagged GPCR with or without 250 ng Gα-encoding plasmid. The transfected cells were harvested by adding 300 µl of 0.53 mM EDTA-containing D-PBS, followed by 300 µl of 5 mM HEPES (pH 7.4)-containing Hank's Balanced Salt Solution (HBSS). The cell suspension was dispensed in a 96-well V-bottom plate (200 µl per well, two wells per sample). After centrifugation at 700 g for 1 min, the cells were washed once with D-PBS and pelleted. Cell pellets were suspended in 2% goat serum- and 2 mM EDTA-containing D-PBS (blocking buffer; 100 µl per well) and incubated for 30 min on ice. After centrifugation at 700 g for 1 min, the cells were stained with anti-FLAG epitope tag monoclonal antibody (Clone 1E6, FujiFilm Wako Pure Chemicals; 10 µg ml$^{-1}$ in the blocking buffer; 50 µl per well) for 30 min on ice. After rinse with D-PBS, cells were labeled with a goat anti-mouse IgG secondary antibody conjugated with Alexa Fluor 488 (Thermo Fisher Scientific; 10 µg ml$^{-1}$ dilution in the blocking buffer; 25 µl per well) for 15 min on ice. The cells were washed once with D-PBS, resuspended in 100 µl of 2 mM EDTA-containing-D-PBS and filtered through a 40 µm filter. The fluorescently labeled cells (approximately 20,000 cells per sample) were analyzed by an EC800 flow cytometer (Sony). Fluorescent signal derived from Alexa Fluor 488 was recorded in an FL1 channel and flow cytometry data were analyzed by a FlowJo software (FlowJo). Values of mean fluorescence intensity (MFI) were used for quantification.

GloSensor cAMP Assay

Plasmid transfection was performed in a 6-well plate with a mixture of 1 µg Glo-22F cAMP biosensor-encoding pCAGGS plasmid (gene synthesized with codon optimization by Genscript), 200 ng AVPR2-encoding plasmid and 100 ng of Gα$_s$-Lg-encoding plasmid or native Gα$_s$-encoding plasmid. After 1-day incubation, the transfected cells were harvested with 0.53 mM EDTA-containing D-PBS, centrifuged at 190 g for 5 min and suspended in 0.01% BSA- and 5 mM HEPES (pH 7.4)-containing HBSS (vehicle; 0.6 ml per well). The cells were seeded in a half-area white 96-well plate (Greiner Bio-one; 30 µL per well) and loaded with D-luciferin potassium solution (10 µL of 8 mM solution per well; FujiFilm Wako Pure Chemical, Japan). After 2 h incubation in the dark at room temperature, the plate was read for its initial luminescent count (integration time of 1 s per well; Spectramax L, Molecular Devices, Japan). The cells were treated with vehicle, arginine vasopressin (Peptide Institutes, Japan) or 10 µM forskolin (FujiFilm Wako Pure Chemical, Japan) (10 µL of 5× solution per well). Kinetics values were measured on the plates for 20 min and expressed as fold-change values. To obtain a concentration-response curve, fold-change luminescent signals at 10-min after compound addition were normalized to that in forskolin-treated condition. Using the Prism 7 software (GraphPad Prism), the cAMP signals were fitted to a four-parameter sigmoidal concentration-response curve, from which EC$_{50}$ values were obtained.

For the chimeric G$_s$-based cAMP assay, ΔG$_s$ cells were transfected with a mixture of 1 µg Glo-22F plasmid, 200 ng GPCR plasmid and 100 ng chimeric Gα$_s$ plasmid containing the backbone of human Gα$_s$ subunit (short isoform, residues 1-374) and a substitution of C-terminal 6-amino acids. The transfected cells were harvested, seeded in the half-area 96-well plate, loaded with D-luciferin and stimulated with a GPCR ligand in the same manner as described above. Scores of G-protein coupling (RAi values) values were calculated as described in the TGFα shedding assay section.

Active RhoA Pulldown Assay

HN12 cells and Cal27 cells were cultured to 50% confluency, and then serum starved overnight. To induce RhoA activation, cells were treated with 5 µM LPA, 1 µM Ang II, or 10 µM CP-55940 for 5 min. Active RhoA levels were measured using the RhoA Pull-Down Activation Assay Biochem Kit (bead pull-down format; Cytoskeleton) following the manufacturer instruction using a modified lysis buffer (50 mM Tris-HCl (pH 7.2), 500 mM NaCl, 10 mM MgCl$_2$, 0.1% SDS, 1% NP-40). Briefly, after stimulation, samples were lysed and protein concentrations were quantified using DC Protein Assay (BioRad). Samples were adjusted to the same concentration with lysis buffer and 500 µg of each protein lysate was added to 15 µL GST-tagged Rhotekin-RBD bound to Sepharose beads. Samples were incubated while rocking at 4° C. for 1.5 h. Beads were then washed, eluted in Laemmli sample buffer, and analyzed by western blot using a mouse monoclonal anti-RhoA antibody (Cytoskeleton).

Ca$^{2+}$ Mobilization Assay

Plasmid transfection was performed in the parental, ΔGq and ΔG12 HEK293 cells by using 5 µg GPCR plasmid (AGTR1 or EDNRA; 5 µg per 10-cm culture dish). After one-day incubation, the transfected cells were harvested with trypsinization. After centrifugation, the cells were suspended in serum-free DMEM at a cell concentration of 5×10$^5$ cells ml$^{-1}$, and 40 µl (per well hereafter) of the cell suspension seeded in a half-area, clear-bottom black plate. The cells were further incubated in the incubator for one day. After loading 40 µl of a Ca$^{2+}$ indicator (FLIPR Calcium 5 Assay Kit, Molecular Devices) according to manufacturer instructions in the presence of 2.5 mM probenecid for 1 h in the incubator, the cell plate was placed in a fluorescence microplate reader (FlexStation 3, Molecular Devices). Fluorescent signal was measured with automated pipetting of test ligands (20 µL of 5× compounds). Fluorescent signals from 40 to 55 sec after ligand addition were averaged and normalized to an initial count and expressed as a relative value to vehicle treatment.

Comparison of Data from the Chimeric G-Protein-Based Assay With Known Couplings

The inventors performed Receiver Operating Characteristic (ROC) analysis to compare the chimeric G-protein-based TGFα shedding assay results to primary or secondary couplings from GtoPdb (Harding et al., 2018), defined as binary classifiers. The inventors defined the optimal LogRAi cutoff as that maximizing the True Positive Rate (TPR, or sensitivity) while minimizing the True Negative Rate (TNR, or 1-specificity). The inventors defined positives as GtoPdb couplings reported in at least 3 references, and negatives as the couplings that were never reported for these more studied receptors. The inventors obtained a value close to −1 as the optimal LogRAi cutoff considering all G-proteins altogether (FIG. 15), which the inventors then considered as a lower and upper confidence bound for positively and negatively coupled receptors.

Sequence-Based Coupling Determinant Features

The inventors first generated a multiple sequence alignments (MSAs) of the 144 Class A GPCR sequences using HMMalign from the HMMer package (Eddy, 1998), using the 7tm_1 Pfam (Finn et al., 2016) Hidden Markov Model (HMM). The inventors subdivided the pool of receptor sequences into positively and negatively coupled to a given G-protein using the optimal LogRAi cutoff as a lower and upper bound. These sub-alignments were used to build corresponding HMM profiles through hmmbuild (http://www.hmmer.org/), leading to 22 models (coupled vs. uncoupled for 11 G-proteins).

From coupled and uncoupled HMM profiles for each G-protein, the inventors then extracted alignment positions present in both HMM models and showing statistically different distributions (Wilcoxon's signed-rank test; p-value<=0.05) of the 20 amino acid bit scores (FIG. 4A). The inventors also considered those alignment positions with consensus columns (i.e. those having a fraction of residues, as opposed to gaps, equal or greater than the hmmbuild's symfrac parameter, using default value of 0.5) present in either of HMM models. In details, if a consensus column was present only in the HMM profile of either the coupled or uncoupled groups, the inventors labelled it as insertion or deletion, respectively. As additional features, the inventors also included length and amino acid composition of the N- and C-termini (N-term and C-term) and the extra- and intra-cellular loops (ECLs and ICLs). For every G-protein, only statistically significant (p-value<0.05; Wilcoxon's rank-sum test) features were considered.

To identify each positions within the alignment, the inventors employed the Ballesteros/Weinstein scheme (Weinstein, 1995), using the consensus secondary structure from the 7tm_1 HMM model to number residues within helices in a consecutive way. Most conserved positions within each helix were defined according to GPCRDB (http://www.arcrdb.ora) (Isberg et al., 2017). The inventors adjusted the B/W numberings for TM6, which they started at position 6.25 (domain position 200) instead of 6.31 (domain position 206), according to visual inspections of recent G protein-GPCRs complexes. If a position lies on an extra-7TM region (e.g. ECLs or ICLs), the inventors use the corresponding label plus the corresponding Pfam domain consecutive numbering in parenthesis.

G-Protein Coupling Predictor

The inventors implemented a predictor for G-protein coupling by using a logistic regression classifier, or Log-reg classifier, available from the scikit-learn package (http://scikit-learn.org) (Pedregosa F, 2011) The possible outcomes in log-reg are modeled using a logistic function, with L1 or L2 based regularization. In this study the inventors used L2 penalized form of log-reg. The target value is expected to be a linear combination of the given features. This property of log-reg can also be exploited to study the weights of its features.

As an optimization problem, binary class L2 penalized logistic regression minimizes the following cost function:

$$\min_{w,c} \frac{1}{2} w^T w + C \sum_{i=1}^{n} \log(\exp(-y_i(X_i^T w + c)) + 1) \quad 1)$$

where X denotes a vector of feature variables, $w \in R\hat{\ }n$ is the weight vector, $c \in R\hat{\ }n$ is the intercept, C is inverse of regularization strength (positive float), y takes values in $\{-1, 1\}$ at trial i and n is the number of trials conducted.

The inventors used the liblinear method as the optimization algorithm as shown to be optimal for relatively small datasets (https://www.csie.ntu.edu.tw/~cjlin/liblinear/).

Training and Cross Validation

The inventors used 7TM domain positions and compositional features for the ICL3 and C-term, which prevail over other extra-7TM domain features, to create a training matrix. In case of significant positional features, two-bit scores (derived from the positive and negative HMMs for a given G-protein) are returned for the corresponding amino acid found at a given position in the input GPCR sequence (FIG. 4A). In case a position was found to be present in either positive or negative HMMs, the single bit score, derived from the respective HMM, was returned. If for any GPCR, no amino acid was present at the given position, it was assigned the highest bit scores from the both models, implying the least conserved scores.

All the features were scaled to the range [0, 1]. Feature scaling aids not only in converging the algorithm faster but also helps in assessing the feature relevance (Dou et al., 2012). A grid search was performed over a stratified 5-fold cross validation (CV) to select the best value of C (inverse of the regularization strength) over a range of [1e-02, 1e05]. In a stratified 5-fold CV, the training matrix is divided randomly into 5 equal sub-matrices, preserving the ratio of positive (coupling) and negative (non-coupling) GPCRs. During each fold, one of the sub matrix is treated as the validation set and the remaining four as the training set.

The inventors assessed the performance of the inventors' predictor using standard metrics (MCC, ACC, PRE, REC, SPE, AUC, F1M;). The parameters showing the best Area Under the Curve (AUC) of the Receiver Operating Curve (ROC) were chosen to create models for every G-protein.

The number of positive (coupling) GPCRs were either more (eg: in GNAI1/3) or less (eg: in GNAS) than the number of negative (non-coupling) GPCRs. Such an imbalance would make the predictor biased to any one of the two classes. In order to counter this problem, the parameter class_weight was set to balanced in the log-reg classifier function. By default, all the classes have same weight. However, by setting the class_weight as balanced, the values of the column with classes (coupling/uncoupling) are used to automatically adjust the weights inversely proportional to their frequencies in the training matrix. To ensure minimal variance due to random division of the training matrix during the cross validation, the aforementioned experiment was repeated ten times for every G-protein group and the standard deviation was recorded. The feature weights were extracted as described elsewhere (Dou et al., 2012) from the trained models and are critical to understand the relative importance of different features (FIG. 4).

Besides performing the above-said steps at LogRAi cutoff of –1.0, the inventors also created models at LogRAi cutoffs –0.5 and –0.1. As it can be seen in FIG. 15A, for most of the G-proteins, –1.0 turns out to be the best LogRAi cutoff during cross-validation (using MCC as the selection criteria).

Randomized Training Test

In order to assess over-fitting, the inventors performed a randomization test (Sgourakis et al., 2005b). For every G-protein, the original labels of the training matrix were replaced with randomly determined labels, while preserving the ratio of number of positive (coupling) and negative (non-coupling) GPCRs. Performance using the randomization training set was lower than that of actual training set, implying that the inventors' strategy is insensitive to the data training set.

Test Set to Benchmark Predictor Performance

To benchmark the inventive method and compare it with Pred Couple (Sgourakis et al., 2005b), a web-server available to predict GPCR-G-protein coupling, the inventors extracted all the GPCRs from GtoPdb that are present in neither the chimeric G-protein-based TGFα shedding assay nor in Pred Couple's training set, thus obtaining a list of 86 unseen GPCRs. As mentioned above, one of the major limitations of GtoPdb is the absence of a definite true negative set, thus, the best measure to compare the inventive predictor with that of Pred Couple is recall, also known as sensitivity or the true positive rate. Since both GtoPdb and Pred Couple provide coupling information at the G-protein family level, the inventors combined the performance of individual G-protein predictors based on their families to compare the performance of the inventive method of the first inventive aspect with Pred-Couple. For example: if a given GPCR was predicted to couple to at least one of the G-proteins of a family, it was annotated as coupling to that G-protein family. The combinations of the inventive predictors at the family level outperformed Pred-Couple over the test set. The individual G-protein predictors' and their combined (G-protein family level) performance over the Test set at different LogRAi cutoffs are reported in FIGS. 15A and 15C, respectively.

To further check the predictor's performance, the inventors trained and tested an additional predictor using exactly the same procedure as reported above using GtoPdb coupling information instead of the TGFα shedding assay (FIG. 4A).

Functional Classification of Coupling Features Through 3D Structure Analysis.

The inventors identified functional positions as those mediating inter- and intra-molecular contacts, i.e. whenever at least one pair of atoms, from either a residue-residue or residue-ligand interface, was found spatially closer than 5 Å. The inventors analysed 246 3D structures, representing 51 members of the GPCR Class A (PFAM: 7tm_1) family using PDB-Swissprot-PFAM correspondences available from SIFT (as of July 2018) (Velankar et al., 2013).

To define GPCR-ligand contact sites, the inventors restricted their analysis only to GPCR putative ligands as defined in GtoPd (Harding et al., 2018). The inventors performed similarity searches between GtoPdb and PDB ligands using topological fingerprints from RDKit (http://www.rdkit.org/) generated from SMILES descriptors and the inventors considered only the best matching GtoPdb ligand for a given PDB component. All the protein residues mediating contacts were mapped to protein sequence position using alignments between Uniprot canonical sequences and corresponding PDB generated through Blast (Altschul et al., 1990). Note that through this procedure the inventors considered contacts mediated by the equivalent residues from different structures only once, thus avoiding over-counting due to PDB redundancy. The inventors then mapped the amino acids found in contact with putative ligands on the PFAM multiple sequence alignments (MSA). Based on available GPCR-G-protein complexes (PDB ID: 3SN6, 5G53, 6D9H, 6GDG, 6DDE, 6DDF, 6CMO and 6D9H) the inventors similarly identified the residues forming the receptor-G-protein interaction interface by using a distance cutoff of 6.5 Å to define atom-pairs forming inter-residue contacts.

Similarly to methods employed to decipher the activation mechanisms of GPCRs and other signaling molecules, the inventors also inspected the network of intramolecular contacts using the same thresholds as above and they similarly mapped the identified positions on Class A 7TM MSA. They then defined a consensus contact network by considering the sequence positions (nodes) found in contact (edges) in at least 50% of the analyzed sequences. They performed network analysis through igraph (Csardi and T., 2006), defining as hub nodes having a degree of at least 4. The inventors generated functional state consensus networks by grouping available structures using ligand classification from GtoPdb (i.e. agonist or antagonist/inverse agonist) or functional classification directly available from the protein databank (i.e. active or inactive), thus defining active-like (i.e. agonist-bound/active) or inactive-like (i.e. antagonist-bound/inactive) states. Structures where this classification was not possible were discarded.

The inventors calculated the shortest paths connecting positions forming the consensus ligand and G-protein binding interfaces within active- and inactive-like networks through the Dijkstra algorithm (Dijkstra, 1959) from igraph. Active-state specific shortest paths were defined as those characterized by having either endpoints, or intermediate connectivity residues, exclusive to active-like state contact network.

$G_{12}$-Coupled DREADD Chimeric Sequences Predictions

In order to inventively predict mutant sequences with enhanced $G_{12/13}$ coupling capabilities, the inventors started from the available DREADD coupled with $G_{q/11}$ (M3D) and $G_{i/o}$ (M4D) (Armbruster et al., 2007). They generated chimeric sequences by swapping on these backbones the ICL3 and C-term sequence stretches derived from each receptor of the chimeric G-protein-based assay panel (148 GPCRs). The inventors first aligned the receptor sequences, including M3D and M4D, to the PFAM 7tm_1 HMM model. They defined ICL3 as the MSA region comprised within HMM positions 173-205, and the C-term as the MSA portion starting after 7tm_1 HMM end (i.e. position 268). They then created hM3D and hM4D chimeras by exchanging their ICL3 and C-term sequences with the corresponding sequences from each receptor testing in the chimeric G-protein-based TGFα shedding assay. They generated 296 chimeric sequences by swapping the ICL3 alone or in combination with the C-termini.

The inventors then predicted the coupling probability to GNA12/GNA13 for each chimeric sequence, ranking them according to their relative coupling probability (i.e. $\Delta Pred\_Coup = Pred\_Coup^{DREADD\_MUT} - Pred\_Coup^{DREADD}$). The inventors selected the top 10 chimeric sequences for experimental validation.

Quantification and Statistical Analysis

Statistical analyses were performed using GraphPad Prism 7 software and methods are described in the legends of the figures. In flow cytometry experiments, approximately 20,000 cells were measured for their fluorescent signals and data were analyzed by FlowJo software. Mean fluorescent intensity was used for quantification of cell surface GPCR expression. Representation of symbols and error bars is described in the ligands. Symbols are either mean values of indicated numbers of independent experiments or datapoint from single experiment. Error bars denote SEM or SD. Concentration-response curves were fitted to all data by the Nonlinear Regression: Variable slope (four parameter) in the Prism 7 tool. Liner regression and representation of 90% confidence bands were performed by the Prism 7 tool. For multiple comparison analysis in the flow cytometry data and G12-DREADD generation, two-way ANOVA and following Dunnet's test and Sidak's test, respectively, was used.

Data and Software Availability

The Python code used for the predictor is available on GitHub (https://github.com/raimondifranc/gpcr_coupling_predictor)

CITED REFERENCES

Altschul, S. F., Gish, W., Miller, W., Myers, E. W., and Lipman, D. J. (1990). Basic local alignment search tool. J Mol Biol 215, 403-410.

Armbruster, B. N., Li, X., Pausch, M. H., Herlitze, S., and Roth, B. L. (2007). Evolving the lock to fit the key to create a family of G protein-coupled receptors potently activated by an inert ligand. Proc Natl Acad Sci USA 104, 5163-5168.

Ataei, F., Torkzadeh-Mahani, M., and Hosseinkhani, S. (2013). A novel luminescent biosensor for rapid monitoring of IP3 by split-luciferase complementary assay. Biosens Bioelectron 41, 642-648.

Capper, M. J., and Wacker, D. (2018). How the ubiquitous GPCR receptor family selectively activates signalling pathways. Nature 558, 529-530.

Chen, P., Zuo, H., Xiong, H., Kolar, M. J., Chu, Q., Saghatelian, A., Siegwart, D. J., and Wan, Y. (2017). Gpr132 sensing of lactate mediates tumor-macrophage interplay to promote breast cancer metastasis. Proc Natl Acad Sci USA 114, 580-585.

Csardi, G., and T., N. (2006). The igraph software package for complex network research. InterJournal Complex Systems.

Denker, B. M., Schmidt, C. J., and Neer, E. J. (1992). Promotion of the GTP-liganded state of the Go alpha protein by deletion of the C terminus. J Biol Chem 267, 9998-10002.

Devost, D., Sleno, R., Petrin, D., Zhang, A., Shinjo, Y., Okde, R., Aoki, J., Inoue, A., and Hebert, T. E. (2017). Conformational Profiling of the AT1 Angiotensin II Receptor Reflects Biased Agonism, G Protein Coupling, and Cellular Context. J Biol Chem 292, 5443-5456.

Dijkstra, E. (1959). A note on two problems in connexion with graphs. Numerische Mathematik 1, 269-271.

Dixon, A. S., Schwinn, M. K., Hall, M. P., Zimmerman, K., Otto, P., Lubben, T. H., Butler, B. L., Binkowski, B. F., Machleidt, T., Kirkland, T. A., et al. (2016). Nano-Luc Complementation Reporter Optimized for Accurate Measurement of Protein Interactions in Cells. ACS chemical biology 11, 400-408.

Dorsam, R. T., and Kunapuli, S. P. (2004). Central role of the P2Y12 receptor in platelet activation. J Clin Invest 113, 340-345.

Dou, Y., Wang, J., Yang, J., and Zhang, C. (2012). Lipred: a sequence-based prediction tool for catalytic residues in enzymes with the L1-logreg classifier. PLoS One 7, e35666.

Eddy, S. R. (1998). Profile hidden Markov models. Bioinformatics 14, 755-763.

Ehlert, F. J., Griffin, M. T., Sawyer, G. W., and Bailon, R. (1999). A simple method for estimation of agonist activity at receptor subtypes: comparison of native and cloned M3 muscarinic receptors in guinea pig ileum and transfected cells. J Pharmacol Exp Ther 289, 981-992.

Finn, R. D., Coggill, P., Eberhardt, R. Y., Eddy, S. R., Mistry, J., Mitchell, A. L., Potter, S. C., Punta, M., Qureshi, M., Sangrador-Vegas, A., et al. (2016). The Pfam protein families database: towards a more sustainable future. Nucleic Acids Res 44, D279-285.

Flock, T., Ravarani, C. N. J., Sun, D., Venkatakrishnan, A. J., Kayikci, M., Tate, C. G., Veprintsev, D. B., and Babu, M. M. (2015). Universal allosteric mechanism for Galpha activation by GPCRs. Nature 524, 173-179.

Gales, C., Rebois, R. V., Hogue, M., Trieu, P., Breit, A., Hebert, T. E., and Bouvier, M. (2005). Real-time monitoring of receptor and G-protein interactions in living cells. Nat Methods 2, 177-184.

Guettier, J. M., Gautam, D., Scarselli, M., Ruiz de Azua, I., Li, J. H., Rosemond, E., Ma, X., Gonzalez, F. J., Armbruster, B. N., Lu, H., et al. (2009). A chemical-genetic approach to study G protein regulation of beta cell function in vivo. Proc Natl Acad SciU S A 106, 19197-19202.

Harding, S. D., Sharman, J. L., Faccenda, E., Southan, C., Pawson, A. J., Ireland, S., Gray, A. J. G., Bruce, L., Alexander, S. P. H., Anderton, S., et al. (2018). The IUPHAR/BPS Guide to PHARMACOLOGY in 2018:

updates and expansion to encompass the new guide to IMMUNOPHARMACOLOGY. Nucleic Acids Res 46, D1091-D1106.

Hauser, A. S., Attwood, M. M., Rask-Andersen, M., Schioth, H. B., and Gloriam, D. E. (2017). Trends in GPCR drug discovery: new agents, targets and indications. Nat Rev Drug Discov 16, 829-842.

Hauser, A. S., Chavali, S., Masuho, I., Jahn, L. J., Martemyanov, K. A., Gloriam, D. E., and Babu, M. M. (2018). Pharmacogenomics of GPCR Drug Targets. Cell 172, 41-54 e19.

Herroeder, S., Reichardt, P., Sassmann, A., Zimmermann, B., Jaeneke, D., Hoeckner, J., Hollmann, M. W., Fischer, K. D., Vogt, S., Grosse, R., et al. (2009). Guanine nucleotide-binding proteins of the G12 family shape immune functions by controlling CD4+ T cell adhesiveness and motility. Immunity 30, 708-720.

Horn, F., van der Wenden, E. M., Oliveira, L., AP, I. J., and Vriend, G. (2000). Receptors coupling to G proteins: is there a signal behind the sequence? Proteins 41, 448-459.

Inoue, A., Ishiguro, J., Kitamura, H., Arima, N., Okutani, M., Shuto, A., Higashiyama, S., Ohwada, T., Arai, H., Makide, K., et al. (2012). TGFalpha shedding assay: an accurate and versatile method for detecting GPCR activation. Nat Methods 9, 1021-1029.

Insel, P. A., and Ostrom, R. S. (2003). Forskolin as a tool for examining adenylyl cyclase expression, regulation, and G protein signaling. Cell Mol Neurobiol 23, 305-314.

Isberg, V., Mordalski, S., Munk, C., Rataj, K., Harpsoe, K., Hauser, A. S., Vroling, B., Bojarski, A. J., Vriend, G., and Gloriam, D. E. (2017). GPCRdb: an information system for G protein-coupled receptors. Nucleic Acids Res 45, 2936.

Kihara, Y., Maceyka, M., Spiegel, S., and Chun, J. (2014). Lysophospholipid receptor nomenclature review: IUPHAR Review 8. Br J Pharmacol 171, 3575-3594.

Leng, W., Pang, X., Xia, H., Li, M., Chen, L., Tang, Q., Yuan, D., Li, R., Li, L., Gao, F., et al. (2013). Novel split-luciferase-based genetically encoded biosensors for noninvasive visualization of Rho GTPases. PLoS One 8, e62230.

Martin, D., Abba, M. C., Molinolo, A. A., Vitale-Cross, L., Wang, Z., Zaida, M., Delic, N. C., Samuels, Y., Lyons, J. G., and Gutkind, J. S. (2014). The head and neck cancer cell oncogenome: a platform for the development of precision molecular therapies. Oncotarget 5, 8906-8923.

Muppidi, J. R., Schmitz, R., Green, J. A., Xiao, W., Larsen, A. B., Braun, S. E., An, J., Xu, Y., Rosenwald, A., Ott, G., et al. (2014). Loss of signalling via Galpha13 in germinal centre B-cell-derived lymphoma. Nature 516, 254-258.

O'Hayre, M., Inoue, A., Kufareva, I., Wang, Z., Mikelis, C. M., Drummond, R. A., Avino, S., Finkel, K., Kalim, K. W., DiPasquale, G., et al. (2016). Inactivating mutations in GNA13 and RHOA in Burkitt's lymphoma and diffuse large B-cell lymphoma: a tumor suppressor function for the Galpha13/RhoA axis in B cells. Oncogene 35, 3771-3780.

Patel, Y. M., Lordkipanidze, M., Lowe, G. C., Nisar, S. P., Garner, K., Stockley, J., Daly, M. E., Mitchell, M., Watson, S. P., Austin, S. K., et al. (2014). A novel mutation in the P2Y12 receptor and a function-reducing polymorphism in protease-activated receptor 1 in a patient with chronic bleeding. J Thromb Haemost 12, 716-725.

Pedregosa F, V. G., Gramfort A, Michel V, Thirion B, Grisel O, Blondel M, Prettenhofer P, Weiss R, Dubourg V, Vanderplas J, Passos A, Cournapeau D, Brucher M, Perrot M, Duchesnay E (2011). Scikit-learn: Machine Learning in Python. J Machine Learning Res 12, 2825-2830.

Rasmussen, S. G., DeVree, B. T., Zou, Y., Kruse, A. C., Chung, K. Y., Kobilka, T. S., Thian, F. S., Chae, P. S., Pardon, E., Calinski, D., et al. (2011). Crystal structure of the beta2 adrenergic receptor-Gs protein complex. Nature 477, 549-555.

Rodriguez, G. J., Yao, R., Lichtarge, O., and Wensel, T. G. (2010). Evolution-guided discovery and recoding of allosteric pathway specificity determinants in psychoactive bioamine receptors. Proc Natl Acad Sci USA 107, 7787-7792.

Sauliere, A., Bellot, M., Paris, H., Denis, C., Finana, F., Hansen, J. T., Altie, M. F., Seguelas, M. H., Pathak, A., Hansen, J. L., et al. (2012). Deciphering biased-agonism complexity reveals a new active AT1 receptor entity. Nat Chem Biol 8, 622-630.

Schrage, R., Schmitz, A. L., Gaffal, E., Annala, S., Kehraus, S., Wenzel, D., Bullesbach, K. M., Bald, T., Inoue, A., Shinjo, Y., et al. (2015). The experimental power of FR900359 to study Gq-regulated biological processes. Nat Commun 6, 10156.

Sgourakis, N. G., Bagos, P. G., and Hamodrakas, S. J. (2005a). Prediction of the coupling specificity of GPCRs to four families of G-proteins using hidden Markov models and artificial neural networks. Bioinformatics 21, 4101-4106.

Sgourakis, N. G., Bagos, P. G., Papasaikas, P. K., and Hamodrakas, S. J. (2005b). A method for the prediction of GPCRs coupling specificity to G-proteins using refined profile Hidden Markov Models. BMC Bioinformatics 6, 104.

Sievers, F., Wilm, A., Dineen, D., Gibson, T. J., Karplus, K., Li, W., Lopez, R., McWilliam, H., Remmert, M., Soding, J., et al. (2011). Fast, scalable generation of high-quality protein multiple sequence alignments using Clustal Omega. Mol Syst Biol 7, 539.

Stallaert, W., van der Westhuizen, E. T., Schonegge, A. M., Plouffe, B., Hogue, M., Lukashova, V., Inoue, A., Ishida, S., Aoki, J., Le Gouill, C., et al. (2017). Purinergic Receptor Transactivation by the beta2-Adrenergic Receptor Increases Intracellular Ca2+ in Nonexcitable Cells. Mol Pharmacol 91, 533-544.

Sugimoto, Y., and Narumiya, S. (2007). Prostaglandin E receptors. J Biol Chem 282, 11613-11617.

Suzuki, N., Hajicek, N., and Kozasa, T. (2009). Regulation and physiological functions of G12/13-mediated signaling pathways. Neurosignals 17, 55-70.

Thomsen, W., Frazer, J., and Unett, D. (2005). Functional assays for screening GPCR targets. Current opinion in biotechnology 16, 655-665.

Urban, D. J., and Roth, B. L. (2015). DREADDs (designer receptors exclusively activated by designer drugs): chemogenetic tools with therapeutic utility. Annu Rev Pharmacol Toxicol 55, 399-417.

Velankar, S., Dana, J. M., Jacobsen, J., van Ginkel, G., Gane, P. J., Luo, J., Oldfield, T. J., O'Donovan, C., Martin, M. J., and Kleywegt, G. J. (2013). SIFTS: Structure Integration with Function, Taxonomy and Sequences resource. Nucleic Acids Res 41, D483-489.

Violin, J. D., Crombie, A. L., Soergel, D. G., and Lark, M. W. (2014). Biased ligands at G-protein-coupled receptors: promise and progress. Trends Pharmacol Sci 35, 308-316.

Waterhouse, A. M., Procter, J. B., Martin, D. M., Clamp, M., and Barton, G. J. (2009). Jalview Version 2—a multiple sequence alignment editor and analysis workbench. Bioinformatics 25, 1189-1191.

Weinstein, J. B. a. H. (1995). Integrated methods for the construction of three-dimensional models and computational probing of structure-function relations in G protein-coupled receptors. Methods Neurosci 25, 366-428.

Wess, J., Nakajima, K., and Jain, S. (2013). Novel designer receptors to probe GPCR signaling and physiology. Trends Pharmacol Sci 34, 385-392.

Wettschureck, N., and Offermanns, S. (2005). Mammalian G proteins and their cell type specific functions. Physiol Rev 85, 1159-1204.

Wheeler, T. J., Clements, J., and Finn, R. D. (2014). Skylign: a tool for creating informative, interactive logos representing sequence alignments and profile hidden Markov models. BMC Bioinformatics 15, 7.

Wong, S. K. (2003). G protein selectivity is regulated by multiple intracellular regions of GPCRs. Neurosignals 12, 1-12.

Woodward, D. F., Jones, R. L., and Narumiya, S. (2011). International Union of Basic and Clinical Pharmacology. LXXXIII: Classification of Prostanoid Receptors, Updating 15 Years of Progress. Pharmacol Rev 63, 471-538.

Yabuki, Y., Muramatsu, T., Hirokawa, T., Mukai, H., and Suwa, M. (2005). GRIFFIN: a system for predicting GPCR-G-protein coupling selectivity using a support vector machine and a hidden Markov model. Nucleic Acids Res 33, W148-153.

The invention claimed is:

1. A Designer Receptor Exclusively Activated by Designer Drugs (DREADD), wherein the DREADD is a $G_{12}$-specific G-protein coupled receptor (GPCR) responding to a ligand and comprises or consists of the amino acid sequence SEQ ID NO: 2, 3 or 4.

\* \* \* \* \*